United States Patent
Kawano et al.

(10) Patent No.: US 8,162,821 B2
(45) Date of Patent: Apr. 24, 2012

(54) BODY-INSERTABLE DEVICE POSITIONING SYSTEM AND IN-VIVO OBSERVATION METHOD

(75) Inventors: Hironao Kawano, Tokyo (JP); Hironobu Takizawa, Tokyo (JP); Hidetake Segawa, Tokyo (JP); Isao Aoki, Kanagawa (JP); Katsumi Hirakawa, Kanagawa (JP); Satomi Kobayashi, Tokyo (JP); Hideo Ito, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1097 days.

(21) Appl. No.: 11/646,878

(22) Filed: Dec. 28, 2006

(65) Prior Publication Data

US 2007/0221233 A1    Sep. 27, 2007

(30) Foreign Application Priority Data

Dec. 28, 2005 (JP) ................................ 2005-380454

(51) Int. Cl.
*A61B 1/00* (2006.01)
*A61B 5/05* (2006.01)
(52) U.S. Cl. ......... 600/117; 600/424; 600/118; 128/899
(58) Field of Classification Search .................. 600/101, 600/109, 114, 117, 118, 424; 348/65; 128/899
See application file for complete search history.

(56) References Cited

U.S. PATENT DOCUMENTS

| | | | |
|---|---|---|---|
| 4,278,077 A | 7/1981 | Mizumoto | |
| 5,681,260 A * | 10/1997 | Ueda et al. | 600/114 |
| 6,240,312 B1 * | 5/2001 | Alfano et al. | 600/476 |
| 2003/0018280 A1 | 1/2003 | Lewkowicz et al. | |
| 2003/0020810 A1 | 1/2003 | Takizawa et al. | |
| 2003/0214580 A1 | 11/2003 | Iddan | |
| 2003/0229268 A1 * | 12/2003 | Uchiyama et al. | 600/109 |
| 2004/0264754 A1 * | 12/2004 | Kleen et al. | 382/128 |

(Continued)

FOREIGN PATENT DOCUMENTS

DE   29 29 429 A1   2/1980

(Continued)

OTHER PUBLICATIONS

Extended Supplementary European Search Report dated Apr. 4, 2011, in counterpart European Patent Application No. 06843617.9.

(Continued)

*Primary Examiner* — John P Leubecker
*Assistant Examiner* — Christopher Sponheimer
(74) *Attorney, Agent, or Firm* — Scully, Scott, Murphy & Presser, P.C.

(57) ABSTRACT

An object of the present invention is to actively control at least one of the position and direction of the imaging field in a subject and to observe a desired observed region in the subject certainly in a short period of time. A body-insertable device system according to the present invention includes a capsule endoscope 1 introduced into a subject and a permanent magnet 3. An imaging unit of the capsule endoscope 1 for taking an image inside the subject is fixed in a casing. The capsule endoscope 1 includes a drive unit for changing at least one of the position and posture of the casing in the liquid 2a which is also introduced in the subject 100. The permanent magnet 3 controls the operation of the drive unit for changing at least one of the position and posture of the casing in the liquid 2a.

16 Claims, 68 Drawing Sheets

U.S. PATENT DOCUMENTS

| | | |
|---|---|---|
| 2005/0036059 A1 | 2/2005 | Goldwasser |
| 2005/0085696 A1 | 4/2005 | Uchiyama et al. |
| 2005/0124875 A1* | 6/2005 | Kawano et al. ............... 600/407 |
| 2005/0216231 A1* | 9/2005 | Aoki et al. .................... 702/183 |
| 2006/0004255 A1* | 1/2006 | Iddan et al. .................... 600/160 |

FOREIGN PATENT DOCUMENTS

| | | |
|---|---|---|
| EP | 1 972 253 A1 | 9/2008 |
| JP | 2003-38424 | 2/2003 |
| JP | 2003-210395 | 7/2003 |
| JP | 2003210395 A * | 7/2003 |
| JP | 2003-275170 A | 9/2003 |
| JP | 2003-325438 | 11/2003 |
| JP | 2005-198879 A | 7/2005 |
| JP | 2005-334331 A | 12/2005 |
| WO | WO 2004/028335 A2 | 4/2004 |
| WO | 2004-529718 | 9/2004 |
| WO | WO 2005/060348 A2 | 7/2005 |

OTHER PUBLICATIONS

Japanese Office Action dated Oct. 25, 2011 in counterpart Japanese Patent Application No. 2007-552983 together with English translation.

* cited by examiner

RING-SHAPED PERMANENT MAGNET 620

BODY-INSERTABLE DEVICE POSITIONING SYSTEM AND IN-VIVO OBSERVATION METHOD

CROSS-REFERENCE TO RELATED APPLICATIONS

This application is based upon and claims the benefit of priority from Japanese Patent Application No. 2005-380454, filed Dec. 28, 2005, the entire contents of which are incorporated herein by reference.

BACKGROUND OF THE INVENTION

1. Field of the Invention

The present invention relates to a body-insertable device system and an in-vivo observation method using a body-insertable device for being introduced into a subject and sequentially taking images in the subject.

2. Description of the Related Art

Recently, in a field of endoscopes, a capsule-shaped body-insertable device (for example, a capsule endoscope) including an imaging function and a radio communication function has been proposed and a body-insertable device system for obtaining an image in a subject using this capsule endoscope has been developed. In order to observe (inspect) inside a subject, a capsule endoscope is swallowed through, for example, a mouth of the subject. Then, until it is naturally discharged, it moves inside a body cavity, such as the stomach or small intestine according to their peristaltic movements and takes images in the subject every 0.5 seconds, for example.

While the capsule endoscope moves inside the subject, the images taken by the capsule endoscope are received via an antenna provided on a body surface of the subject and shown on an external image display. The image display includes a radio communication function for the capsule endoscope and an image memory function for sequentially storing images received from the capsule endoscope in the subject. A doctor or a nurse displays images stored in the image display, that is, images of digestive canal in the subject to observe (inspect) inside the subject and provides diagnosis.

As such a body-insertable device, there is an in-vivo sensing device having a specific gravity that allows the device to float in liquid introduced in a subject and taking an image of a body cavity as being carried by flow of the liquid in the body cavity of the subject (See PCT National Publication No. 2004-529718).

However, the above described conventional body-insertable device is moved in the subject by the flow of the liquid filling the body cavity so that it is often difficult to move actively without relying on the flow of the fluid and the position or direction of imaging field in the body cavity cannot be changed actively. Thus, it is often difficult to take an entire image of a desired observed region in the subject, for example, the digestive canal such as the stomach or large intestine and it becomes difficult to observe every part of the observed region. Accordingly, there have been problems that it takes long time to observe inside the subject and that there is a possibility of overlooking an affected area or a bleeding area in the observed region, for example.

SUMMARY OF THE INVENTION

At least one object of the present invention is to solve the problems.

A body-insertable device system according to one aspect of the present invention includes a casing to be introduced into a subject and including at least one imaging unit having a specific observing direction for the subject; liquid to be introduced into the subject; and a drive unit which changes at least one of a position and posture of the casing in the liquid.

An in-vivo observation method according to another aspect of the present invention includes a casing introducing step of introducing a casing for obtaining an image into a subject; a liquid introducing step of introducing liquid into the subject; and a position/posture changing step of changing at least one of the position and posture of the casing in the liquid introduced in the casing introducing step.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Preferred embodiments of a body-insertable device, body-insertable device system, and an in-vivo observation method according to the present invention will be described with reference to the drawings. It is noted that the present invention is not limited to what is described in the embodiments.

First Embodiment

Figure 1:
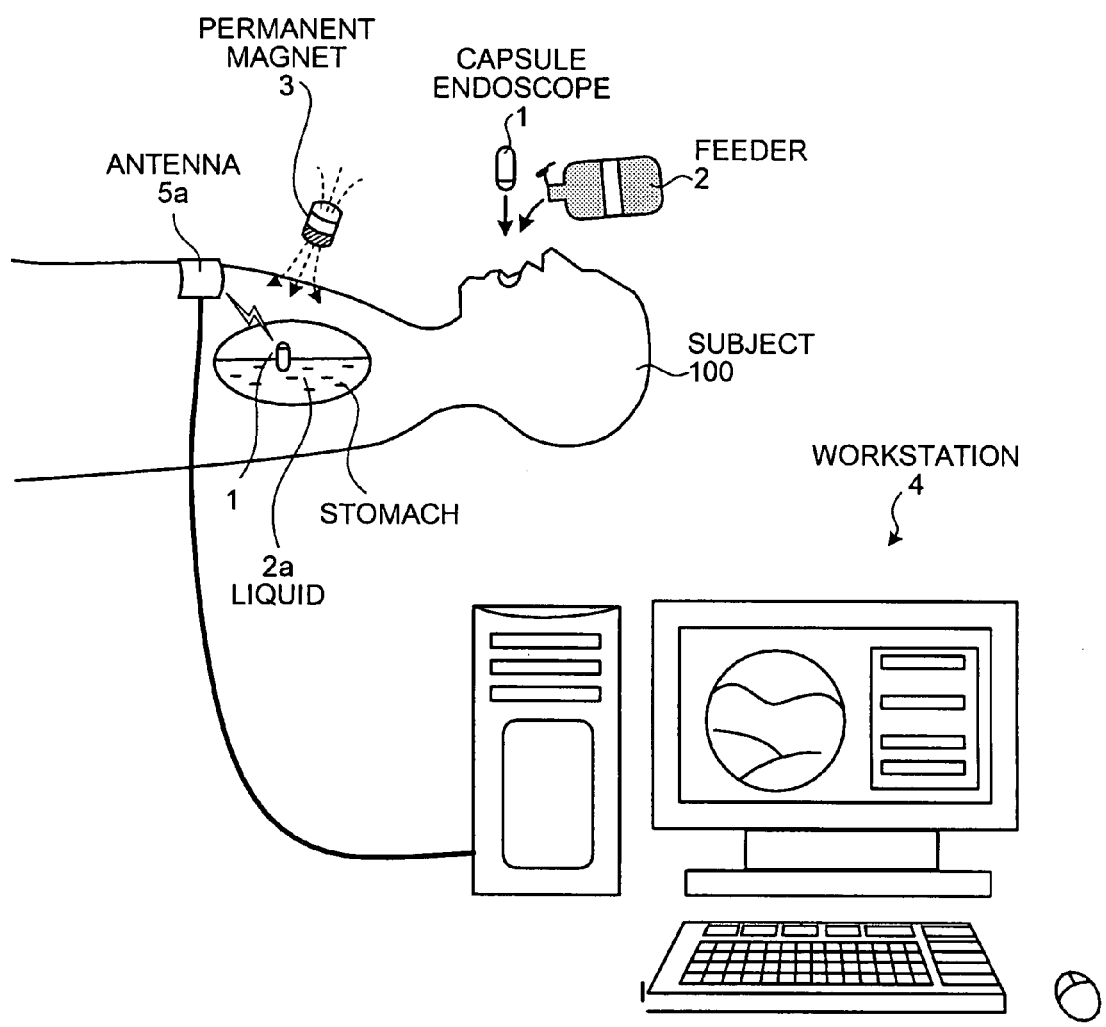
FIG. 1 is a schematic view schematically showing a configuration example of a body-insertable device system according to a first embodiment of the present invention.

FIG. 1 is a schematic view schematically showing a configuration example of a body-insertable device system according to a first embodiment of the present invention. As shown in FIG. 1, the body-insertable device system of the first embodiment includes a capsule endoscope 1 for being inserted into a subject 100 and imaging inside a digestive canal of the subject 100, a feeder 2 for introducing liquid 2a, in which the capsule endoscope 1 floats, into the subject 100, a permanent magnet 3 for controlling at least one of position and posture of the capsule endoscope 1 floating in the liquid 2a, and a workstation 4 for displaying an image taken by the capsule endoscope 1 on a screen.

The capsule endoscope 1 includes an imaging function for imaging inside the subject 100 and a radio communication function for sending various information such as an image to the workstation 4. Further, the capsule endoscope 1 is made in a size easily insertable into the subject 100 and has specific gravity equal to or smaller than that of the liquid 2a. When swallowed by the subject 100, this type of capsule endoscope 1 moves in the digestive canal by a peristaltic movement or the like of the subject 100 and sequentially images inside the digestive canal at a predetermined interval, for example, every 0.5 seconds. Further, the capsule endoscope 1 sends an image of the inside of the digestive canal to the workstation 4.

The feeder 2 feeds liquid 2a into the subject 100 so that the capsule endoscope 1 floats in the liquid 2a. Concretely, the feeder 2 contains desired liquid 2a, for example, water or normal saline solution or the like and feed the liquid 2a into body via a mouth of the subject 100. The liquid 2a fed by such feeder 2 is introduced into, for example, the stomach of the subject 100 and the capsule endoscope 1 floats in the liquid 2a in the stomach.

The permanent magnet 3 works as a control means for controlling at least one of the position and posture of the capsule endoscope 1 in the subject 100. Concretely, the permanent magnet 3 generates magnetic field for the capsule endoscope 1 introduced in the inside of the subject 100 (for example, inside of the stomach) and controls an operation (that is, a movement of the casing) of the capsule endoscope 1 in the liquid 2a with a magnetic force of the magnetic field. The permanent magnet 3 controls the operation of the capsule endoscope 1 to control at least one of the position and posture of the capsule endoscope 1 in the subject 100. In this case, the capsule endoscope 1 includes a magnet for moving the casing in response to the magnetic force applied by the permanent magnet 3.

As the permanent magnet 3, a permanent magnet having a predetermined magnetic force may be employed; however, more desirably, a plurality of permanent magnets having different magnetic forces are prepared and one of the plurality of permanent magnet is selected and employed. In this case, the permanent magnet 3 having a proper magnetic field may be selected according to a body type (for example, height, weight, waist size, and the like) or the operation of the controlled capsule endoscope 1 (for example, movement, wobble, or both).

The workstation 4 includes a radio communication function for receiving various information such as image taken from the capsule endoscope 1 and a display function for displaying the image received from the capsule endoscope 1 on the screen. Concretely, the workstation 4 includes an antenna 5a for sending and receiving radio signal to and from the capsule endoscope 1, and, for example, receives various information from the capsule endoscope 1 via the antenna 5a disposed on the body surface of the subject 100. Further, the workstation 4 may send a control signal (for example, a control signal for starting or stopping the imaging operation of the capsule endoscope 1) via the antenna 5a to control the drive of the capsule endoscope 1.

The antenna 5a is provided with, for example, a loop antenna to send and receive a radio signal between the capsule endoscope 1 and the workstation 4. Concretely, as shown in FIG. 1, the antenna 5a is located at a predetermined position on the body surface of the subject 100, for example, near the stomach of the subject 100. In this case, the antenna 5a realizes radio communication between the capsule endoscope 1 in the stomach of the subject 100 and the workstation 4. The antenna 5a may be located on the body surface of the subject 100 corresponding to the pathway of the capsule endoscope 1 in the subject 100. Further, the number of the antenna 5a to be provided is not limited to one and more than one antennas 5a may be provided.

Figure 2:
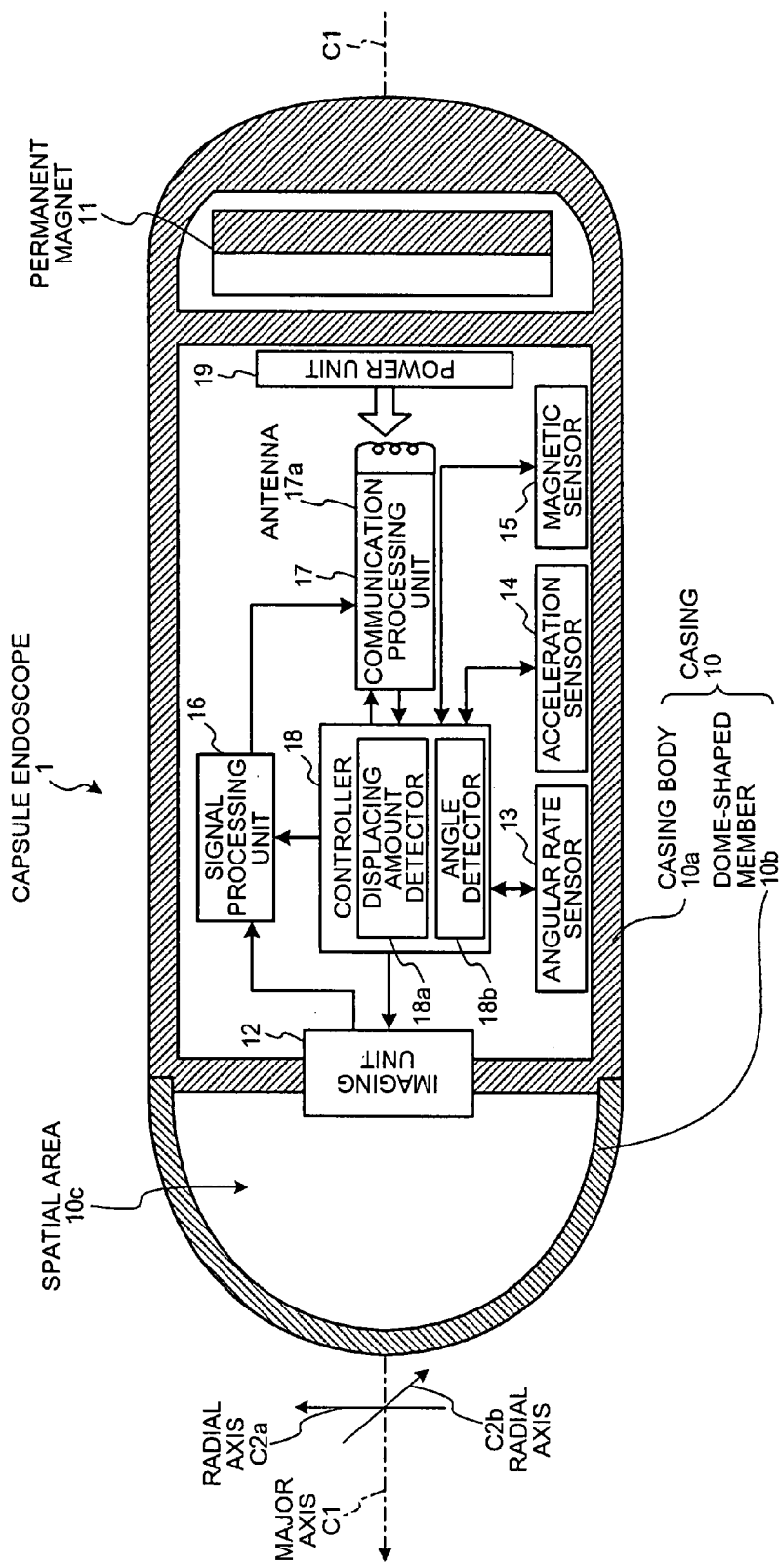
FIG. 2 is a schematic view showing a configuration example of the body-insertable device system according to the first embodiment of the present invention.

Next, a structure of the capsule endoscope 1 as an example of the body-insertable device according to the present invention will be described in detail. FIG. 2 is a schematic view showing a configuration example of the capsule endoscope 1. As shown in FIG. 2, the capsule endoscope 1 includes a capsule-shaped casing 10 formed in a size easily insertable into the subject 100 and a permanent magnet 11 for moving the casing 10 according to the magnetic force of the permanent magnet 3. Further, the capsule endoscope 1 includes an imaging unit 12 for imaging inside the subject 100, an angular rate sensor 13 for detecting a angular rate when the casing 10 wobbles, an acceleration sensor 14 for detecting an acceleration when the casing 10 moves, and a magnetic sensor 15 for detecting a magnetic field strength generated by the permanent magnet 3 toward the capsule endoscope 1. Also, the capsule endoscope 1 includes a signal processing unit 16 for generating an image signal corresponding to an image taken by the imaging unit 12, an antenna 17a for sending and receiving a radio signal with the external antenna 5a, and a communication processing unit 17 for modulating various signal such as the image signal to be transmitted to the external workstation 4 into a radio signal or demodulating a radio signal received via the antenna 17a. In addition, the capsule endoscope 1 includes a control unit 18 for controlling drive of each element of the capsule endoscope 1 and a power unit 19 for supplying driving power to each component of the capsule endoscope 1.

The casing 10 is a capsule-shaped member formed in a size easily inserted into the subject 100 and is provided with a casing body 10a for containing each element of the capsule endoscope 1 and a dome-shaped member 10b for forming a front-end part of the casing 10. As shown in FIG. 2, the casing body 10a is provided with, for example, the permanent magnet 11 and the power unit 19 at a rear portion of the casing 10 and the imaging unit 12 at the front-end part. The dome-shaped member 10b is a substantially transparent dome-shaped member having an optical transparency and attached to the front-end part of the casing body 10a so as to cover the imaging unit 12. In this case, the dome-shaped member 10b forms a spatial area 10c surrounded by the inner wall of the dome-shaped member 10b and the front-end part of the casing body 10a. The casing 10 provided with such casing body 10a and dome-shaped member 10b has a specific gravity which is equal to or smaller than that of the liquid 2a and the center of gravity is in its rear portion.

The permanent magnet 11 functions as a driver for moving the casing 10 by a magnetic force of a magnetic field generated outside the subject 100. Concretely, the permanent magnet 11 becomes magnetized in a longitudinal direction of the casing 10 and, for example, when the external permanent magnet 3 generates a magnetic field toward the permanent magnet 11, the permanent magnet 11 moves or wobbles the casing 10 in the liquid 2a according to the magnetic force applied by the magnetic field. With this, the permanent magnet 11 can change at least one of the posture and position of the capsule endoscope 1 in the liquid 2 by the magnetic force.

The posture of the capsule endoscope 1, mentioned here, is the posture of the casing 10 at predetermined space coordinates xyz. Concretely, the posture of the capsule endoscope 1, mentioned here, is determined by the direction of the major axis C1 on space coordinates xyz when the major axis C1 extending from the rear-end part toward the front-end part is set as an axis vector on a central axis of the casing 10 in its longitudinal direction. Further, the position of the capsule endoscope 1, mentioned here, is determined by the position of the casing 10 on the space coordinates xyz. That is, when the capsule endoscope 1 is introduced into the subject 100, the posture of the capsule endoscope 1 in the subject 100 is determined based on the direction of the major axis C1 on the space coordinates xyz and the position of the capsule endoscope 1 in the subject 100 is determined based on the position of the casing 10 on the space coordinates xyz.

The imaging unit 12 is configured to, for example, image inside the digestive canal of the subject 100. Concretely, the imaging unit 12 is provided with an imaging device such as a CCD or CMOS, a light emitting device such as an LED for illuminating the imaging field of the imaging device, and an optical system such as a lens for focusing catoptric lights from the imaging field toward the imaging device. The imaging unit 12 is fixed in the front-end part of the casing body 10a, as described above, focuses catoptric lights from the imaging field received via the dome-shaped member 10b, and, for example, images inside the digestive canal of the subject 100. The imaging unit 12 sends the obtained image information to the signal processing unit 16. Here, the optical system of the imaging unit 12 is desirably wide-angle. With this, the imaging unit 12 can have, for example, a viewing angle of 100 to 140 degree angle so that a wide imaging field can be obtained. Since the body-insertable device system according to the first embodiment of the present invention includes the capsule endoscope 1 having such a wide imaging field, the observation of the subject 100 can be improved.

The direction of the imaging field of the imaging unit 12 fixed inside the casing 10 is determined by the direction of the casing 10 on the space coordinates xyz. That is, the acceptance surface of the imaging unit 12 is placed vertically with respect to a predetermined direction related with the casing 10, for example, the major axis C1. In this case, the central axis (that is, the optical axis) of the imaging field of the imaging unit 12 substantially corresponds with the major axis C1 and the acceptance surface of the imaging unit 12 is parallel to the two radial axes C2a, C2b which are axis vector perpendicular to the major axis C1. The radial axes C2a, C2b are axis vectors of the casing 10 in the radial direction and the major axis C1 and the radial axes C2a, C2b are perpendicular to each other. In such an imaging unit 12, the normal direction of the acceptance surface, that is the direction of the imaging field, is determined based on the direction of the major axis C1 on the space coordinates xyz and the rotation angle of the acceptance surface, that is the rotation angle of the imaging field which rotates about the major axis C1, is determined based on the rotation angle of the radial axis C2a which rotates about the major axis C1

The angular rate sensor 13 is configured to detect an angular rate of the casing 10 when the posture of the capsule endoscope 1 changes. Concretely, the angular rate sensor 13 is provided with an MEMS gyro or the like and detects the angular rate when the casing 10 wobbles, that is, an angular rate of the major axis 10 whose direction changes on the space coordinates xyz. Further, the angular rate sensor 13 detects the angular rate of the casing 10 when the casing 10 rotates about the major axis C1. In this case, the angular rate sensor 13 detects the angular rate of the radial axis C2a which rotates around the major axis C1. The angular rate sensor 13 sends each detection results of the angular rate to the control unit 18.

The acceleration sensor 14 is configured to detect an acceleration of the casing 10 when the capsule endoscope 1 displaces. Concretely, the acceleration sensor 14 detects the acceleration when the casing 10 moves, that is, an acceleration of the casing 10 whose position changes on the space coordinates xyz. In this case, the acceleration sensor 14 detects the magnitude and direction of the acceleration of the casing 10. The acceleration sensor 14 sends the detection result of the acceleration to the control unit 18.

The magnetic sensor 15 is configured to detect an external magnetic field strength which effects on the capsule endoscope 1. Concretely, the magnetic sensor 15 detects magnetic field strength of the permanent magnet 3, for example, when the external permanent magnet 3 generates a magnetic field toward the capsule endoscope 1. The magnetic sensor 15 sends the detection result of the magnetic field strength to the control unit 18.

For the detection of the magnetic field strength toward the capsule endoscope 1, it is not limited to the magnetic sensor 15 and the angular rate sensor 13 or the acceleration sensor 14 may be used. In this case, the control unit 18 detects a direction change or a displacement of the capsule endoscope 1 made by the magnetic field of the external permanent magnet 3 based on the detection result from the angular rate sensor 13 or the acceleration sensor 14 and detects the magnetic field strength of the permanent magnet 3 based on the direction change or displacement of the capsule endoscope 1.

The signal processing unit 16 is configured to generate an image signal corresponding to an image taken by the imaging unit 12. Concretely, the signal processing unit 16 generates an image signal including the image information received from the imaging unit 12. Further, the signal processing unit 16 includes movement information (described later) of the casing 10 received from the control unit 18 in a blanking period of the image signal. With this, the signal processing unit 16 relates the image taken by the imaging unit 12 to the movement information of the casing 10 at the imaging operation. The signal processing unit 16 sends an image signal including the image information and the movement information to the communication processing unit 17.

The communication processing unit 17 performs a predetermined modulation process on the image signal received from the signal processing unit 16 to modulate the image signal into a radio signal. In a similar way, the communication processing unit 17 modulates a magnetic field detection signal (described later) received from the control unit 18 into a radio signal. The communication processing unit 17 outputs the radio signal generated in such way to the antenna 17a. The antenna 17a is, for example, a coil antenna and sends the radio signal received from the signal processing unit 17 to, for example, the external antenna 5a. In this case, the radio signal is received by the workstation 4 via the antenna 5a. On the other hand, the communication processing unit 17 receives the radio signal from, for example, the workstation 4 via the antenna 17a. In this case, the communication processing unit 17 performs a predetermined demodulation process on the radio signal received via the antenna 17a to demodulate the radio signal from, for example, the workstation 4 into a control signal. Then, the communication processing unit 17 sends the obtained control signal to the control unit 18.

The control unit 18 controls drive of the imaging unit 12, angular rate sensor 13, acceleration sensor 14, magnetic sensor 15, signal processing unit 16, and communication processing unit 17 and controls inputs and outputs of signals in each element. In this case, the control unit 18 controls an operation timing of the imaging unit 12, angular rate sensor 14, and acceleration sensor 14 so as to cause the imaging unit 12 to detect the angular rate and acceleration of the casing 10 at an imaging operation. Further, the control unit 18 starts or stops the drive of the imaging unit 12 based on the control signal when the control signal of the workstation 4 from the communication processing unit 17. In this case, the control unit 18 controls the drive of the imaging unit 12 so as to image inside the subject 100 at a predetermined interval, for example, every 0.5 seconds, according to the imaging-start control signal and stops the drive of the imaging unit 12 according to imaging-stop control signal. Further, the control unit 18 obtains the external magnetic field strength based on the detection result received from the magnetic sensor 15 and sends magnetic field detection signal corresponding to the magnetic field strength to the communication processing unit 17.

The control unit 18 may control the drive of the imaging unit 12 according to the control signal from the workstation 4, as described above. Also, the control unit 18 may start to control the drive of the imaging unit 12 when a predetermined time has passed since the driving power is supplied by the power unit 19.

Further, the control unit 18 includes a displacing amount detector 18a for detecting displacing amount of the casing 10 when the capsule endoscope 1 displaces and an angle detector 18b for detecting a rotation angle of the casing 10 when the posture of the capsule endoscope 1 changes. The displacing amount detector 18a performs a predetermined integral process on the acceleration detected by the acceleration sensor 14 to calculate the displacing amount of the casing 10 on the space coordinates xyz. The displacing amount calculated by the displacing amount detector 18a is a vector quantity showing distance and direction of the displacement of the casing 10 on the space coordinates xyz. On the other hand, the angle detector 18b performs a predetermined integral process on the angular rate detected by the angular rate sensor 13 to calculate a rotation angle on the major axis C1 and the rotation angle of the radial axis C2a on the space coordinates xyz. The control unit 18 sends the displacing amount detected by the displacing amount detector 18a and the rotation angle detected by the angle detector 18b as movement information of the casing 10 to the signal processing unit 16.

Figure 3:
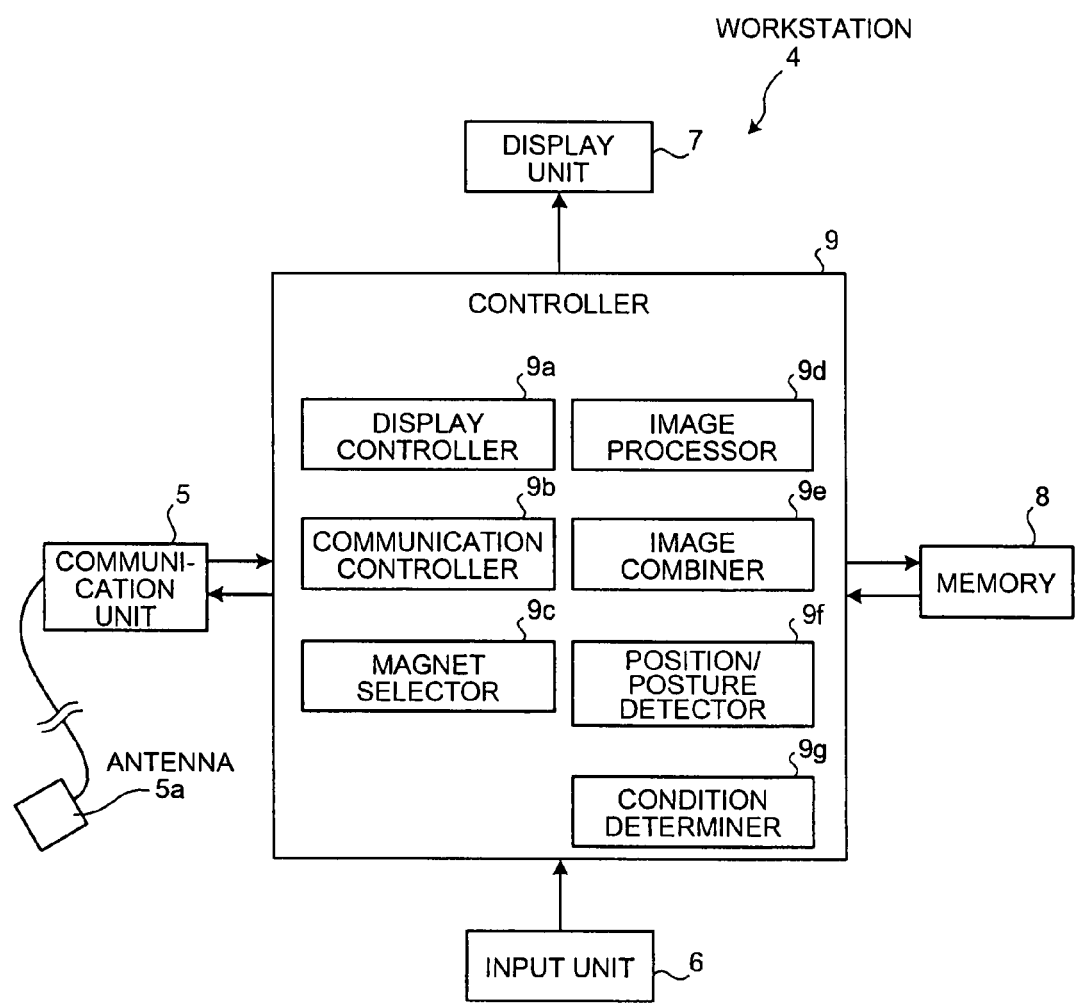
FIG. 3 is a block diagram schematically showing a configuration example of a workstation according to the first embodiment.

Next the workstation 4 of the body-insertable device system according to the first embodiment of the present invention will be described in detail. FIG. 3 is a block diagram schematically showing a configuration example of the workstation 4. As shown in FIG. 3, the workstation 4 includes a communication unit 5 for communicating with the capsule endoscope 1 via the antenna 5a, an input unit 6 for inputting each instruction information or the like to the workstation 4, a display unit 7 for displaying image or the like taken by the capsule endoscope 1, a memory 8 for storing various information such as image information, and a control unit 9 for controlling drives of each element of the workstation 4.

The communication unit 5 is connected to the antenna 5a via a cable and performs a predetermined demodulation process on the radio signal received via the antenna 5a to obtain various information sent from the capsule endoscope 1. In this case, the communication unit 5 obtains image information taken by the imaging unit 12 and the movement information of the casing 10 and sends the obtained image information and the movement information to the control unit 9. Further, the communication unit 5 obtains a magnetic field detection signal corresponding to the detection result of magnetic field strength by the magnetic sensor 15 and sends the obtained magnetic field detection signal to the control unit 9. On the other hand, the communication unit 5 performs a predetermined modulation process or the like on a control signal which is addressed to the capsule endoscope 1 from the control unit 9 to modulate the control signal into a radio signal. In this case, the communication unit 5 sends the generated radio signal to the antenna 5a and transmit the radio signal to the capsule endoscope 1 via the antenna 5a. With this, the communication unit 5 can send, for example, a control signal for instructing to start driving of the imaging unit 12 to the capsule endoscope 1.

The input unit 6 is provided with a keyboard, a mouse, or the like and various information is input to the control unit 9 by an input operation by an examiner such as a doctor or a nurse. In this case, the input unit 6 is input, for example, various instruction information for instructing the control unit 9 or patient information of the subject 100. As the instruction information, for example, there are instruction information for displaying an image obtained from the capsule endoscope 1 on the display unit 7, instruction information for processing the image obtained from the capsule endoscope 1, and the like. Also, as the patient information, for example, there are information for specifying the subject 100 such as name (patient name), sex, date of birth, or patient ID, physical information such as height, weight, waist size of the subject, and the like.

The display unit 7 is provided with a display such as a CRT display or an LCD display and displays various information according to a displaying instruction by the control unit 9. In this case, the display unit 7 observes, for example, the image took by the capsule endoscope 1 and the inside of the subject 100 based on the patient information of the subject 100 and displays various information necessary for a diagnosis. Further, the display unit 7 displays an image on which a predetermined processing is performed by the control unit 9.

The memory 8 stores various information according to writing instruction of the control unit 9. Concretely, the memory 8 stores, for example, various information received from the capsule endoscope 1, various information input by the input unit 6, and image information on which a predetermined processing is performed by the control unit 9. In this case, the memory 8 associates the image information and the movement information and stores them. Further, the memory 8 sends information to the control unit 9 according to a reading instruction from the control unit 9.

The control unit 9 performs drive control of each element of the workstation 4, such as the communication unit 5, input unit 6, display unit 7, and memory 8. Also the control unit 9 performs an input/output control of each elements and information processing for inputting and outputting various information to and from the elements. Further, the control unit 9 outputs various control signal regarding the capsule endoscope 1 to the communication unit 5 according to the instruction information input from the input unit 6. In this case, the control signal for the capsule endoscope 1 is sent to the capsule endoscope 1 via the antenna 5a. That is, the workstation 4 functions as a control unit for controlling the drive of the capsule endoscope 1.

The control unit 9 includes a display controller 9a for controlling an operation of displaying various information by the display unit 7, and a communication controller 9b for controlling the drive of the communication unit 5. Further, the control unit 9 includes a magnet selector 9c for selecting a permanent magnet which generates a magnetic field sufficient to move the capsule endoscope 1 in the liquid 2a, and an image processor 9d for generating an image inside, for example, the subject 100 based on the image signal received from the capsule endoscope 1. Further, the control unit 9 includes an image combiner 9e for compositing a common part of a plurality of images generated by the image processor 9d and combining, for example, the plurality of images inside the subject 100, a position/posture detector 9f for detecting the position and posture of the capsule endoscope 1, and a condition determiner 9g for determining whether or not the movement of the capsule endoscope 1 is controllable by the magnetic field of the permanent magnet 3.

The magnet selector 9c selects a permanent magnet which generates a magnetic field sufficient to move the capsule endoscope 1 in the liquid 2a based on the determination result of the condition determiner 9g. In this case, the condition determiner 9g detects the magnetic field strength of the permanent magnet 3 toward the capsule endoscope 1 based on the magnetic field detection signal received from the capsule endoscope 1 and performs a comparison process for comparing the detected magnetic field strength and a predetermined magnetic field strength range. The condition determiner 9g determines whether or not the movement of the capsule endoscope 1 is controllable by the magnetic field of the permanent magnet 3 based on the result of the comparison process. That is, when the detected magnetic field strength is within the predetermined magnetic field strength range, the condition determiner 9g determines that the magnetic field strength of the permanent magnet 3 is sufficient to control the movement of the capsule endoscope 1. Further, when the detected magnetic field strength is smaller than the predetermined magnetic field strength range, the condition determiner 9g determines the magnetic field strength of the permanent magnet 3 is not sufficient. When the magnetic field strength is greater than the predetermined magnetic field strength range, the condition determiner 9g determines the magnetic field strength of the permanent magnet 3 is excessive. The magnet selector 9c selects the permanent magnet which is determined to have a sufficient magnetic field strength by the condition determiner 9g. Further, when the condition determiner 9g determines the magnetic field strength is not sufficient, the magnet selector 9c selects a permanent magnet which generates a greater magnetic field than the current permanent magnet. When the condition determiner 9g determines the magnetic field strength is excessive, the magnet selector 9c selects a permanent magnet which generates a smaller magnetic field than the current permanent magnet. The display controller 9a causes the display unit 7 to display a permanent magnet selection result of the magnet selector 9c. In this case, the examiner sees and checks the permanent magnet selection result shown on the display unit 7 so that the examiner can easily select a desired permanent magnet for controlling the movement of the capsule endoscope 1 among a plurality of permanent magnets.

The condition determiner 9g determines the condition of the magnetic field strength of the permanent magnet 3 (that is, the strength condition such as excess or deficiency of the magnetic field to be applied to the capsule endoscope 1) so that the condition determiner 9g can determine whether or not the capsule endoscope 1 is led as desired and cause the display unit 7 to display the determination result whether or not the capsule endoscope 1 responds to the external magnetic field of the permanent magnet 3. With this, it becomes possible to see whether of not the magnetic field strength of the current external permanent magnet 3 and the contact of the subject 100 and the body surface are sufficient and this prevents an oversight of the portion to be observed due to the excess or deficiency of the magnetic field strength applied to the capsule endoscope 1.

Further, such determination of whether or not the capsule endoscope 1 responds to the external magnetic field is made not only by the angular rate sensor 13, acceleration sensor, or magnetic sensor 15 and a sensor that has a position detecting function for detecting the position of the capsule endoscope 1 in the digestive canal may be provided. Further, it is desirable that kinds of permanent magnets having different magnetic field strength are prepared to be selected as the external permanent magnet 3, and those permanent magnets are selectively employed according to the determination result of the condition determiner 9g (for example, excess or deficiency of external magnetic field applied to the capsule endoscope 1). Further, the strength of the external permanent magnet 3 to be employed may be determined according to the body type of the subject 100. In other words, the magnetic field strength of the external permanent magnet 3 is determined according to weight, height, waist size, or the like of the subject 100. In this case, a selection of the permanent magnet to be employed will be implemented more appropriately and easily if a sheet used for determining the external permanent magnet 3 according to each value of the weight, height, and waist size of the subject 100. Accordingly, by absorbing individual differences of the body types of the subject 100, a testing can be more accurately and effectively. The control unit 9 may include a program for determining the external permanent magnet 3 to be employed when each value of weight, height, waist size of the subject 100 is input. Or, instead of the data such as weight, height, and waist size, CT data previously obtained by CT scanning or the like may be employed.

The image processor 9d generates an image taken by the capsule endoscope 1 based on the image signal from the capsule endoscope 1. In this case, the display controller 9a causes the display unit 7 to display the images generated by the image processor 9d in time sequence order. Further, the image combiner 9e performs an image combining process for combining a plurality of images generated by the image processor 9d into a single image. The display controller 9a causes the display unit 7 to display a processed image combined by the image combiner 9e (for example, a panoramic image in the digestive canal of the subject 100). The image combining process of the image combiner 9e will be described later.

The position/posture detector 9f detects the position and posture of the capsule endoscope 1 on the space coordinates xyz according to the movement information received from the capsule endoscope 1. Concretely, the position/posture detector 9f firstly sets space coordinates xyz for determining the position of posture of the capsule endoscope 1. Here, the space coordinates xyz is, for example, a space coordinates in which the position of the capsule endoscope 1 in a resting state is set as an original point O and the radial axes C2a, C2b and the major axis C1 of the capsule endoscope 1 are set so as to correspond to the axes x, y, and z.

Next, the position/posture detector 9f sequentially detects the position (x, y, z) of the capsule endoscope 1 that moves or wobbles on the coordinates and the direction of the major axis C1 based on the original point O. In this case, the position/posture detector 9f obtains the displacing amount (vector quantity) of the casing 10, the rotation angle of the major axis C1, and the rotation angle of the radial axis C2a when the capsule endoscope 1 moves or wobbles on the space coordinates xyz, based on the movement information received from the capsule endoscope 1. The position/posture detector 9f detects the relative position of the casing 10 with respect to the original point 0, that is the position (x, y, z) of the casing 10 on the space coordinates xyz, and the vector direction of the major axis C1 on the space coordinates xyz based on the successively obtained displacing amount of the casing 10, the rotation angle of the major axis C1, and the rotation angle of the radial axis C2a. The position (x, y, z) of the casing 10 and the vector direction of the major axis C1 detected by the position/posture detector 9f represent the position and posture of the capsule endoscope 1 on the space coordinates xyz, respectively.

Further, the position/posture detector 9f detects an inclination of the radial axis C2a with respect to the axis z of the space coordinates xyz based on the rotation angle of the radial axis C2a. Here, the radial axis C2a is a axis vector determining the upward direction of the acceptance surface of the imaging unit 12 and determines the upward direction of an image taken by the imaging unit 12. Thus, the position/posture detector 9f can detect the inclination of the image having the major axis C1 as a normal vector (that is, the image taken by the imaging unit 12) with respect to the axis z by detecting the inclination of the radial axis C2a with respect to the axis z.

The control unit 9 stores the position and posture of the capsule endoscope 1, which are detected by the position/posture detector 9f and the inclination of the image taken by the imaging unit 12 with respect to axis z as position/posture information to the memory 8. In this case, the control unit 9 obtains the position/posture information for each image information received from the capsule endoscope 1 and relates the image information and the position/posture information to store in the memory 8 sequentially.

Figure 4:
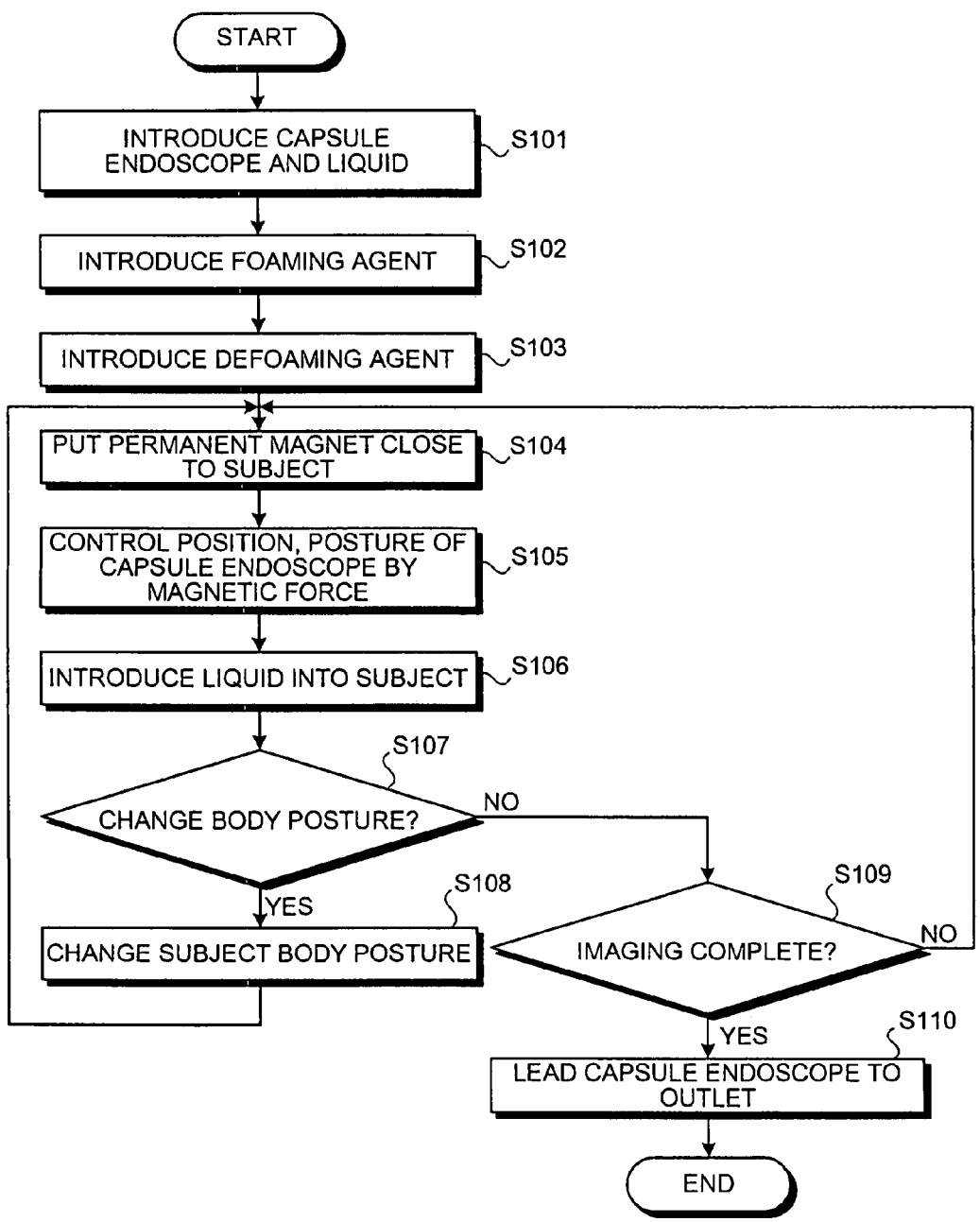
FIG. 4 is a flow chart showing a procedure for observing an inside of digestive canal of a subject with an image inside the digestive canal by the body-insertable device according to the first embodiment.

Next, a procedure for observing inside the digestive canal (for example, stomach and the like) of the subject 100 with the image taken by the capsule endoscope 1. FIG. 4 is a flow chart showing a procedure for observing an inside of digestive canal of the subject 100 with an image inside the digestive canal taken by the capsule endoscope 1 in the subject 100

According to FIG. 4, firstly the examiner starts the imaging operation of the capsule endoscope 1 with the workstation 4 or a predetermined starter, introduces the capsule endoscope 1 into the subject 100, and introduces the liquid 2a into the subject 100 with the feeder 2 (step S101). In this case, the capsule endoscope 1 and the liquid 2a are, for example, swallowed through the mouth of the subject 100 and then reaches a desired digestive canal in the subject 100, which is to be observed. The examiner causes the workstation 4 to display the image taken by the capsule endoscope 1 and finds the position of the capsule endoscope 1 in the subject 100 by the image. The examiner may operate the workstation 4 to cause the capsule endoscope 1 to start an imaging operation after introducing the capsule endoscope 1 into the subject 100.

Next, the examiner introduces foaming agent and a proper amount of water into the subject 100 (step S102) to expand the desired digestive canal in which the capsule endoscope 1 is introduced. With this, the capsule endoscope 1 can easily take the digestive canal to be observed within the imaging field and easily take an image in the digestive canal. After a imaging field of the capsule endoscope 1 in the digestive canal is ensured as described above, the examiner introduces defoaming agent into the digestive canal in the subject 100, where the foaming agent has been introduced (step S103) to defoam the foams generated on the surface of the liquid 2a by the foaming agent. With this, the capsule endoscope 1 can take an image in the digestive canal without being disturbed by the foams generated by the foaming agent.

Then, the examiner puts the permanent magnet 3 close to the subject 100 in which the capsule endoscope 1 is introduced (step S104) to generate a magnetic field toward the capsule endoscope 1 in the subject 100. Concretely, the permanent magnet 3 is put closer to the body surface of the subject 100 close to the digestive canal in which the capsule endoscope 1 is introduced. The permanent magnet 3 for generating a magnetic field toward the capsule endoscope 1 may be provided with a single magnet having a predetermined magnetic force, but more desirably, one permanent magnet is selected among a plurality of permanent magnets having different magnetic forces. In this case, the examiner may refer to the permanent magnet selection result shown on the workstation 4 and select a permanent magnet based on the selection result. With this, the examiner can select a permanent magnet generating a magnetic field having a proper magnetic field strength toward the capsule endoscope 1.

When the permanent magnet 3 is put close to the subject 100, the examiner operates the permanent magnet 3 to adjust the strength and direction of the magnetic field toward the capsule endoscope 1 and controls at least one of the position and posture of the capsule endoscope 1 by the magnetic force of the permanent magnet 3 (step S105). In this case, the permanent magnet 11 of the capsule endoscope 1 responds to the magnetic force applied by the permanent magnet 3 and moves the casing 10. With this effect of the permanent magnet 11, the capsule endoscope 1, for example, horizontally moves or wobbles in the liquid 2a and changes at least one of its position and posture in the digestive canal as an observed region. With this, the capsule endoscope 1 sequentially takes images in the digestive canal while changing the direction of the imaging field and the position of the casing 10 in the digestive canal.

Further, the examiner additionally introduces liquid 2a into the subject 100 (step S106) to increase the amount of the liquid 2a in the digestive canal as an observed region. Here, the capsule endoscope 1, as described above, has a specific gravity which is equal to or smaller than that of the liquid 2a and the center of gravity is in the rear portion of the casing 10. Accordingly, the capsule endoscope 1 floats in the surface of the liquid 2a while directing the imaging field in a substantially vertical direction and moves vertically as the increase of the liquid 2a (that is, a rise of the water level) in the digestive canal. In this case, the capsule endoscope 1 can change the position of an image to be obtained (observed region).

Then, the examiner maintains the body posture of the subject 100 without changing the posture (step S107, No), and when the imaging in the digestive canal as an observed region is continued (step S109, No), the above described procedure subsequent to step S104 is repeated. In this case, the examiner refers to the image in the digestive canal shown on the workstation 4 to increase or reduce the amount of the liquid 2a in the digestive canal, or operates the permanent magnet 3 to control the position and posture of the capsule endoscope 1 in the digestive canal to make a desired condition.

On the other hand, when the body posture of the subject 100 is changed to another posture and continues to image in the digestive canal (step S107, Yes), the examiner changes the current body posture (for example, a supine position) of the subject 100 to another desired body posture (for example, a right lateral supine position) (step S108). Then, the examiner repeats the above described procedure subsequent to step S104.

As described above, controlling at least one of the position and posture of the capsule endoscope 1 in the digestive canal as an observed region allows the capsule endoscope 1 to image the whole region in the digestive canal. Since the images taken by the capsule endoscope 1 are shown on the workstation 4, the examiner can observe every part in the digestive canal as an observed region of the subject 100.

Then, the examiner completes the observation of the digestive canal as an observed region, and, when the observation in the digestive canal is completed (step S109, Yes), leads the capsule endoscope 1 to the outlet port of the digestive canal (step S110). In this case, the capsule endoscope 1 is led to the outlet port by a peristalsis of the digestive canal or the flow of the liquid 2a. Or, the capsule endoscope 1 is led to the outlet port by the magnetic force of the permanent magnet 3 put close to the body surface of the subject 100. Then, the capsule endoscope 1 moves into another digestive canal. With this, the capsule endoscope 1 completes imaging in the digestive canal as an observed region. After that, the capsule endoscope 1 images inside digestive canals in the subject 100 while moving by peristalsis of each digestive canal, the flow of the liquid 2a, or the magnetic force of the permanent magnet 3 and is discharged to outside of the subject 100.

The examiner can display the images taken by the capsule endoscope 1 on the workstation 4 and observe inside each digestive canals of the subject 100. On the other hand, the examiner may operate the workstation 4 and send a control signal for stopping the imaging operation to stop the imaging operation of the capsule endoscope 1 which has already completed to image the desired observed regions.

Further, the above described foaming agent in step S102 and the defaming agent in step S103 may be introduced into the subject 100 according to need. Concretely, the examiner observes the images in the subject 100 shown on the workstation 4 and, foaming agent and defoaming agent may be introduced in order when it is found that the digestive canal needs to be observed more closely, for example.

Figure 5:
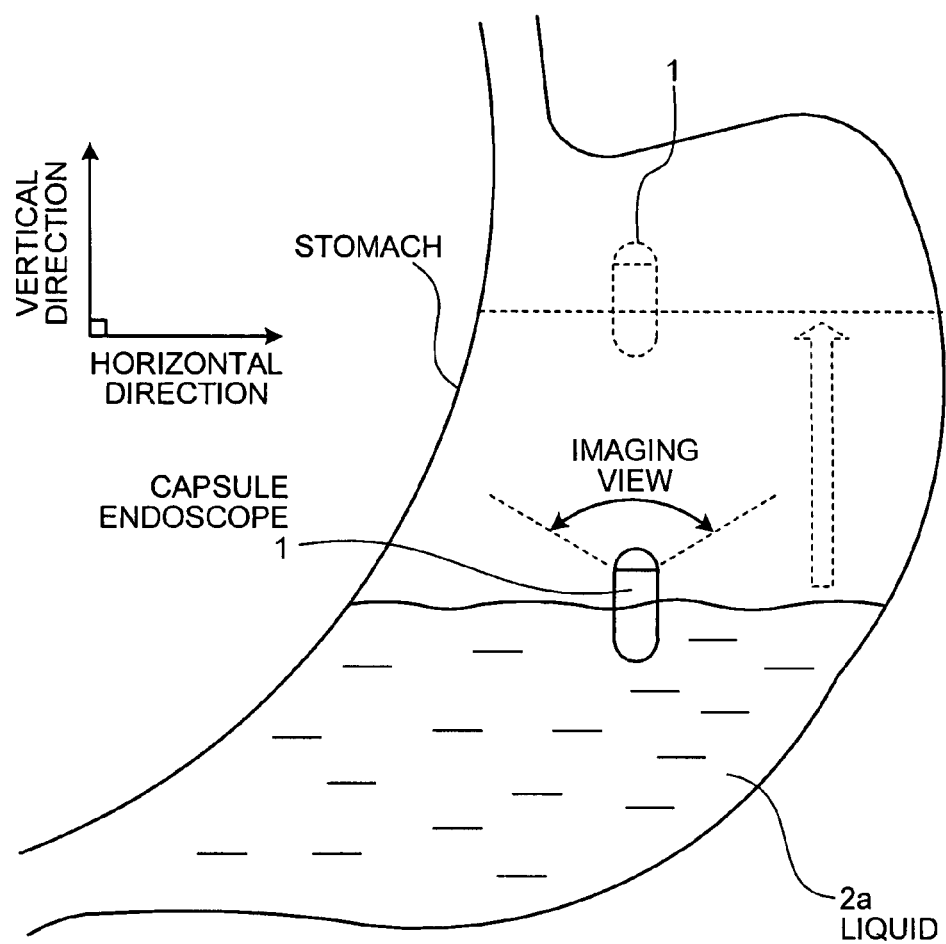
FIG. 5 is a schematic view showing an operation of vertical displacement of the body-insertable device according to the first embodiment.

Next, an operation for controlling at least one of the position and posture of the capsule endoscope 1 introduced into the stomach as an observed region will be described in detail with reference to an example in which the examiner observes the stomach of the subject 100. FIG. 5 is a schematic view showing an operation of the capsule endoscope 1 introduced in the subject 100, which displaces in a vertical direction.

The capsule endoscope 1 and the liquid 2a swallowed through the mouth of the subject 100 passes through the esophagus, and then, reaches, for example, the stomach as an observed region, as shown in FIG. 5. Here, as described above, the capsule endoscope 1 has specific gravity which is equal to or smaller than that of the liquid 2a and the center of gravity is in the rear portion of the casing 10. Accordingly, the capsule endoscope 1 in the liquid 2 floats in the surface of the liquid 2a while directing the imaging field in a substantially vertical direction, as shown in FIG. 5. Here, the imaging field is kept above the liquid 2a.

Such a capsule endoscope 1 can keep the stomach wall vertically above the liquid 2a, that is, the stomach wall expanded by the above described foaming agent, within an imaging field without relaying on the magnetic field of the permanent magnet 3. Further, the capsule endoscope 1 changes its position in vertical direction with the changes in water level of the liquid 2a. Thus, the capsule endoscope 1 can move vertically upward by, for example, increasing the amount of the liquid 2a in the stomach (that is, a rise of the water level) so that the observing position can be changed and an enlarged image of the stomach wall can be taken. As described above, it is possible to control the vertical position of the capsule endoscope 1 in the stomach by increasing or decreasing the amount of the liquid 2a in the stomach.

Regarding the capsule endoscope 1 floating at the surface of the liquid 2a, the center of gravity may be placed at the center portion or the front portion of the casing 10 and the imaging field is directed upward from the liquid 2a in a vertical direction by the magnetic force applied by the permanent magnet 3. However, it is desirable that the center of gravity is placed at the rear portion of the casing 10, as described above. With this structure, the imaging field of the capsule endoscope 1 faces upward in the vertical direction by the buoyant force of the liquid 2a so that the movement of the capsule endoscope 1 can be controlled by a permanent magnet having a smaller magnetic force. Accordingly, the permanent magnet 3 for controlling the movement of the capsule endoscope 1 can be downsized.

Figure 6:
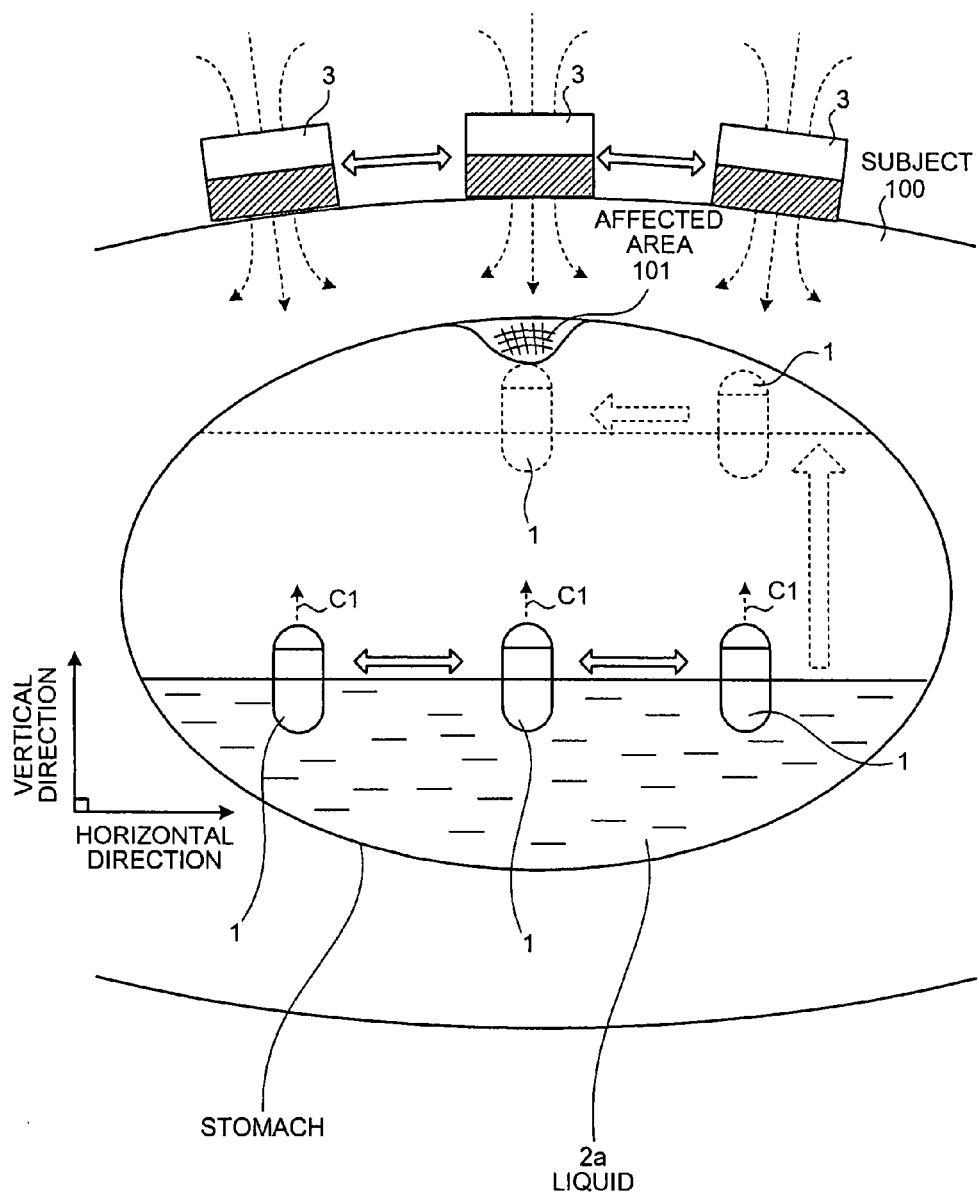
FIG. 6 is a schematic view showing an operation of a permanent magnet for horizontally displacing the body-insertable device according to the first embodiment.

Next, an operation of the capsule endoscope 1 introduced into the digestive canal as an observed region (for example, stomach) in the subject 100, which displaces in a horizontal direction will be described in detail. FIG. 6 is a schematic view showing an operation of the permanent magnet 3 for displacing the capsule endoscope 1 in the subject 100 in a horizontal direction.

As shown in FIG. 6, the permanent magnet 3 put closer to the body surface of the subject 100 generates a predetermined magnetic field toward the capsule endoscope 1 in the liquid 2, for example, in stomach, and captures the capsule endoscope 1 by the magnetic force of the magnetic field. The permanent magnet 3 capturing the capsule endoscope 1 is moved on the body surface of the subject 100 in a substantially horizontal direction to change the position and direction of the magnetic field toward the capsule endoscope 1. In this case, the capsule endoscope 1 moves in the liquid 2a in the horizontal direction following the movement of the permanent magnet 3, and, at the same time, the capsule endoscope 1 sequentially images inside the stomach while displacing the imaging field in the stomach.

As described above, since the horizontal movement of the capsule endoscope 1 is controlled by the magnetic force of the permanent magnet 3, the capsule endoscope 1 can image every part of, for example, the stomach wall, that is the wall of the stomach expanded by the above described foaming agent, above the liquid 2 in a vertical direction. With this, the capsule endoscope 1 can surely take an image of the affected area 101 of the stomach wall, for example. This applies to the case in which the amount of the liquid 2a, in which the capsule endoscope 1 floats, is increased or reduced. In other words, the capsule endoscope 1 displaces in the vertical direction according to the changes in water level of the liquid 2a. In addition, for example, as shown in FIG. 6, the capsule endoscope 1 can change the observing position and move closer to the stomach wall to take an enlarged image of the stomach wall. In this case, the capsule endoscope 1 can move closer to the affected area 101 of the stomach wall, for example, and take an enlarged image of the affected area 101.

Figure 7:
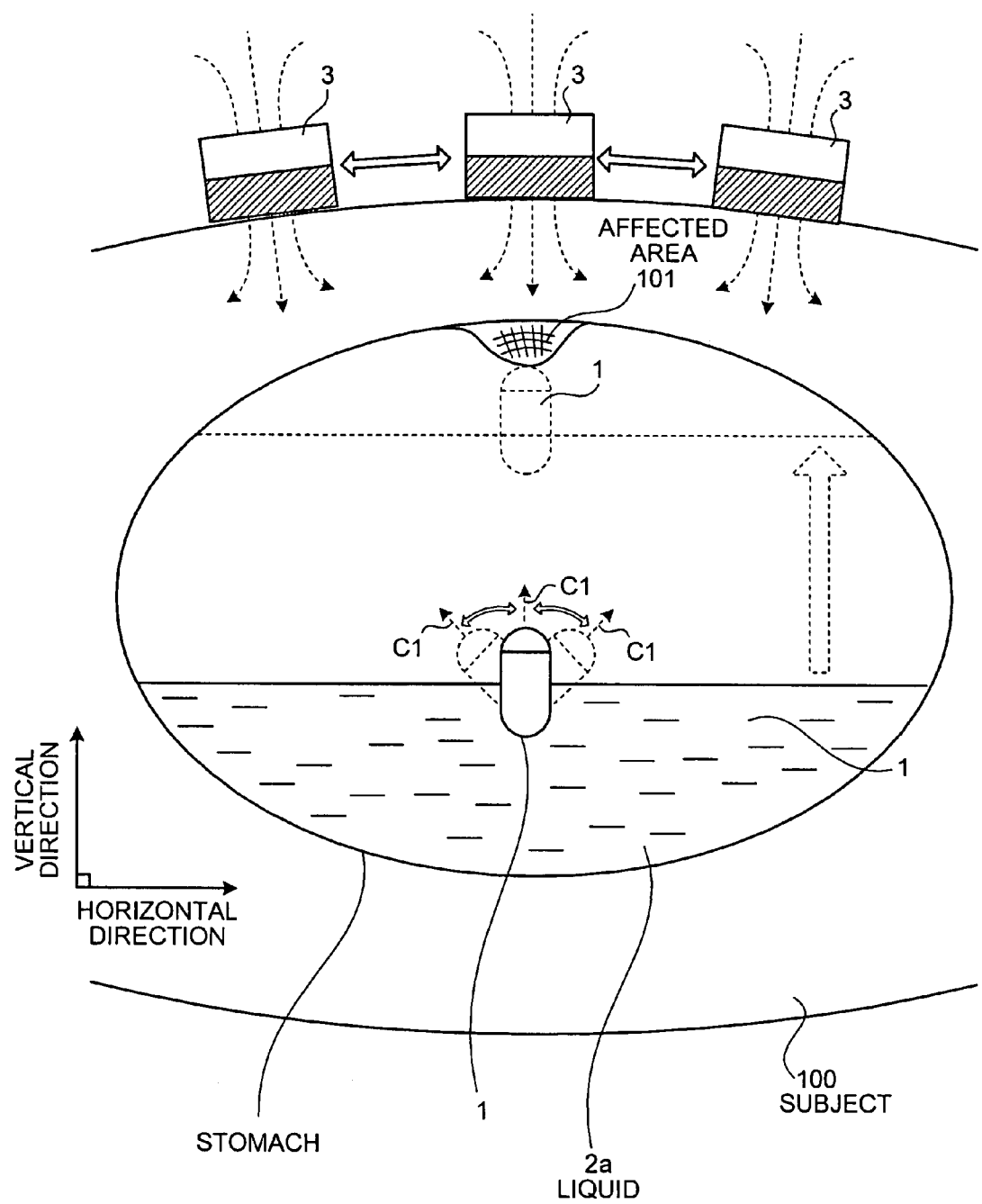
FIG. 7 is a schematic view showing an operation of the permanent magnet for changing a posture of the body-insertable device according to the first embodiment.

Next, an operation for changing the posture of the capsule endoscope 1 introduced into the digestive canal as an observed region (for example, stomach) of the subject 100 will be described in detail. FIG. 7 is a schematic view showing an operation of the permanent magnet 3 for changing the posture of the capsule endoscope 1 introduced into the subject 100.

As shown in FIG. 7, the permanent magnet 3 put closer to the body surface of the subject 100 captures the capsule endoscope 1 by its magnetic force as described above. The permanent magnet 3 capturing the capsule endoscope 1 in this way wobbles and moves on the body surface of the subject 100 in the substantially horizontal direction to change the position and direction of the magnetic field toward the capsule endoscope 1. In this case, the capsule endoscope 1 moves in the liquid 2a following the movement of the permanent magnet 3 and the vector direction of the major axis C1 is directed to the position of the permanent magnet 3. At the same time, the capsule endoscope 1 sequentially images inside the stomach while changing the direction of the image view in the stomach.

Since the wobbling of the capsule endoscope 1 is controlled by the magnetic force of the permanent magnet 3, the capsule endoscope 1 can image every part of the stomach wall, that is the wall of stomach expanded by the above described foaming agent, above the liquid 2a in a vertical direction, for example. With this, the capsule endoscope 1 can surely images inside the affected area 101 of the stomach wall, for example. This applies to the case in which the amount of the liquid 2a, in which the capsule endoscope 1 floats, is increased or reduced. In other words, the capsule endoscope 1 displaces in vertical direction according to a change in the water level of the liquid 2a and, for example, as shown in FIG. 7, moves close to the stomach wall to take an enlarged image of the stomach wall. In this case, the capsule endoscope 1 can move close to the affected area 101 of the stomach wall, for example, and take an enlarged image of the affected area 101.

Figure 8:
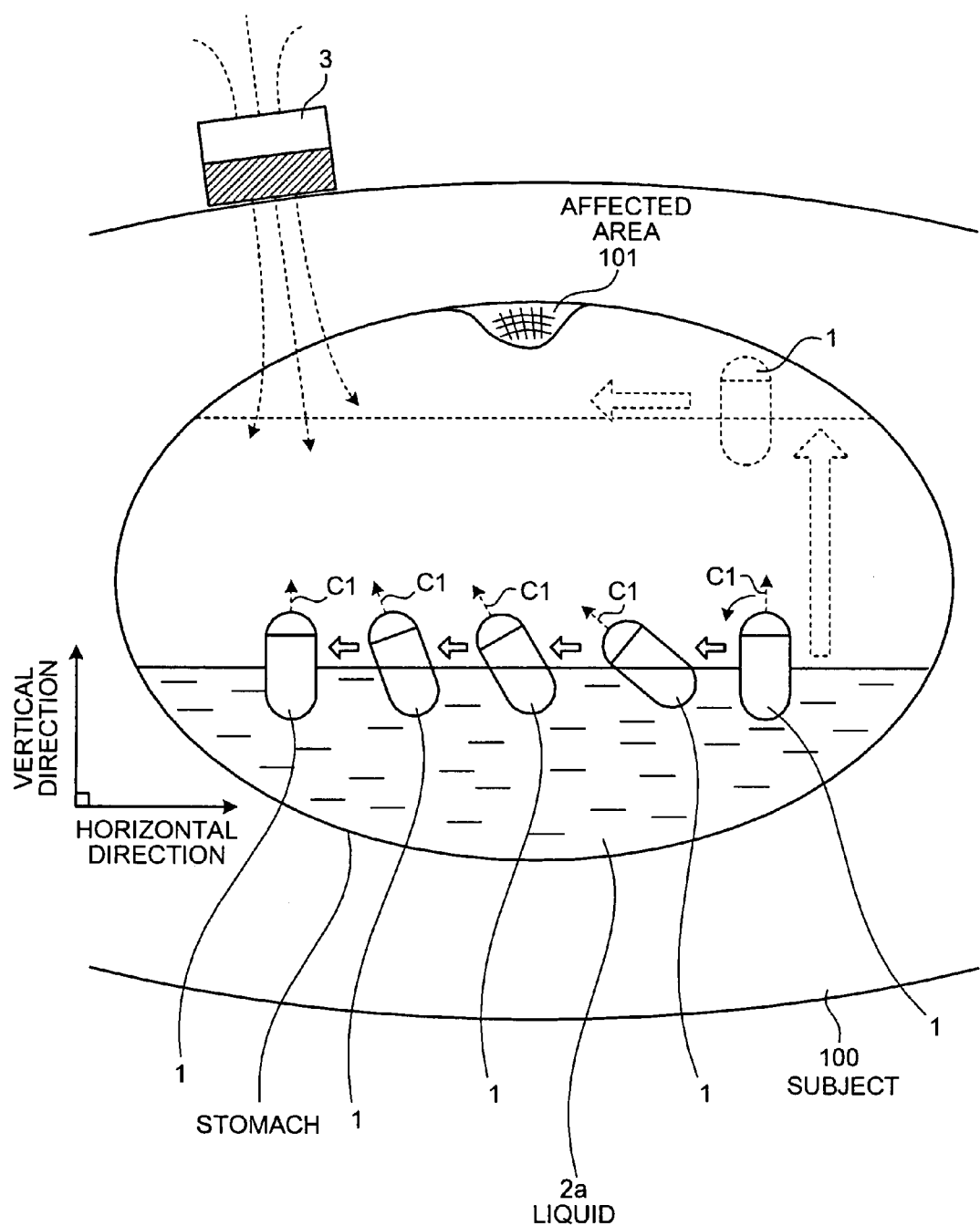
FIG. 8 is a schematic view showing an operation of the permanent magnet for changing a horizontal position and a posture of the body-insertable device according to the first embodiment.

Next, an operation for changing the horizontal position and posture of the capsule endoscope 1 introduced into the digestive canal as an observed region (for example, the stomach) in the subject 100 will be described in detail. FIG. 8 is a schematic view showing an operation of the permanent magnet 3 for changing the horizontal position and posture of the capsule endoscope 1 in the subject 100.

As shown in FIG. 8, the permanent magnet 3 put close to the body surface of the subject 100 generates a predetermined magnetic field toward the capsule endoscope 1 in the liquid 2 in, for example, the stomach. In this case, the capsule endoscope 1 moves as if being captured by the magnetic field generated by the permanent magnet 3. Concretely, the capsule endoscope 1 moves horizontally toward the permanent magnet 3 while wobbling to direct the vector direction of the major axis C1 to the position of the permanent magnet 3. At the same time, the capsule endoscope 1 sequentially images inside the stomach while changing the position and direction of the imaging field in the stomach. Here, it is desirable that the center of gravity of the capsule endoscope 1 is placed such that the magnetization direction of the permanent magnet 11 in the capsule endoscope 1 maintains 10 degree or larger with respect to the surface of the liquid (the center of gravity is displaced from the center of the capsule endoscope 1 by 10 degree or larger with respect to the magnetization direction of the permanent magnet 11) under a condition in which there is no magnetic field generated outside the subject 100. Since the magnetization direction of the permanent magnet 11 before generating the magnetic field outside the subject 100 corresponds to the direction of the permanent magnet 11 after generating the magnetic field, the permanent magnet 3 may be put close to the subject 100 so as to make the magnetization direction of the permanent magnet 3 and the magnetization direction of the permanent magnet 11 be the same direction in order to lead the capsule endoscope 1 in the subject 100. Since the controllability is improved and generating magnetic torque is not required, the capsule endoscope 1 can be led effectively and the permanent magnet 11 and the permanent magnet 3 can be downsized. The permanent magnet 3 may be put close to the liquid in the subject 100 from beneath in a vertical direction. Further, the strength of the magnetic field strength near the permanent magnet 11 may be controlled by changing the distance from the permanent magnet 3 to the subject 100 to change the movement speed of the capsule endoscope 1 in the subject 100. Further, according to the first embodiment, the horizontal position of the capsule endoscope 1 of the subject 100 is controlled by changing the horizontal position of the permanent magnet 3. However, there may be provided with a plurality of electromagnet (magnetic field generating elements) arranged on a horizontal plane in array and a control unit (magnetic field strength changing unit) for controlling current applied to the plurality of electromagnet and the horizontal position of the capsule endoscope 1 in the subject 100 may be controlled by switching the electrical magnet to be magnetized.

Since the permanent magnet 3 controls the horizontal position and posture of the capsule endoscope 1 with its magnetic force in this way, the capsule endoscope 1 can image every part of the stomach wall, that is, the wall of the stomach expanded by the above described foaming agent, above the liquid 2a in a vertical direction, for example. With this, the capsule endoscope 1 can surely take an image of the affected area 101 of the stomach wall, for example. This applies to the case in which the amount of the liquid 2a in which the capsule endoscope 1 floats is increased or reduced. That is, the capsule endoscope 1 vertically displaces according to a change in the water level of the liquid 2a and, for example, as shown in FIG. 8, it is possible to change the observing position and move closer to the stomach wall to take an enlarged image of the stomach wall. In this case, the capsule endoscope 1 can move close to the affected area 101 of the stomach wall, for example, and take an enlarged image of the affected area 101.

On the other hand, when the capsule endoscope 1 completes to image inside the stomach as a desired observed region, the capsule endoscope 1 moves to the next digestive canal (for example, duodenum) by the above described procedure in step S110. Concretely, the capsule endoscope 1 moves to the pyloric part from the stomach by the magnetic force applied by the permanent magnet 3 placed near the pyloric part of the subject 100. In this case, the examiner may change the body posture of the subject 100 to, for example, a right lateral supine position, move the permanent magnet 3 toward the body surface near the pyloric part of the subject 100, and lead the capsule endoscope 1 to pyloric part by the magnetic force applied by the permanent magnet 3.

Figure 9:
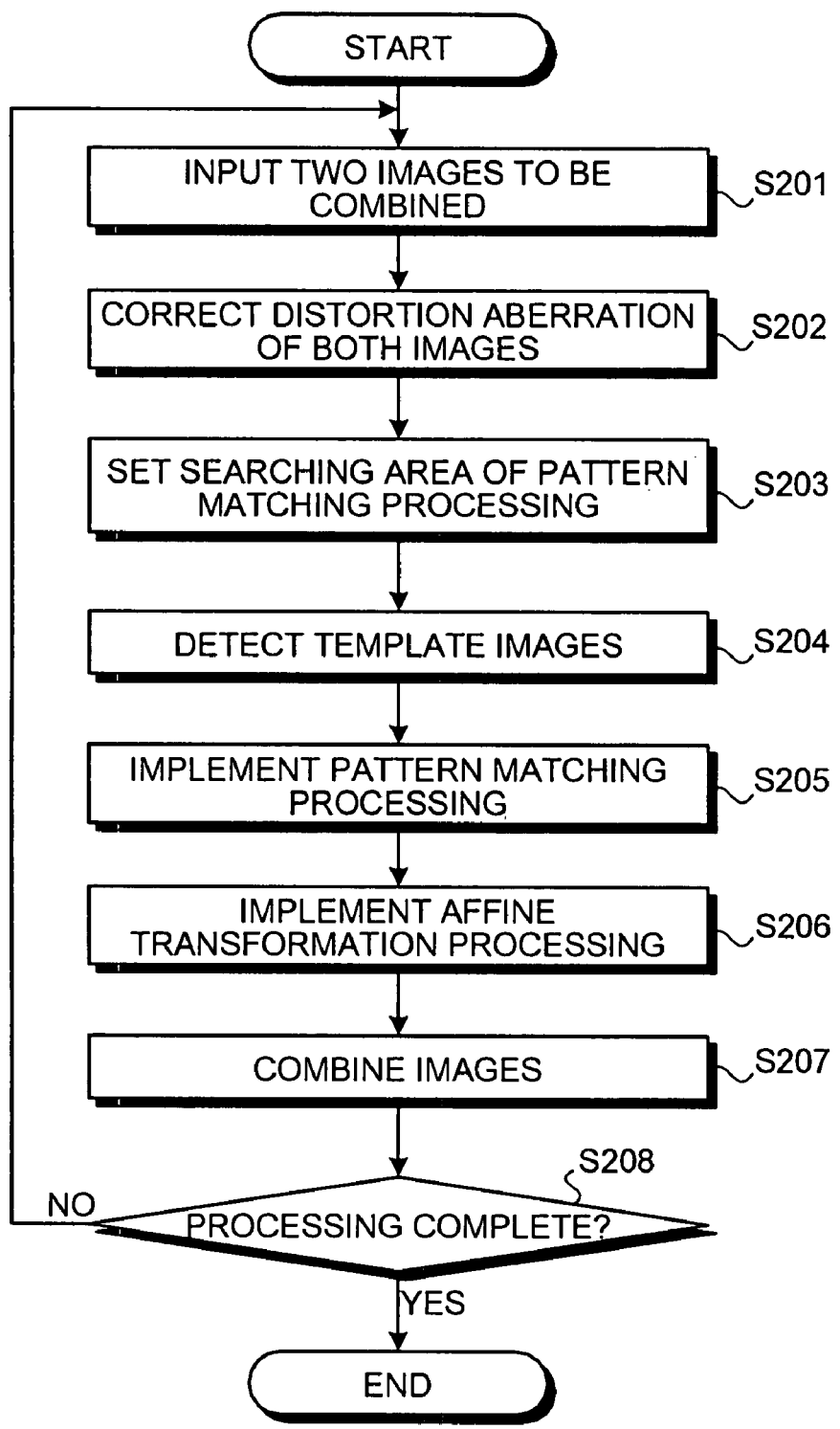
FIG. 9 is a flow chart showing a procedure of an image combining process implemented by a control unit of the workstation.
Figure 10:
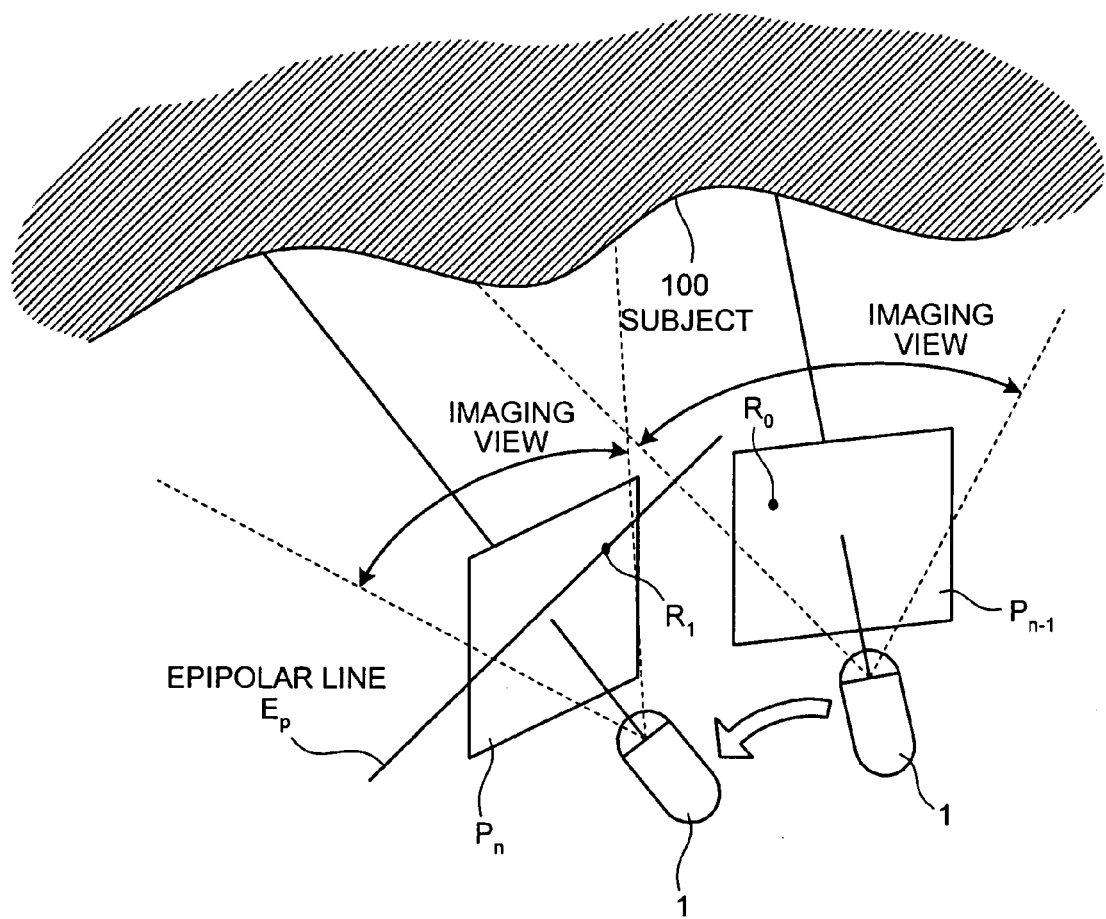
FIG. 10 is a schematic view showing an operation of the control unit for combining a plurality of images.

Next, the image combining process for combining a plurality of images of inside view of the subject 100 taken by the capsule endoscope 1 will be described in detail. FIG. 9 is a flow chart showing a procedure of image combining process implemented by the control unit 9 of the workstation 4. FIG. 10 is a schematic view showing an operation of the control unit 9 for combining the plurality of images.

The control unit 9 of the workstation 4 finds the relative position and the relative direction of the plurality of images taken by the capsule endoscope 1 based on the image information obtained from the capsule endoscope 1 and the position/posture information corresponding to image information and combines the images based on epipolar geometry. In other words, according to FIG. 9, the control unit 9 firstly inputs two images to be combined (step S201). In this case, the input unit 6 inputs information specifying the two images to be combined to the control unit 9 according to the input by the examiner. The control unit 9 reads the two pictures $P_n$, $P_{n-1}$ to be combined from the memory 8 based on the input information from the input unit 6. At the same time, the control unit 9 reads the position/posture information corresponding to each image $P_n$, $P_{n-1}$ from the memory 8. The image combiner 9e recognizes the position and posture of the capsule endoscope 1 and the inclination of the image with respect to the axis z at the time of taking the images $P_n$, $P_{n-1}$ based on the position/posture information of each images $P_n$, $P_{n-1}$.

Next, the control unit 9 corrects the distortion aberrations of the two read images $P_n$, $P_{n-1}$ (step S202). In this case, the image combiner 9e corrects each distortion aberration of the images $P_n$, $P_{n-1}$. With this, the image combiner 9e can conflate the pixel regions showing a common object (that is, similar object) and combine the images $P_n$, $P_{n-1}$ when a common object is shown in the two images $P_n$, $P_{n-1}$.

Then, the control unit 9 sets a searching area of pattern matching processing for searching similar pixel regions between the two images $P_n$, $P_{n-1}$ (step S203). In this case, the image combiner 9e calculates a plurality of reference points on the image $P_{n-1}$ and epipolar lines on the image $P_n$ which correspond to the reference points based on the epipolar geometry.

Here, the images $P_n$, $P_{n-1}$ are images taken before and after the capsule endoscope 1 changes at least one of the position and posture. Concretely, the image $P_{n-1}$ is, as shown in FIG. 10, an image inside the subject 100 taken by the capsule endoscope 1 and the image $P_n$ is an image inside the subject 100 taken by the capsule endoscope 1 after the capsule endoscope 1 changes its position and posture. Such images $P_n$, $P_{n-1}$ includes pixel regions which are highly similar to each other if those images include an image of the same object. The image combiner 9e sets a plurality of (for example, six or more) reference points on the image $P_{n-1}$ corresponding to the highly similar pixel regions and sets epipolar lines on the image $P_n$, which correspond to the reference points.

For example, as shown in FIG. 10, the image combiner 9e sets a reference point $R_0$ on the image $P_{n-1}$ and an epipolar line $E_p$ on the image $P_n$, which corresponds to the reference point $R_0$. When the reference point $R_0$ represents a position on the coordinates of highly similar pixel region between the images $P_n$, $P_{n-1}$, the image combiner 9e can set the epipolar line $E_p$ on the image $P_n$, for example, between two opposite vertexes on the image $P_n$. On such an epipolar line $E_p$, a corresponding point $R_1$ corresponding to the reference point $R_0$ is included. This corresponding point $R_1$ represents a position on the coordinates of the highly similar pixel region on the image $P_n$ with respect to the pixel region on the image $P_{n-1}$ where the position on the coordinates is set by the reference point $R_0$.

As described above, the image combiner 9e sets a plurality of (for example, six or more) reference points on the image $P_{n-1}$, and further, sets epipolar lines on the image $P_n$, which corresponds to the reference points, respectively. In this case, the image combiner 9e sets each pixel region near the respective epipolar lines as the searching area of the pattern matching processing.

Then, the control unit 9 detects pixel regions (template image) as a criterion of pattern matching processing based on the image $P_{n-1}$ (step S204). In this case, the image combiner 9e detects a plurality of (for example, six or more) template images corresponding to the reference points shown as the above example of the reference point $R_0$, respectively.

After that, the control unit 9 implements the pattern matching processing for detecting the highly similar pixel regions on the image $P_n$ compared to the template images detected as described above (step S205). In this case, the image combiner 9e sets, for example, the pixel region near the epipolar line $E_p$ on the image $P_n$ as a searching area of the pattern matching processing and detects a pixel region on the image $P_n$ highly similar to the template image corresponding to the reference point $R_0$. Then, the image combiner 9e calculates corresponding point $R_1$ determining the position on the coordinates in the highly similar pixel region on the image $P_n$. The image combiner 9e repeats such a pattern matching processing on the template images and the epipolar lines and detects, for example, six or more pixel regions respectively corresponding to the six or more template images. Then, the image combiner 9e calculates six or more corresponding points on the image $P_n$ respectively corresponding to six or more coordinate points, that is, the six or more reference points shown as the above example of the reference point $R_0$, for determining the positions of the six or more pixel regions on the coordinates.

When, for example, six or more reference points and corresponding points on the images $P_n$, $P_{n-1}$ are calculated, the control unit 9 implements an affine transformation processing on the images $P_n$, $P_{n-1}$ (step S206). In this case, the image combiner 9e calculates an affine parameter based on least squares by using the six or more calculated reference points and corresponding points. The image combiner 9e converts, for example, the coordinate system on the image $P_{n-1}$ into the coordinate system on the image $P_n$ based on the calculated affine parameter and completes the affine transformation processing of the images $P_n$, $P_{n-1}$.

Then, the control unit 9 conflates the images $P_n$, $P_{n-1}$ on which the affine transformation processing has been performed (step S207) and combines the images $P_n$, $P_{n-1}$ into a single processed image (for example, panoramic image). In this case, the image combiner 9e conflates the pixel regions (that is, highly similar pixel regions) which are common to the images $P_n$, $P_{n-1}$ on which the affine transformation processing has been performed and generates a processed image in which the images $P_n$, $P_{n-1}$ are combined.

After that, when the image combining process is continuously implemented (step S208, No), the control unit 9 repeats the above described procedure subsequent to step S201. In this case, the image combiner 9e can sequentially combine a plurality of images taken by the capsule endoscope 1 and generate a panoramic image showing the entire wall of the observed region, for example, inner wall of the stomach, in the subject 100. On the other hand, when information for completing the process is input by the input unit 6, the control unit 9 completes the image combining process (step S208, Yes). In this case, the control unit 9 stores the processed image generated in the image combining process to the memory 8.

Here, the control unit 9 can generate a cylindrical processed image showing the inside of the digestive canal in the subject 100 substantially in three dimensions based on the processed image generated in the image combining process, for example, a strip-shaped panoramic image. In this case, the image combiner 9e converts a rectangular coordinate system of the strip-shaped panoramic image into a cylindrical coordinate system and generates a cylindrical processed image by combining both ends in a longitudinal direction of the strip-shaped panoramic image together. The control unit 9 stores the cylindrical processed image to the memory 8.

Figure 11:
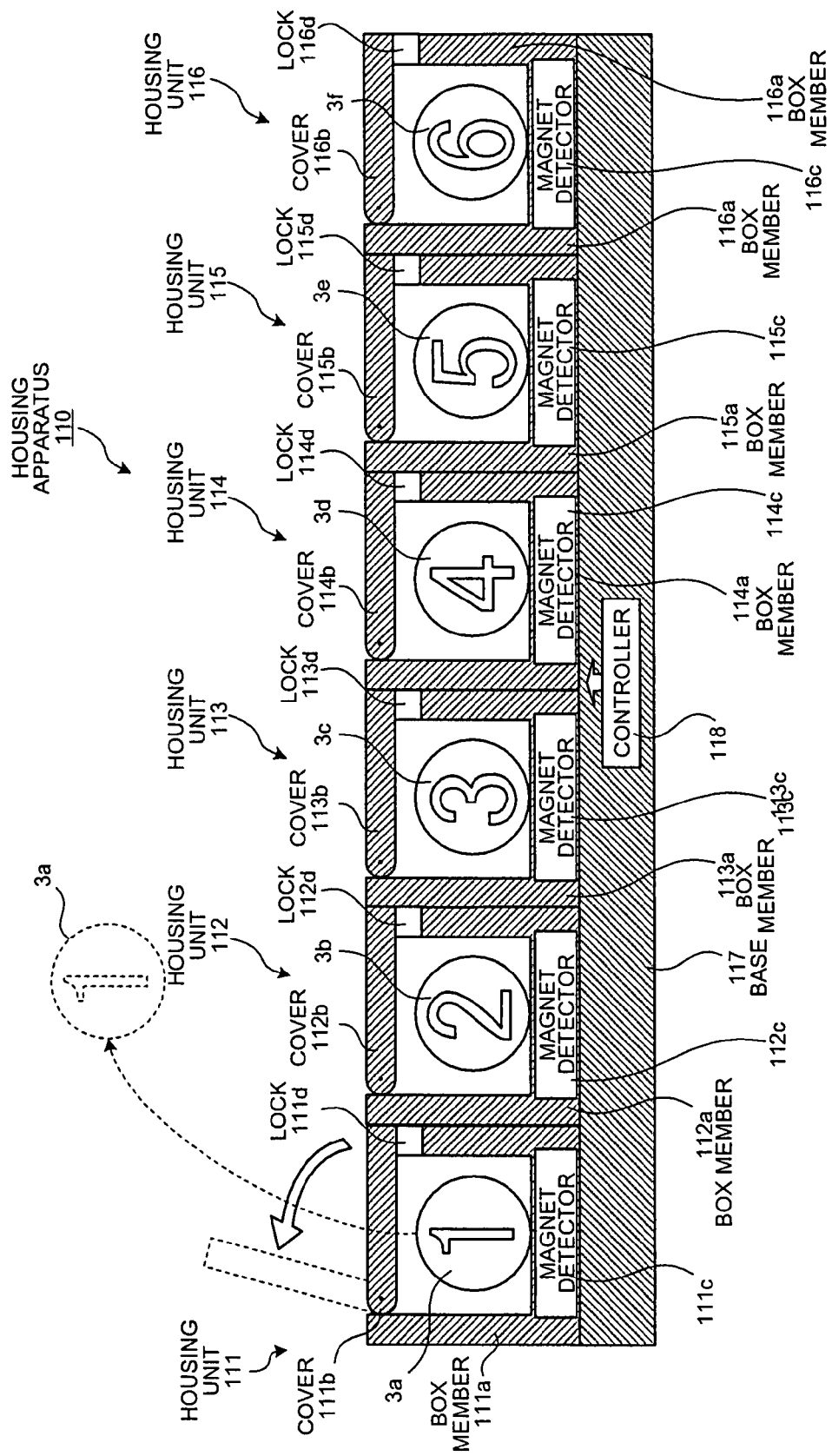
FIG. 11 is a schematic view schematically showing a configuration example of a housing apparatus for housing a plurality of permanent magnets.

Next, the housing apparatus for containing the plurality of permanent magnets prepared to be selected as the permanent magnet 3 for controlling the movement of the capsule endoscope 1 will be described. FIG. 11 is a schematic view schematically showing a configuration example of a housing apparatus for housing a plurality of permanent magnets. Hereinafter, a housing apparatus for housing six permanent magnets 3a to 3f to be selected as the permanent magnet 3 will be described as an example. It is noted that the number of the permanent magnets may be two or more and it should not limit the configuration of the housing apparatus.

As shown in FIG. 11, the housing apparatus 110 includes six housing units 111 to 116 for accommodating the permanent magnets 3a to 3f, a base 117 for integrally connecting the housing units 111 to 116, and a control unit 118 for controlling opening/closing drive of the housing units 111 to 116. The permanent magnets 3a to 3f are denoted with magnet numbers 1 to 6 for specifying them. In this case, regarding the permanent magnets 3a to 3f, the magnet with larger magnet number has larger magnetic force.

The housing unit 111 accommodates the permanent magnet 3a of magnet number 1. Concretely, the housing unit 111 includes a box member 111a for accommodating the permanent magnet 3a, a cover 111b for opening and closing an opening of the box member 111a, a magnet detector 111c for detecting the permanent magnet 3a in the box member 111a, and a lock 111d for locking the cover 111b. The box member 111a is, for example, a member having a concaved sectional side view and the cover 111b is rotatably provided at the opening of the box member 111a. The permanent magnet 3a accommodated in the box member 111a is put in and out by opening and closing the cover 111b. When the permanent magnet 3a is accommodated in the box member 111a, the magnet detector 111c detects the magnetic field or the weight of the permanent magnet 3a and detects the pretense or absence of the permanent magnet 3a in the box member 111a according to the detection result. The magnet detector 111c informs the detection result of the permanent magnet 3a to the control unit 118. The lock 111d locks or unlocks the cover 111b according to the control of the control unit 118.

Further, the housing units 112 to 116 accommodate the permanent magnets 3b to 3f of magnet numbers 2 to 6, respectively, and their structures and functions are substantially the same as those of the housing unit 111. That is, the housing units 112 to 116 includes box members 112a to 116a for individually accommodating permanent magnets 3b to 3f, covers 112b to 116b for opening and closing openings of the box members 112a to 116a, magnet detectors 112c to 116c for individually detecting the permanent magnets 3b to 3f in the box members 112a to 116a, and locks 112d to 116d for locking the covers 112b to 116b, respectively. In this case, the box members 112a to 116a have functions substantially the same as those of the box member 111a of the housing unit 111 and the covers 112b to 116b have functions substantially the same as those of the cover 111b of the housing unit 111. Further, the magnet detectors 112c to 116c have functions substantially the same as those of the magnet detector 111c of the housing unit 111 and the locks 112d to 116d have functions substantially the same as those of the lock 111d of the housing unit 111.

The control unit 118 is disposed, for example, on the base 118 and controls each drive of the magnet detectors 111c to 116c and the locks 111d to 116d. Concretely, the control unit 118 obtains each detection result of the permanent magnets 3a to 3f from the magnet detectors 111c to 116c and controls each drive of the locks 111d to 116d based on each obtained detection result of the permanent magnet 3a to 3f. In this case, when the control unit 118 obtains detection results indicating the presence of the permanent magnet from all of the magnet detectors 111c to 116c, the control unit 118 performs a drive control for unlocking the locks 111d to 116d.

On the other hand, when the control unit 118 obtains detection result indicating absence of the permanent magnet from one of the magnet detector 111c to 116c, the control unit 118 performs a drive control for unlocking the lock of the housing unit that has the magnet detector having notified the detection result of absence of the permanent magnet, that is the lock (one of the locks 111d to 116d) of the housing unit from which the permanent magnet has been removed. At the same time, the control unit 118 performs a drive control for locking the covers on the rest of housing units that have magnet detectors having notified detection results of presence of the permanent magnets, that is, the lock (some of the locks 111d to 116d) of the housing units in which the permanent magnets are accommodated.

Such controller 118 performs controls drive so that one of the permanent magnets 3a to 3f respectively accommodated in the housing units 111 to 116 can be taken out and, at the same time, other permanent magnets cannot be taken out. For example, as shown in FIG. 11, when the examiner takes the permanent magnet 3a out among the permanent magnets 3a to 3f, the control unit 118 obtains a detection result indicating absence of the permanent magnet from the magnet detector 111c and also detection results indicating presence of the permanent magnets from the other magnet detectors 112c to 116C. In this case, the control unit 118 performs a drive control for unlocking the cover on the lock 111d and a driving control for locking the covers on the other locks 112d to 116d. With this, the examiner can take only a necessary permanent magnet from the housing apparatus 110 and securely observe the inside of the subject 100 since it can be prevented that, for example, a plurality of permanent magnets are unintentionally put close to the subject 100 having the capsule endoscope 1 inside.

As described above, according to the first embodiment of the present invention, an imaging unit for imaging inside view of a subject is fixed inside a casing so that the position and posture of the imaging field can be determined by the position on the coordinates of the casing on a predetermined space coordinates and a vector direction, and further, a permanent magnet for moving the casing responding to an external magnetic field is fixed inside the casing so that at least one of the position on the coordinates and the vector direction of the casing can be changed in a predetermined liquid introduced into a digestive canal of the subject. Accordingly, at least one of the positions on the coordinates and the vector direction of the casing introduced in the subject can be actively changed. Accordingly, the position and direction of the imaging field in the digestive canal of the subject can be easily changed so that a body-insertable device capable of imaging every part in a desired digestive canal as an observed region is achieved. Further, buoyant force works on the body-insertable device by the liquid introduced into the subject and a gravity generated on the body-insertable device is reduced, or further, canceled corresponding to the buoyant force. Accordingly, at least one of the position and posture of the body-insertable device can be easily changed, and a drive unit (for example, a permanent magnet installed in the body-insertable device) for changing at least one of the position and posture of the body-insertable device can be downsized. As a result, the body-insertable device itself can be downsized so that the facility for introducing the body-insertable device into the subject is improved.

Further, a permanent magnet for generating a magnetic field toward such body-insertable device is employed to move the body-insertable device in a predetermined liquid introduced into a digestive canal of the subject and to change at least one of the position and posture of the body-insertable device. Accordingly, at least one of the position and posture of the body-insertable device in the liquid introduced in the digestive canal can be actively changed, and, with this, the position and direction of the imaging field with respect to the inside of the digestive canal of the subject can be easily changed. As a result, a body-insertable device system capable of observing every part of a desired digestive canal as an observed region in a short time can be achieved.

Further, since the specific gravity of the body-insertable device is set equal to or smaller than that of the predetermined liquid, the body-insertable device floats in the surface of the liquid introduced into a digestive canal without relying on the external magnetic field strength, the external permanent magnet for controlling the movement of the body-insertable device can be downsized, and the body-insertable device is easily displaced or wobbled in a horizontal direction by a magnetic field generated by the external permanent magnet. Further, the body-insertable device can be easily displaced in a vertical direction by increasing or reducing the amount of the predetermined liquid for floating the body-insertable device.

Further, since a dome-shaped member as a part of the casing of the body-insertable device for covering the imaging unit is able to be put in the predetermined liquid, a liquid membrane is formed on a blemish generated on the dome-shaped member. Accordingly, the blemish on the dome-shaped member falls into obscurity so that a clearer image can be taken when an image of inside view of the digestive canal is taken.

Modification of First Embodiment

Next, a modification of the first embodiment of the present invention will be described. The above described first embodiment employs the capsule endoscope 1 that floats at the surface of the liquid 2a in the digestive canal introduced in the subject 100 and directs an imaging field above the surface of the liquid 2a in a vertical direction. However, a body-insertable device system according to the modification of the first embodiment includes a capsule endoscope that floats in the surface of the liquid 2a and directs an imaging field under the surface of the liquid 2a in a vertical condition, in place of the capsule endoscope 1.

Figure 12:
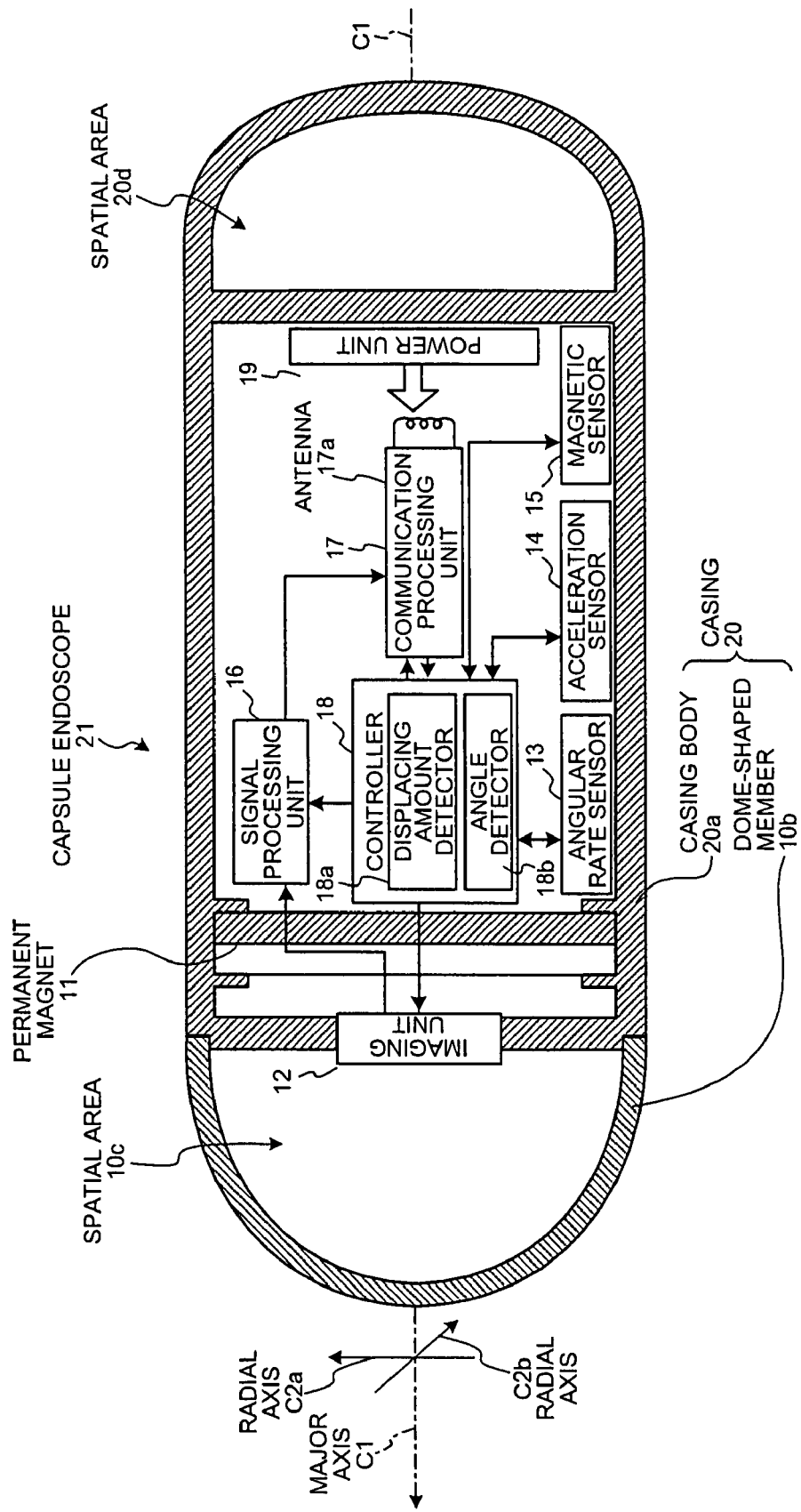
FIG. 12 is a schematic view showing a configuration example of the body-insertable device according to a modification of the first embodiment of the present invention.

FIG. 12 is a schematic view showing a configuration example of the body-insertable device according to the modification of the first embodiment of the present invention. As shown in FIG. 12, a capsule endoscope 21, as an example of the body-insertable device, includes a casing 20, in place of the casing 10 of the capsule endoscope 1 in the first embodiment. The casing 20 includes a casing body 20a in place of the casing body 10a of the casing 10. Other structures are the same as those in the first embodiment and the same elements are represented by the same reference numbers.

The casing 20 is a capsule-shaped member made in a size easily inserted into the subject 100 and provided with a dome-shaped member 10b attached to a front-end part of the casing body 20. The casing body 20a accommodates each element of the capsule endoscope 21 and includes a permanent magnet 11 in a front portion with respect to the center portion of the casing 20. In this case, an imaging unit 12 is fixed to the front-end part of the casing body 20a, similarly to the case of the capsule endoscope 1. Further, a spatial area 20d is formed in a rear portion of the casing body 20a. Such a casing 20 provided with the casing body 20a and the dome-shaped member 10b has specific gravity equal to or less than that of the liquid 2a, similarly to the casing 10 of the capsule endoscope 1 and has the center of gravity at its front portion.

In order to set the specific gravity of the casing 20 to be equal to or smaller than that of the liquid 2a and set the center of gravity at the front portion, the casing body 20a is not limited to the arrangement of the permanent magnet 11 or forming of a spatial area 20d, as shown in shown in FIG. 12.

A weight made of such as steel or lead may be put near the front-end part not to make the specific gravity greater than that of the liquid 2a, a spatial area may be added near the rear-end part, or the location of a power unit 19 may be changed to the front portion.

Figure 13:
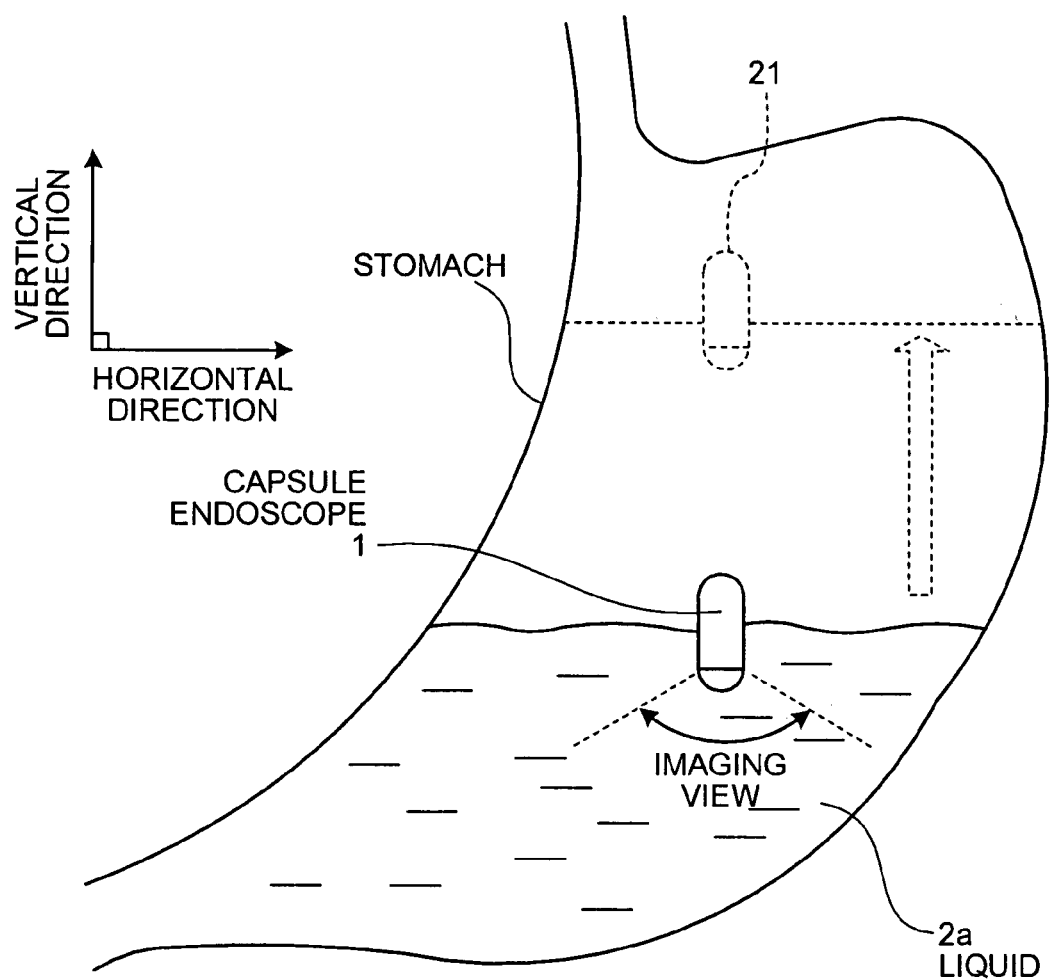
FIG. 13 is a schematic view showing a condition in which the body-insertable device is inserted into the digestive canal, according to the modification of the first embodiment of the present invention.

The capsule endoscope 21 having such casing 20 floats in the surface of the liquid 2a introduced into a digestive canal of the subject 100 and directs an imaging field under the surface of the liquid 2a in a vertical direction. FIG. 13 is a schematic view showing a condition of the capsule endoscope 21 and the liquid 2a introduced into the digestive canal. As shown in FIG. 13, for example, when the capsule endoscope 21 and the liquid 2a are introduced into the stomach of the subject 100, the capsule endoscope 21 floats in the surface of the liquid 2a in the stomach and directs the imaging field under the surface of the liquid 2a in a vertical direction. In this case, the imaging field is placed completely under the water.

Here, the stomach wall (that is, the wall of the stomach under the surface of the liquid 2a in a vertical direction) captured in the imaging field of the capsule endoscope 21 extends with the liquid 2a introduced in the stomach without using the foaming agent as described in the first embodiment.

Further, the capsule endoscope 21 changes its vertical position according to a change in water level of the liquid 2a, similarly to the case of the first embodiment. Accordingly, after introduced into the subject 100, the capsule endoscope 21 can change observed region, image every part in the stomach, for example, and, further, take an enlarged image of the stomach wall by repeating the above described procedure subsequent to step S104. With this, the effect as the first embodiment can be provided.

Such a capsule endoscope 21 is configured to have center of gravity at the center or rear portion of the casing 20. The capsule endoscope 21 may direct the imaging field under the liquid 2a in a vertical direction by the magnetic force applied by the permanent magnet 3; however, as described above, it is more desired to set the center of gravity at a front portion. With this structure, since the imaging field of the capsule endoscope 21 is directed downward by the buoyant force of the liquid 2a, the movement of the capsule endoscope 21 can be controlled by a permanent magnet having a smaller magnetic force so that the permanent magnet 3 for controlling the movement of the capsule endoscope 21 can be downsized.

As described above, according to the modification of the first embodiment of the present invention, since the capsule endoscope having the center of gravity displaced in a front portion is employed in place of the capsule endoscope 1 of the first embodiment, the capsule endoscope floats while directing the imaging field under the surface of the liquid introduced into the digestive canal of the subject. Accordingly, inside the digestive canal can be captured in the imaging field through the liquid. Also, without the foaming agent, it is possible to take an image in the digestive canal which is extended with the liquid. As a result, the same effect as the first embodiment can be provided and a clearer image in the subject can be taken. Further, buoyant force works on the body-insertable device (for example, the capsule endoscope 21) by the liquid introduced into the subject and the gravity generated on the body-insertable device can be reduced or canceled as much as the amount of this buoyant force. Accordingly, at least one of the position and posture of the body-insertable device can be easily changed and the drive unit (for example, a permanent magnet installed in the body-insertable device) for changing at least one of the position and posture of the body-insertable device can be downsized. As a result, since the body-insertable device itself can be downsized, the facility of introducing the body-insertable device into the subject can be improved.

Second Embodiment

Next, a second embodiment of the present invention will be described. The above described first embodiment employs a capsule endoscope 1 having specific gravity equal to or smaller than the that of the liquid 2a introduced into a digestive canal of the subject 100; however a body-insertable device system according to the second embodiment employs a capsule endoscope having specific gravity greater than that of the liquid 2a, in place of the capsule endoscope 1.

Figure 14:
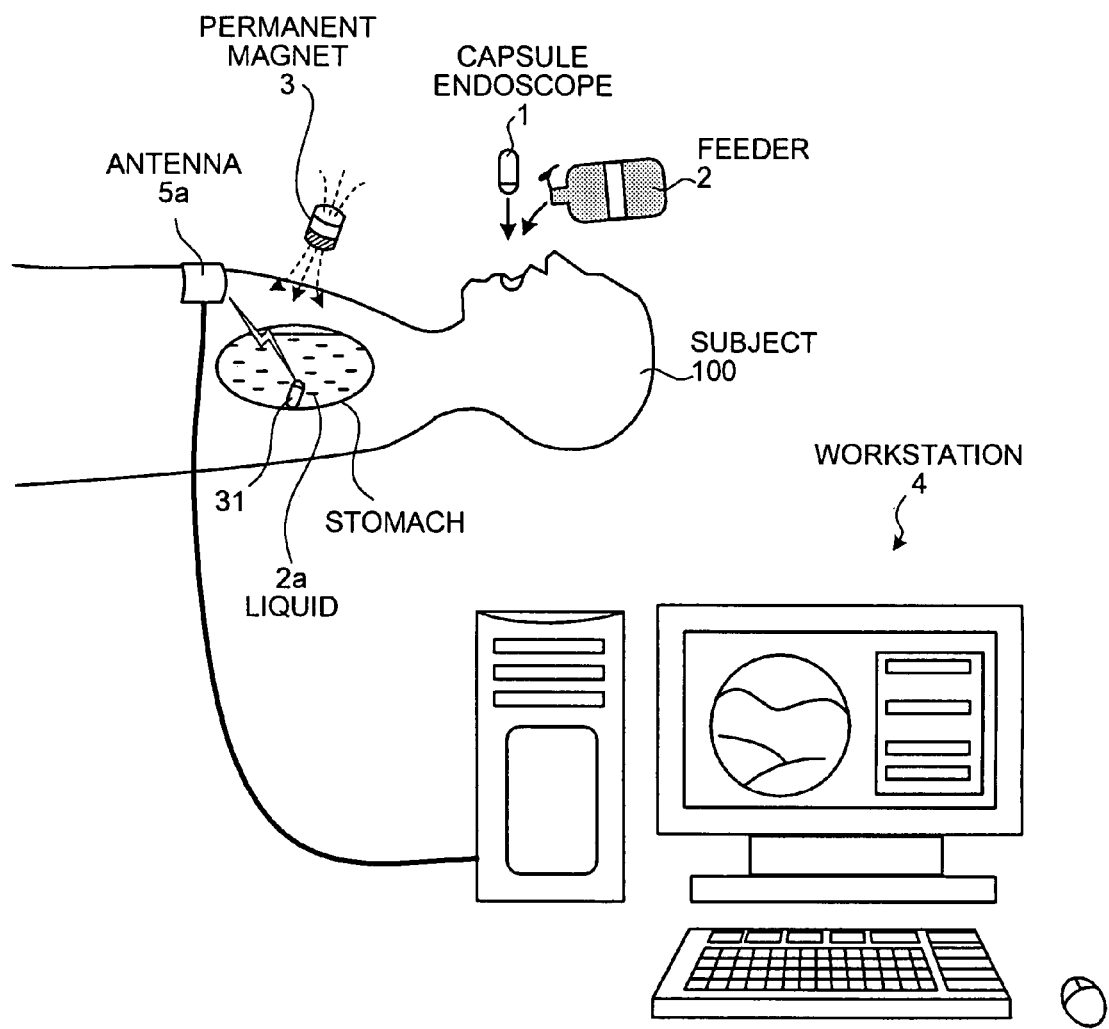
FIG. 14 is a schematic view showing a configuration example of a body-insertable device system according to a second embodiment of the present invention.

FIG. 14 is a schematic view showing a configuration example of a body-insertable device system according to the second embodiment of the present invention. As shown in FIG. 14, the body-insertable device system of the second embodiment includes a capsule endoscope 31, in place of the capsule endoscope 1 of the body-insertable device system according to the first embodiment. Other elements are the same as those in the first embodiments and the same elements are represented by the same reference numbers.

The capsule endoscope 31 has the imaging function and radio communication function as the capsule endoscope 1 of the first embodiment and has specific gravity greater than that of the liquid 2a introduced into digestive channel of the subject 100. Such capsule endoscope 31 sinks in the liquid 2a and wobbles or moves in the liquid 2a corresponding to a magnetic force applied by a permanent magnet 3. In this way, the capsule endoscope 31 sequentially take images in the digestive canal while changing at least one of the position and direction of the imaging field in the digestive canal.

Figure 15:
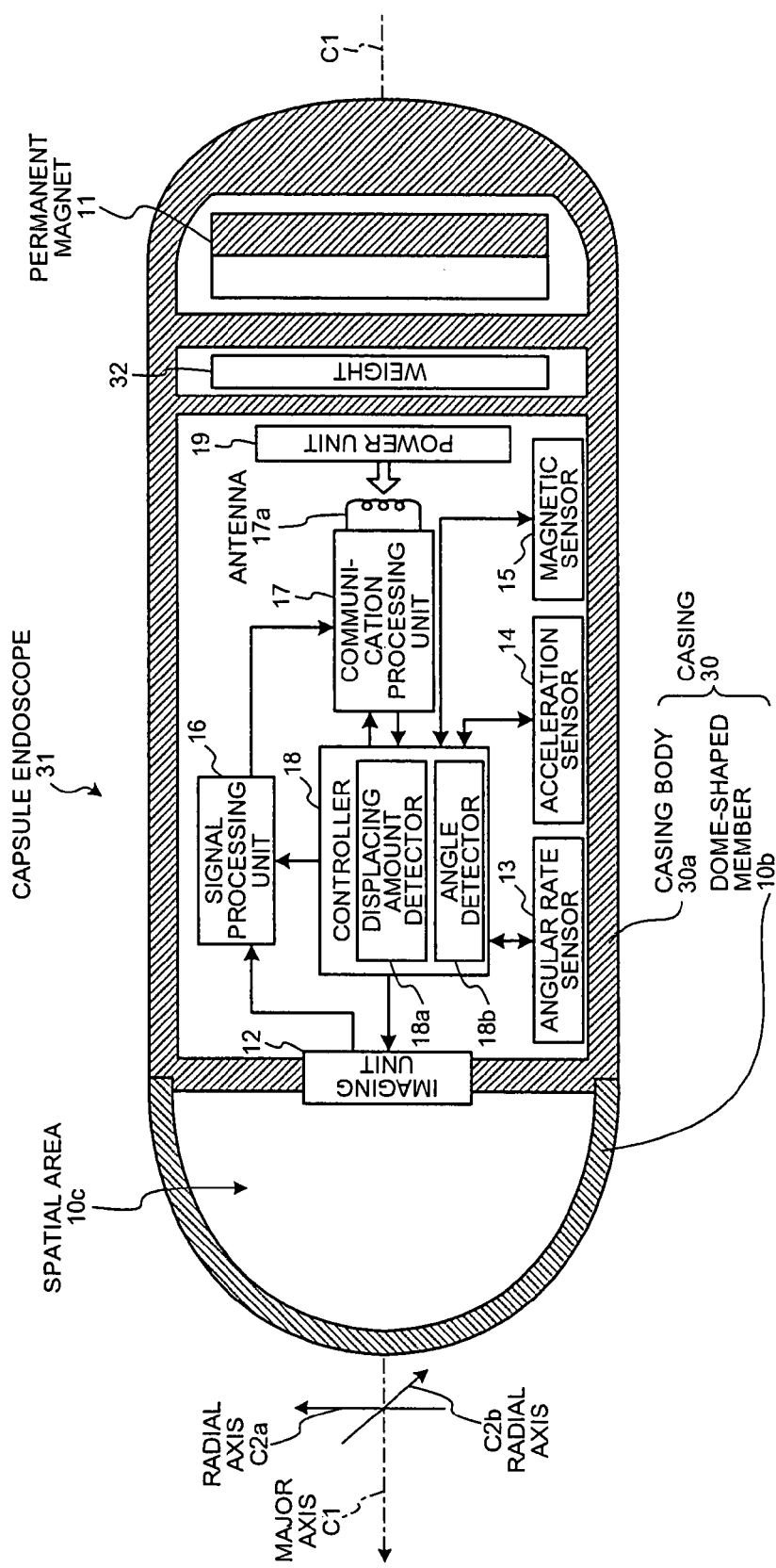
FIG. 15 is a schematic view showing a configuration example of the body-insertable device according to the second embodiment of the present invention.

Next, the structure of the capsule endoscope 31 of the second embodiment of the present invention will be described. FIG. 15 is a schematic view showing a configuration example of the body-insertable device according to the second embodiment of the present invention. As shown in FIG. 15, the capsule endoscope 31, as an example of the body-insertable device, includes a casing 30, in place of the casing 10 of the capsule endoscope 1 in the first embodiment. The casing 30 includes a casing body 30a, in place of the casing body 10a of the casing 10. Further, the casing body 30a includes a weight 32 therein. Other elements are the same as those of the first embodiment and the same elements are represented by the same reference numbers.

The casing 30 is a capsule-shaped member formed in a size easily insertable into the subject 100 and provided with a dome-shaped member 10b at a front-end part of the casing body 30a. The casing body 30a accommodates each element of the capsule endoscope 31. In this case, the casing body 30a includes an imaging unit 12 fixed to its front-end part and permanent magnet 11 and a weight 32 at a center or rear portion of the casing 30 as the capsule endoscope does. The weight 32 is a member made of such as steel or lead for adding a predetermined weight to the casing 30. The casing 30 provided with the casing body 30a to which a predetermined number of the weights 32 are added and the dome-shaped member 10b has specific gravity greater than that of the liquid 2a and the center of gravity is placed at a rear portion of the casing 30.

In order to set the specific gravity of the casing 30 greater than that of the liquid 2a, the spatial area in the casing body 30a may be reduced to increase its density and it should not be limited to the addition of the weights 32, as shown in FIG. 15. Further, the density of the casing 30 may be increased by reducing a spatial area 10c formed with the dome-shaped member 10*b* and the front-end part of the casing body 30*a*. The capsule endoscope 31 can be downsized by increasing the density of the casing 30.

The capsule endoscope 31 having such casing 30 sinks in the liquid 2*a* introduced into a digestive canal of the subject 100 and the inside of the digestive canal is captured in an imaging field through the liquid 2*a*. In this case, since the capsule endoscope 31 has the center of gravity at the rear portion of the casing 30, the capsule endoscope 31 can direct the imaging field upward in a vertical direction by a buoyant force of the liquid 2*a*, for example, without relying on the magnetic force of the permanent magnet 3. Further, since the capsule endoscope 31 can take images in the digestive canal through the liquid 2*a*, a clearer image in the digestive canal expanded by the liquid 2*a* can be taken without using the above described foaming agent.

After introduced into the subject 100, such capsule endoscope 31 can image every part of the desired observed region, for example, the stomach by repeating the above described procedure subsequent to step S104. With this, the same effect as the first embodiment can be provided.

Figure 16:
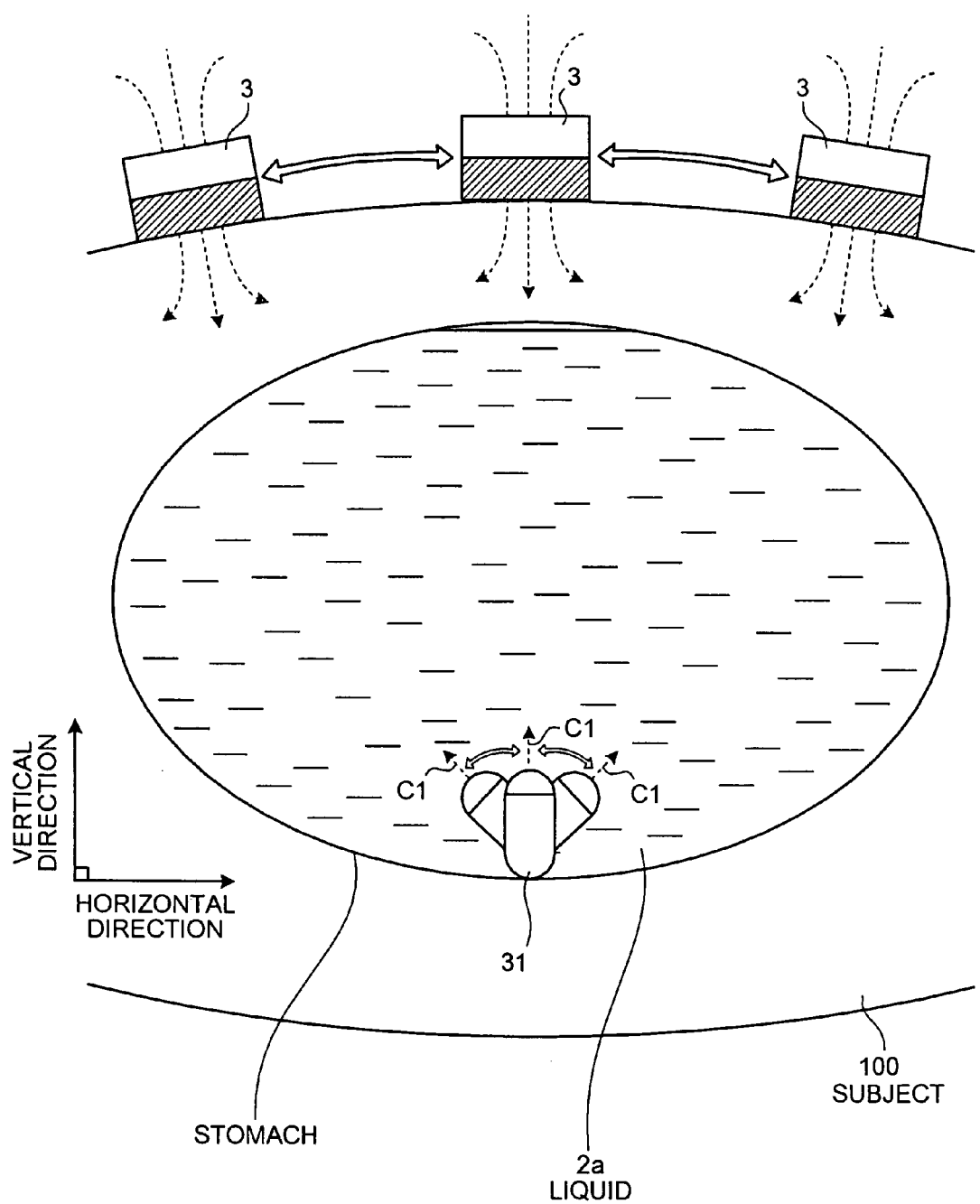
FIG. 16 is a schematic view showing an operation of a permanent magnet for changing a posture of the body-insertable device according to the second embodiment.

Next, an operation of changing the position and posture of the capsule endoscope 31 in the liquid 2*a* with the steps S104 and S105 will be described. Firstly, an operation of changing the posture of the capsule endoscope 31 introduced into the digestive canal as an observed region (for example, the stomach) of the subject 100 will be described in detail. FIG. 16 is a schematic view showing an operation of the permanent magnet 3 for changing the posture of the capsule endoscope 31 under the liquid 2*a*.

As shown in FIG. 16, when the permanent magnet 3 is put close to a body surface of the subject 100 close to, for example, the stomach, the permanent magnet 3 captures the capsule endoscope 31 under the liquid 2*a* in the stomach by its magnetic force. The permanent magnet 3 capturing the capsule endoscope 31 is, for example, horizontally wobbled on the body surface of the subject 100 to change the position and the direction of the magnetic field toward the capsule endoscope 31. In this case, the capsule endoscope 31 wobbles at the bottom of the liquid 2*a* corresponding to the wobbling of the permanent magnet 3 and directs the vector direction of the major axis C1 toward the position of the permanent magnet 3. At the same time, the capsule endoscope 31 sequentially images inside the stomach while changing the direction of the imaging field in the stomach. Here, it is desirable that the magnetization direction of the permanent magnet 11 in the capsule endoscope 31 is 80 degree or smaller toward the direction of the observing view. The direction of the imaging field can be changed according to the direction of the magnetic field generated toward the permanent magnet 11 by adjusting the magnetization direction of the permanent magnet 11 in this way.

The capsule endoscope 31 can image every part of the stomach expanded with the liquid 2*a* by controlling the wobbling of the capsule endoscope 31 by the magnetic force of the permanent magnet 3. Further, when the specific gravity of the capsule endoscope 31 is greater than that of the liquid, the capsule endoscope 31 sink to the bottom of the liquid and contact with the stomach wall. With the friction at the contact point, this contact point works as a supporting point. As a result, the direction of the imaging field can be changed. Further, although not shown in the drawing, a plurality of electromagnet may be arranged on a horizontal plane and the direction of the magnetic field of the permanent magnet 11 of the capsule endoscope 31 may be changed by changing the magnetic field of each electrical magnet by a magnetic field strength changing unit instead of changing the position of the permanent magnet 3 in a horizontal direction. The concrete structure of the plurality of electromagnet may be provided as shown in later described in FIGS. 32 and 35.

Figure 17:
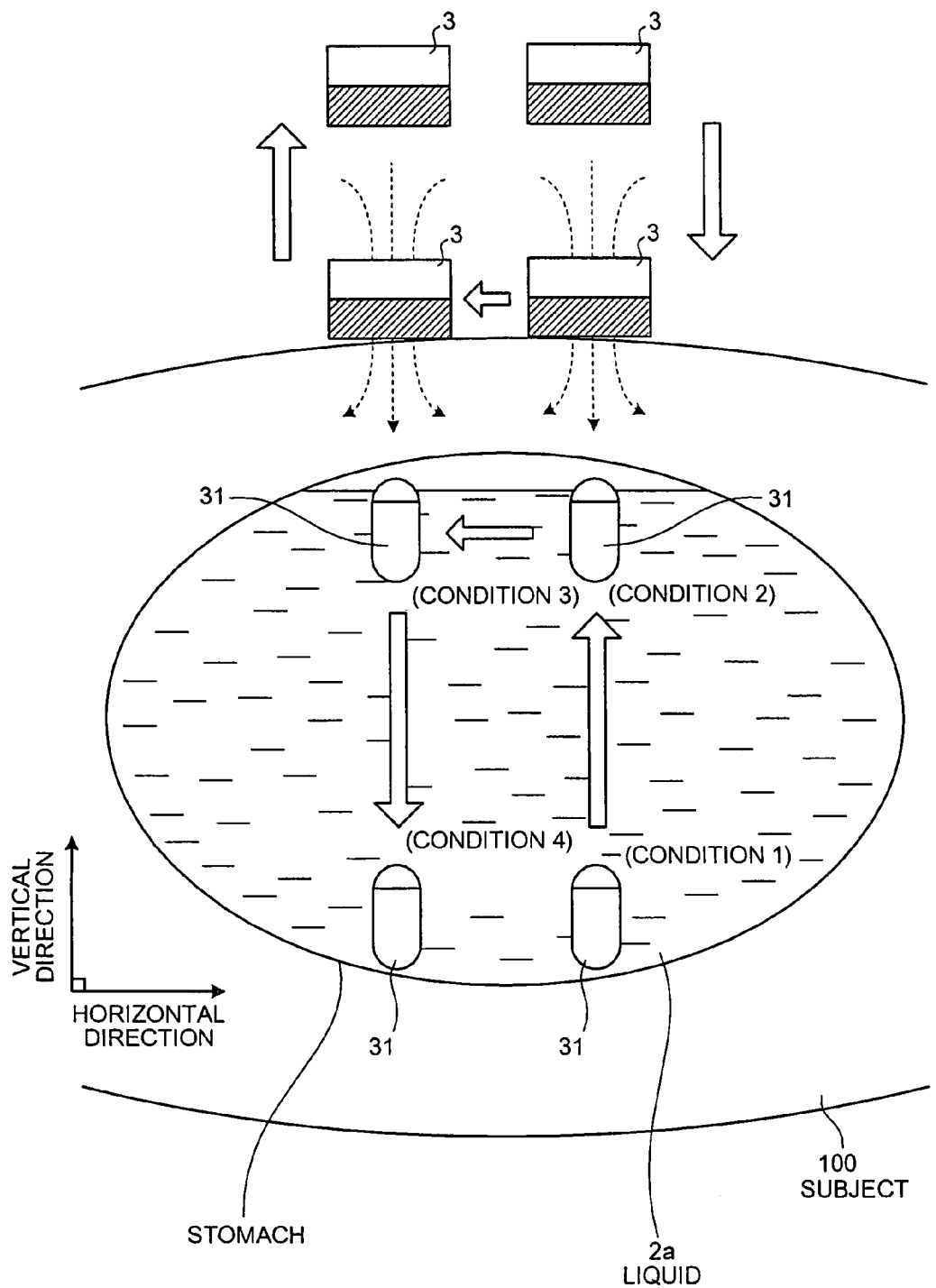
FIG. 17 is a schematic view showing an operation of the permanent magnet for vertically or horizontally displacing the body-insertable device according to the second embodiment.

Next, an operation of vertically or horizontally displacing the capsule endoscope 31 introduced into the digestive canal as an observed region (for example, the stomach) of the subject 100 will be described in detail. FIG. 17 is a schematic view showing an operation of the permanent magnet 3 for vertically or horizontally displacing the capsule endoscope 31 sunken in the liquid 2*a*. The permanent magnet 3 used here has a magnetic field of a magnetic field strength sufficient for attracting the capsule endoscope 31 sunken in the liquid 2*a* upward in a vertical direction. In this case, the permanent magnet 3 adjusts the distance to the body surface of the subject 100 to adjust the magnetic field strength working on the capsule endoscope 31.

As shown in FIG. 17, when the permanent magnet 3 is put close to the body surface of the subject 100 close to, for example, the stomach, at a predetermined distance, the permanent magnet 3 captures the capsule endoscope 31 sunken to the bottom of the liquid 2*a* (condition 1). Then, the permanent magnet 3 capturing the capsule endoscope 31 is put closer to the body surface of the subject 100 to generate stronger magnetic field toward the capsule endoscope 31 sunken to the bottom of the liquid 2*a*. With this, the capsule endoscope 31 is drawn toward the magnetic force of the permanent magnet 3 and moves upward to the surface of the liquid 2*a* (condition 2). In such a way, the capsule endoscope 31 can be displaced upward and, at the same time, sequentially take images of the inside view in the stomach while changing the imaging field in the stomach.

Further, after attracting the capsule endoscope 31 up to the surface of the liquid 2*a*, the permanent magnet 3 horizontally moves on the body surface of the subject 100 to change the position and direction of the magnetic field toward the capsule endoscope 31. In this case, the capsule endoscope 31 horizontally moves in the liquid 2*a* following the movement of the permanent magnet 3 (condition 3), and, at the same time, sequentially take images of inside view of the stomach while displacing the imaging field in the stomach.

After that, the permanent magnet 3 moves away from the body surface of the subject 100 to reduce the magnetic field strength toward the capsule endoscope 31. In this case, the capsule endoscope 31 is released form the magnetic force of the permanent magnet 3 and displaces downward to the bottom of the liquid 2*a* (condition 4). At the same time, the capsule endoscope 31 sequentially takes images in the stomach while changing the imaging field in the stomach.

As described above, the capsule endoscope 31 can take every part in the stomach expanded with the liquid 2*a* by controlling the displacing operation of the capsule endoscope 31 by the magnetic force of the permanent magnet 3. In this case, the capsule endoscope 31 can move closer to a desired place in the stomach wall and take an enlarged image of the stomach wall. Further, since it can be prevented that the capsule endoscope 31 contact with the stomach wall when horizontally moving in the liquid 2*a*, so that the capsule endoscope 31 can move smoothly in a horizontal direction without generating fiction. Here, the strength of the magnetic fields generated toward the capsule endoscope 31 can be changed by changing the distance between the permanent magnet 3 and the subject 100. Further, an electrical magnet may be employed in place of the permanent magnet 3. Further, the permanent magnet 3 may be fixed to a structure such as an arm and the strength of the magnetic field generated toward the capsule endoscope 31 may be changed by changing the position of the fixing unit.

Such capsule endoscope 31 may be provided with the center of gravity placed at the center or front portion of the casing 30 and direct the imaging field upward with the magnetic force generated by the permanent magnet 3. However, it is desirable that the center of gravity is placed at the rear portion of the casing 30, as described above. With this, since the imaging field of the capsule endoscope 31 can be directed upward in a vertical direction by the buoyant force of the liquid 2a, the movement of the capsule endoscope 31 can be controlled with a permanent magnet having a small magnetic force. Accordingly, the permanent magnet 3 for controlling the capsule endoscope 31 can be downsized. Further, the posture of the capsule endoscope 31 when it moves can be controlled by changing the posture of the permanent magnet 3.

As described above, according to the second embodiment of the present invention, a capsule endoscope, which is corresponding to the capsule endoscope 1 of the first embodiment, having specific gravity greater than that of a predetermined liquid is employed, so that an imaging field can be changed while sunken in the liquid introduced into a digestive canal of a subject. Accordingly, inside view of the digestive canal can be captured in the imaging field through the liquid and an image in the digestive canal expanded with the liquid can be obtained without using foaming agent. As a result, the same effect as the first embodiment can be provided and a clearer image in the subject can be observed. Further, a buoyant force of the liquid introduced into the subject works on the body-insertable device (for example, the capsule endoscope 31) and gravity generated on the body-insertable device can be reduced or canceled as much as the amount of the buoyant force. Accordingly, at least one of the position and posture of the body-insertable device can be easily changed and a drive unit (for example, a permanent magnet installed in the body-insertable device) for changing at least one of the position and posture of the body-insertable device can be downsized. As a result, since the body-insertable device it self can be downsized, the facility of introducing the body-insertable device into the subject can be improved.

Third Embodiment

Next, a third embodiment of the present invention will be described. The above first embodiment employs the permanent magnet 3 for controlling the capsule endoscope 1 by its magnetic force. However, a body-insertable device system of the third embodiment employs an electrical magnet, in place of the permanent magnet 3.

Figure 18:
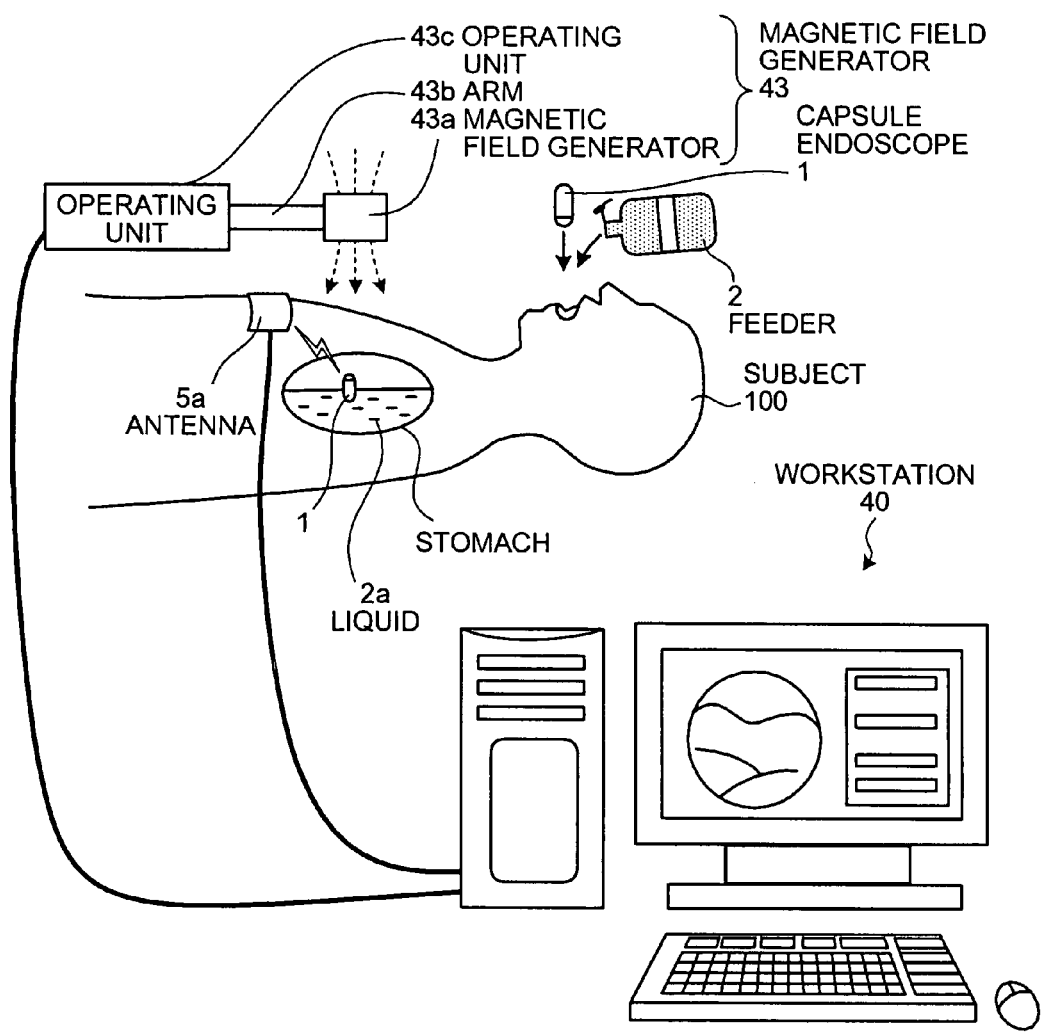
FIG. 18 is a schematic view showing a configuration example of a body-insertable device system according to a third embodiment of the present invention.

FIG. 18 is a schematic view showing a configuration example of the body-insertable device system according to the third embodiment of the present invention. The body-insertable device system in the third embodiment includes a magnetic field generator 43, in place of the permanent magnet 3 of the body-insertable device system in the first embodiment, and a workstation 40, in place of the workstation 4. Other elements are the same as those of the first embodiment and the same elements are represented by the same reference numbers.

The magnetic field generator 43 includes a magnetic field generator 43a for generating a magnetic field toward the capsule endoscope 1, an arm 43b for connecting the magnetic field generator 43a to an end thereof, and an operating unit 43c for operating the magnetic field generator 43a via the arm 43b. Such magnetic field generator 43 is electrically connected to the workstation 40 via a cable and the like and controlled by the workstation 40.

Figure 19:
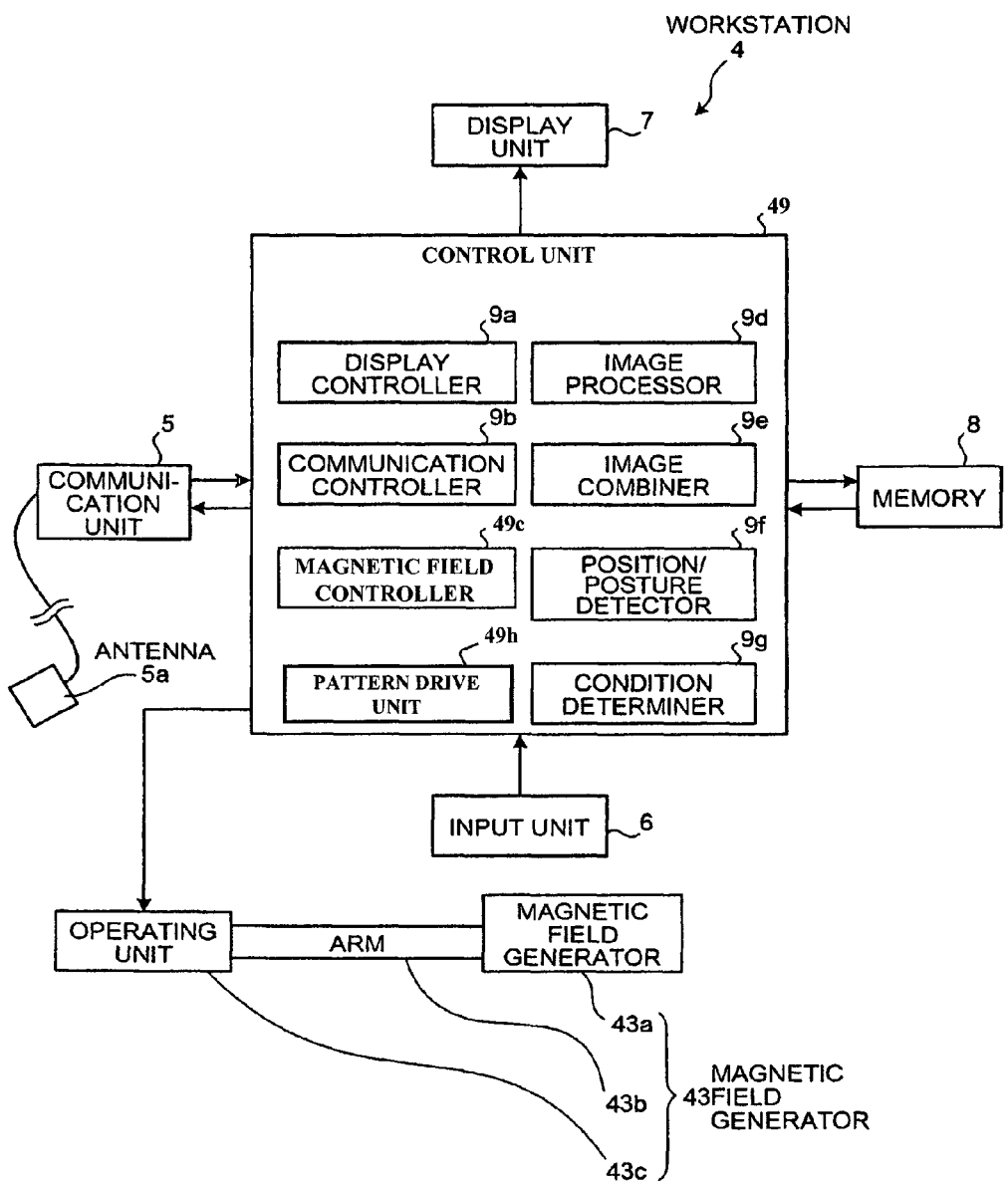
FIG. 19 is a block diagram schematically showing a configuration example of a workstation and a magnetic field generator according to the third embodiment.

Next, structures of the workstation 40 and the magnetic field generator 43 will be described in detail. FIG. 19 is a block diagram schematically showing a configuration example of the workstation 40 and the magnetic field generator 43. As shown in FIG. 19, the workstation 40 includes a control unit 49, in place of the control unit 9 of the workstation 4 of the body-insertable device system in the first embodiment. The control unit 49 includes a magnetic field controller 49c, in place of the magnet selector 9c of the control unit 9 of the workstation 4. Further, the operating unit 43c of the magnetic field generator 43 is electrically connected to the control unit 49 via a cable and the like. Other elements are the same as those of the first embodiment and the same elements are represented by the same reference numbers.

The magnetic field generator 43a generates a magnetic field for controlling the movement of the capsule endoscope 1 in the liquid 2a introduced into the digestive canal of the subject 100. Concretely, the magnetic field generator 43a is provided with an electrical magnet or the like and generates a magnetic field by drive power supplied by the operating unit 43c via the arm 43b. In this case, the magnetic field generator 43a is put close to the body surface of the subject 100 and controls at least one of the position and posture of the capsule endoscope 1 that floats, for example, in the surface of the liquid 2a by the magnetic field generated with the drive power. On the other hand, the arm 43b has an end connected to the magnetic field generator 43a and another end connected to the operating unit 43c so as to connect the magnetic field generator 43a and the operating unit 43c electrically.

The operating unit 43c operates the magnetic field generator 43a disposed at the end of the arm 43b. Concretely, the operating unit 43c is held by the examiner to adjust the position of the magnetic field generator 43a with respect to the subject 100 according to the examiner's operation. Further, drive power is supplied to the operating unit 43c from the control unit 9 and the operating unit 43c adjusts and supplies the drive power to the magnetic field generator 43a. In this case, the operating unit 43c includes an adjusting switch (not shown) for adjusting the drive power to be supplied to the magnetic field generator 43a and adjust the drive power to be supplied to the magnetic field generator 43a according to the examiner's operation of the adjusting switch.

On the other hand, the control unit 49 of the workstation 40 has the function similar to the control unit 9 of the workstation 4, and, in addition, controls a drive of the magnetic field generator 43. Concretely, the control unit 49 further includes a magnetic field controller 49c for controlling the magnetic field strength of the magnetic field generator 43a. The magnetic field controller 49c controls the drive power to be supplied to the magnetic field generator 43 according to determination result of a magnetic field strength by the condition determiner 9g. With this structure the magnetic field strength of the magnetic field generator 43 is controlled. In this case, the condition determiner 9g determines the magnetic field strength of the magnetic field generator 43a toward the capsule endoscope 1 based on a magnetic field detection signal received from the capsule endoscope 1.

Such magnetic field controller 49c initializes the drive power to be supplied to the magnetic field generator 43 based on the patient information of the subject 100 input from the input unit 6, for example. Then the magnetic field controller 49c adjusts the drive power according to the determination result of the magnetic field strength by the condition determiner 9g. The magnetic field generator 43 controlled by the magnetic field controller 49c generates a magnetic field sufficient to move the capsule endoscope 1 in the liquid 2a introduced in the digestive canal of the subject 100. In this case, the examiner can observe every part in a desired observed region such as stomach by implementing above described procedures from step S101.

Figure 20:
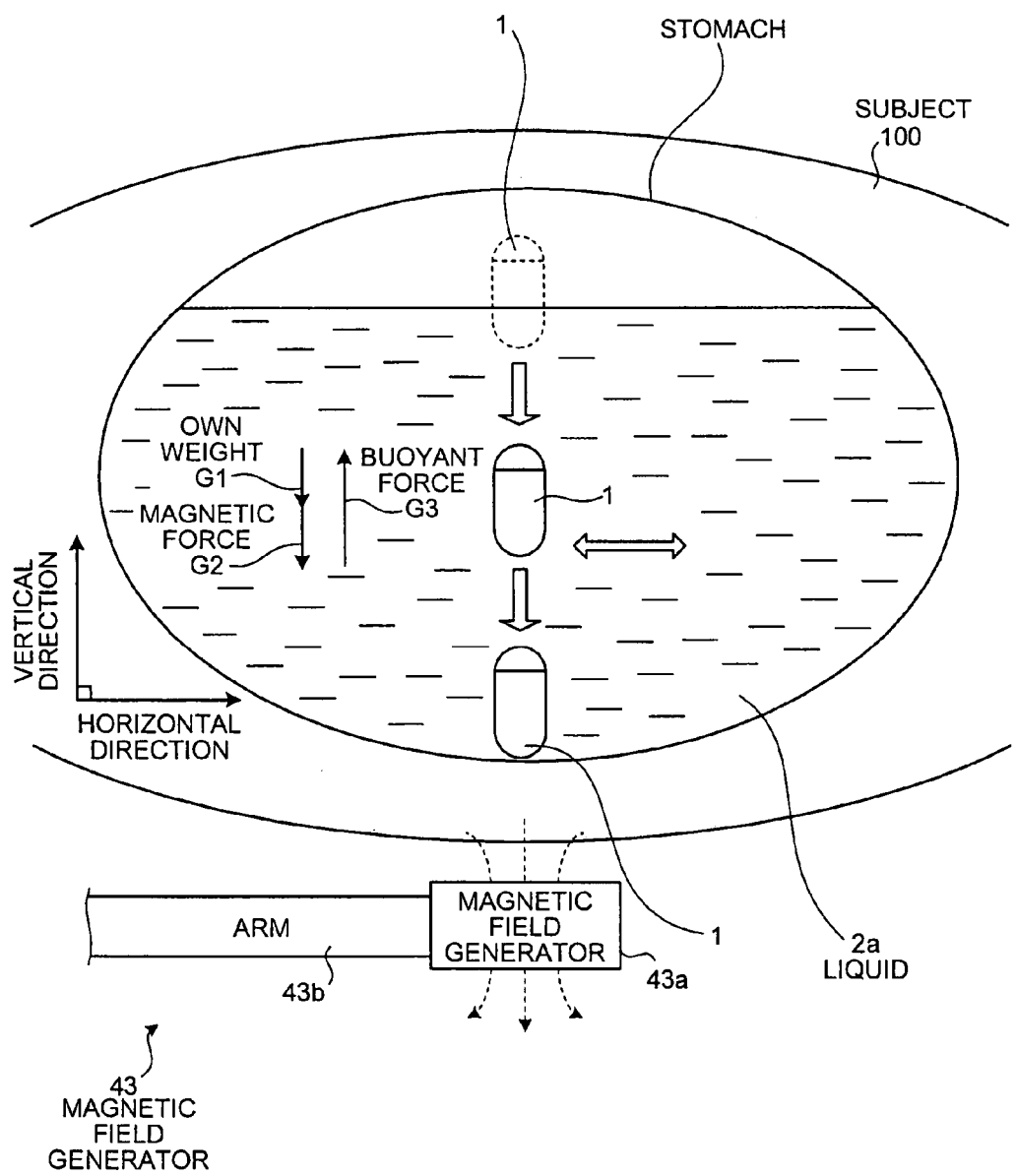
FIG. 20 is a schematic view showing an operation of a control unit for controlling a magnetic field strength of the magnetic field generator according to the third embodiment.

Further, the magnetic field controller 49c can control the magnetic field strength of the magnetic field generator 43a so as to keep the capsule endoscope 1 under the liquid 2a by controlling the drive power supplied to the magnetic field generator 43a. FIG. 20 is a schematic view showing an operation of the control unit 49 for controlling the magnetic field strength of the magnetic field generator 43.

Firstly, the control unit 49 supplies drive power to the magnetic field generator 43 which is put close to the body surface of the subject 100 and to generate a magnetic field toward the capsule endoscope 1 introduced in the stomach, for example. In this case, the magnetic field controller 49c controls the drive power supplied to the magnetic field generator 43 and the magnetic field strength of the magnetic field generator 43. The magnetic field generator 43a generates a magnetic field with the drive power controlled by the magnetic field controller 49c and, for example, as shown in FIG. 20, captures the capsule endoscope 1 that floats in the surface of the liquid 2a by its magnetic force.

Next, the control unit 49 controls the drive power to the magnetic field generator 43 based on, for example, instruction information from the input unit 6, so as to set the magnetic field strength for keeping the capsule endoscope 1 under the surface of the liquid 2a. In this case, the magnetic field controller 49c controls the drive power to the magnetic field generator 43 based on position/posture information of the capsule endoscope 1 and controls the magnetic field strength to keep the capsule endoscope 1 under the surface of the liquid 2a by the magnetic field of the magnetic field generator 43.

Here, when the magnetic field generator 43a generates a magnetic field for attracting the capsule endoscope 1 in the liquid 2, as shown in FIG. 20, for example, the capsule endoscope 1 receives the magnetic force G2 from the magnetic field generator 43a and the buoyant force G3 from the liquid 2a in addition to own weight G1. In this case, the direction of forces of the weight G1 and the magnetic force G2 is downward in a vertical direction and the direction of force of the buoyant force G3 is upward in a vertical direction. In other words, when the buoyant force G3 is greater than the sum of the weight G1 and the magnetic force G2, the capsule endoscope 1 moves upward toward the surface of the liquid 2a. When the buoyant force G3 is smaller than the sum of the weight G1 and the magnetic force G2, the capsule endoscope 1 moves downward toward the bottom of the liquid 2a. When the buoyant force G3 is substantially equal to the sum of the weight G1 and the magnetic force G2, the capsule endoscope 1 stays in the liquid 2a.

Therefore, the magnetic field controller 49c controls the magnetic field strength of the magnetic field generator 43, that is, the magnetic force G2, based on the position/posture information of the capsule endoscope 1 to keep the capsule endoscope 1 under the surface of the liquid 2a. In this case, the magnetic field controller 49c determines whether or not the capsule endoscope 1 is kept under the surface of the liquid 2a based on the position/posture information of the capsule endoscope 1 and controls the drive power supplied to the magnetic field generator 43 based on the determination result. The magnetic field generator 43a adjusts the magnetic field strength, that is, the magnetic force G2, with the drive power controlled by the magnetic field controller 49c, generates, for example, a magnetic field to sink the capsule endoscope 1 under the liquid 2a, and then, generates an imaging field to keep the capsule endoscope 1 under the surface of the liquid 2a.

As described above, the magnetic field generator 43 can displace the capsule endoscope 1 in the liquid 2 upward or downward in vertical direction by operating the adjusting switch of the operating unit 43c and adjusting the drive power supplied to the magnetic field generator 43a under a condition in which a magnetic field to keep the capsule endoscope 1 under the surface of the liquid 2a is generated. Concretely, the magnetic field generator 43 reduces the magnetic force G2 by reducing the drive power to move the capsule endoscope 1 upward toward the surface of the liquid 2a according to the operation of the adjusting switch of the operating unit 43c. Further, the magnetic field generator 43 increases the magnetic force G2 by increasing the drive power to move the capsule endoscope 1 downward toward the bottom of the liquid 2a according to the operation of the adjusting switch of the operating unit 43c.

Figure 21:
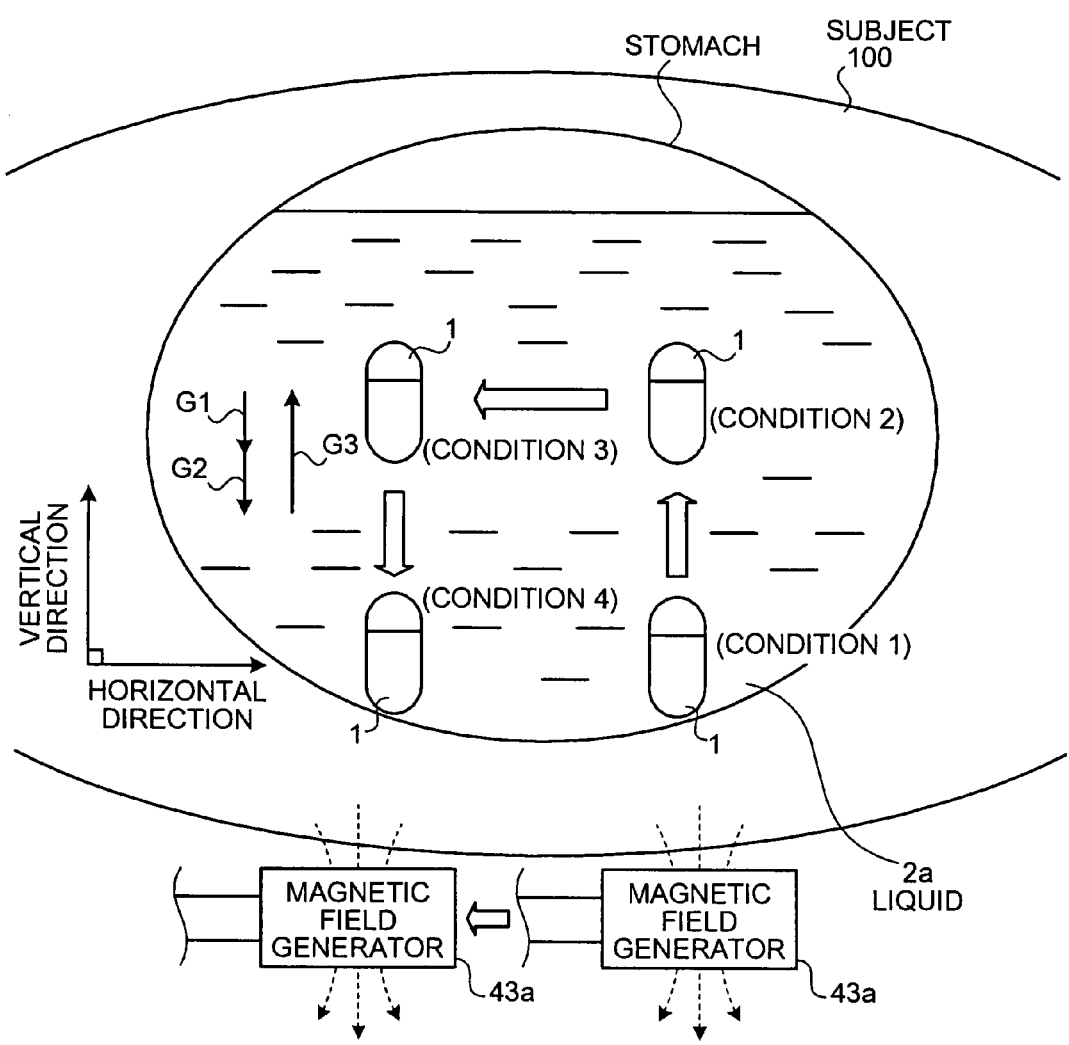
FIG. 21 is a schematic view showing an operation of the magnetic field generator for displacing the body-insertable device while keeping the body-insertable device under liquid.

Further, the magnetic field generator 43 can dispose the capsule endoscope 1 while keeping the capsule endoscope 1 under the surface of the liquid 2a by moving the magnetic field generator 43 on the body surface of the subject 100 while adjusting the magnetic field strength based on the control of the magnetic field controller 49c. FIG. 21 is a schematic view showing an operation of the magnetic field generator 43 for displacing the capsule endoscope 31 while keeping the capsule endoscope 1 in the liquid 2a.

As shown in FIG. 21, the magnetic field generator 43 generates a magnetic field to keep the capsule endoscope 1 under the surface of the liquid 2a, for example, in the stomach according to the control by the magnetic field controller 49c and keep the capsule endoscope 1 under the surface of the liquid 2a with its magnetic force. After that, the magnetic field generator 43 increase the magnetic force G2 according to the operation of the adjusting switch of the operating unit 43c and moves the capsule endoscope 1 downward to the bottom of the liquid 2a (condition 1).

Next, the magnetic field generator 43 reduces the magnetic force G2 according to the operation of the adjusting switch of the operating unit 43c and moves the capsule endoscope 1 upward between the surface and the bottom of the liquid 2a (condition 2). Here, the magnetic field generator 43 moves the magnetic field generator 43a on the body surface of the subject 100 in a substantially horizontal direction according to the operation of the operating unit 43c to change the position and the direction of the magnetic field of the capsule endoscope 1. In this case, the capsule endoscope 1 moves in the liquid 2a in a substantially horizontal direction following the movement of the magnetic field generator 43a (condition 3).

Then, the magnetic field generator 43 increases the magnetic force G2 by the operation of the adjusting switch of the operating unit 43c and moves the capsule endoscope 1 downward to the bottom of the liquid 2a (condition 4). In this way, the magnetic field generator 43 can displace the capsule endoscope 1 while keeping the capsule endoscope 1 under the surface of the liquid 2a. In this case, the capsule endoscope 1 sequentially takes images in the stomach while displacing the imaging field in the stomach while moving from condition 1 to condition 4. Further, although not shown in the drawings, the posture of the capsule endoscope 1 may be controlled by changing the direction of the magnetic field generator 43a. With this, the position (in vertical and horizontal conditions) and the posture of the capsule endoscope 1 in the liquid 2a can be controlled. Further, the control unit 49 may include a pattern drive unit which is not shown and the pattern drive unit may control magnetic field generator 43a, and the arm 43b based on a predetermined pattern to control the position (in vertical and horizontal directions) and the posture of the capsule endoscope 1.

As described above, since the magnetic field generator 43 controls the displacement of the capsule endoscope 1 with its magnetic force, the capsule endoscope 1 can image every part of the stomach wall expanded with the liquid 2a. In this case, the capsule endoscope 1 can move close to a desired place of the stomach wall and take an enlarged image of the stomach wall. Further, there is gas above the liquid according to the third embodiment; however, when the stomach is filled with the liquid, it is difficult to move the capsule endoscope 1 since the capsule endoscope 1 contacts with the upper face in the stomach. In this case, the position of the capsule endoscope 1 can be controlled without being disturbed by the upper face in the stomach by attracting the capsule endoscope 1 into the liquid and moving the capsule endoscope 1 horizontally, enhancing controllability.

As described above, according to the third embodiment of the present invention, the movement of the capsule endoscope in the first embodiment is controlled by a magnetic field of an electrical magnet. Accordingly, the capsule endoscope can be easily kept in a predetermined liquid introduced into a digestive canal of a subject and the position and posture of an imaging field of the capsule endoscope introduced into the digestive canal can be easily changed. The inside of the digestive canal can be captured in the imaging field through the predetermined liquid and clearer images in the digestive canal expanded with the predetermined liquid can be taken without using the foaming agent. Thus, the same effect as the above described first embodiment can be provided and the inside of the subject can be easily observed.

Further, the structure for controlling the movement of the capsule endoscope according to the third embodiment by the magnetic field of the electrical magnet can be applied not only to the first embodiment but to the modification of the first embodiment and the second embodiment. When the third embodiment is combined with the modification of the first embodiment or the second embodiment, the effects described above can be provided, and, the position and direction of the imaging field of the capsule endoscope introduced into the digestive canal can be easily changed so that the inside of the subject can be easily observed. Further, buoyant force of the liquid introduced in the subject works on the body-insertable device (for example, the capsule endoscope 1) and the gravity generated on the body-insertable device can be reduced or, further, canceled as much as the amount of the buoyant force. Accordingly, at least one of the position and posture of the body-insertable device can be easily changed and the driving unit (for example, a permanent magnet installed in the body-insertable device) for changing one of the position and posture of the body-insertable device can be downsized. As a result, the body-insertable device itself can be downsized so that the facility of introducing the body-insertable device into the subject can be improved.

Fourth Embodiment

Next, a fourth embodiment of the present invention will be described. According to the above described third embodiment, the movement of a capsule endoscope in a liquid is controlled by a single electrical magnet. However, a body-insertable device system according to the fourth embodiment is configured to include an electrical magnet for generating a horizontal magnetic field and an electrical magnet for generating a vertical magnetic field toward a capsule endoscope so as to control the movement of the capsule endoscope in a liquid by magnetic fields of the electromagnet.

Figure 22:
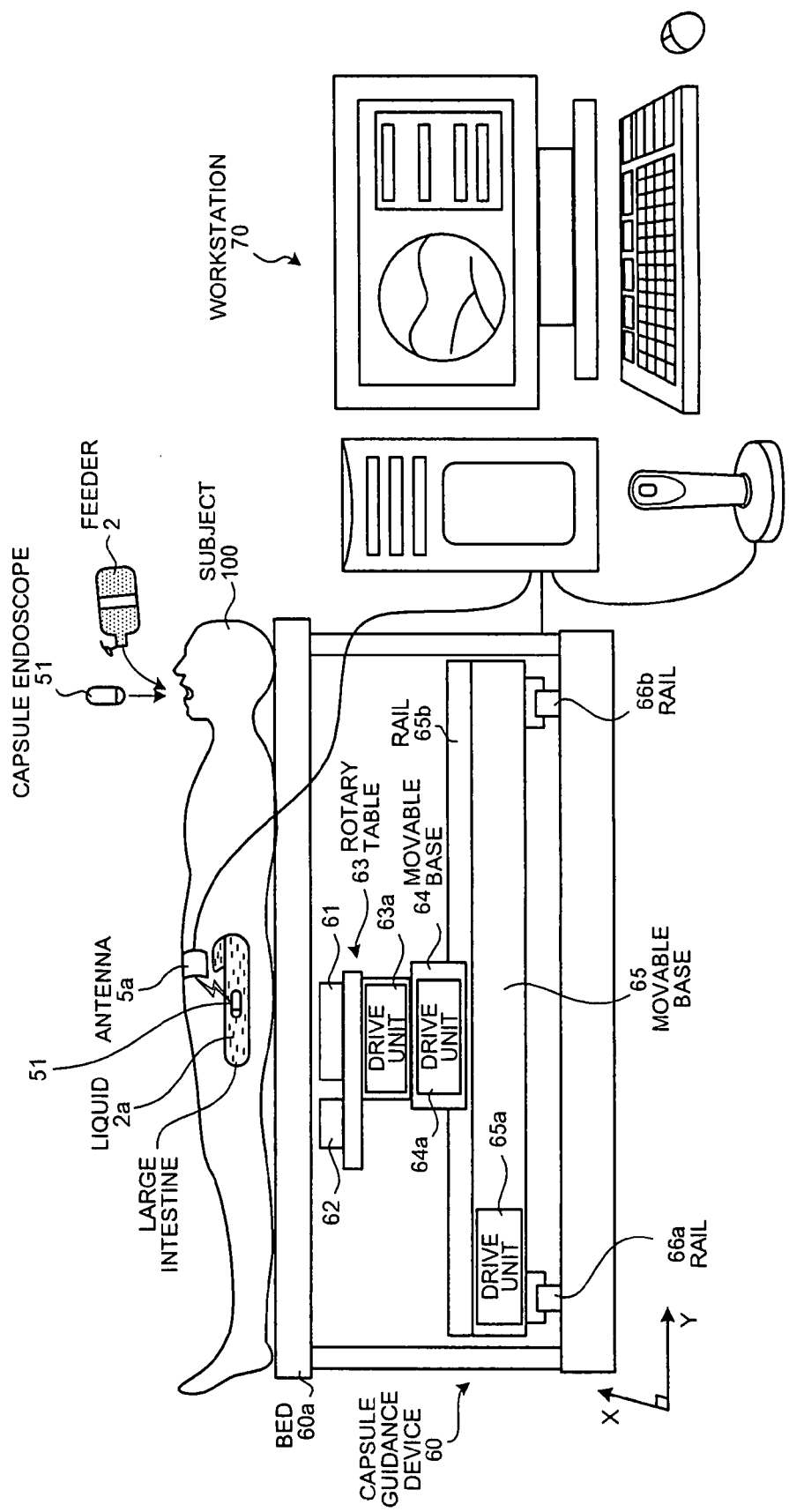
FIG. 22 is a schematic view showing a configuration example of a body-insertable device system according to a fourth embodiment of the present invention.

FIG. 22 is a schematic view showing a configuration example of the body-insertable device system according to the fourth embodiment of the present invention. As shown in FIG. 22, the body-insertable device system according to the fourth embodiment includes a capsule endoscope 51, in place of the capsule endoscope 1 of the body-insertable device system in the third embodiment, a capsule guidance device 60, in place of the magnetic field generator 43, and a workstation 70, in place of the workstation 40. Other elements are the same as those of the third embodiment and the same elements are represented by the same reference numbers.

The capsule endoscope 51 has the same imaging function and radio communication function as the capsule endoscope 1 of the first embodiment and includes a magnet that is magnetized in a radial direction, in place of a longitudinal direction. Further, the capsule endoscope 51 has specific gravity equal to or smaller than that of the liquid 2a and the center of gravity is placed at a center portion of the casing. The capsule endoscope 51 may be configured to have the center of gravity at a front portion or a rear portion of the casing 50; however, it is desirable to place the center of gravity at the center portion of the casing 50, as described above. With this, since the magnetic torque required to change the posture of the capsule endoscope 51 is substantially constant, the facility of controlling the posture of the capsule endoscope 51 is improved and more secure observation can be obtained.

The capsule guidance device 60 is mounted on a bed 60a which is a subject placement unit where the subject 100 is placed in a desired body posture. The capsule guidance device 60 controls the movement of the capsule endoscope 51 in the liquid 2a introduced in the subject 100 and leads the capsule endoscope 51 to a desired position in the subject 100. Such capsule endoscope 60 includes a vertical magnetic field generator 61 for generating a magnetic field toward the capsule endoscope 51 in the subject 100 on the bed 60a (or toward the subject placement unit) in a substantially vertical direction and a horizontal magnetic field generator 62 for generating a magnetic field for the capsule endoscope 51 in a substantially horizontal direction. Further, the capsule guidance device 60 includes a rotary table 63 for mounting the vertical magnetic field generator 61 and the horizontal magnetic field generator 62, a movable base 64 for moving the rotary table 63 in a longitudinal direction of the bed 60a (direction of axis Y), and a movable base 65 for moving the movable base 64 along in a widthwise direction of the bed 60a (direction of axis X).

The vertical magnetic field generator 61 and the horizontal magnetic field generator 62, disposed near the subject placement unit of the bed 60a while mounted on the rotary table 63, generate magnetic fields toward the capsule endoscope 51 in the subject 100 placed on the subject placement unit, via the subject placement unit. In this case, the vertical magnetic field generator 61 generates a magnetic field applying a magnetic force, in a substantially vertical direction, toward the capsule endoscope 51 in the subject 100. Further, the horizontal magnetic field generator 62 generates a magnetic field applying a magnetic force, in a horizontal direction, toward the capsule endoscope 51 in the subject 100.

The rotary table 63 places the vertical magnetic field generator 61 and the horizontal magnetic field generator 62 thereon near the subject placement unit on the bed 60a. Further, the rotary table 63 has a drive unit 63a and rotates the vertical magnetic field generator 61 and the horizontal magnetic field generator 62 mounted thereon. In this case, the drive unit 63a rotates the horizontal magnetic field generator 62 around the vertical magnetic field generator 61 with a coil axis of the vertical magnetic field generator 61 as a rotation center.

The movable base 64 is configured to move the vertical magnetic field generator 61 and the horizontal magnetic field generator 62 on the bed 60a in a direction of the axis Y of the bed 60a. Concretely, the movable base 64 includes a drive unit 64a and mounts a rotary table 63 on which the vertical magnetic field generator 61 and the horizontal magnetic field generator 62 are mounted. The drive unit 64a moves the movable base 64 along a rail 65b disposed on the movable base 65, that is, in the direction of the axis Y of the bed 60a.

The movable base 65 is configured to move the vertical magnetic field generator 61 and the horizontal magnetic field generator 62 in a direction of the axis X of the bed 60a. Concretely, the movable base 65 includes a drive unit 65a and mounts the movable base 64 on which the rotary table 63 is mounted. The drive unit 64a moves the movable base 65 along a pair of rails 66a, 66b provided on the bottom face of the bed 60a, that is, in the direction of the axis X of the base 60a.

Such movable bases 64, 65 move the vertical magnetic field generator 61 and the horizontal magnetic field generator 62 on the rotary table 63 to a desired position of the subject placement unit of the bed 60a, that is, a desired position on the coordinates on the rectangular coordinate system XY of the longitudinal axis (axis Y) and the widthwise axis (axis X) of the bed 60a. Further, the rotary table 63 rotates the vertical magnetic field generator 61 and the horizontal magnetic field generator 62 at the desired position on the rectangular coordinate system XY under a condition in which a plane of the rectangular coordinate system XY and the coil axis of the vertical magnetic field generator 61 are orthogonal.

The workstation 70 has the substantially same function as the workstation 40 in the third embodiment and further includes an operating function of the capsule guidance device 60. Concretely, the workstation 70 is electrically connected to the capsule guidance device 60 via a cable and controls drives of the above described vertical magnetic field generator 61, horizontal magnetic field generator 62, and drive units 63a, 64a, 65a.

Figure 23:
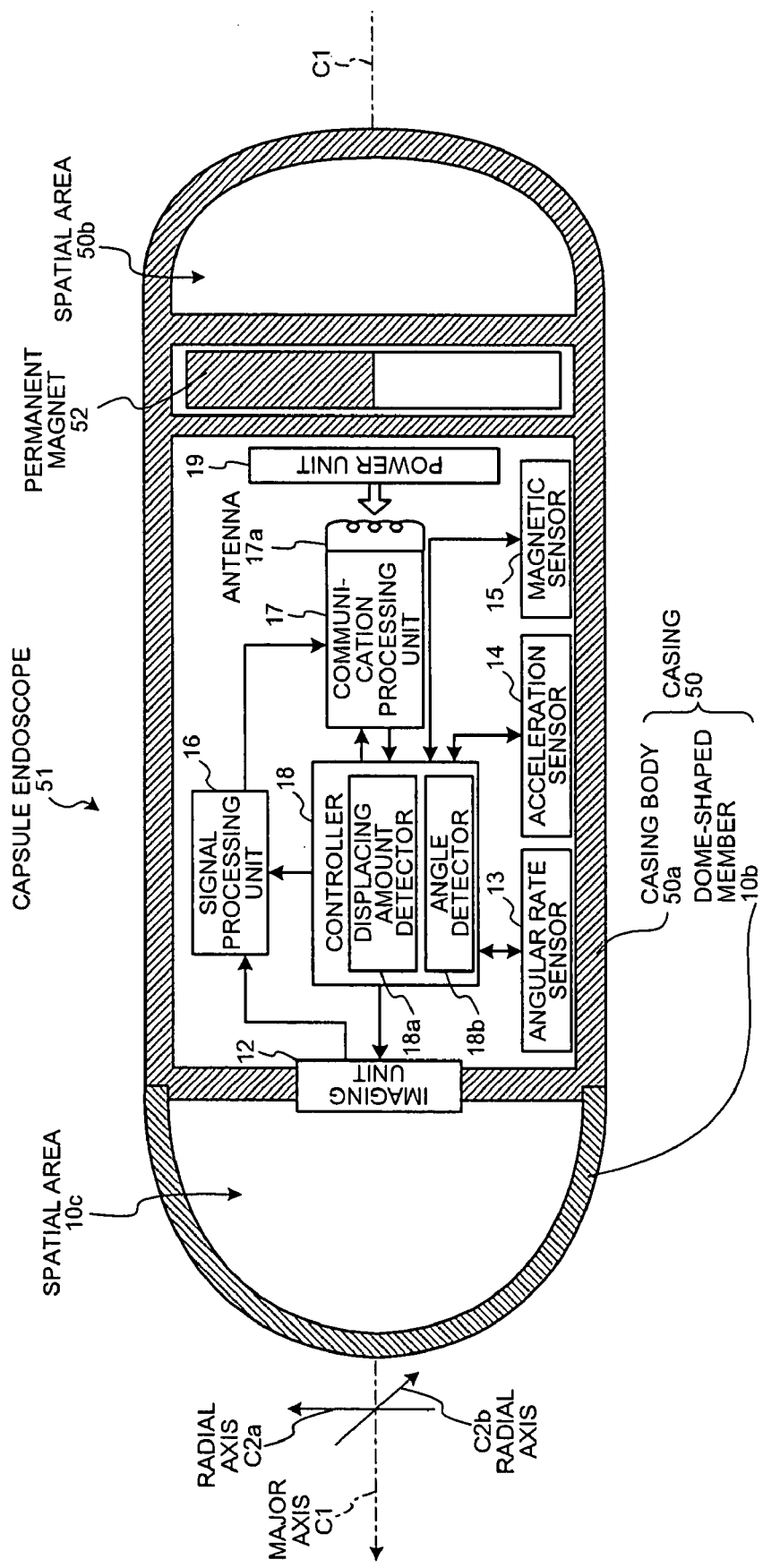
FIG. 23 is a schematic view showing a configuration example of the body-insertable device according to the fourth embodiment of the present invention.

Next, a structure of the capsule endoscope 51 according to the fourth embodiment of the present invention will be described. FIG. 23 is a schematic view showing a configuration example of the body-insertable device according to the fourth embodiment of the present invention. As shown in FIG. 23, the capsule endoscope 51, as an example of the body-insertable device includes a casing 50, in place of the casing 10 of the capsule endoscope 1, and a permanent magnet 52, in place of the permanent magnet 11. The casing 50 includes a casing body 50a, in place of the casing body 10a of the casing 10. Other elements are the same as those in the first embodiment and the same elements are represented by the same reference numbers.

The casing 50 is a capsule-shaped member formed in a size easily insertable into the subject 100 and provided with a dome-shaped member 10b attached to a front-end part of the casing body 50a. The casing body 50a accommodates each element of the capsule endoscope 51. In this case, an imaging unit 12 is fixed in the front-end part of the casing body 50a, similarly to the capsule endoscope 1. Further, a spatial area 50d is formed in the rear-end part of the casing body 50a. The casing 50 provided with the casing body 50a and the dome-shaped member 10b has specific gravity equal to or smaller than that of the liquid 2a and the center of gravity is placed near a center portion.

The permanent magnet 52 functions as a driver for driving the casing 50 with a magnetic force of a magnetic field generated outside. Concretely, the permanent magnet 52 magnetizes in a radial direction of the casing 50 (for example, the direction of the radial axis C2a) and, when the vertical magnetic field generator 61 and the horizontal magnetic field generator 62 generate magnetic fields toward the permanent magnet 52, the permanent magnet 52 moves or wobbles the casing 50 in the liquid 2a with the magnetic forces applied by the magnetic fields. With this, the permanent magnet 52 can change at least one of the position and posture of the capsule endoscope 51 in the liquid 2a with the magnetic force.

Figure 24:
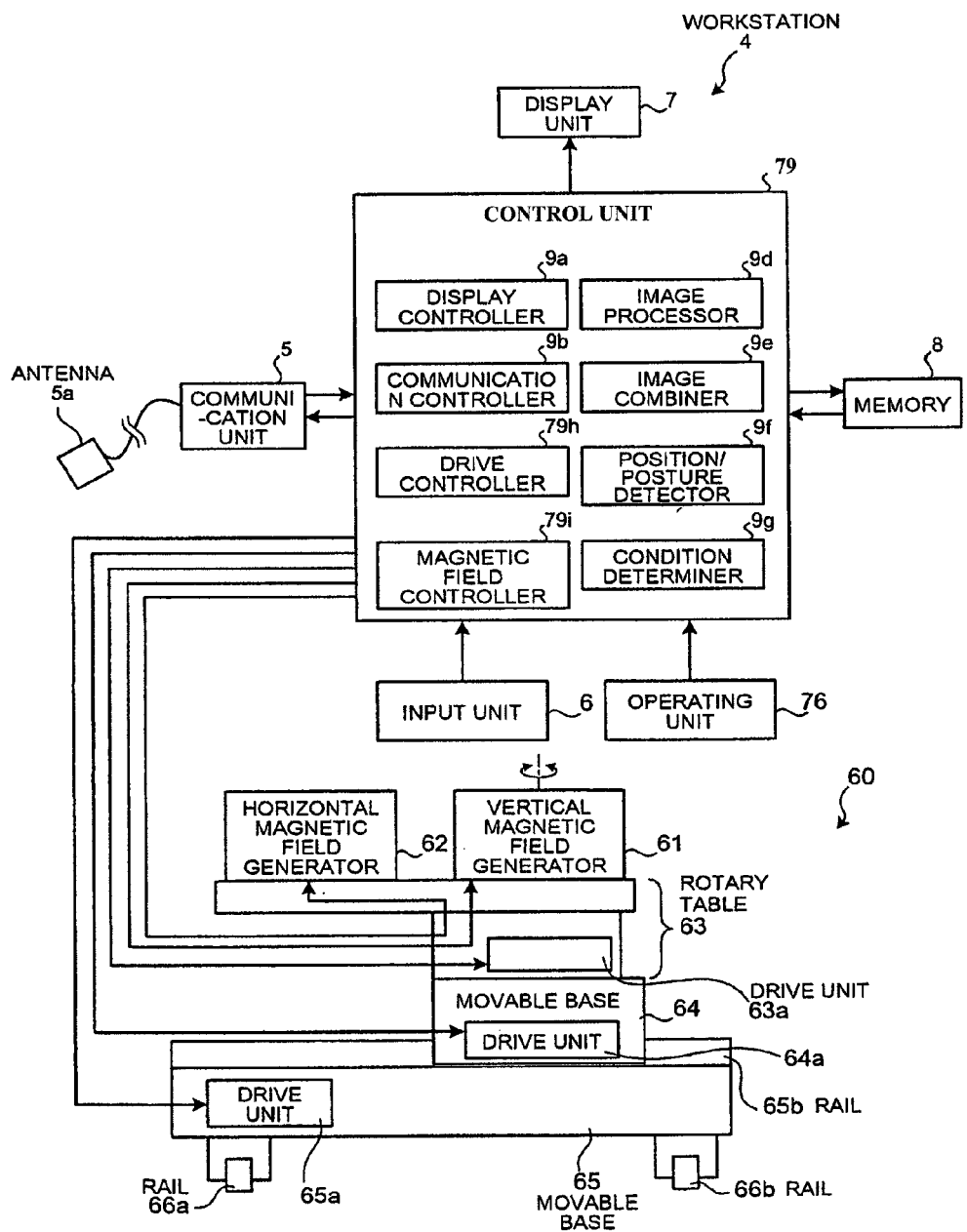
FIG. 24 is a block diagram schematically showing a configuration example of a workstation according to the fourth embodiment.

Next, a structure of the workstation 70 will be described. FIG. 24 is a block diagram schematically showing a configuration example of the workstation 70. As shown in FIG. 24, the workstation 70 includes a control unit 79, in place of the control unit 49 of the workstation 40 in the third embodiment and, further, the operating unit 76 for operating the capsule guidance device 60. The control unit 79 includes a magnetic field controller 79i, in place of the magnetic field controller 49c of the control unit 49 and, further, a drive controller 79h for controlling the drive of the capsule guidance device 60. In this case, the control unit 79 is electrically connected to the capsule guidance device 60 via a cable or the like. Other elements are the same as those of the third embodiment and the same elements are represented by the same reference numbers.

The operating unit 76 is for controlling the capsule guidance device 60. Concretely, the operating unit 76 includes an operating lever for operating the drive of each drive units 63a, 64a, 65a of the capsule guidance device 60 and an adjusting switch for adjusting each magnetic field strength of the vertical magnetic field generator 61 and the horizontal magnetic field generator 62. The operating unit 76 inputs instruction information for instructing a drive of the capsule guidance device 60 into the control unit 79.

The control unit 79 has the substantially same function as the control unit 49 of the workstation 40 and controls the drive of the capsule guidance device 60. Such controller 79 further includes the magnetic field controller 79i for controlling each magnetic field strength of the vertical magnetic field generator 61 and the horizontal magnetic field generator 62 and the drive controller 79h for controlling each drive of the drive units 63a, 64a, and 65a.

The drive controller 79h controls each drive of the drive units 63a, 64a, 65a based on instruction information input from the operating unit 76 by the examiner's operation. In this case, the drive controller 79h rotates the horizontal magnetic field generator 62 around the vertical magnetic field generator 61 by controlling the drive of the drive unit 63a, as described above. Further, the drive controller 79h controls the drive of the drive unit 64a to move the movable base 64 along the rail 65b and controls the drive of the drive unit 65a to move the movable base 65 along the pair of the rails 66a, 66b.

Similarly to the above described magnetic field controller 49c of the control unit 49, the magnetic field controller 79i controls drive power supplied to the vertical magnetic field generator 61 and the horizontal magnetic field generator 62 based on the determination result of the condition determiner 9g or the position/posture information of the capsule endoscope 51 to control each magnetic field strengths of the vertical magnetic field generator 61 and the horizontal magnetic field generator 62. Or, the magnetic field controller 79i controls each magnetic field strength of the vertical magnetic field generator 61 and the horizontal magnetic field generator 62 based on the patient information of the subject 100 input by the input unit 6 or the instruction information input by the operating unit 76.

Figure 25:
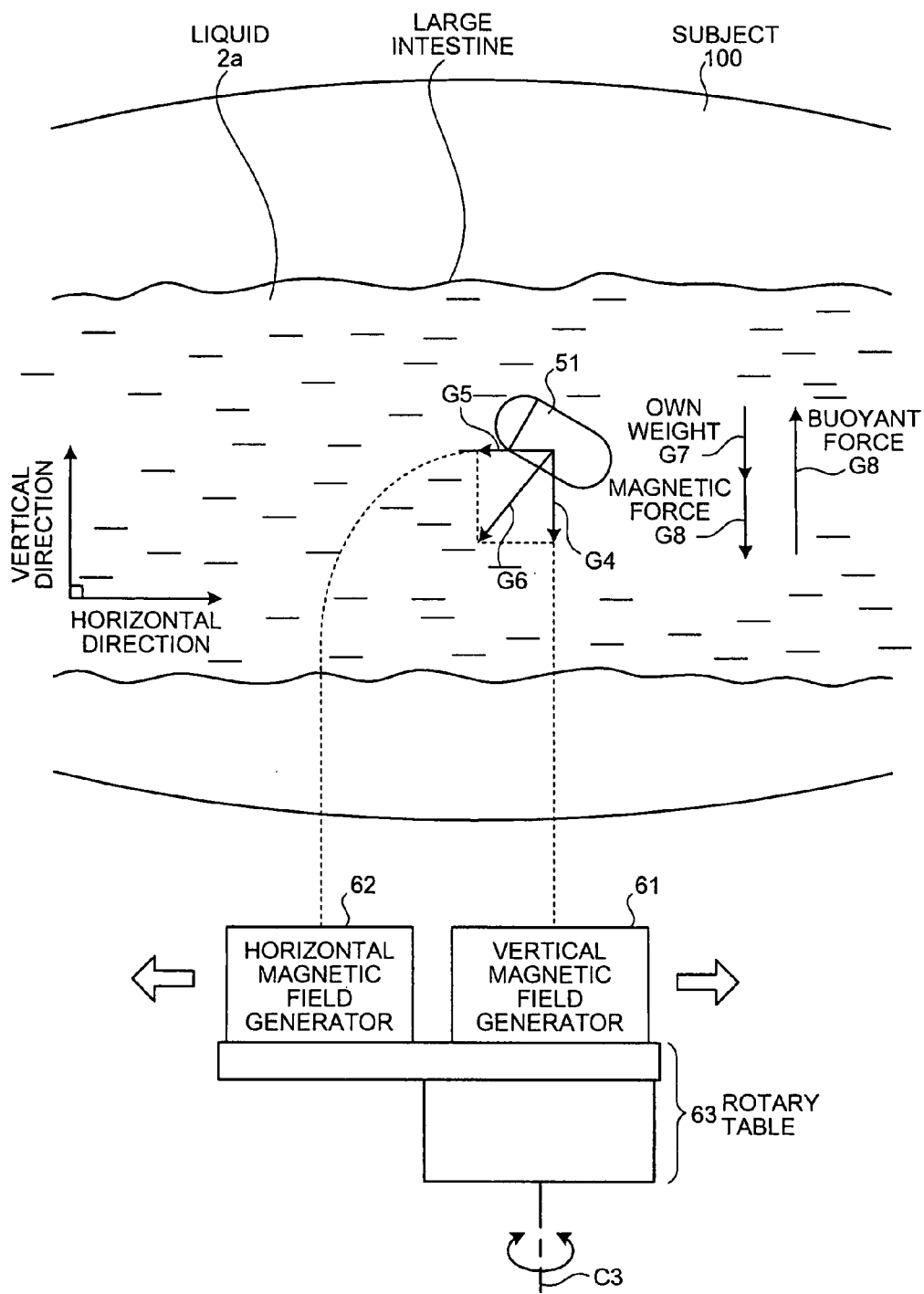
FIG. 25 is a schematic view showing an operation of a control unit for controlling a drive of the body-insertable device according to the fourth embodiment.

Such a controller 79 can control the position and posture of the capsule endoscope 51 in the liquid 2a introduced into the digestive canal of the subject 100 by controlling the drive of the capsule guidance device 60. FIG. 25 is a schematic view showing an operation of the control unit 79 for controlling the drive of the capsule guidance device 60. Hereinafter, an example of introducing the capsule endoscope 51 and the liquid 2a into the large intestine of the subject 100 will be described.

Firstly, the control unit 79 moves the vertical magnetic field generator 61 and the horizontal magnetic field generator 62 to the position where magnetic force can be applied to the capsule endoscope 51 in the liquid 2a introduced in the large intestine of the subject 100. In this case, the drive controller 79h controls the drives of the drive units 63a, 64a, 65a based on the instruction information from the operating unit 76 or the position/posture information of the capsule endoscope 51 and moves the vertical magnetic field generator 61 and the horizontal magnetic field generator 62 to the position where the capsule endoscope 51 can be captured by the magnetic forces.

Next, the control unit 79 controls the drives of the vertical magnetic field generator 61 and the horizontal magnetic field generator 62 so as to capture the capsule endoscope 51 by the magnetic forces. In this case, the magnetic field controller 79i controls the drive power supplied to the vertical magnetic field generator 61 and the horizontal magnetic field generator 62 as described above to control the magnetic field strength of the vertical magnetic field generator 61 and the horizontal magnetic field generator 62. Under the control of the magnetic field controller 79i, the vertical magnetic field generator 61 and the horizontal magnetic field generator 62 respectively generate a magnetic field in a substantially vertical direction and a magnetic field in a substantially horizontal direction toward the capsule endoscope 51. In this case, the capsule endoscope 51 is captured by the magnetic forces applied by the vertical magnetic field generator 61 and the horizontal magnetic field generator 62.

Here, the capsule endoscope 51 captured by the magnetic forces of the vertical magnetic field generator 61 and the horizontal magnetic field generator 62 is, for example, as shown in FIG. 25, applied with the magnetic force G4 of the vertical magnetic field and the magnetic force G5 of the horizontal magnetic field. In this case, the combined magnetic force G6 of the combined magnetic field with the vertical magnetic field and the horizontal magnetic field is applied to the capsule endoscope 51 and the position and posture of the capsule endoscope 51 in the liquid 2a is controlled based on the combined magnetic force G6. The control unit 79 can change the posture of the capsule endoscope 51 by controlling the drive of the rotation of the rotary table 63 about the coil axis C3 of the vertical magnetic field generator 61 and changing the vector direction of the magnetic force 5 (that is, the vector direction of the combined magnetic force 6). Further, the control unit 79 can change the position of the capsule endoscope 51 by controlling the drive of the movable bases 64, 65 and changing the position of the magnetic forces G4, G5 (that is, the position of the combined magnetic force G6).

Figure 26:
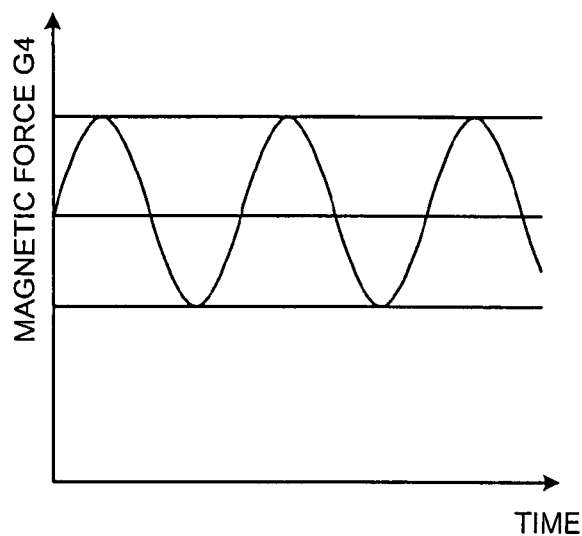
FIG. 26 is a schematic view showing a strength change of a vertical magnetic field controlled by the magnetic field controller.

Further, the control unit 79 can control the vertical position of the capsule endoscope 51 in the liquid 2a by controlling the magnetic field strength of the vertical magnetic field generator 61. Concretely, the magnetic field controller 79i, for example, as shown in FIG. 26, controls to increase or decrease the magnetic field strength of the vertical magnetic field generator 61 at a predetermined cycle to increase and decrease the vertical magnetic force G4 applied to the capsule endoscope 51 at a predetermined cycle. When the buoyant force G8 is greater than the sum of the weight G7 and the magnetic force G4, the capsule endoscope 51 moves upward in the liquid 2a. When the buoyant force G8 is smaller than the sum of the weight G7 and the magnetic force G4, the capsule endoscope 51 moves downward in the liquid 2a. And, when the buoyant force G8 is substantially equal to the sum of the weight G7 and the magnetic force G4, the capsule endoscope 51 stays in the liquid 2a.

Therefore, the magnetic field controller 79i can control the vertical position of the capsule endoscope 51 in the liquid 2a, similarly to the case of the third embodiment and keep the capsule endoscope 51 at a desired position in a vertical direction by controlling the magnetic field strength of the vertical magnetic field generator 61, that is, the magnetic force G4 based on the position/posture information of the capsule endoscope 51. Further, the magnetic field controller 79i may control increase or decrease of the magnetic force G4 based on the instruction information or the like from the operating unit 76 to control the vertical position of the capsule endoscope 51 in the liquid 2a.

Further, the control unit 79 can control the reciprocating movement of the capsule endoscope 51 that repeatedly and reciprocatingly changes the direction of the major axis C1 in the liquid 2a at a predetermined cycle by repeatedly and reciprocatingly changing the direction of the magnetic field strength and the magnetic field direction of the vertical magnetic field generator 61 and the horizontal magnetic field generator 62 at a predetermined cycle based on the instruction information from the input unit 6 or the operating unit 76. In this case, the capsule endoscope 51 in the liquid 2a automatically repeat reciprocating movements of the predetermined position of the casing 50 as the rotation center based on the control of the control unit 79 to repeatedly and reciprocatingly change the direction and the position of the imaging field of the subject 100. With the reciprocating movement, the capsule endoscope 51 can easily take images of a wide area (wide angle) in the digestive canal. Desirably, the control unit 79 controls the reciprocating movement of the capsule endoscope 51 corresponding to imaging timing of the imaging unit 12. With this, the control unit 79 can prevent a wobbling of the image when the capsule endoscope 51 is moved reciprocatingly.

Figure 27:
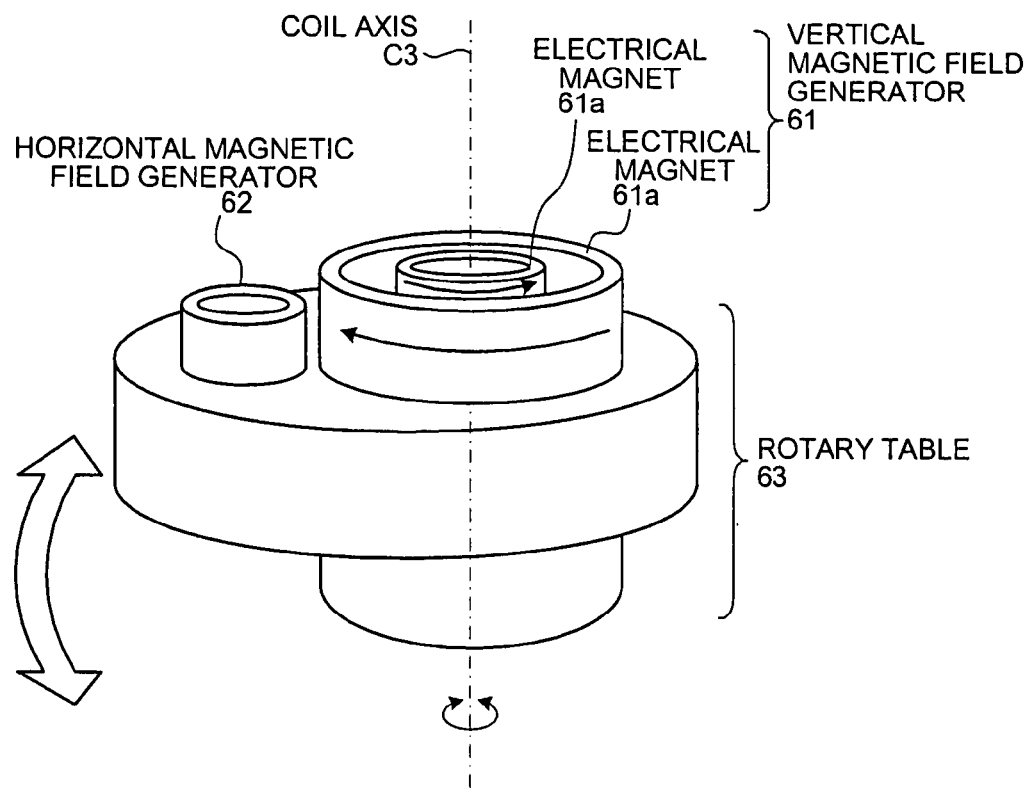
FIG. 27 is a schematic view showing a configuration example of a vertical magnetic field generator and a horizontal magnetic field generator according to the fourth embodiment.

The vertical magnetic field generator 61 and the horizontal magnetic field generator 62 are realized by using a desired number of electromagnet. In this case, desirably, the vertical magnetic field generator 61, for example, as shown in FIG. 27, is configured to include two electromagnet 61a, 61b in a concentric fashion and drive current is applied to the electromagnet 61a, 61b in different directions. With this structure, the vertical magnetic field generator 61 can generate a magnetic field in a reverse direction outside the magnetic field generated by the electrical magnet 61a so that a magnetic gradient toward the coil axis C3 from the outside can be increased. The vertical magnetic field generator 61 can easily capture the capsule endoscope 51 in the liquid 2a introduced in the large intestine of the subject 100, for example, by generating such magnetic fields. This helps to improve controllability of the position and posture of the capsule endoscope 51.

On the other hand, desirably the capsule endoscope 51 has specific gravity which is equal to or smaller than that of the liquid 2a introduced into the subject 100, and, more desirably, has specific gravity which is greater than the half of the specific gravity of the liquid 2a. The reason is as follows. That is, when the specific gravity of the capsule endoscope 51 is smaller than the half of that of the liquid 2a, the difference between the buoyant force generated on the capsule endoscope 51 in the liquid 2a and the weight of the capsule endoscope 51 becomes larger than the weight. In this case, the magnetic force necessary for the operation control of the capsule endoscope 51 (that is, the magnetic force applied to each of the vertical magnetic field generator 61 and the horizontal magnetic field generator 62) is larger than the magnetic force necessary for the operation control of the capsule endoscope 51 arranged outside the liquid 2a, or in the air for example. Accordingly, it is necessary to increase the magnetic force necessary for the operation control of the capsule endoscope 51, and it becomes difficult to realize the downsizing or electrical power saving of the vertical magnetic field generator 61 and the horizontal magnetic field generator 62. That is, when the specific gravity of the capsule endoscope 51 is set greater than the half of the specific gravity of the liquid 2 specific gravity, the downsizing and electrical power saving of the vertical magnetic field generator 61 and the horizontal magnetic field generator 62 can be enhanced.

Further, the capsule endoscope 51 includes the permanent magnet 52 magnetized in a radial direction of the casing 50; however, the capsule endoscope 51 may include a permanent magnet magnetized in the direction of major axis C1, similarly to the capsule endoscope 1 of the first embodiment. The capsule endoscope 51 having such a structure can restrict the vector direction of the major axis C1 by the horizontal magnetic field, that is, the magnetic force applied in a horizontal direction. With this structure, the posture control of the capsule endoscope 51 by the capsule guidance device 60 becomes more secure and the posture controllability for the capsule endoscope 51 in liquid 2a is improved.

Figure 28:
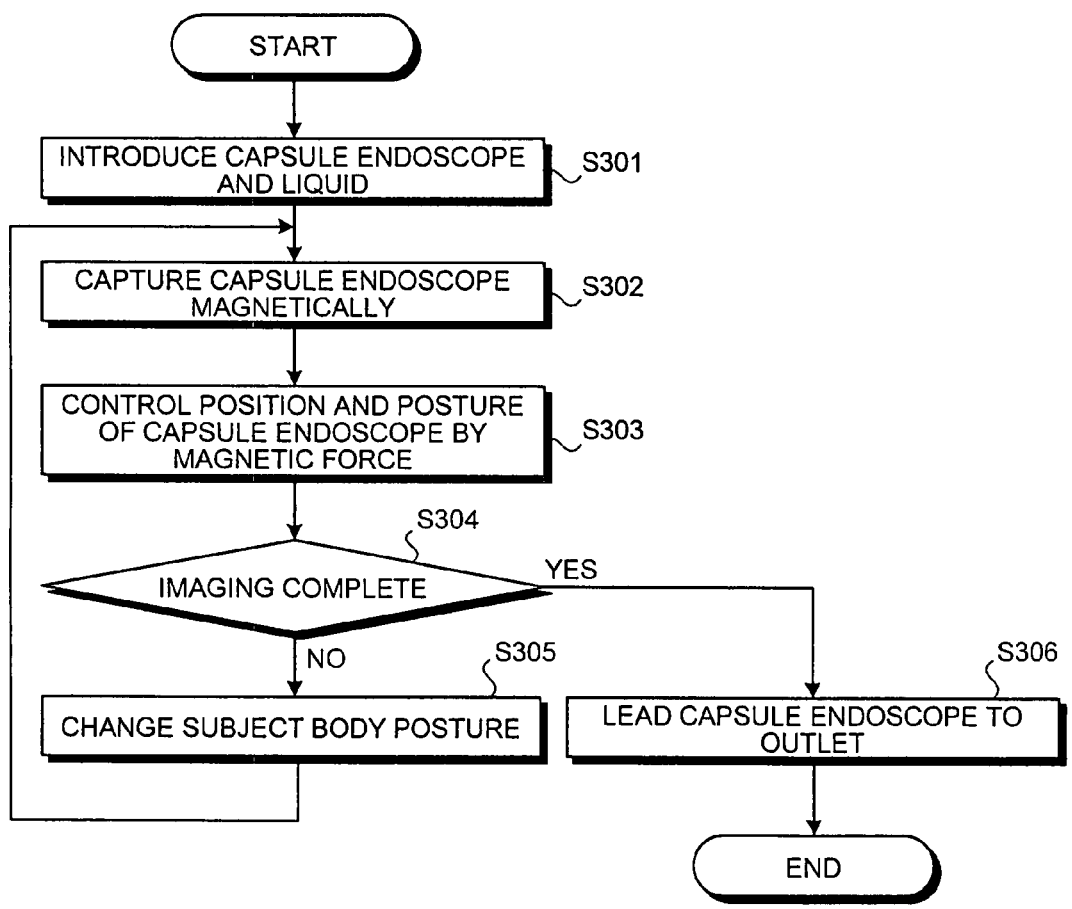
FIG. 28 is a flow chart showing a procedure of observing an inside of digestive canal of a subject with an image inside the digestive canal by the body-insertable device according to the fourth embodiment.

Next, a procedure of observing the digestive canal of the subject 100 (for example, the large intestine) with an image taken by the capsule endoscope 51 will be described. FIG. 28 is a flow chart showing a procedure of observing the digestive canal of the subject 100 with an image of digestive canal taken by the capsule endoscope 51 introduced into subject 100.

In FIG. 28, firstly, the examiner starts an imaging operation of the capsule endoscope 51 by using the workstation 70 or a predetermined starter and introduces liquid 2a into the subject 100 by using a feeder 2 (step S301). In this case, the capsule endoscope 51 and the liquid 2a are swallowed, for example, through the mouth of the subject 100, and then reaches to a desired digestive canal (for example, the large intestine) of the subject 100. The examiner displays the image taken by the capsule endoscope 51 on the workstation 70 and finds the position of the capsule endoscope 51 in the subject 100 by seeing the image. After introducing the capsule endoscope 51 into the subject 100, the examiner may operate the workstation 70 to start imaging operation of the capsule endoscope 51. Further, the capsule endoscope 51 and the liquid 2a may be introduced into the subject 100 through the transanal route. For example, when observing only the large intestine, introduction of the capsule endoscope 51 and the liquid 2a through the transanal route can reduce the time that the capsule endoscope 51 and the liquid 2 reach to the large intestine so that inspection time can be shortened.

Here, when the capsule endoscope 51 and the liquid 2a introduced into the subject 100 reach to, for example, a digestive canal of thin pipes such as the large intestine, the liquid 2a expands the digestive canal. Accordingly, the capsule endoscope 51 in the liquid 2a can ensure an imaging field of the digestive canal because of the effect of the liquid 2a and take images of the expanded digestive canal.

Next, the examiner operates the operating unit 76 of the workstation 70 to magnetically capture the capsule endoscope 51 in the digestive canal (step S302). In this case, the controller 79 controls the drive of the capsule guidance device 60 based on the instruction information input from, for example, the operating unit 76 according to the examiner's operation. The capsule guidance device 60 magnetically captures the capsule endoscope 51 according to the control of the control unit 79. Concretely, the vertical magnetic field generator 61 and the horizontal magnetic field generator 62 move close to the capsule endoscope 51 in the digestive canal by the drives of the rotary table 63 and the movable bases 64, 65 and generate magnetic fields in vertical and horizontal direction toward the capsule endoscope 51. The capsule endoscope 51 is captured by the magnetic forces of the magnetic fields, as described above.

When capturing the capsule endoscope 51 with the magnetic forces in this way, the examiner operates the operating unit 76 to drive the capsule guidance device 60 and control the position and posture of the capsule endoscope 51 (step S303). In this case, magnetic forces in vertical and horizontal direction are applied to the capsule endoscope 51 in the liquid 2a in the digestive canal and the capsule endoscope 51 wobbles and moves vertically in the liquid with the effect of the vertical and horizontal magnetic forces. Further, the capsule endoscope 51 horizontally moves in the digestive canal by the drive of the capsule guidance device 60. As described above, the capsule guidance device 60 changes at least one of the position and posture of the capsule endoscope 51 in a desired digestive canal as an observed region according to the control of the control unit 79. In this case, the capsule endoscope 51 sequentially take images in the digestive canal that is expanded by the liquid 2a while changing the direction of the imaging field in the digestive canal with the movement of the casing 50.

Next, when the imaging operation is continued to take images of other parts in the digestive canal (step S304, No), the examiner changes the current body posture (for example, a supine position) of the subject 100 to another desired body posture (for example, left supine position) (step S305), and then, repeats the above described procedure subsequent to step S302. In this case, the examiner operates the operating unit 76 or the like to drive the capsule guidance device 60 and controls the position and posture of the capsule endoscope 51 in the digestive canal to a desired position while referring to the image in the digestive canal shown on the workstation 70.

By repeating the procedures in step S302 to S305, the capsule endoscope 51 can sequentially take images as moving with the liquid 2a through, for example, the ascending colon, transverse colon, and descending colon in the large intestine to the anus so that substantially whole area in the digestive canal (for example, the large intestine) can be taken. The examiner can observe every part in the desired digestive canal as an observed region of the subject 100 by displaying the images taken by the capsule endoscope 51 on the workstation 70.

Then, when the observation of the digestive canal as an observed region is completed and the imaging the digestive canal is to be completed (step S304, Yes), the examiner operates the operating unit 76 or the like to drive the capsule guidance device 60 to lead the capsule endoscope 51 toward the outlet port of the digestive canal (step S306), and the imaging in the large intestine is completed.

When moving into another digestive canal, the capsule endoscope 1 take images in the digestive canal while moving in the subject 100 by the peristalsis of the following digestive canals, flow of the liquid 2a, or the magnetic force of the capsule guidance device 60 and discharged to the outside.

Figure 29:
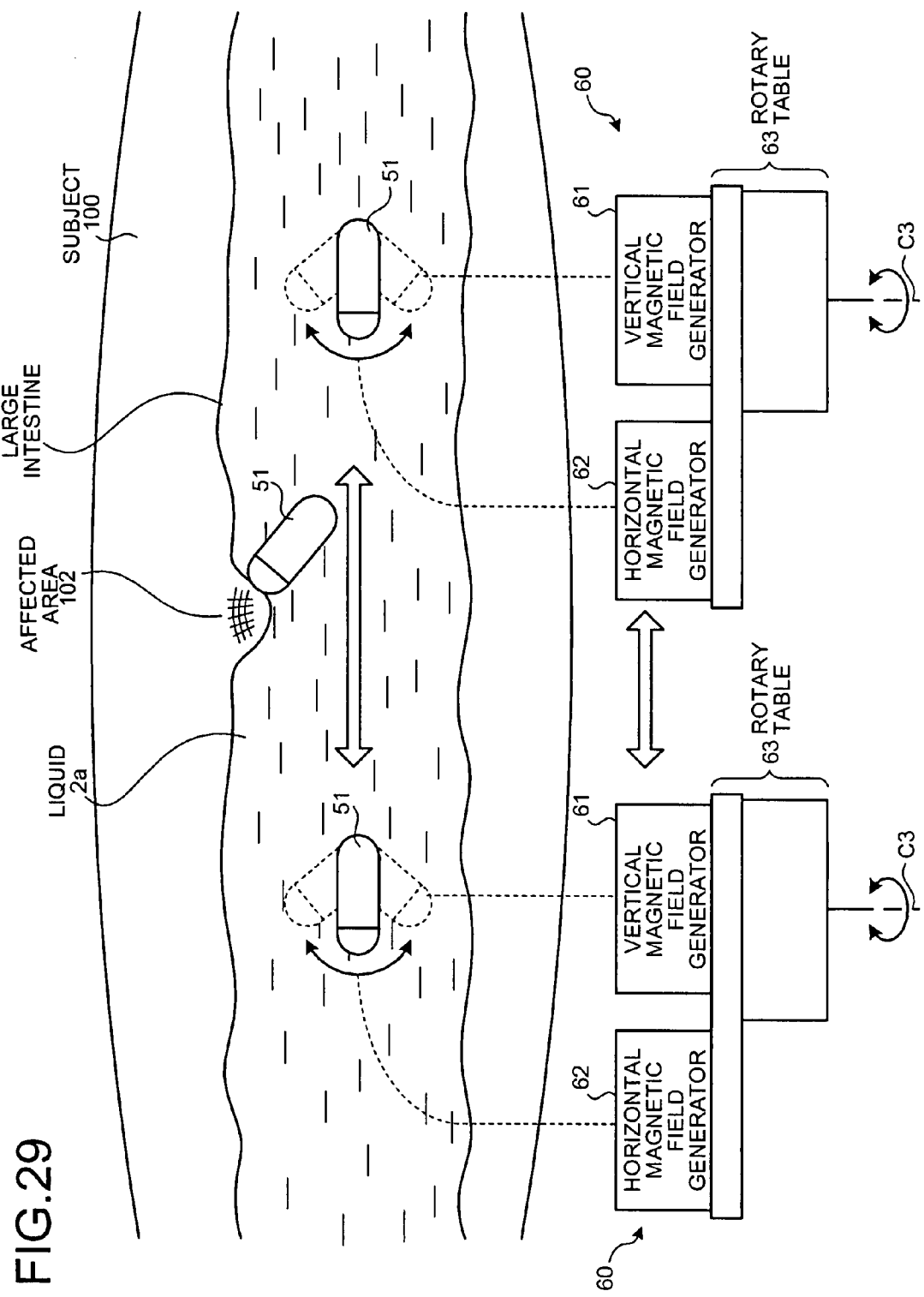
FIG. 29 is a schematic view showing an operation of a capsule guidance device for controlling a position and a posture of the body-insertable device according to the fourth embodiment.

Next, an operation for controlling the position and posture of the capsule endoscope 51 introduced into the large intestine as an observed region will be described in detail with an example of observing the large intestine of the subject 100. FIG. 29 is a schematic view showing an operation of the capsule guidance device 60 for controlling the position and posture of the capsule endoscope 51 introduced in the subject.

As shown in FIG. 29, the capsule guidance device 60 moves the vertical magnetic field generator 61 and the horizontal magnetic field generator 62 close to the capsule endoscope 51 in the large intestine of the subject 100 to magnetically capture the capsule endoscope 51 in the liquid 2a, according to the control of the control unit 79. In this case, the vertical magnetic field generator 61 applies a vertical magnetic force to the capsule endoscope 51 and the horizontal magnetic field generator 62 applies a horizontal magnetic force to the capsule endoscope 51.

Next, the capsule guidance device 60 adjusts each magnetic field strength of the vertical magnetic field generator 61 and the horizontal magnetic field generator 62, the rotation position of the horizontal magnetic field generator 62 changed by the rotation drive of the rotary table 63 (that is, the position around the vertical magnetic field generator 61), and the positions of the vertical magnetic field generator 61 and the horizontal magnetic field generator 62 changed by the drives of the movable bases 64, 65 (that is, the positions on the rectangular coordinate system XY), according to the control of the control unit 79, and controls the position and posture of the capsule endoscope 51 in the large intestine.

According to the control of the capsule guidance device 60, the capsule endoscope 51 in the large intestine stays or moves vertically or horizontally. Further, the capsule endoscope 51 in the large intestine wobbles in the liquid 2a or moves reciprocatingly at a predetermined cycle. The capsule guidance device 60 changes the position and posture of the capsule endoscope 51 in the liquid 2a in the large intestine to desired position and posture and sequentially changes the position or direction of the imaging field in the large intestine. With this, the capsule endoscope 51 can take substantially whole area in the large intestine which is expanded by the liquid 2a.

Further, when the examiner finds an affected area 102, for example, in the large intestine through the images displayed on the workstation 70 and operates the operating unit 76 with reference to the image of the affected area 102, the control unit 79 controls the drive of the capsule guidance device 60 based on the instruction information input from the operating unit 76. The capsule guidance device 60 leads the capsule endoscope 51 in the liquid 2a according to the control of the control unit 79 to move the capsule endoscope 51 close to the affected area 102 in the large intestine. With this, the capsule endoscope 51 can take an enlarged image of the affected area 102.

Further, when a desired position on the coordinates in the image displayed on the display unit 7, for example, information specifying the position on the coordinates of the affected area 102 in the image, is input from the input unit 6, the control unit 79 can move the capsule endoscope 51, for example, close to the affected area 102 by controlling the drive of the capsule guidance device 60 based on the specifying information of the position on the coordinates and the position/posture information of the capsule endoscope 51. In this case, the capsule guidance device 60 can control the position and posture of the capsule endoscope 51 in the liquid 2a based on the control of the control unit 79 to automatically move the capsule endoscope 51 close to the affected area 102 in the large intestine.

As described above, in the fourth embodiment of the present invention, an imaging unit for imaging the subject is fixed inside the casing and a permanent magnet magnetized in a predetermined direction toward the casing is disposed in the casing, a permanent magnet moves the casing corresponding to the combined magnetic field, so that at least one of the position on the coordinates and a vector direction of the casing in a predetermined liquid introduced into a digestive canal of a subject can be changed. Accordingly, similarly to the third embodiment, the casing can be kept in a liquid in the subject and at least one of the positions on the coordinates and vector direction of the casing can be changed. With this, the same effect as the third embodiment can be provided and a preferred body-insertable device capable of easily changing the position and direction of an imaging field in the digestive canal in liquid introduced into the digestive canal such as small intestine or the large intestine with thin pipes and taking images in such digestive canal with thin pipes can be realized.

Further, a plurality of electromagnet for generating vertical and horizontal magnetic field towards the body-insertable device are employed to control the position and posture of the body-insertable device by applying magnetic force of the combined magnetic field toward the body-insertable device in the predetermined liquid introduced in a digestive canal of the subject. Accordingly, the position and posture of the body-insertable device can be actively changed in a liquid introduced in the digestive canal of thin pipes such as the small intestine and the large intestine so as to change the position and direction of the imaging field in the digestive canal. Thus, a body-insertable device system capable of observing every part in the digestive canal of thin pipes in a short period of time can be realized. Further, a buoyant force of the liquid introduced in the subject works on the body-insertable device (for example, the capsule endoscope 51) so that the gravity generated on the body-insertable device is reduced or canceled as much as the amount of the buoyant force. Accordingly, at least one of the position and posture of the body-insertable device can be easily changed and the drive unit (for example, a permanent magnet installed in the body-insertable device) for changing at least one of the position and posture of the body-insertable device can be downsized. As a result, the body-insertable device itself can be downsized so that the facility of introducing the body-insertable device into the subject can be improved.

First Modification of Fourth Embodiment

A first modification of a fourth embodiment of the present invention will be described. In the fourth embodiment, the single horizontal magnetic field generator 62 is rotated around the vertical magnetic field generator 61 to change the posture of the capsule endoscope 51. However, according to the first modification of the fourth embodiment, a body-insertable device system includes a plurality of horizontal magnetic field generators around the vertical magnetic field generator 61 and the posture of the capsule endoscope 51 is changed by switching the plurality of horizontal magnetic field generator for generating horizontal magnetic field.

Figure 30:
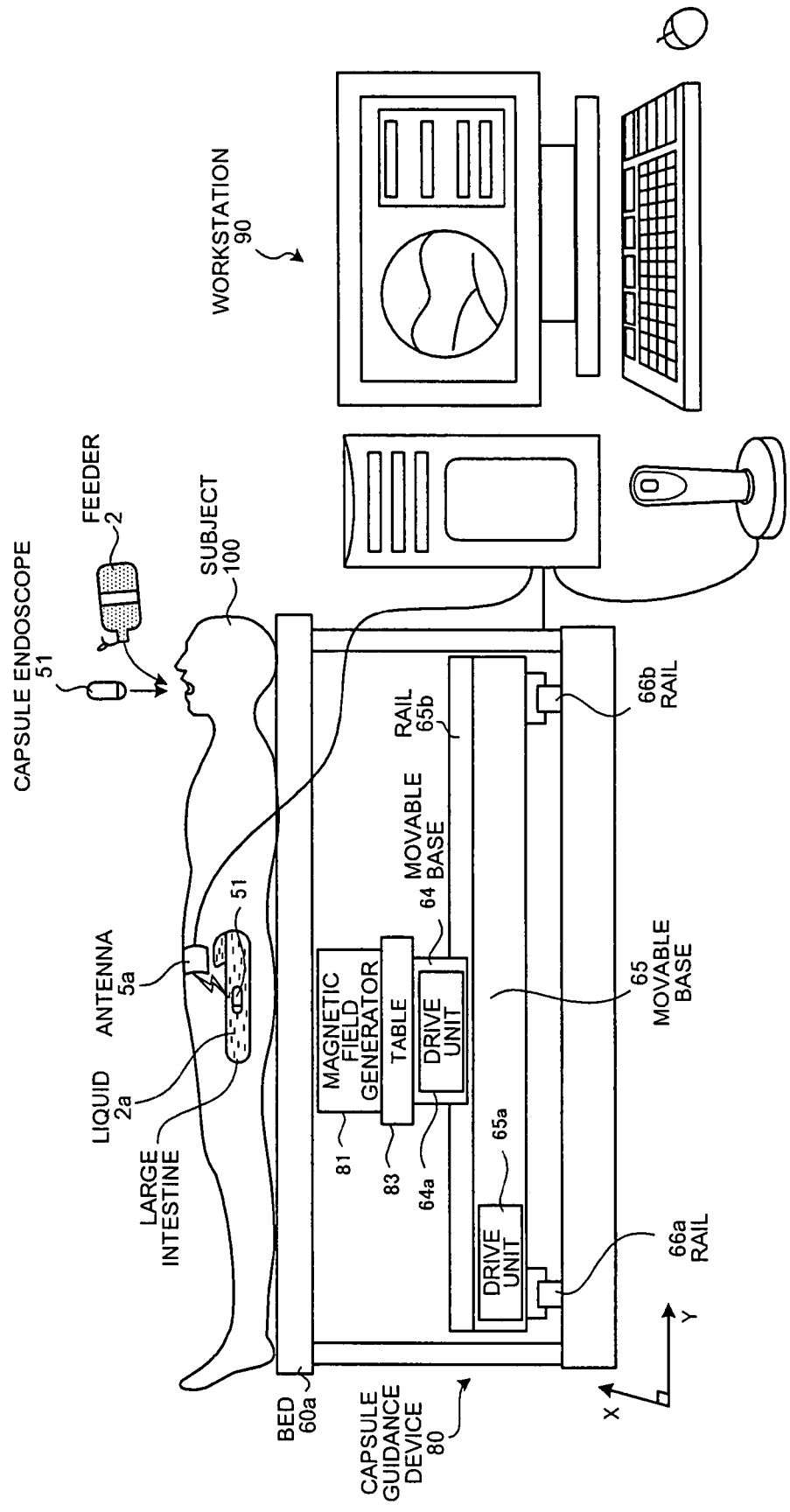
FIG. 30 is a schematic view showing a configuration example of a body-insertable device system according to a first modification of the fourth embodiment of the present invention.

FIG. 30 is a schematic view showing a configuration example of the body-insertable device system according to the first modification of the fourth embodiment of the present invention. As shown in FIG. 30, the body-insertable device system of the first modification of the fourth embodiment includes a capsule guidance device 80, in place of the capsule guidance device 60 of the body-insertable device system in the fourth embodiment and a workstation 90, in place of the workstation 70. The capsule guidance device 80 includes a magnetic field generator 81, in place of the vertical magnetic field generator 61 and the horizontal magnetic field generator 62 of the capsule guidance device 60 and a table 83, in place of the rotary table 63. Other elements are the same as the fourth embodiment and the same elements are represented by the same reference numbers.

The magnetic field generator 81 is mounted on the table 83 fixed to the movable base 64 and generates vertical and horizontal magnetic fields toward the capsule endoscope 51 in the subject 100. The magnetic field generator 81 has, for example, a vertical magnetic field generator at a central portion of the table 83 and a plurality of horizontal magnetic field generators around the vertical magnetic field generator.

The workstation 90 has the substantially same function as the workstation 70 in the fourth embodiment. The workstation 90 is electrically connected to the capsule guidance device 80 via a cable or the like and controls the capsule guidance device 80.

Figure 31:
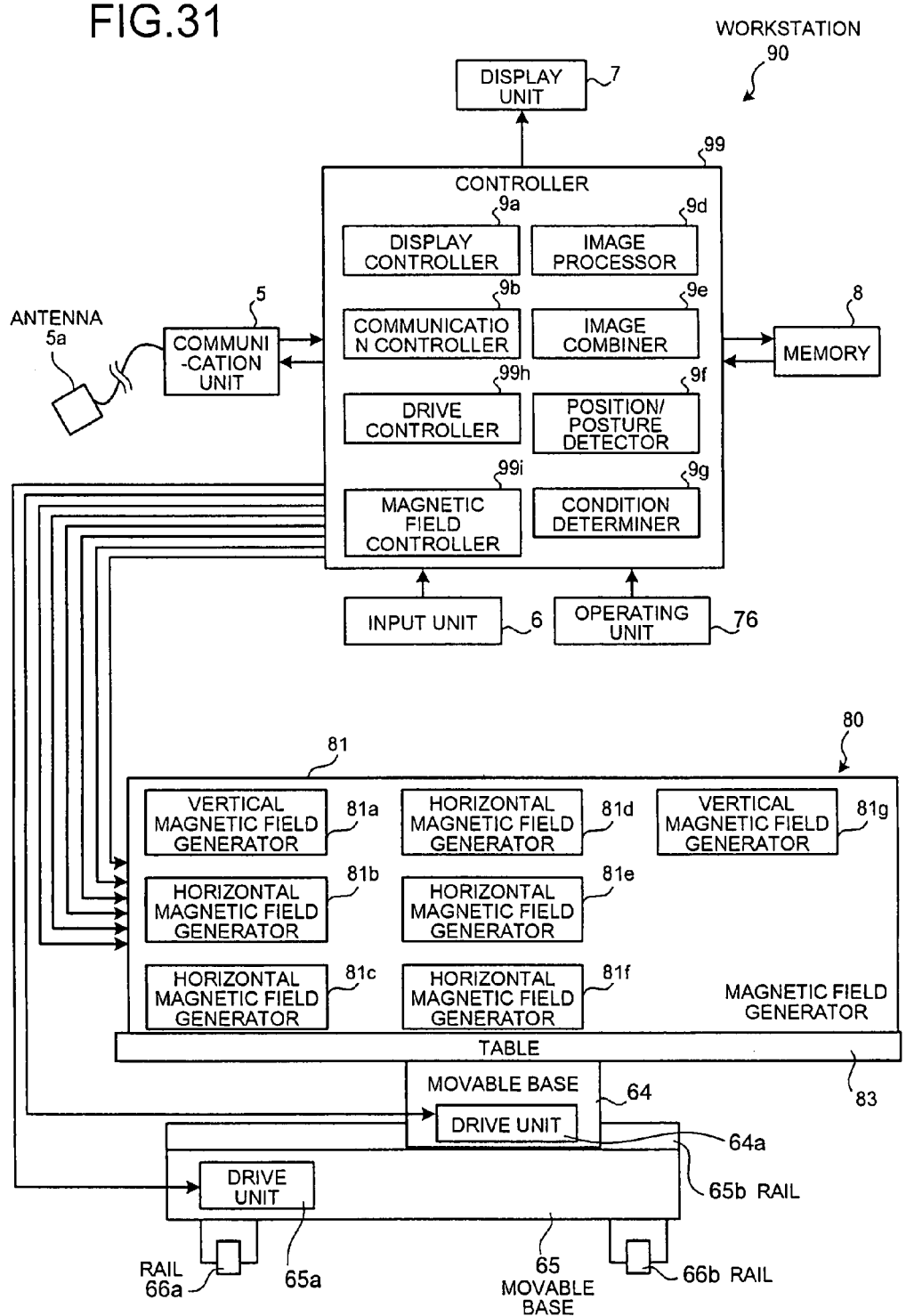
FIG. 31 is a block diagram schematically showing a configuration example of the capsule guidance device and a workstation according to the first modification of the fourth embodiment of the present invention.
Figure 32:
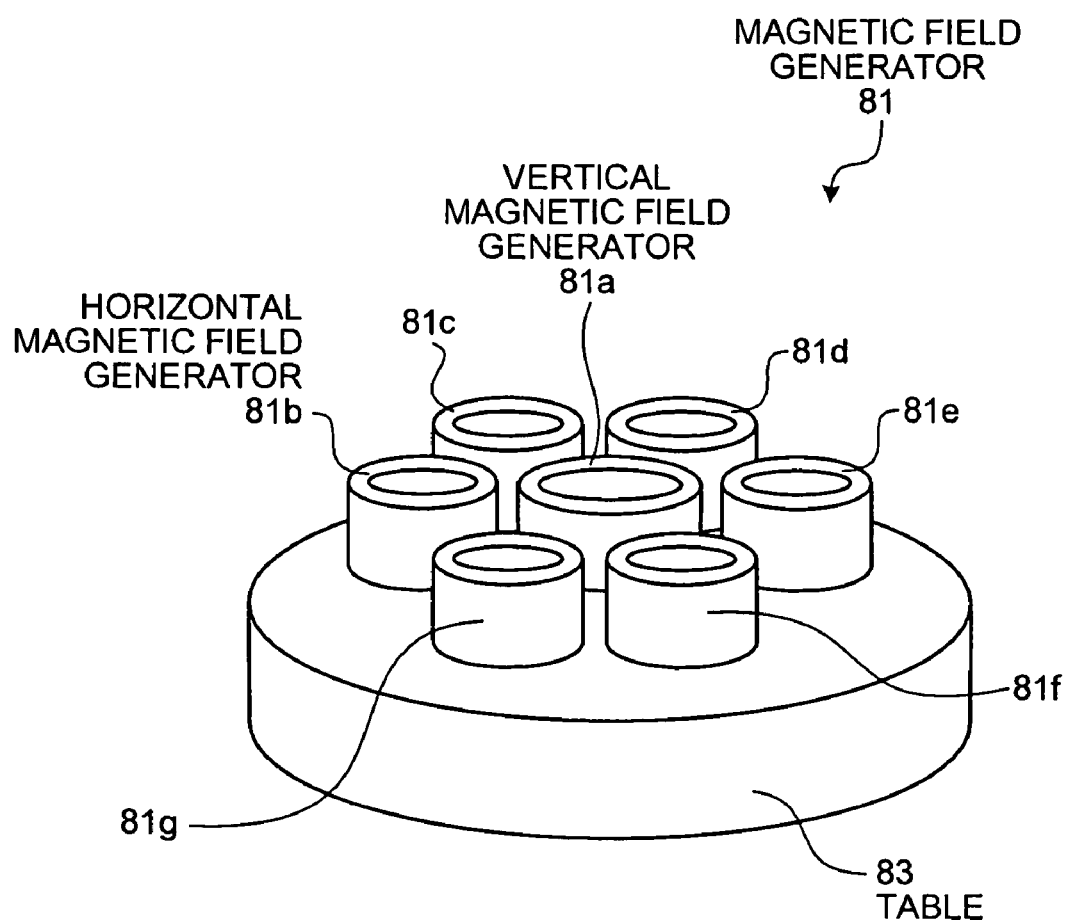
FIG. 32 is a schematic view showing a arrangement example of the vertical magnetic field generator and the horizontal magnetic field generator of the capsule guidance device according to the first modification of the fourth embodiment.

Next, each structure of the capsule guidance device 80 and the workstation 90 will be explained. FIG. 31 is a block diagram schematically showing a configuration example of the capsule guidance device 80 and the workstation 90. FIG. 32 is a schematic view showing an example of alignment of the vertical magnetic field generator and the horizontal magnetic field generators of the capsule guidance device 80.

As shown in FIG. 31, the magnetic field generator 81 of the capsule guidance device 80 includes a vertical magnetic field generator 81a and six horizontal magnetic field generators 81b to 81g. The vertical magnetic field generator 81a has similar function as the vertical magnetic field generator 61 of the capsule guidance device 60 and its drive is controlled by the control unit 99. The horizontal magnetic field generators 81b to 81g have similar function as the horizontal magnetic field generator 62 of the capsule guidance device 60 and their drives are controlled by the control unit 99.

The vertical magnetic field generator 81a and the horizontal magnetic field generators 81b to 81g are, for example, arranged on the table 83 as shown in FIG. 32. Concretely, the vertical magnetic field generator 81a is arranged at the substantially center of the table 83 and the horizontal magnetic field generators 81b to 81g are arranged around the vertical magnetic field generator 81a at substantially equal intervals. Here, the number of the horizontal magnetic field generators only has to be more than one and should not be limited to six.

On the other hand, the workstation 90 includes a control unit 99, in place of the control unit 79 of the workstation 70. In this case, the control unit 99 includes a drive controller 99h, in place of the drive controller 79h of the control unit 79 and a magnetic field controller 99i, in place of the magnetic field controller 79i. Other elements are the same as those of the fourth embodiment and the same elements are represented by the same reference numbers.

The control unit 99 has the substantially same function as the control unit 79 of the workstation 70. Further, the control unit 99 controls the drive of the capsule guidance device 80 similarly to the control unit 79. Concretely, the drive controller 99h controls drives of the drive unit 64a of the movable base 64 and the drive unit 65a of the movable base 65 similarly to the drive controller 79h. By the control of the drive controller 99h, the movable bases 64, 65 can move the table 83 having the magnetic field generator 81 mounted thereon to a desired position on the rectangular coordinate system XY.

The magnetic field controller 99i controls the vertical magnetic field strength and the horizontal magnetic field strength generated by the magnetic field generator 81, similarly to the magnetic field generator 79i. In this case, the magnetic field controller 99i controls the drive of the vertical magnetic field generator 81a in the same way as the control on the vertical magnetic field generator 61 by the magnetic field generator 79i. Further, the magnetic field controller 99i selects one of the six horizontal magnetic field generators 81b to 81g for generating a horizontal magnetic field based on the instruction information input from the operating unit 76.

The magnetic field controller 99i controls the drive of one of the selected horizontal magnetic field generator 81b to 81g in the same way as the control on the horizontal magnetic field generator 62 by the magnetic field generator 79i. In this case, the magnetic field controller 99i sequentially switches the horizontal magnetic field generator for generating a magnetic field according to the instruction information input from the operating unit 76.

By the control of the magnetic field controller 99i, the magnetic field generator 81 can control the posture and the vertical position of the capsule endoscope 51 in the liquid 2a, similarly to the fourth embodiment without rotation drive of the table 83. Further, by the controls of the drive controller 99h and the magnetic field controller 99i, the magnetic field generator 81 can move the capsule endoscope 51 to a desired position on the rectangular coordinate system XY while capturing the capsule endoscope 51 in the liquid 2a by the magnetic force of the combined magnetic field. With this, the magnetic field generator 81 can control the horizontal position of the capsule endoscope 51 in the liquid 2a similarly to the fourth embodiment.

As described above, the first modification of the fourth embodiment of the present invention has the substantially same functions as those of the fourth embodiment. Further, a plurality of horizontal magnetic field generators are provided around a vertical magnetic field generator for generating a vertical magnetic field toward a capsule endoscope and the plurality of horizontal magnetic field generator are switched for generating a horizontal magnetic field. With this, the same effects as the fourth embodiment can be provided. In addition, a capsule guidance device for controlling the position and posture of the capsule endoscope can be enhanced.

Second Modification of Fourth Embodiment

Next, a second modification of the fourth embodiment of the present invention will be described. In the first modification of the fourth embodiment, a vertical magnetic field of the vertical magnetic field generator 81a and a horizontal magnetic field of one of the horizontal magnetic field generators 81b to 81g are generated toward the capsule endoscope 51. However, a body-insertable device system of the second modification of the fourth embodiment includes a magnetic field generator for generating a rotational magnetic field toward the capsule endoscope 51 and controls the position and posture of the capsule endoscope 51 by the rotational magnetic field.

Figure 33:
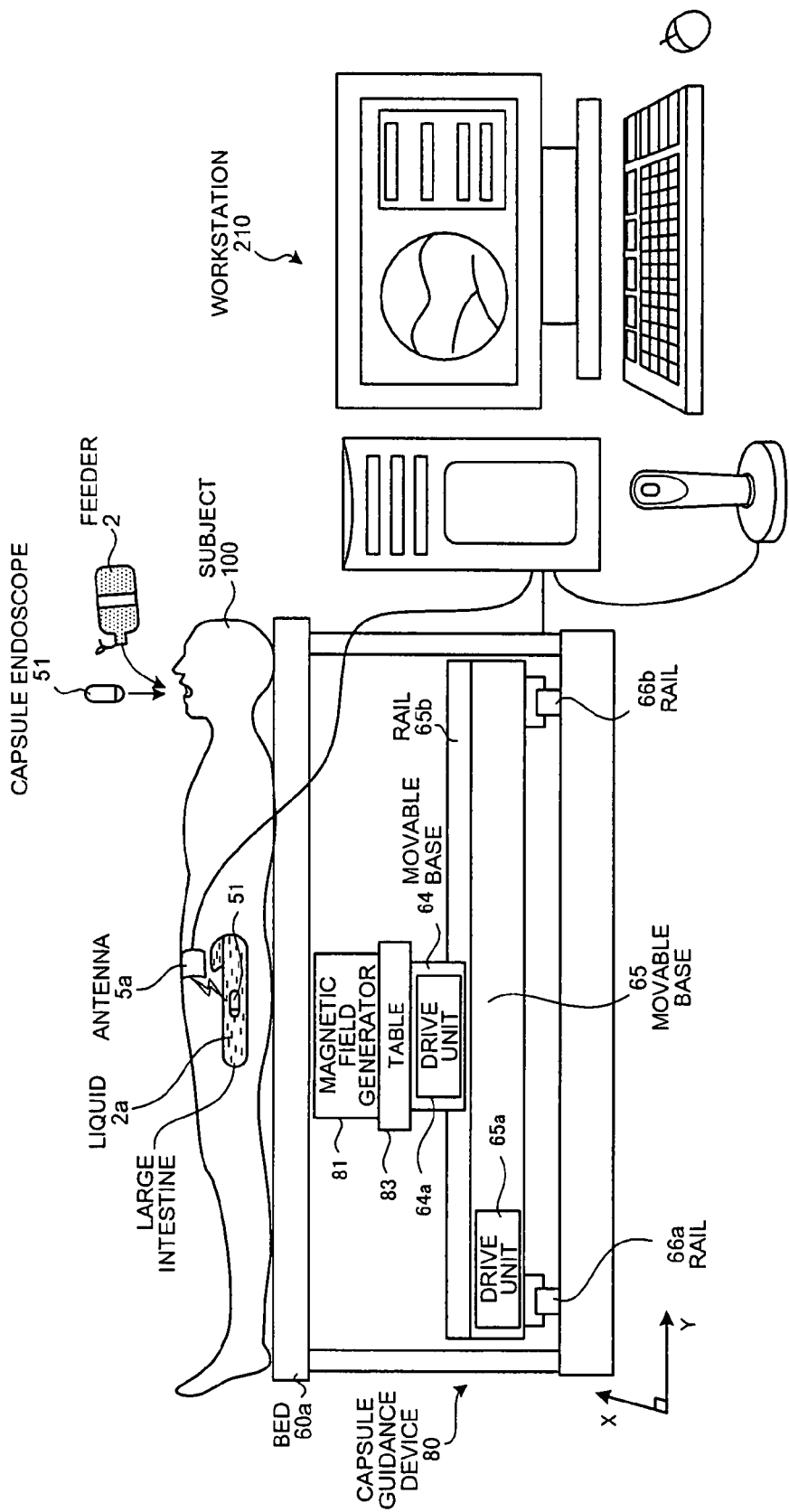
FIG. 33 is a schematic view showing a configuration example of a body-insertable device system according to a second modification of the fourth embodiment of the present invention.

FIG. 33 is a schematic view showing a configuration example of the body-insertable device system according to the second modification of the fourth embodiment of the present invention. As shown in FIG. 33, the body-insertable device system of the second modification of the fourth embodiment includes a capsule guidance device 200, in place of the capsule guidance device 80 of the body-insertable device system in the first modification of the fourth embodiment and a workstation 210, in place of the workstation 90. The capsule guidance device 200 includes a magnetic field generator 201, in place of the magnetic field generator 81 of the capsule guidance device 80. Other elements are the same as the first modification of the fourth embodiment and the same elements are represented by the same reference numbers.

The magnetic field generator 201 is mounted on a table 83 fixed to the movable base 64 and generates a rotational magnetic field toward the capsule endoscope 51 introduced in the subject 100. Such magnetic field generator 201 includes, for example, a vertical magnetic field generator at the center portion of the table 8 and, a plurality of horizontal magnetic field generators around the vertical magnetic field generator.

The workstation 210 has the substantially same function as the workstation 90 of the first modification of the fourth embodiment. In this case, the workstation 210 is electrically connected to the capsule guidance device 200 via a cable or the like and controls the drive of the capsule guidance device 200.

Figure 34:
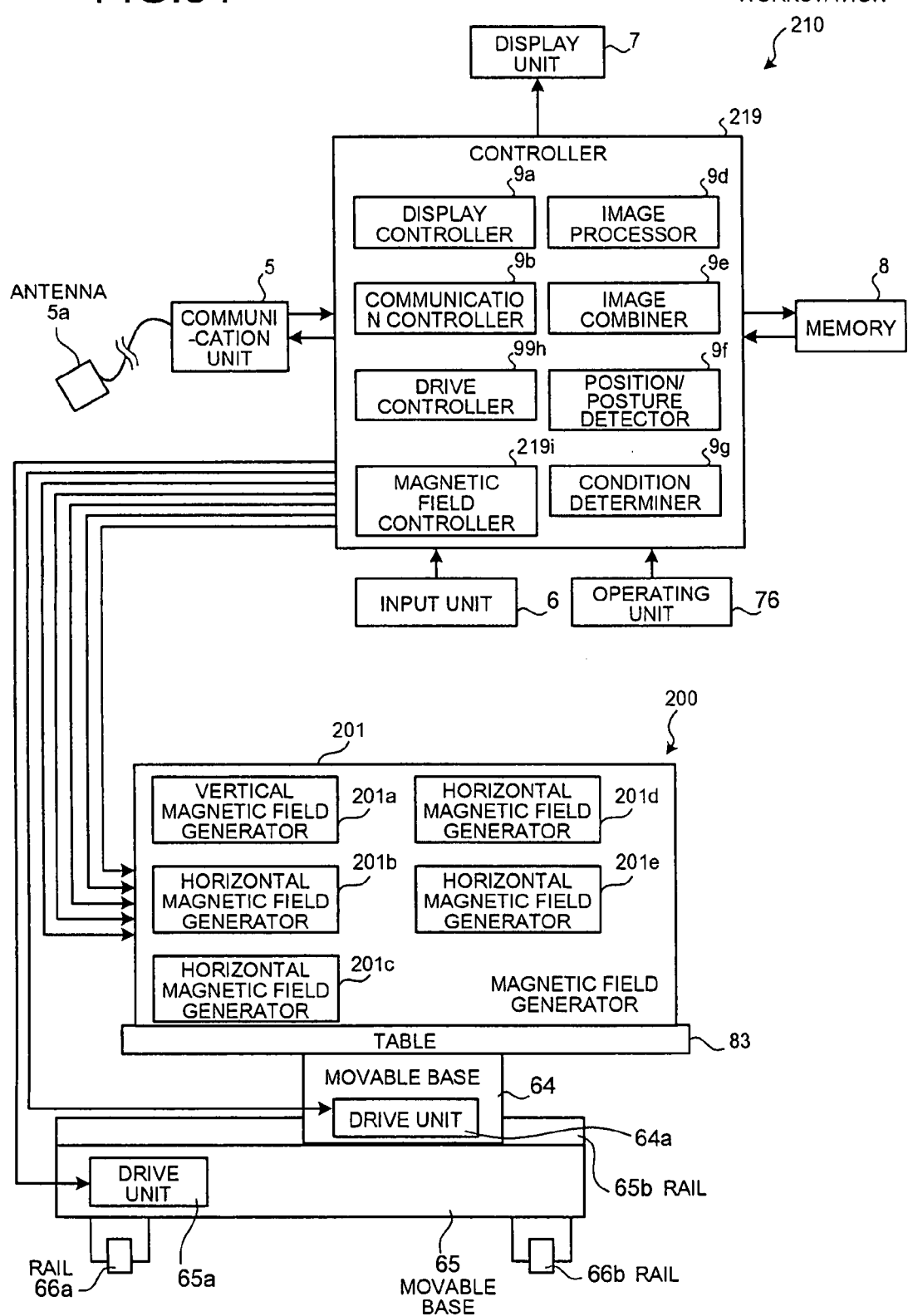
FIG. 34 is a block diagram schematically showing a configuration example of a capsule guidance device and a workstation according to the second modification of the fourth embodiment.
Figure 35:
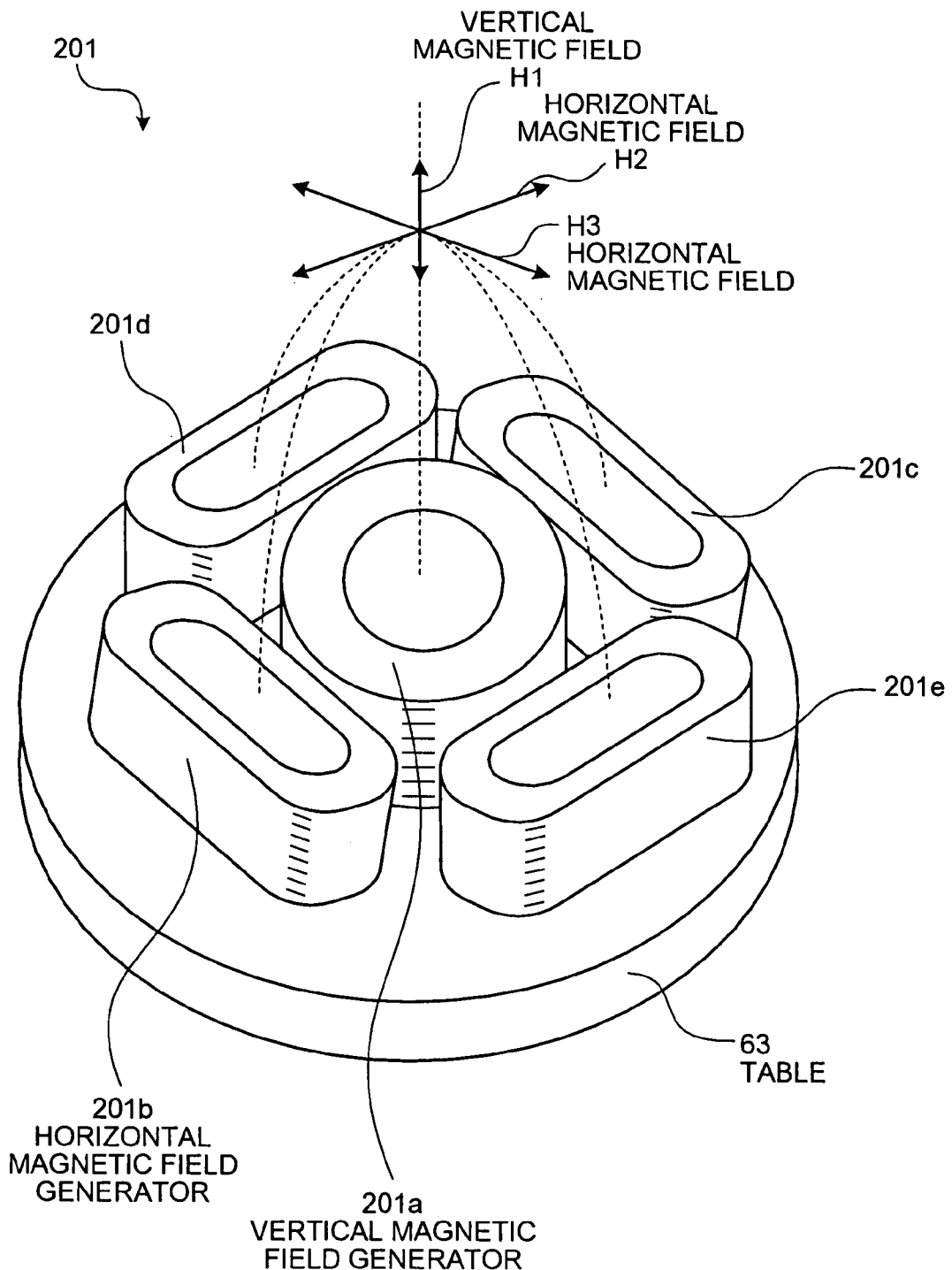
FIG. 35 is a schematic view showing a configuration example of a magnetic field generator of a capsule guidance device for generating a rotational magnetic field.

Next, each structure of the capsule guidance device 200 and the workstation 210 will be described. FIG. 34 is a block diagram schematically showing a configuration example of the capsule guidance device 200 and the workstation 210. FIG. 35 is a schematic view showing a configuration example of the magnetic field generator of the capsule guidance device 200 for generating a rotational magnetic field.

As shown in FIG. 35, the magnetic field generator 201 of the capsule guidance device 200 includes a single vertical magnetic field generator 201a and two pairs of horizontal magnetic field generators 201b to 201e. The vertical magnetic field generator 201a functions to generate a vertical alternating-current magnetic field toward the capsule endoscope 51. Further, the two pairs of horizontal magnetic field generators 201b to 201e function to generate a circular alternating-current magnetic field applying horizontal magnetic force toward the capsule endoscope 51.

Such vertical magnetic field generator 201a and the horizontal magnetic field generators 201b to 201e are arranged on the table 83 as shown in FIG. 35, for example. Concretely, the vertical magnetic field generator 201a is arranged at the substantially center portion of the table 83 and the horizontal magnetic field generators 201b to 201e are arranged around the vertical magnetic field generator 201a at substantially equal intervals. In this case, the vertical magnetic field generator 201a generates a vertical magnetic field H1 which is a vertical alternating-current magnetic field. Further, the pair of horizontal magnetic field generators 201b, 201c generates a horizontal magnetic field H2 which is a circular alternating-current magnetic field and the pair of the horizontal magnetic field generators 201d, 201e generates a horizontal magnetic field H3 which is a circular alternating-current magnetic field. The horizontal magnetic fields H2, H3 are mutually vertical and form horizontal magnetic fields above the vertical magnetic field H1. Further, the horizontal magnetic field H2 or the horizontal magnetic field H3 and the vertical magnetic field H1 are combined to each other to form a rotational magnetic field. Here, the number of horizontal magnetic field generators is any even number and should not be limited to four. Although the second modification of the fourth embodiment of the present invention describes a rotational magnetic field to be generated. However, the magnetic field generator 201 can generate magnetic fields toward any direction, so that it should not be limited to the rotational magnetic field and it is possible to control the posture of the capsule endoscope 1 as described above in the first embodiment. Further, in the first embodiment, it is possible to capture the capsule endoscope 1 by the magnetic field generated by the vertical magnetic field generator 201a. Therefore, the horizontal position of the capsule endoscope 1 may be controlled by moving the horizontal position of the vertical magnetic field generator 201.

On the other hand, as shown in FIG. 34, the workstation 210 includes a control unit 219, in place of the control unit 99 of the workstation 90. In this case, the control unit 219 includes a magnetic field controller 219i, in place of the magnetic field controller 99i of the control unit 99. Other elements are the same as those of the first modification of the fourth embodiment and the same elements are represented by the same reference numbers.

The control unit 219 has the substantially same function as the control unit 99 of the workstation 90. In this case, the control unit 219 controls drives of the drive unit 64a of the movable base 64 and the drive unit 65a of the movable base 65, similarly to the control unit 99. By the control of the control unit 219, the movable bases 64, 65 can move the table 83 having the magnetic field generator 201 thereon to a desired position on the rectangular coordinate system XY.

The magnetic field controller 219i controls the drive of the magnetic field generator 201 so as to generate the rotational magnetic field toward the capsule endoscope 51 in the subject 100. Concretely, the magnetic field controller 219i controls the drive of the vertical magnetic field generator 201a so as to form the vertical magnetic field H1, for example, with an alternating-current magnetic field of cosine wave.

Further, the magnetic field controller 219i selects a pair of horizontal magnetic field generators for generating a horizontal magnetic field (one of the horizontal magnetic fields H2, H3), for example, as an alternating-current magnetic field of sine wave among four horizontal magnetic field generators 201b to 201e based on the instruction information input from the operating unit 76. Then, the magnetic field controller 219i controls the drives of the selected pair of horizontal magnetic field generators, that is, the horizontal magnetic field generators 201b and 201c, or the horizontal magnetic field generators 201d and 201e so as to form the horizontal magnetic field H2 or the horizontal magnetic field H3. In this case, the magnetic field controller 219i sequentially switches the pair of horizontal magnetic field generators for generating the horizontal magnetic field based on the instruction information sequentially input from the operating unit 76.

Figure 36:
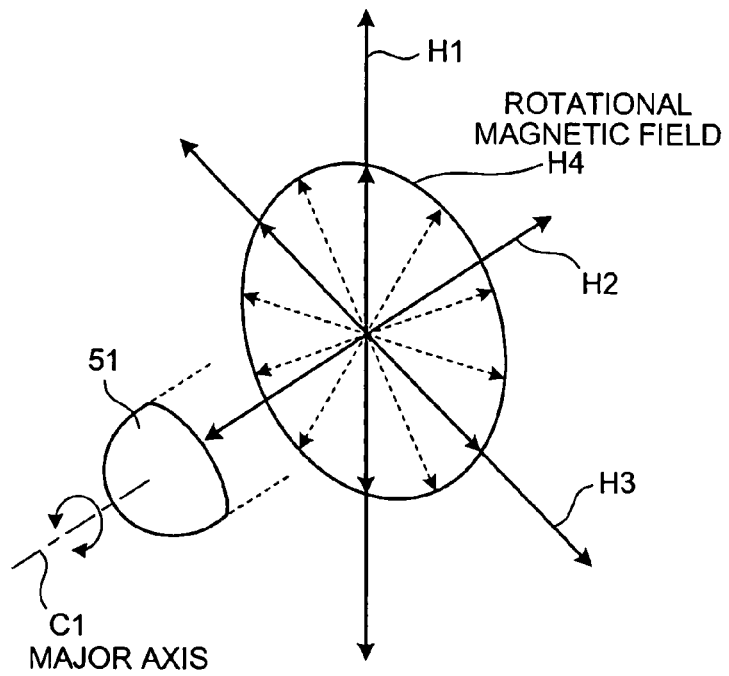
FIG. 36 is a schematic view showing a rotational magnetic field generated for the body-insertable device.

By the control of the magnetic field controller 219i, one of the pairs of the horizontal magnetic field generators 201b to 201e and the vertical magnetic field generator 201a respectively generate the horizontal magnetic field and the vertical magnetic field and the horizontal magnetic field, and the vertical magnetic field are combined to form a rotational magnetic field. In this case, for example, a pair of horizontal magnetic field generators 201d, 201e and the vertical magnetic field generator 201a, as shown in FIG. 36, respectively generate the horizontal magnetic field H3 and the vertical magnetic field H1, and the horizontal magnetic field H3 and the vertical magnetic field H1 are combined to form the rotational magnetic field H4. Here, the pair of horizontal magnetic field generators 201b, 201c and the vertical magnetic field generator 201a forms a rotational magnetic field perpendicular to the rotational magnetic field H4.

The rotational magnetic field is applied to the capsule endoscope 51 in a digestive canal of the subject 100, for example, in the large intestine and the capsule endoscope 51 rotates about the major axis C1 in the liquid 2a and the alternating magnetic field is applied in a direction of magnetic field (that is, the radial direction of the casing 50) of the installed permanent magnet 52. By such effect of the rotational magnetic field, the position and posture of the capsule endoscope 51 in the liquid 2a is controlled, similarly to the fourth embodiment. That is, by the control of the magnetic field controller 219i, the magnetic field generator 201 can control the posture and the horizontal direction of the capsule endoscope 51 in the liquid 2a without rotation drive of the table 83 similarly to the fourth embodiment. Further, by the control of the drive controller 99h and the magnetic field controller 219i, the magnetic field generator 201 can move the capsule endoscope 51 in the liquid 2a to the desired position on the rectangular coordinate system XY while capturing the capsule endoscope 21 with the magnetic force of the rotational magnetic field. With this, the magnetic field generator 201 can control the horizontal position of the capsule endoscope 51 in the liquid 2a, similarly to the fourth embodiment.

Figure 37:
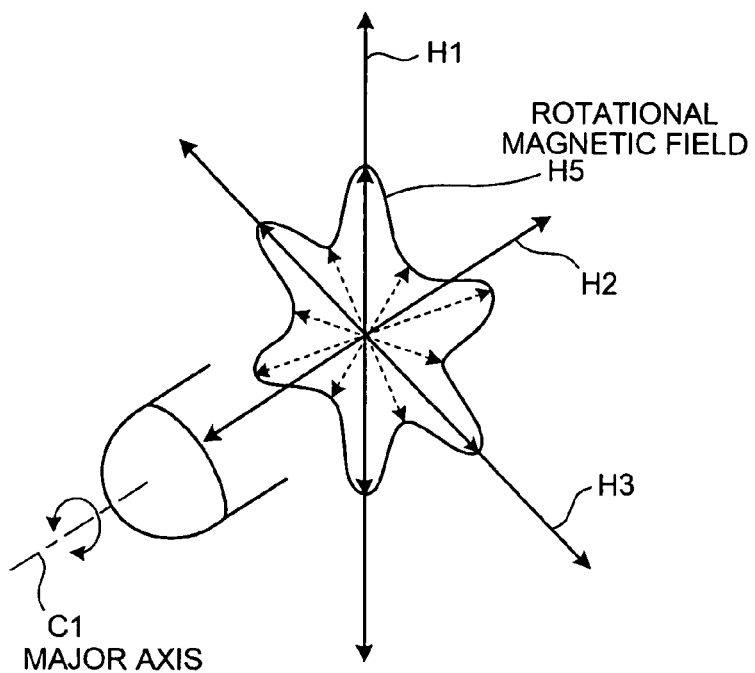
FIG. 37 is a schematic view showing another aspect of the rotational magnetic field.

Here, the magnetic field controller 219i controls the drive of the vertical magnetic field generator 201a and one pair of the horizontal magnetic field generators 201b to 201e to add an oscillating magnetic field component of the a frequency greater than the rotational frequency to the rotational magnetic field (for example, the rotational magnetic field H4) generated toward the capsule endoscope 51. With this, as shown in FIG. 37, a pair of horizontal magnetic field generators 201d, 201e and the vertical magnetic field generator 201a form the rotational magnetic field H5 generated by changing the predetermined cycle of the magnetic field strength of the rotational magnetic field H4. In this case, when the magnetic field strength of the rotational magnetic field H5 is greater, the capsule endoscope 51 is drawn to the magnetic field generator 201. On the other hand, when the magnetic field strength of the rotational magnetic field H5 is smaller, the buoyant force becomes greater than the attracting force effective on the capsule endoscope 51 so that the capsule endoscope 51 moves upward. Therefore, the capsule endoscope 51 automatically moves upward and downward with respective to a predetermined position in the liquid 2a so that an image of wide range in the large intestine can be easily obtained.

As described above, the second modification of the fourth embodiment of the present invention includes the substantially same function as the first modification of the fourth embodiment. Further, the position and posture of a capsule endoscope can be controlled by the rotational magnetic field by generating a rotational magnetic field of the capsule endoscope. Therefore, the same effect as the first modification of the fourth embodiment can be provided and the position and posture of the capsule endoscope can be securely controlled.

Fifth Embodiment

Next, a fifth embodiment of the present invention will be described. In the first embodiment, at least one of the position and posture of the capsule endoscope 1 having specific gravity equal to or smaller than that of the liquid 2a introduced into a digestive canal is controlled by a magnetic force. However, a body-insertable device system according to the fifth embodiment includes a capsule endoscope having a vibration motor so that the capsule endoscope wobbles by driving the vibration motor. Further, the condition of the specific gravity of the capsule endoscope is changed from a condition greater than that of the liquid 2a to a condition smaller than that of the liquid 2a.

Figure 38:
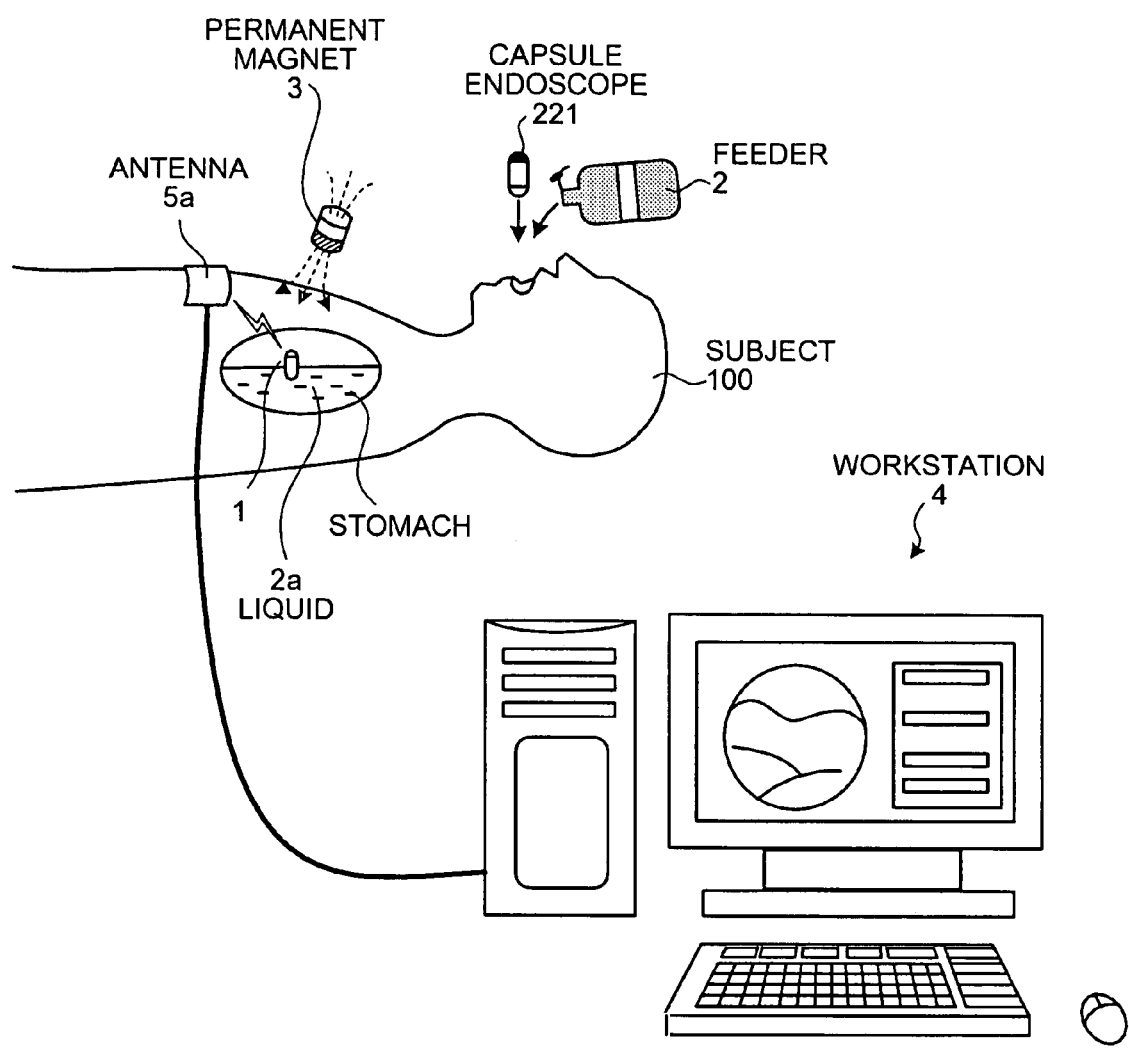
FIG. 38 is a schematic view showing a configuration example of a body-insertable device system according to a fifth embodiment of the present invention.

FIG. 38 is a schematic view showing a configuration example of the body-insertable device system according to the fifth embodiment of the present invention. As shown in FIG. 38, the body-insertable device system of the fifth embodiment includes a capsule endoscope 221, in place of the capsule endoscope 1 of the body-insertable device system in the first embodiment and a workstation 230, in place of the workstation 4. Other elements are the same as those of the first embodiment and the same elements are represented by the same reference numbers.

The capsule endoscope 221 has the same imaging function and radio communication function as those of the capsule endoscope 1 in the first embodiment, and further, includes a function for changing the specific gravity of the capsule endoscope 221 with respect to that of the liquid 2a introduced into the digestive canal of the subject 100 from smaller specific gravity to larger specific gravity. Further, the capsule endoscope 221 wobbles according to the control signal received from the workstation 230 and functions for changing the position and direction of imaging field in the subject 100.

The workstation 230 includes the substantially same function as the workstation 4 in the first embodiment. In this case, the workstation 230 has a drive control function for controlling the operation of the capsule endoscope 221, in place of the magnet selection function and magnetic field strength determining function of the workstation 4. Concretely, the workstation 230 sends a control signal to the capsule endoscope 221 via an antenna 5a to wobble the capsule endoscope 221 or change the specific gravity of the capsule endoscope 221 according to the control signal.

Figure 39:
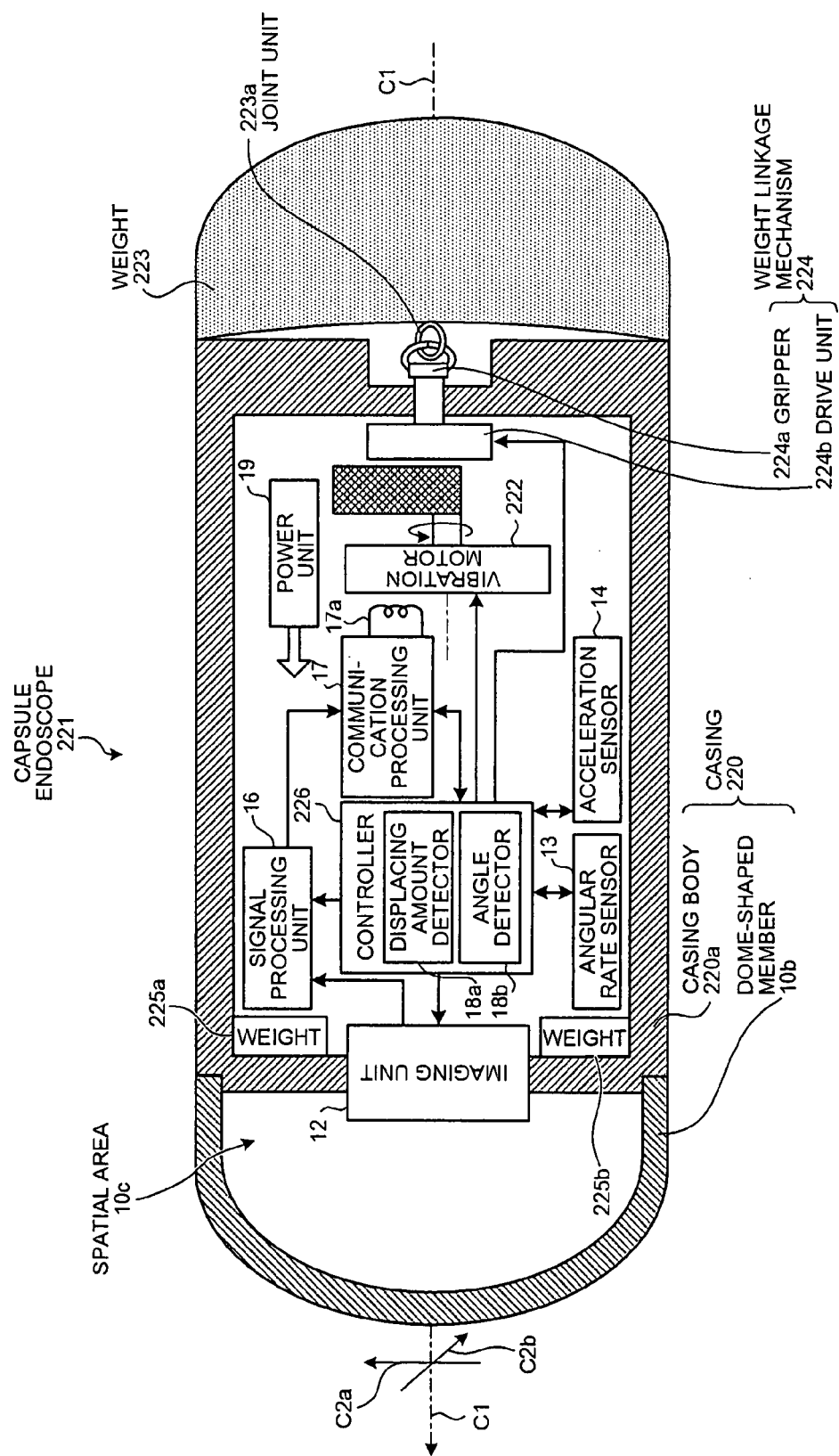
FIG. 39 is a schematic view showing a specific example of the body-insertable device according to the fifth embodiment of the present invention.

Next, a structure of the capsule endoscope 221 will be described. FIG. 39 is a schematic view showing an illustrative example of the body-insertable device according to the fifth embodiment of the present invention. As shown in FIG. 39, the capsule endoscope 221 as an example of the body-insertable device includes a casing 220, in place of the casing 10 of the capsule endoscope 1 according to the first embodiment and the control unit 226, in place of controller 18. The casing 220 includes a casing body 220a, in place of the casing body 10a of the casing 10. Further, the capsule endoscope 221 includes the weight 233 at an outer wall of a rear-end part of the casing 220 and a weight linkage mechanism 224 is disposed near an inner wall of the rear-end part of the casing 220. Further, the capsule endoscope 221 includes the vibration motor 222 and weights 225a, 225b in the casing 220. Other elements are the same as those of the first embodiment and the same elements are represented by the same numbers.

The casing 220 is a capsule-shaped member formed in a size easily insertable into the subject 100 and provided with a dome-shaped member 10b attached to a front-end of the casing body 220a. The casing body 220a connects the weight 223 to the rear-end part from outside. Further, inside the rear-end part of the casing body 220a, the weight linkage mechanism 224 for removably linking the weight 223 is placed. On the other hand, the weights 225a, 225b are fixed near the front-end part of the casing body 220a. The weights 225a, 225b work to place the center of gravity of the casing 220 at a front portion, where the weight 223 is not connected. The weights 225a, 225b do not make the specific gravity of the casing 220 to be greater than that of the liquid 2a. On the other hand, other elements of the capsule endoscope 221 are placed at predetermined positions in the casing body 220a.

The casing 220 provided with the casing body 220a and the dome-shaped member 10b has specific gravity smaller than that of the liquid 2a and the center of gravity is placed at a front portion. Further, the casing 220 having the weight 223 linked to the rear-end part thereof changes to have specific gravity which is greater than that of the liquid 2a and the center of gravity is moved to a rear portion. That is, the casing 220 having such structure can change its condition of specific gravity from greater specific gravity to smaller specific gravity in comparison to the liquid 2a by attaching and removing the weight to and from the rear-end part and the position of the center of gravity changes from a rear portion to a front portion according to the change in the specific gravity.

The vibration motor 222 functions as a vibrator for vibrating the casing 220 and wobbling the casing 220 in the liquid 2a. Concretely, the vibration motor 222 is provided with a pager motor or the like and controlled by the control unit 226. In this case, the vibration motor 222 wobbles the casing 220 in the liquid 2a introduced into the digestive canal of the subject 100 by vibrating and changes the position and direction of the imaging field in the liquid 2a in the digestive channel.

The weight 223 is made of a member having a great specific gravity in comparison to the liquid 2a such as steal and provided a joint unit 223a is placed at a predetermined position. The weight 223 is connected to the rear-end part of the casing body 220a from outside by the joint unit 223a being held by the weight linkage mechanism 224. By linking to the casing body 220a, the weight 223 changes the specific gravity of the casing 220 larger than that of the liquid 2a and the center of gravity of the casing 220 is displaced to the rear potion.

The weight linkage mechanism 224 is for linking the weight 223 to the rear-end part of the casing body 220a. Concretely, the weight linkage mechanism 224 includes a gripper 224a for gripping the joint unit 223a of the weight 223 and a drive unit 224b for driving the gripper 224a. The gripper 224a is disposed though the wall of the rear-end part of the casing body 220a and grips the joint unit 223a from the inside of the casing body 220a via the wall of the rear-end part of the casing body 220a. The drive unit 224b drives the gripper 224a according to the control of the control unit 226. That is, the gripper 224a removably grips the joint unit 223a according to the drive of the drive unit 224b. The weight linkage mechanism 224 having such gripper 224a and the drive unit 224b functions as a specific gravity changing unit for changing the specific gravity of the casing 220 as described above.

The control unit 226 is configured to control the drives of each elements of the capsule endoscope 221. Concretely, the control unit 226 has the same function as the control unit 18 of the capsule endoscope 1 and controls each drive of the vibration motor 222 and the drive unit 224b. In this case, the control unit 226 performs a radio communication with the workstation 230 and controls the drive of the vibration motor 222 or the drive unit 224b based on the control signal from the workstation 230 input from the communication processing unit 17. Further, the control unit 226 changes the position and direction of the imaging field in the subject by wobbling the casing 220 in the liquid 2a, or changes the specific gravity of the capsule endoscope 221 from greater to smaller with respect to the specific gravity of the liquid 2a.

Figure 40:
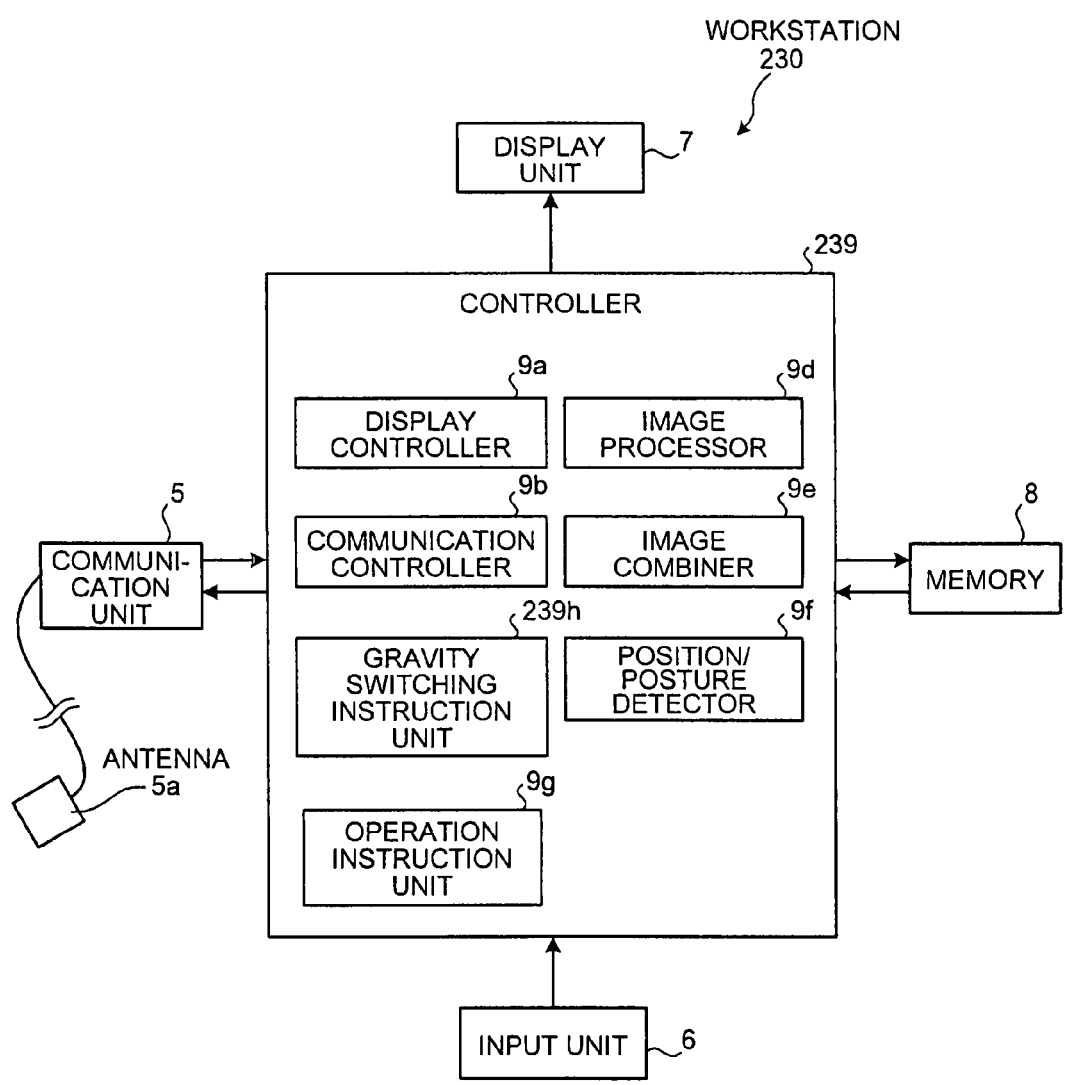
FIG. 40 is a block diagram schematically showing a configuration example of a workstation according to the fifth embodiment.

Next, a structure of the workstation 230 will be described. FIG. 40 is a block diagram schematically showing a configuration example of the workstation 230. As shown in FIG. 40, the workstation 230 includes a control unit 239, in place of the control unit 9 of the workstation 4. The control unit 239 includes a specific gravity switching instruction unit 239h, in place of the condition determiner 9g and the magnet selector 9c of the control unit 9 and an operation instruction unit 239i. Other elements are the same as those of first embodiment and the same elements are represented by the same reference numbers.

The control unit 239 has the substantially same function as the workstation 4 of the control unit 9. In this case, the control unit 239 includes an instruction function to provide instruction for switching specific gravity to the capsule endoscope 221, in place of a magnet selection function and a magnetic field strength determining function and a drive control function for starting or stopping the wobble of the capsule endoscope 221. Concretely, the specific gravity switching instruction unit 239h generates a control signal for switching the specific gravity of the capsule endoscope 221 according to the instruction information input from the input unit 6. The control signal generated by the specific gravity switching instruction unit 239h is sent by radio to the capsule endoscope 221 via the communication unit 5. On the other hand, the operation instruction unit 239i generates a control signal for stating or stopping the wobble of the capsule endoscope 221 based on the instruction information input from the input unit 6. The control signal generated by the operation instruction unit 239i is sent by radio to the capsule endoscope 221 via the communication unit 5 or the like.

Figure 41:
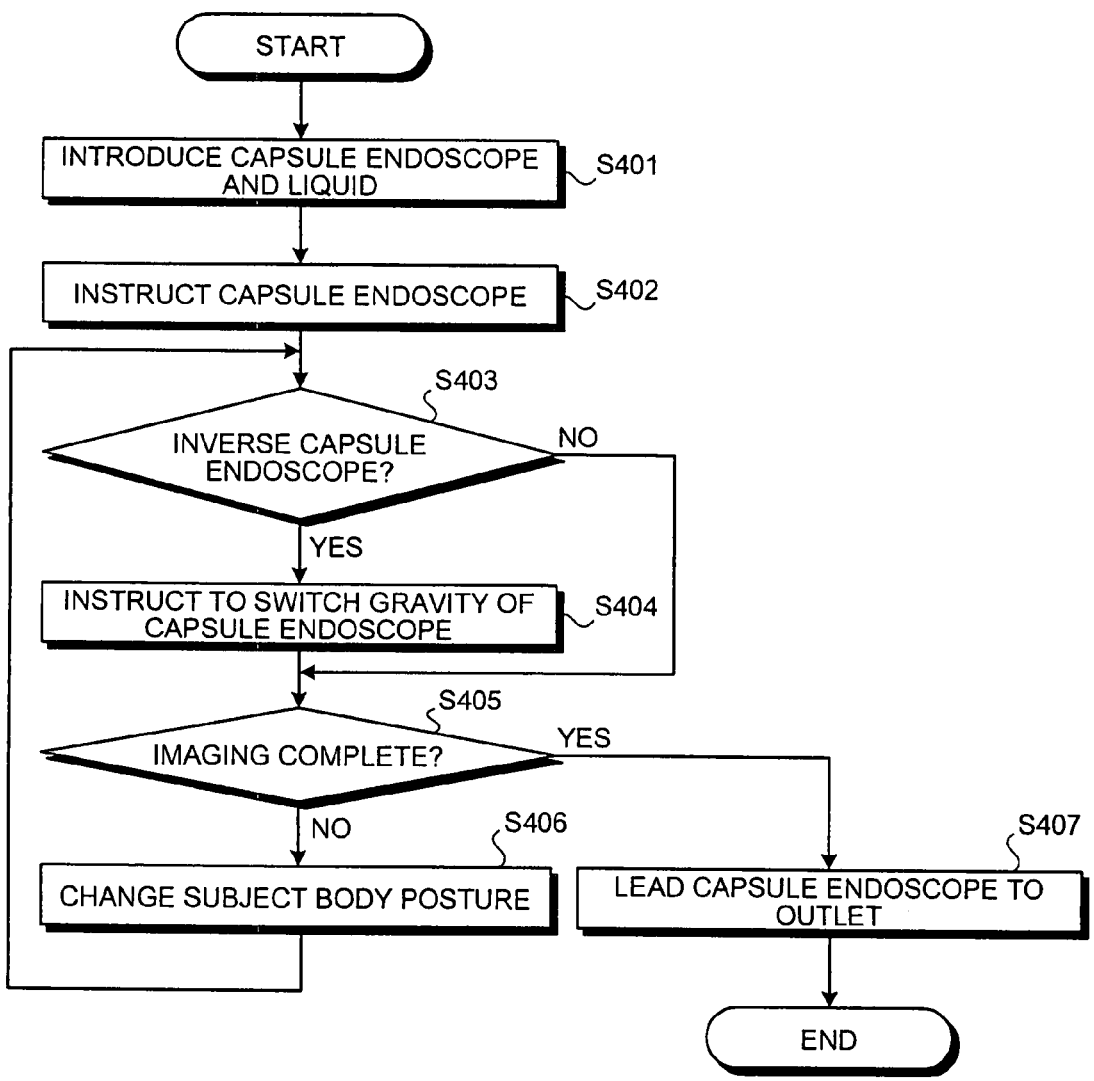
FIG. 41 is a flow chart showing a procedure for observing an inside of digestive canal of a subject with an image inside the digestive canal by the body-insertable device according to the fifth embodiment.
Figure 42:
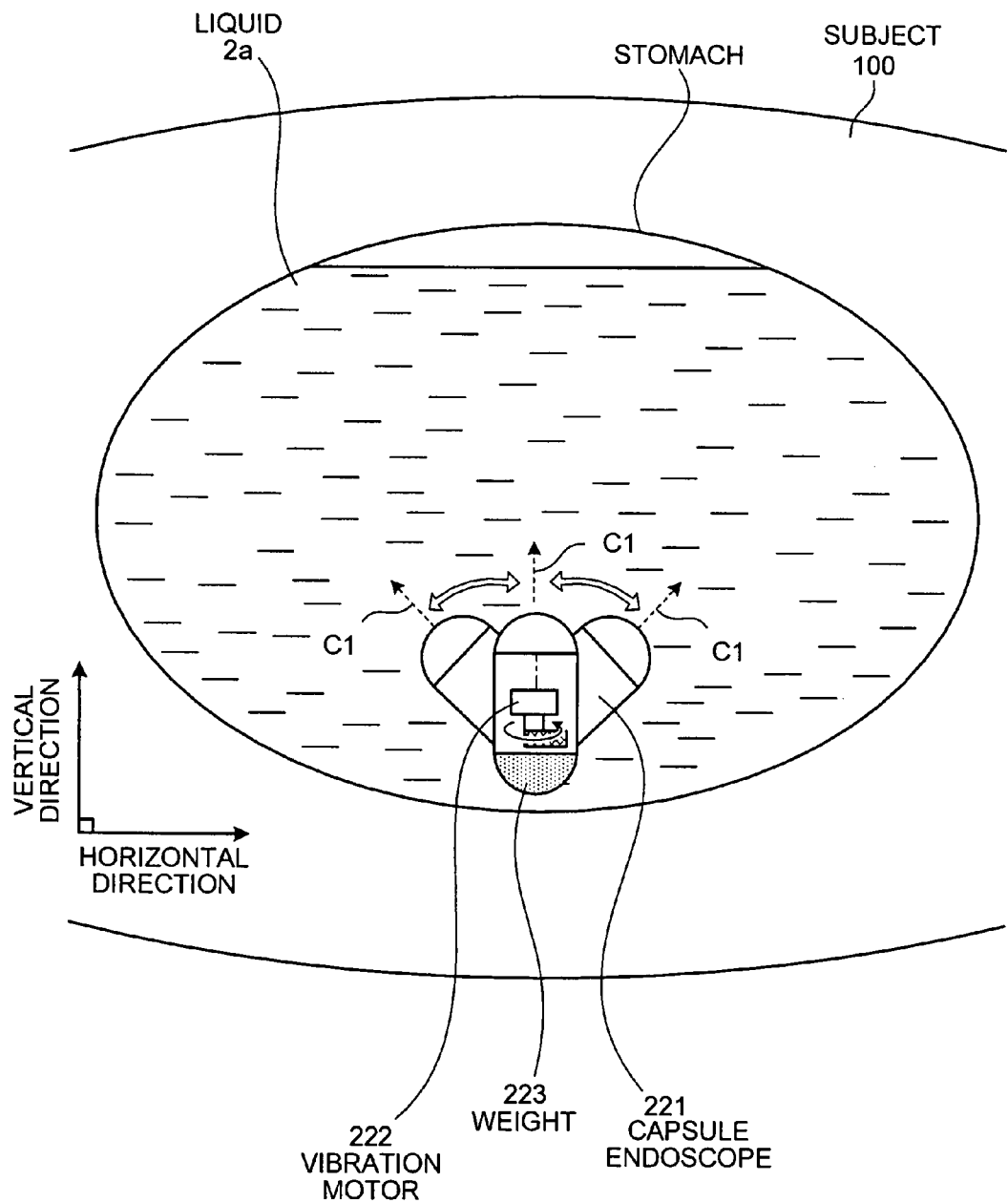
FIG. 42 is a schematic view showing an operation of the body-insertable device that wobbles as the bottom of the casing containing liquid is vibrated.
Figure 43:
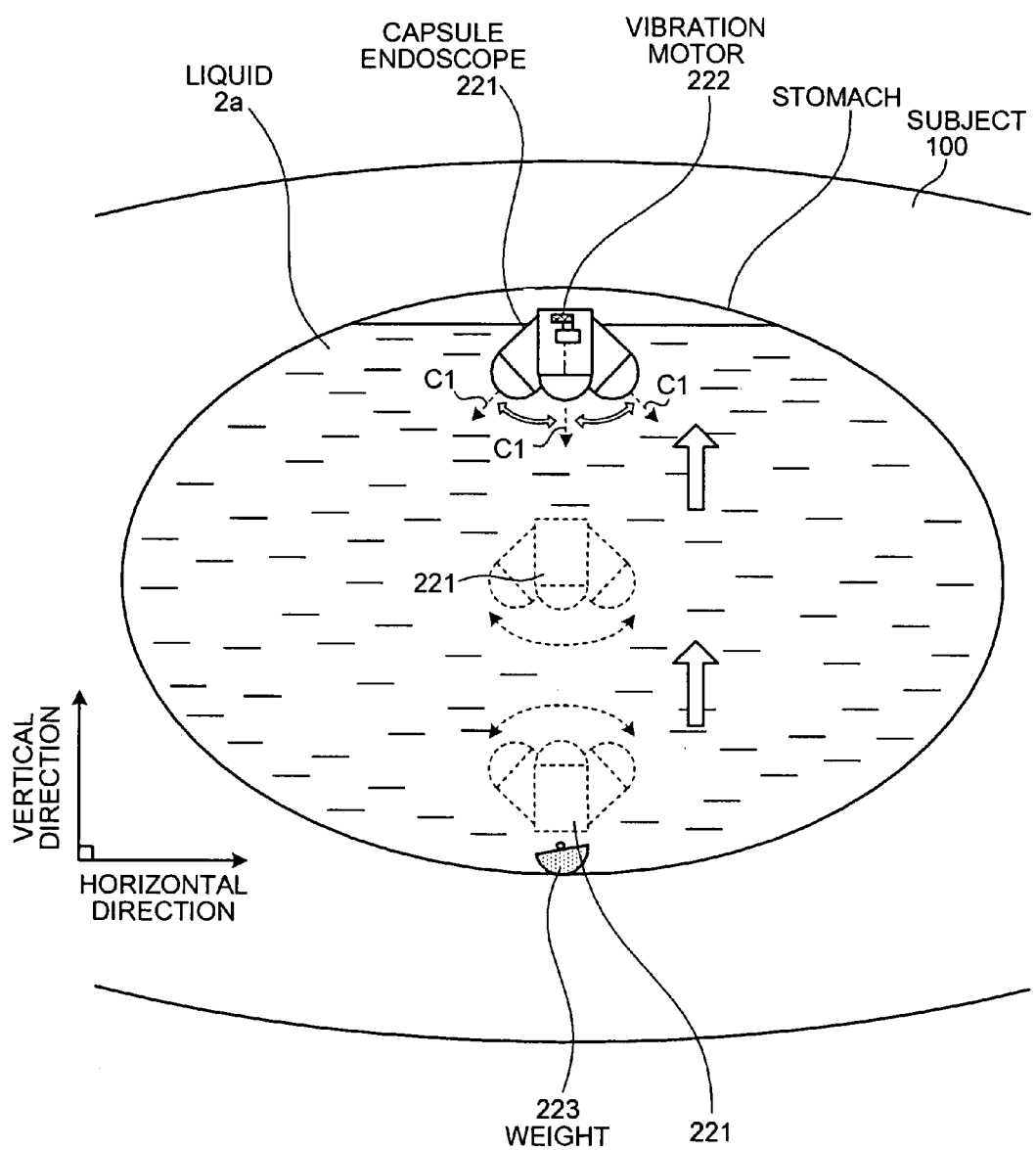
FIG. 43 is a schematic view showing an operation of the body-insertable device when specific gravity is changed from higher to lower with respect to the liquid to reverse an image view.

Next, a procedure of observing a digestive canal (for example, the stomach) of the subject 100 with an image taken by the capsule endoscope 221. FIG. 41 is a flow chart showing a procedure of observing a digestive canal of the subject 100 with an image in the digestive canal taken by the capsule endoscope 221 introduced into the subject 100. FIG. 42 is a schematic view showing an operation of the capsule endoscope 221 which wobbles by vibrating the casing 220 under the liquid 2a. FIG. 43 is a schematic view showing an operation of the capsule endoscope 221 for changing the specific gravity from larger to smaller with respect to the specific gravity of the liquid 2a to invert the imaging field.

In FIG. 41, the examiner uses the workstation 230 or a predetermined starter to start an imaging operation of the capsule endoscope 221 and introduces the capsule endoscope 221 into the subject 100 and then liquid 2a into the subject 100 by using the feeder 2 (step S401). In this case, the capsule endoscope 221 and the liquid 2a are, for example, swallowed through the mouth of the subject 100, and then, reaches to a desired digestive canal in the subject 100. Further, the amount of the liquid 2a is to fill a desired digestive canal, for example, the stomach and the liquid 2a sufficiently expand the digestive canal. Since the capsule endoscope 221 is connected with the weight 223, the capsule endoscope 221 sinks to the bottom of the liquid 2a. The examiner finds the position of the capsule endoscope 221 in the subject 100 while seeing the image taken by the capsule endoscope 221 and displayed on the workstation 230. The examiner may operate workstation 230 to start the imaging operation of the capsule endoscope 221 after introducing the capsule endoscope 221 into the subject 100.

Next, the examiner operates the input unit of the workstation 230 and instructs an operation of the capsule endoscope 221 (step S402). In this case, the control unit 239 receives instruction information from the input unit 6 to start the operation of the capsule endoscope 221. The operation instruction unit 239i generates control signal for instructing a start of the operation based on the instruction information. The control signal generated in this way is transmitted to the capsule endoscope 221 by radio communication drive of the communication unit 5. In this case, the control unit 226 of the capsule endoscope 221 stars the drive of the vibration motor 222 based on the control signal from the workstation 230 to start the drive and wobbles the casing 220 in the liquid 2a. The capsule endoscope 221, for example, as shown in FIG. 42, wobbles the imaging field under the condition that the imaging field is directed above in a vertical direction under the liquid. With this, the capsule endoscope 221 sequentially takes images while changing the position and direction of the imaging field in the digestive canal.

Then, when the direction of the imaging field in the digestive canal is changed by inverting the capsule endoscope 221 (step S403, Yes), the examiner operates the input unit 6 and inputs instruction information for changing the specific gravity of the capsule endoscope 221 (step S404). In this case, the control unit 239 receives the instruction information for changing the specific gravity from the input unit 6 and the specific gravity switching instruction unit 239 generates a control signal for instructing switching of the specific gravity based on the instruction information. The control signal generated in this way is transmitted to the capsule endoscope 221 by the radio communication drive of the communication unit 5

In this case, the control unit 226 of the capsule endoscope 221 controls the drive of the drive unit 224b based on the control signal from the workstation 230 to unlock the gripping condition of the joint unit 223a by the gripper 224a. With this, the capsule endoscope 221 is released from the weight 223 and moves upward, as shown in FIG. 43. Then, the capsule endoscope 221 inverts the imaging field downward and moves up to the surface of the liquid 2a, while wobbling in the liquid 2a. During this, the capsule endoscope 221 sequentially takes images in the digestive canal (for example, the stomach wall) while repeating wobbling. Here, the specific gravity of the weight 223 released from the capsule endoscope 221 is greater than that of the liquid 2a. Further, desirably the weight 223 is provided at an opposite side of the place where the imaging unit 12 is provided. Accordingly, the imaging unit 12 can obverse under the water all the time.

After that, when the examiner change the body posture of the subject 100 to another body posture and imaging operation in the digestive canal as an observed region continues (step S405, No), the current body posture of the subject (for example, supine position) may be changed to another desired body posture (for example a right lateral supine position) (step S406). Then, the examiner repeat the above procedure subsequent to step S403. When the capsule endoscope 221 is not inverted in step S403 (step S403, No), the examiner repeats the procedure subsequent to step S405.

In this way, the capsule endoscope 221 can image substantially whole region in the digestive canal by changing at least one of the position and posture of the capsule endoscope 221 in the digestive canal as an observed region. The examiner can observe ever part in the desired digestive canal as an observed region of subject 100 by displaying the image taken by the capsule endoscope 221 on the workstation 230.

When the examiner completes the observation in the digestive canal as an observed region and the imaging of the digestive canal is completed (step S405, Yes), the capsule endoscope 221 is led to an outlet of the digestive canal (step S407). In this case, the capsule endoscope 221 is led to the outlet by the peristalsis of the digestive canal and flow of the liquid 2a and moves into the following digestive canal. With this, the capsule endoscope 221 completes imaging in the digestive canal as an observed region. Then, the capsule endoscope 221 is moved by the peristalsis of each digestive canal or flow of the liquid 2a in the subject 100 while taking images in the digestive canal and then discharged outside the subject 100.

Here, the examiner may observe the digestive canal of the subject 100 while displaying the images taken by the capsule endoscope 221 on the workstation 230. On the other hand, the examiner may operate workstation 230 and send a control signal for stopping the imaging operation to stop the imaging operation of the capsule endoscope 221 which has completed imaging of the desired observed region.

As described above, according to the fifth embodiment of the present invention, the imaging unit for taking images in the digestive canal of the subject is fixed in the casing and the vibration motor is disposed in the casing, and the vibration motor vibrates the casing in the liquid to change the position and direction of the imaging field. Further, a weight is removably attached to the outside of the casing whose specific gravity is smaller than that of the liquid to set the specific gravity of the casing greater than the specific gravity of the liquid and the linkage of the weight may be released at a desired timing. Accordingly, a body-insertable device and a body-insertable device system can be easily realized, in which the position and direction of the imaging field in the liquid introduced into the digestive canal are easily changed and the same effect as the first embodiment can be provided. Further, a buoyant force of the liquid in the subject works on the body-insertable device and the gravity generated on the body-insertable device can be reduced or even canceled as much as the amount of the buoyant force. Accordingly, at least one of the position and posture of the body-insertable device can be easily changed and the drive unit (for example, a vibration motor installed in the body-insertable device) for changing at least one of the position and posture of the body-insertable device can be downsized. As a result, the body-insertable device itself can be downsized so that the facility of introducing the body-insertable device into a subject can be improved.

First Modification of Fifth Embodiment

A first modification of the fifth embodiment will be described. According to the fifth embodiment, the specific gravity of the capsule endoscope 221 is changed from greater to smaller with respect to the specific gravity of the liquid 2a. A body-insertable device system according to the first modification of the fifth embodiment includes a capsule endoscope for changing the specific gravity from smaller to larger with respect to the specific gravity of the liquid 2a, in place of the capsule endoscope 221.

Figure 44:
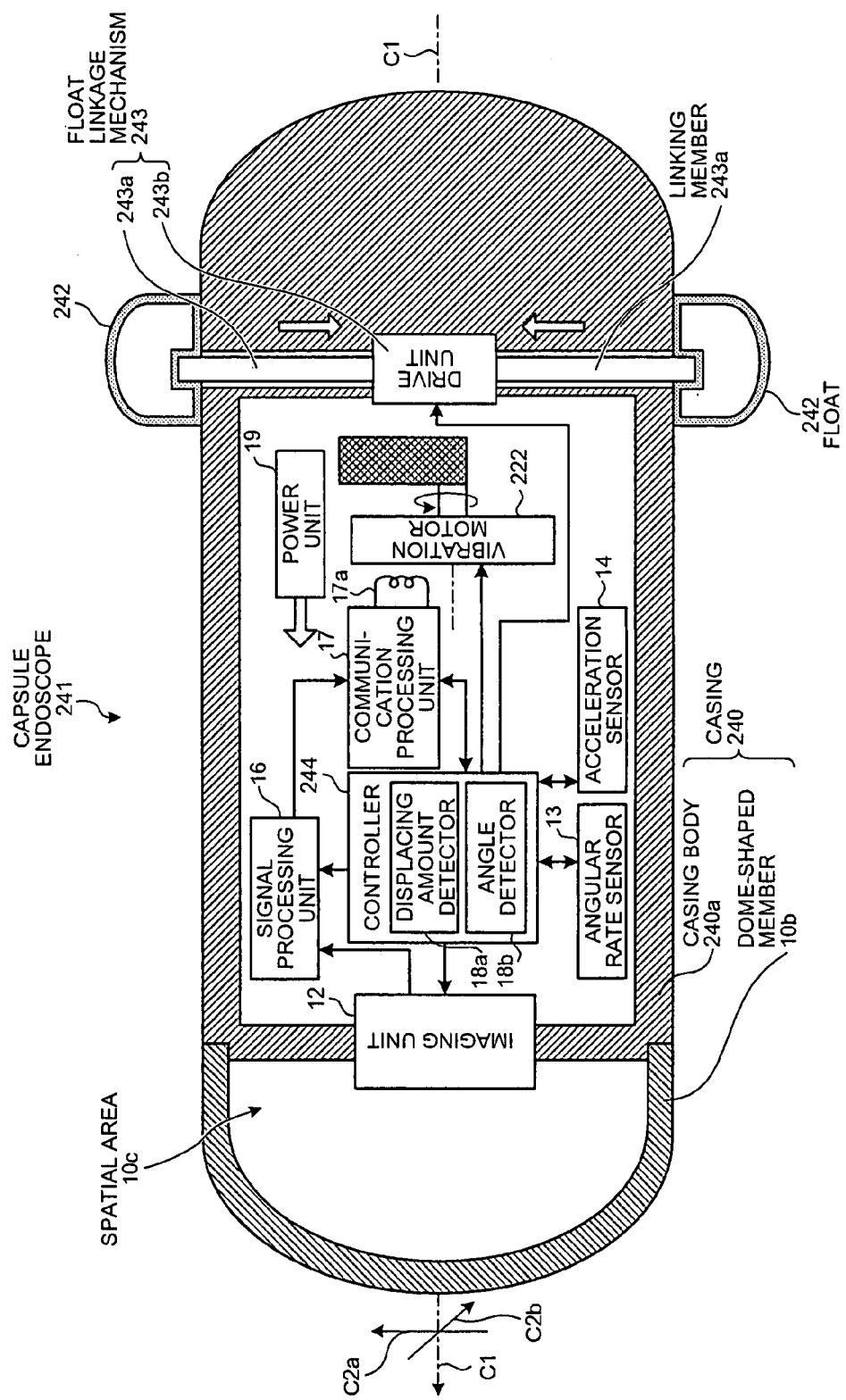
FIG. 44 is a schematic view showing a configuration example of a body-insertable device according to a first modification of the fifth embodiment of the present invention.

FIG. 44 is a schematic view showing a configuration example of the body-insertable device according to the first modification of the fifth embodiment of the present invention. As shown in FIG. 44, a capsule endoscope 241 as an example of the body-insertable device includes a casing 240 in place of the casing 220 of the capsule endoscope 221 in the fifth embodiment, a float 242, in place of the weight 223, a float linkage mechanism 243, in place of the weight linkage mechanism 224, and a control unit 244, in place of the control unit 226. Further, the casing 240 includes a casing body 240a, in place of the casing body 220a of the casing 220. Other elements are the same as those of the fifth embodiment and the same elements are represented by the same reference numbers.

The casing 240 is a capsule-shaped member formed in a size easily insertable into the subject 100 and provided with a dome-shaped member 10b attached to a front-end part of the casing body 240a. The float 242 is removably attached to a side wall of a rear-end part of the casing body 240a and a float linkage mechanism 243 is installed near a linking unit of the float 242. Further, other elements of the capsule endoscope 241 are placed at predetermined places in the casing body 240a.

The casing 240 provided with the casing body 240a and the dome-shaped member 10b has specific gravity greater than that of the liquid 2a and the center of gravity is placed at rear portion. Further, the casing 240 having the float 242 connected at the rear-end part thereof changes to have specific gravity smaller than that of the liquid 2a and displaces the center of gravity to the front portion. That is, the casing 240 having such a structure can change the condition of specific gravity from smaller to larger with respect to the specific gravity of the liquid 2a by attaching or removing the float 242 to or from the side wall of the rear-end part thereof. The center of gravity of the casing 240 displaces from the front portion to the rear portion according to the changes of the specific gravity.

The float 242 is a circular member including gas such as air and removably linked to the side wall of the rear-end part of the casing body 240*a* in a manner of putting the casing body 240*a* into a inner through hole. Concretely, the float 242 is removably linked to the side wall of the rear-end part of the casing body 240*a* by being supported by the float linkage mechanism 243 while putting the casing body 240*a* into the inner through hole. The float 242 change the specific gravity of the casing 240 smaller with respect to that of the liquid 2*a* and displaces the center of gravity of the casing 240 to the front portion by being linked to the casing body 240*a* in such manner.

The float linkage mechanism 243 is configured to connect the float 242 to the side wall of the rear-end part of the casing body 240*a*. Concretely, the float linkage mechanism 243 includes a linking member 243*a* for supporting the float 242 from inside of the casing body 240*a* and a drive unit 243*b* for driving the linking member 243*a*. The linking member 243*a* attaches and removes the float 242 by a reciprocating movement in the through hole formed at the rear-end part of the casing body 240*a*. That is, the linking member 243*a* supports the float 242 by being inserted through the through hole and projected from the side wall of the casing body 240*a* and releases linked condition of the float 242 by being accommodated in the through hole. The drive unit 243*b* operates the linking member 243*a* according to the control of the control unit 244. The float linking member 243 including the linking member 243*a* and the drive unit 243*b* functions as a specific gravity changing unit for changing the specific gravity of the casing 240 as described above by attaching or removing the float 242.

The control unit 244 is configured to control drives of each elements of the capsule endoscope 241. Concretely, the control unit 244 has the same function as the control unit 226 of the capsule endoscope 221, and further controls the drive of the drive unit 243*b* of the float linkage mechanism 243, in place of the drive unit 224*b* of the weight linkage mechanism 224. In this case, the control unit 244 controls the drive of the vibration motor 222 or the drive unit 243*b* based on the control signal received from the workstation 230 by a radio communication, similarly to the control unit 226. The control unit 244 changes the specific gravity of the capsule endoscope 241 from a smaller specific gravity to a larger specific gravity with respect to the specific gravity of the liquid 2*a* by changing the position and direction of the imaging field in the subject 100 by wobbling the casing 240 in the liquid 2*a*.

Figure 45:
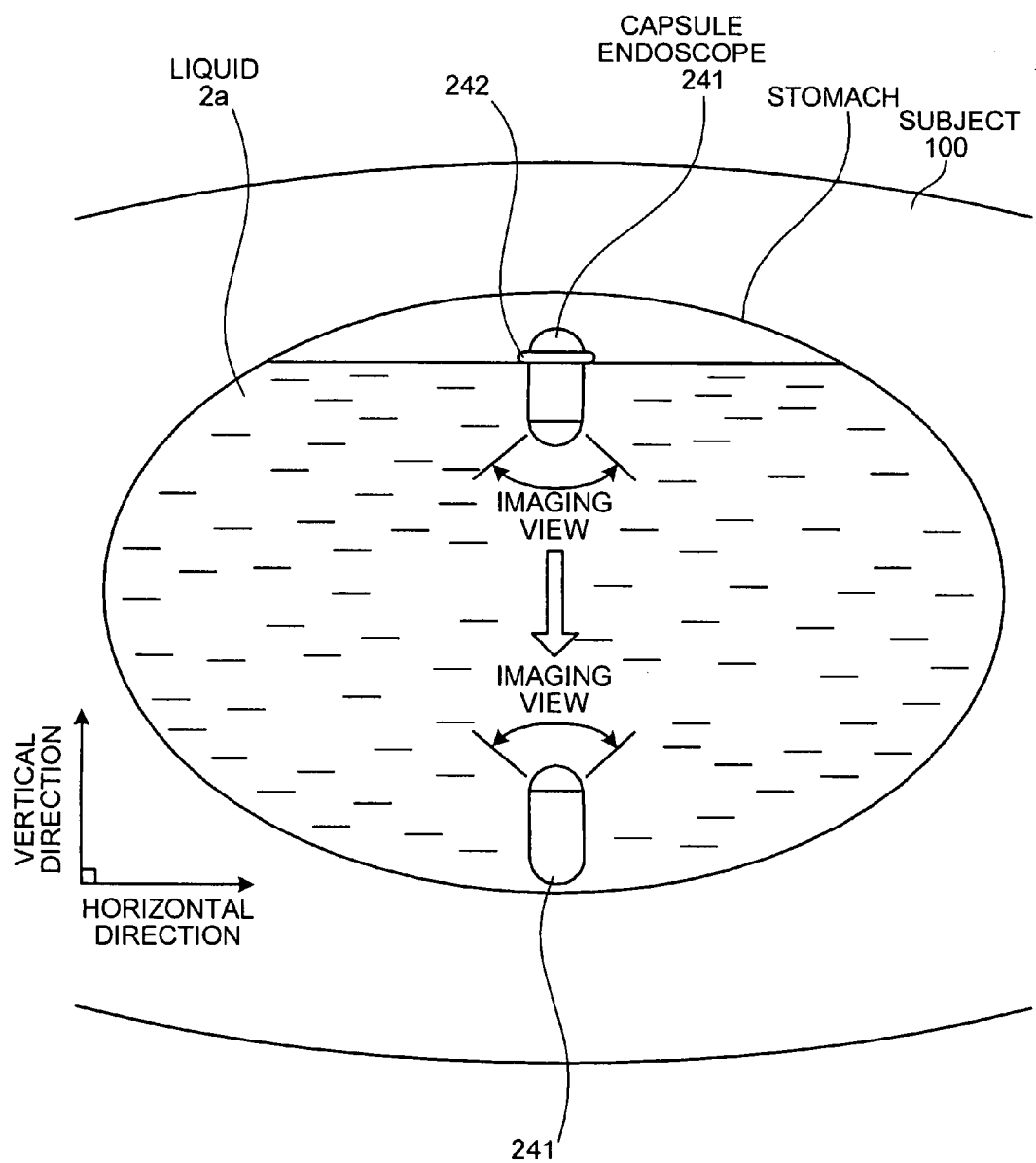
FIG. 45 is a schematic view showing an operation of the body-insertable device for reversing an imaging field in liquid by attaching or detaching a float.

With the body-insertable device system including the capsule endoscope 241 having such a structure, the examiner can observe every part in the desired digestive canal of the subject 100 such as stomach by following steps S401 to S407 in the same way as the above described fifth embodiment. In this case, as shown in FIG. 45, the capsule endoscope 241 floats in the liquid 2*a* introduced into the stomach, for example, and sequentially take images of the stomach wall while wobbling with the imaging field directed downward in the condition. After that, the capsule endoscope 241 releases the casing 240 from the float 242 and sinks to the bottom of the liquid 2*a* and sequentially take images in the stomach wall while wobbling the imaging field directed upward in the condition. Here, the specific gravity of the float 242 released from the capsule endoscope 241 is smaller than the specific gravity of the liquid. Further, desirably, the float 242 is provided in an opposite side of the imaging unit 12. With this, the imaging unit 12 can observe under the water. Further, the linking part of the float 242 and casing 240 may be made of a material that is resoluble in a human body. In this case, after a predetermined period of time has passed after a capsule endoscope having a resoluble linkage is introduced into a subject, the linkage resolves. As a result, the float 242 is released from the casing 240.

According to the above described capsule endoscope 241, the float 242 is linked to the side wall near the rear-end part of the casing body 240*a* with the float linkage mechanism 243; however, it should not be limited to this and the float 242 may be adhered to the side wall of the casing body 240*a* by an adhesive such as starch or gelatin. Such adhesive resolves by soaking in the liquid 2*a*, stomach fluid or the like for a predetermined period of time so that the float 242 can be removably attached to the side wall of the casing body 240*a*. Further, the float 242 may be made of a resoluble material such as gelatin that resolves by soaking in the liquid 2*a*, stomach fluid or the like for a predetermined period of time. The capsule endoscope 241 having such a structure loses the float 242 by being soaked the liquid 2*a*, stomach fluid or the like for a predetermined period of time and changes the specific gravity condition from a smaller specific gravity to a larger specific gravity with respect to the specific gravity of the liquid 2*a*.

Figure 46:
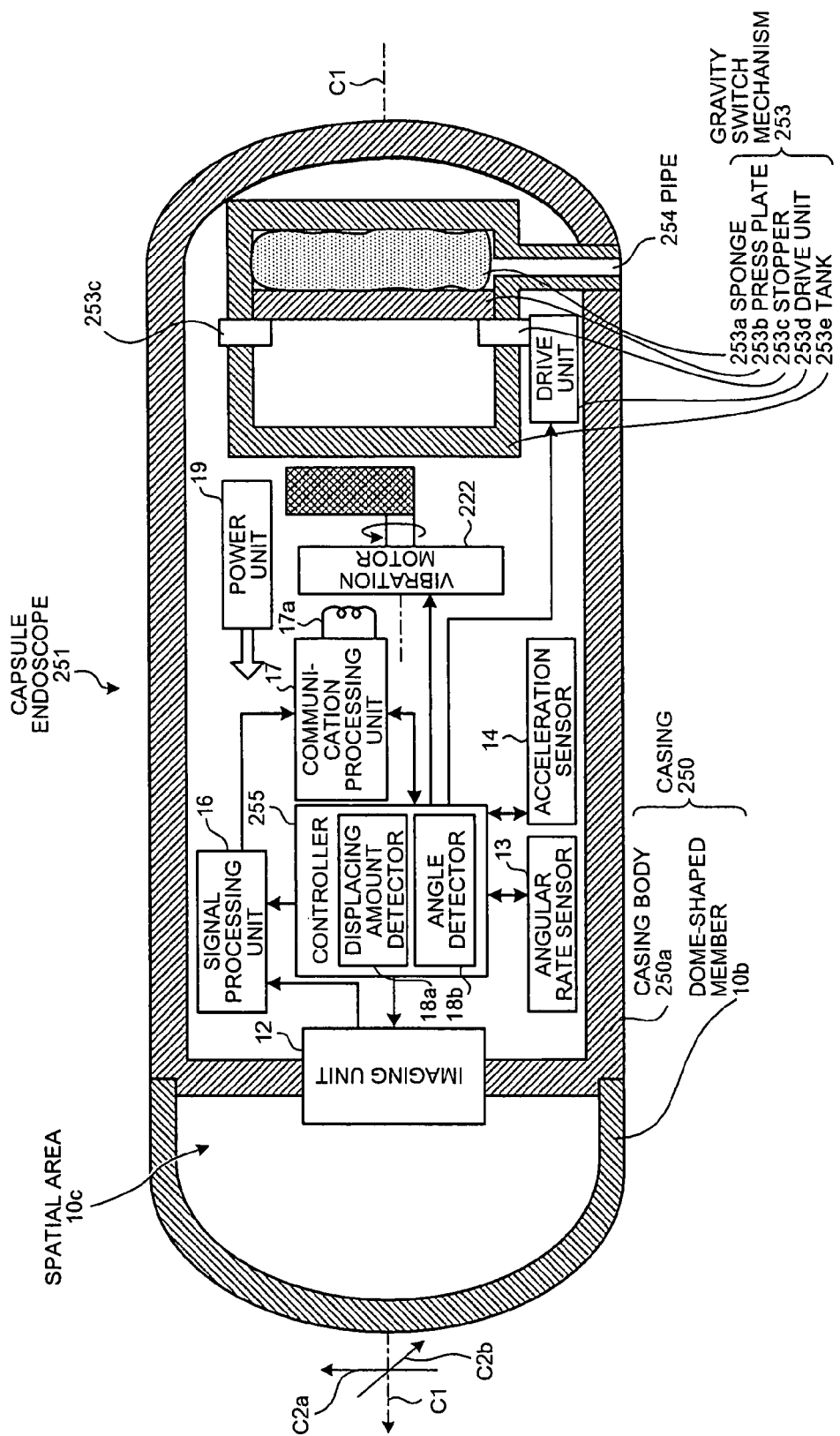
FIG. 46 is a schematic view showing a configuration example of a capsule endoscope as another aspect according to the first modification of the fifth embodiment of the present invention.

Further, the capsule endoscope according to the first modification of the fifth embodiment of the present invention should not be limited to the float 242 and may employ other specific gravity changing units for changing a smaller specific gravity to a larger specific gravity with respect to the specific gravity of the liquid 2*a*. FIG. 46 is a schematic view showing a configuration example of a capsule endoscope of another aspect of the first modification of the fifth embodiment of the present invention. Concretely, as shown in FIG. 46, a capsule endoscope 251 as anther aspect of the first modification of the fifth embodiment includes a casing 250, in place of the casing 240 of the capsule endoscope 241 and a specific gravity switch mechanism 253, in place of the float 242 and the float linkage mechanism 243, and a control unit 255, in place of the control unit 244. The casing 250 has a casing body 250*a* in place of the casing body 240*a* of the casing 240. Other elements are the same as the first modification of the fifth embodiment and the same elements are represented by the same reference numbers.

The casing 250 is a capsule-shaped member formed in a size easily insertable into the subject 100 and provided with a dome-shaped member 10*b* attached to a front-end part of the casing body 250*a*. The casing body 250*a* has the specific gravity switch mechanism 253 in the rear-end part and a pipe 254 for communicating the specific gravity switch mechanism 253 and the outside of the casing body 250 is formed near the specific gravity switch mechanism 253. Further, other elements of the capsule endoscope 251 are placed at predetermined positions in the casing body 250*a*.

The specific gravity switch mechanism 253 changes the specific gravity condition of the capsule endoscope 251 from a smaller specific gravity to a larger specific gravity with respect to the specific gravity of the liquid 2*a* by introducing the liquid 2*a*, for example. Concretely, the specific gravity switch mechanism 253 includes a sponge 253*a* for absorbing the liquid 2*a* or the like via the pipe 254, a press plate 253*b* for pressing the sponge 253*a*, a stopper 253*c* for stopping the movement of the press plate 253*b* pressing the sponge 253*a*, a drive unit 253*d* for drive of the stopper 253*c*, and a tank 253*e* containing the sponge 253*a* and the press plate 253*b*.

The tank 253*e* communicates with the outside of the casing body 250*a* via the pipe 254 of the casing body 250*a*. The sponge 253*a* is disposed near a communication unit of the tank 253e and the pipe 254. The press plate 253b presses the sponge 253a against the inner wall of the tank 253e to compress the sponge 253a. The sponge 253a compressed by the press plate 253b hardly absorbs the liquid 2a, for example. In this case, the tank 253e forms a spatial area in the opposite side of the sponge 253a via the press plate 253b therebetween. The tank 253e makes the specific gravity of the casing 250 smaller than the specific gravity of the liquid 2a and displaces the center of gravity of the casing 250 to the front portion.

On the other hand, when the drive unit 253d moves the stopper 253c and release the press plate 253b, the sponge 253a starts to expand and absorb the liquid 2a vie the pipe 254. In this case, the press plate 253b slides in the tank 253e according to the expansion of the sponge 253a to reduce the spatial area in the tank 253e. With the effect of the sponge 253a and the press unit 253b, the tank 253e reduces the spatial area and increases the area dominated by the sponge 253a for absorbing the liquid 2a. Such a tank 253e makes the specific gravity of the casing 250 greater than that of the liquid 2a and displaces the center of gravity of the casing 250 to the rear portion.

Here, when most part of the tank 253e is filled with the spatial area, the casing 250 has specific gravity smaller than that of the liquid 2a and the center of gravity is placed at the front portion. On the other hand, when most part of the tank 253e is filled with the sponge 253a, the casing 250 has specific gravity greater than that of the liquid 2a and the center of gravity is placed at the rear portion. In other words, with the effect of the specific gravity switch mechanism 253, the casing 250 changes its condition of specific gravity from a smaller specific gravity to a larger specific gravity with respect to the specific gravity of the liquid 2a and the position of the center of gravity is displaced from the front portion to the rear portion according to the change of specific gravity.

The control unit 255 is configured to control drives of each elements of the capsule endoscope 251. Concretely, the control unit 255 has the same function as the control unit 226 of the capsule endoscope 221 and further, controls the drive of the drive unit 253d of the specific gravity switch mechanism 253, in place of the drive unit 224b of the weight linkage mechanism 224. In this case, the control unit 255 controls the drive of the vibration motor 222 or the drive unit 253d based on the control signal received from the workstation 230 by a radio communication, similarly to the above described controller 226. The control unit 255 changes the position and direction of the imaging field in the subject 100 by wobbling the casing 250 in the liquid 2a and changes the specific gravity condition of the capsule endoscope 251 from a smaller specific gravity to a larger specific gravity with respect to the specific gravity of the liquid 2a.

Figure 47:
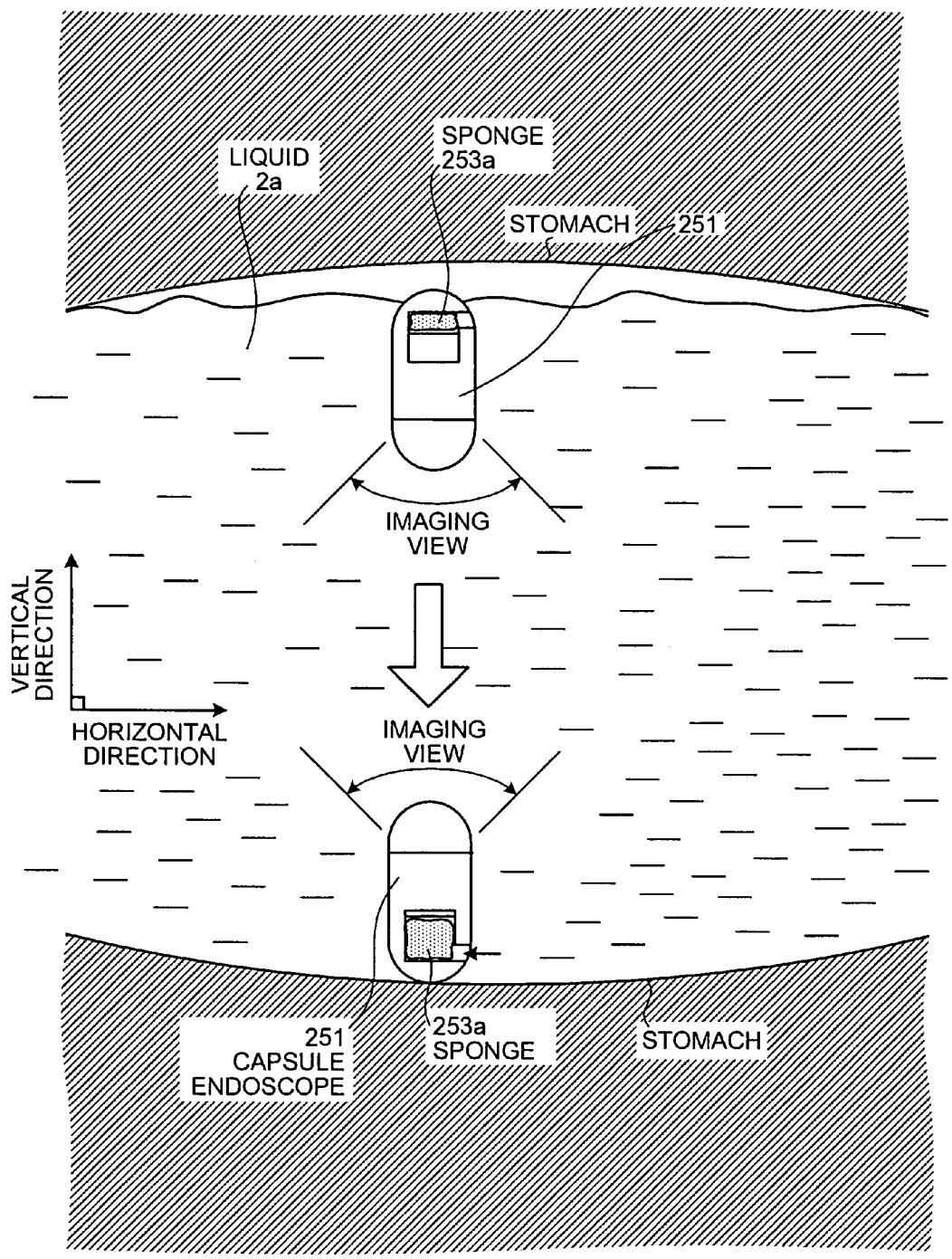
FIG. 47 is a schematic view sowing an operation of the body-insertable device for reversing an imaging field in liquid by absorption of water of a sponge.

With the body-insertable device system including such a capsule endoscope 251 having such a structure, the examiner can observe every part in the desired digestive canal of the subject 100 such as the stomach by following the procedure of steps S401 to S407, similarly to the case of the above described fifth embodiment. In this case, the capsule endoscope 251 floats, as shown in FIG. 47, in the surface of the liquid 2a introduced into the stomach, for example, and sequentially take images of stomach wall while wobbling the imaging field directed downward in the condition. Then, the capsule endoscope 251 make the sponge 253a absorbs the liquid 2a to sink to the bottom of the liquid 2a and sequentially take images of the stomach wall while wobbling the imaging field upward in the condition.

As described above, the first modification of the fifth embodiment of the present invention has the substantially same function as the fifth embodiment and the condition of specific gravity is changed from a smaller specific gravity to a greater specific gravity with respect to the specific gravity of the liquid introduced into the digestive canal. Accordingly, the same effect as the fifth embodiment can be provided.

Second Modification of Fifth Embodiment

A second modification to the fifth embodiment of the present invention will be described. According to the first modification of the fifth embodiment, the specific gravity condition of the capsule endoscope 251 is changed from a smaller specific gravity to a greater specific gravity with respect to the specific gravity of the liquid 2a. However, a body-insertable device system according to the second modification of the fifth embodiment includes a capsule endoscope for reversibly changing the specific gravity condition of the capsule endoscope 251 to a smaller specific gravity or a greater specific gravity, in place of the capsule endoscope 251.

Figure 48:
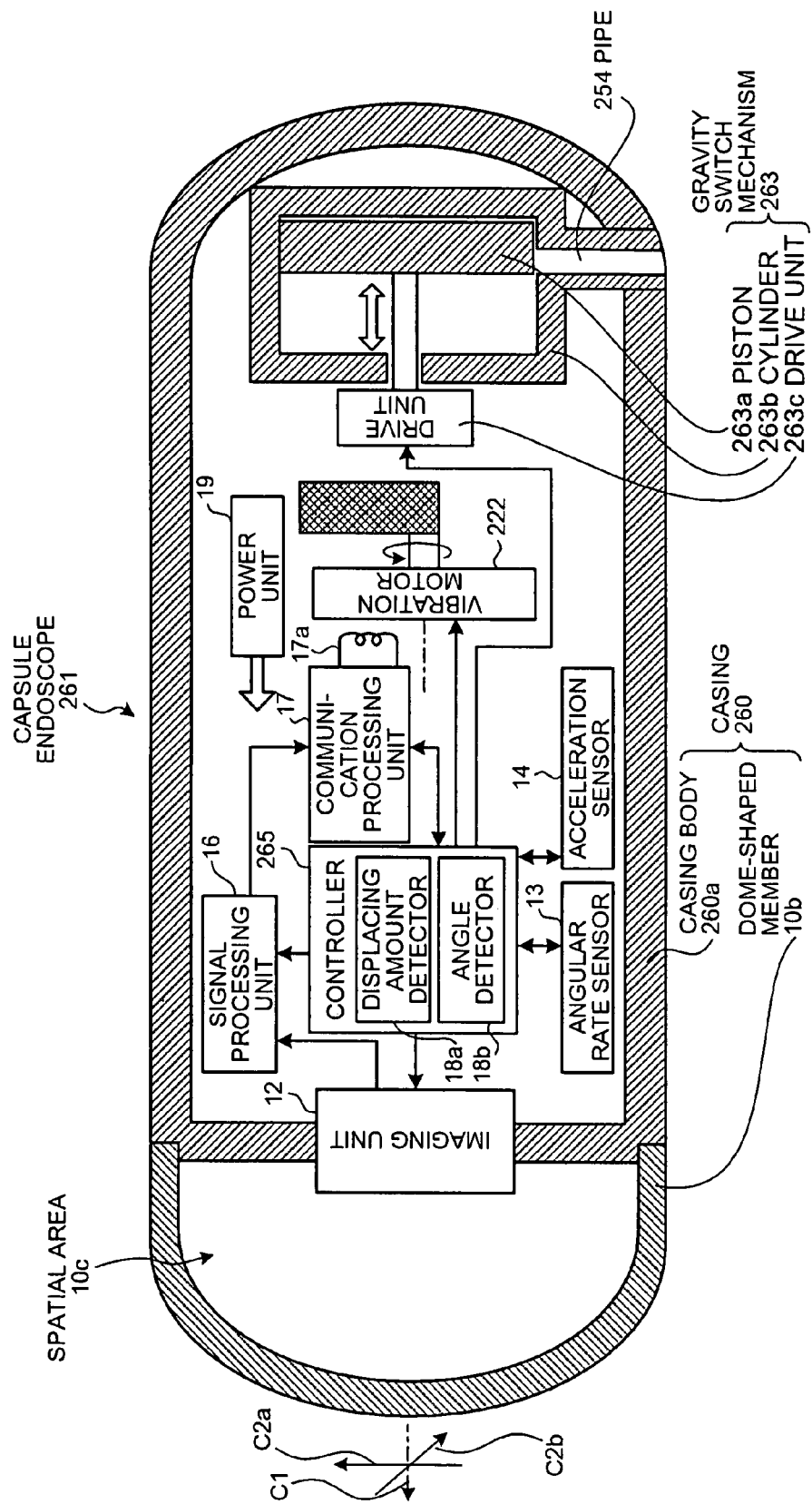
FIG. 48 is a schematic view of a configuration example of a body-insertable device according to a second modification of the fifth embodiment of the present invention.

FIG. 48 is a schematic view showing a configuration example of the body-insertable device according to the second modification of the fifth embodiment of the present invention. As shown in FIG. 48, a capsule endoscope 261, as an example of the body-insertable device, includes a casing 260, in place of the casing 250 of the capsule endoscope 251 as another aspect of the first modification of the fifth embodiment, a specific gravity switch mechanism 263, in place of the specific gravity switch mechanism 253, and a control unit 265, in place of the control unit 255. Further, the casing 260 has a casing body 260a, in place of the casing body 250a of the casing 250. Other elements are the same as those of the aspect of the first modification of the fifth embodiment and the same elements are represented by the same reference number.

The casing 260 is a capsule-shaped member formed in a size easily insertable into the subject 100 and provided with a dome-shaped member 10b attached to a front-end part of the casing body 260a. The casing body 260a includes a specific gravity switch mechanism 263 at the rear-end part and a pipe 264 for communicating the specific gravity switch mechanism 263 and the outside of the casing body 260a is formed near the specific gravity switch mechanism 263. Further, other elements of the capsule endoscope 261 are placed at predetermined positions in the casing body 260a.

The specific gravity switch mechanism 263 reversibly changes the specific gravity of the capsule endoscope 261 to a smaller or greater specific gravity with respect to the specific gravity of the liquid 2a by introducing and discharging the liquid 2a, for example. Concretely, the specific gravity switch mechanism 263 includes a piston 263a for introducing and discharging the liquid 2a or the like via the pipe 264, a cylinder 263b for storing the liquid 2a or forming spatial area according to the slide of the piston 263a, and a drive unit 263c for sliding the piston 263a in the cylinder 263b.

The cylinder 263b communicates with the outside of the casing body 260a via the pipe 264 of the casing body 260a. With the effect of the drive unit 263c, the piston 263a slides in the cylinder 263b, for example, in a longitudinal direction of the casing 260 to introduce or discharge the liquid 2a to and from between the cylinder 263b and the outside.

When the most part of the cylinder 263b is filled with the spatial area by the slide of the piston 263a, the casing 260 has specific gravity smaller than the specific gravity of the liquid 2a and the center of gravity is placed at a front portion. On the other hand, when most part the cylinder 263b is filled with the liquid 2a by the slide of the piston 263a, the casing 260 has specific gravity greater than the specific gravity of the liquid 2a and the center of gravity is placed at a rear portion. In other words, with the effect of the specific gravity switch mechanism 263, the condition of specific gravity the casing 260 changes from a smaller specific gravity to a greater specific gravity with respect to the liquid 2a and the center of gravity displaces from the front portion to the rear portion according to the change of the specific gravity. Further, with the effect of the specific gravity switch mechanism 263, the condition of specific gravity of the casing 260 changes from a greater specific gravity to a smaller specific gravity with respect to the specific gravity of the liquid 2a and the center of gravity changes front the rear portion to the front portion according to the change of specific gravity.

Figure 49:
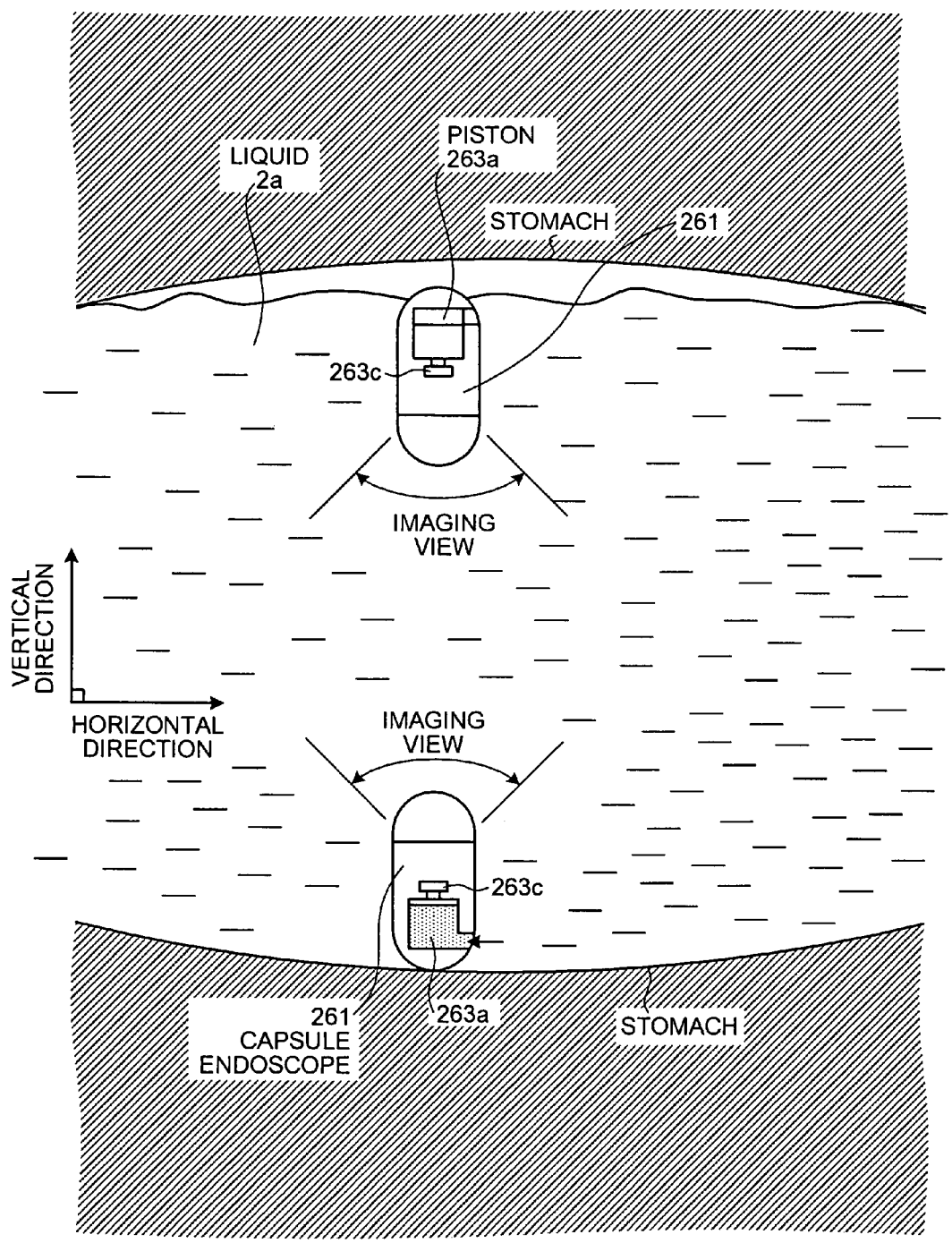
FIG. 49 is a schematic view of an operation of the body-insertable device for reversing an imaging field in liquid by introducing or discharging liquid.

The control unit 265 is configured to control the drives of the each element of the capsule endoscope 261. Concretely, the control unit 265 has the same function as the above described controller 255 of the capsule endoscope 251, and further, controls the drive of the drive unit 263c of the specific gravity switch mechanism 263, in place of the drive unit 253d of the specific gravity switch mechanism 253. In this case, the control unit 265 controls the drive of the vibration motor 222 or the drive unit 263c according to the control signal received from the workstation 230 by a radio communication, similarly to the above described controller 255. The control unit 265 changes the position and direction of the imaging field in the subject 100 while wobbling the casing 260 in the liquid 2a. Also, the control unit 265 reversibly changes the condition of the specific gravity of the capsule endoscope 261 from a smaller specific gravity to a greater specific gravity with respect to the specific gravity of the liquid 2a. With the body-insertable device system including the capsule endoscope 261 having such a structure, the examiner can observe every part in the desired digestive canal of the subject 100 such as the stomach, by following the procedure of steps S401 to S407 of the above described fifth embodiment. In this case, the capsule endoscope 261 floats at the surface of the liquid 2a introduced into the stomach, for example as shown in FIG. 49, and sequentially images the stomach wall while wobbling the imaging view being directed downward in the condition. Further, the capsule endoscope 261 sinks to the bottom of the liquid 2a by introducing the liquid 2a with the piston 263a and sequentially take images of the stomach wall while wobbling the imaging field directed upward in the condition. The capsule endoscope 261 can repeat this operation.

As described above, the second modification of the fifth embodiment of the present invention has the substantially same function as the first modification of the fifth embodiment and reversibly changes the condition of specific gravity of the casing from a smaller specific gravity or a larger specific gravity with respect to the specific gravity of the liquid introduced in the digestive canal. Accordingly, the same effect as the first embodiment of the fifth embodiment can be provided and the images in the digestive canal are taken more certainly so that the facility of observing inside the digestive canal can be improved.

Sixth Embodiment

A sixth embodiment of the present invention will be described. According to the fifth embodiment, the position and direction of the imaging field are changed by wobbling the capsule endoscope with a vibration motor. However, in the body-insertable device system according to the sixth embodiment, the position and direction of the imaging field is changed in a horizontal direction by propelling the capsule endoscope that floats in the surface of the liquid.

Figure 50:
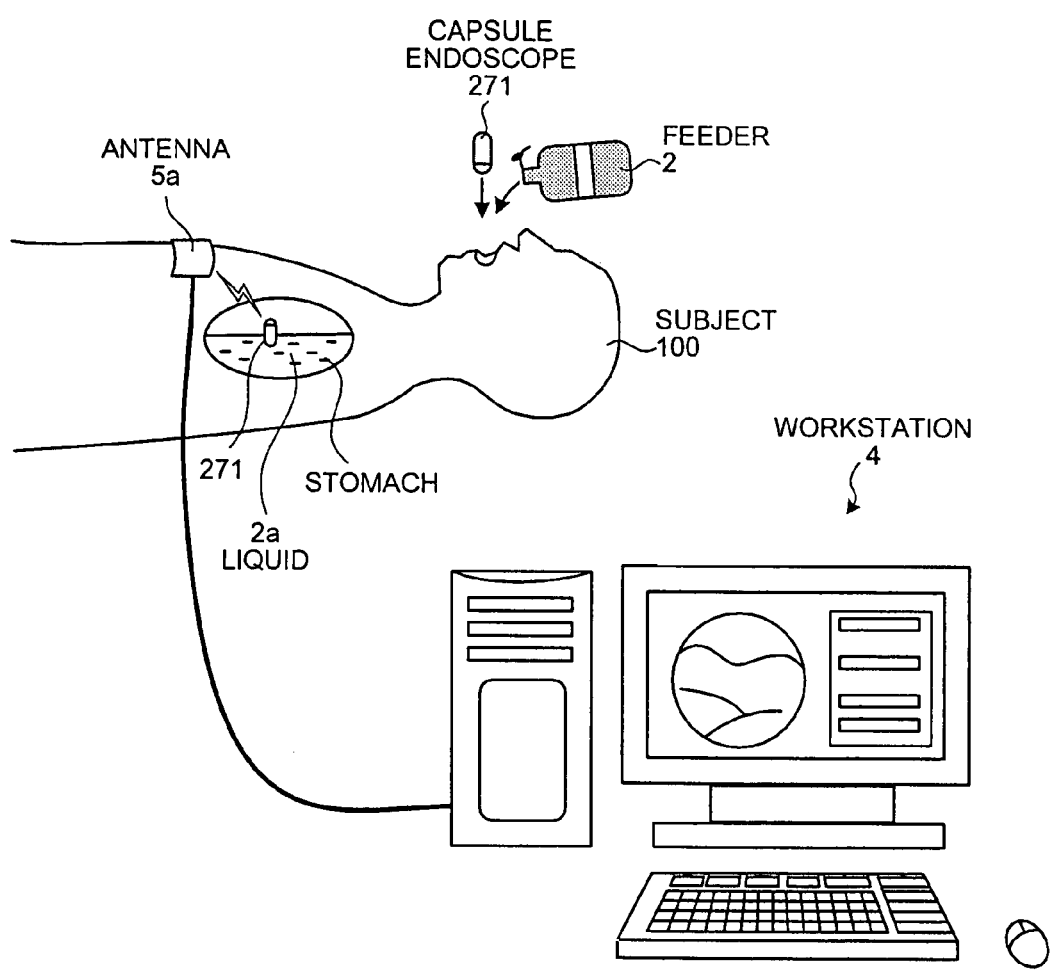
FIG. 50 is a schematic view showing a configuration example of a body-insertable device system according to a sixth embodiment of the present invention.

FIG. 50 is a schematic diagram showing a configuration example of the body-insertable device system according to the sixth embodiment of the present invention. As shown in FIG. 50, the body-insertable device system according to the sixth embodiment includes a capsule endoscope 271, in place of the capsule endoscope 221 of the body-insertable device system in the fifth embodiment and a workstation 280, in place of the workstation 230. Other elements are the same as those of the fifth embodiment and the same elements are represented by the reference numbers.

The capsule endoscope 271 has the same imaging function and radio communication function as the capsule endoscope 221 of the fifth embodiment, and further, has a function for floating at the surface of the liquid 2a and propelling in a horizontal direction. In this case, the capsule endoscope 271 is propelled in the liquid 2a based on a control signal from the workstation 280 to change the position and direction of the imaging field of the subject 100.

The workstation 280 has the substantially same function as the workstation 230 in the fifth embodiment. In this case, the workstation 280 has drive control function for controlling propelling operation of a capsule endoscope 271, in place of the specific gravity switch instruction function and vibration instruction function of the workstation 230. Concretely, the workstation 280 sends a control signal to the capsule endoscope 271 via an antenna 5a to propel the capsule endoscope 271 in the liquid 2a based on the control signal.

Figure 51:
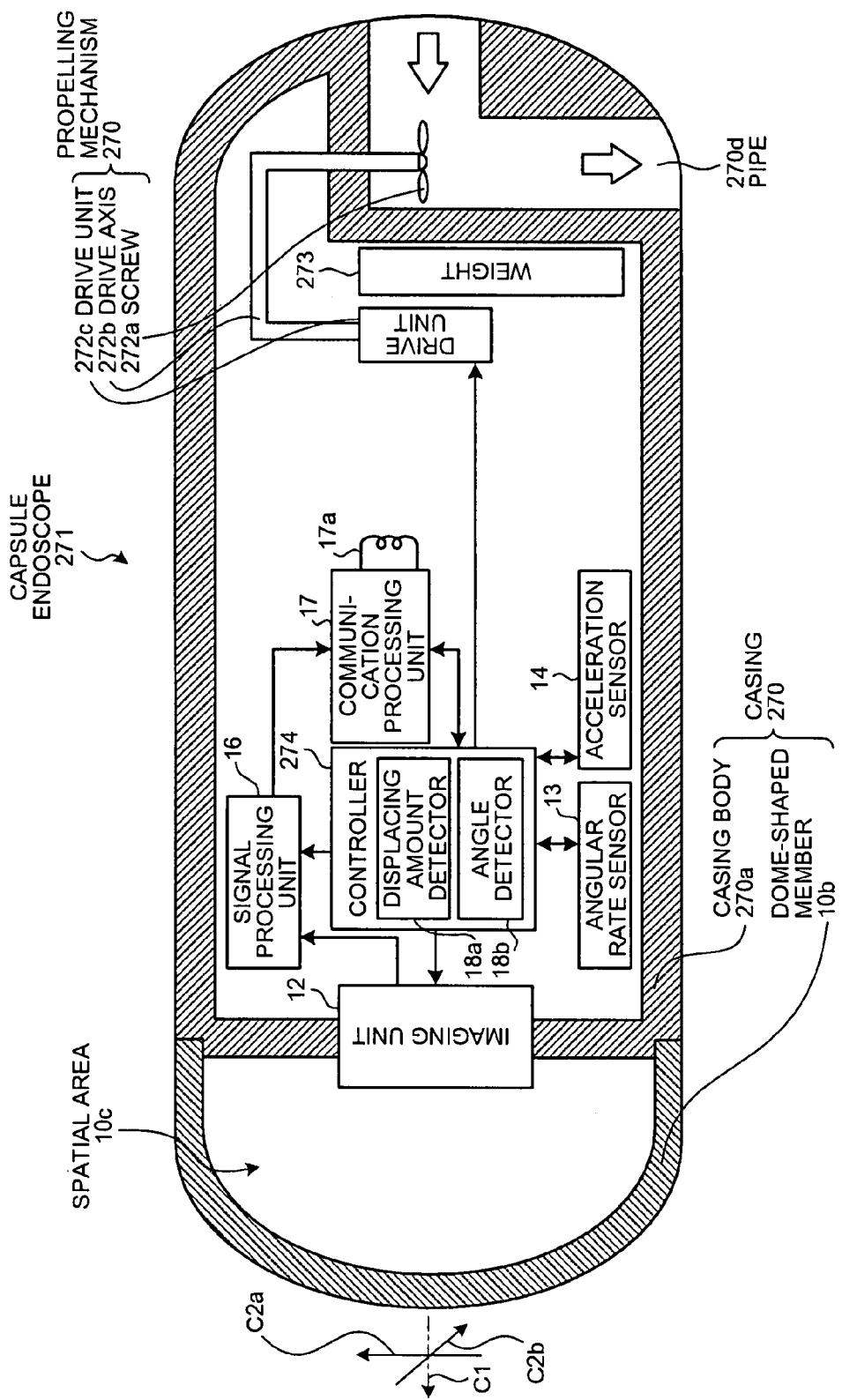
FIG. 51 is a schematic view showing a specific example of the body-insertable device according to the sixth embodiment of the present invention.

Next, a structure of the capsule endoscope 271 will be described. FIG. 51 is a schematic view showing an illustrative example of the body-insertable device according to the sixth embodiment of the present invention. As shown in FIG. 51, a capsule endoscope 271, as an example of the body-insertable device, includes a casing 270, in place of the casing 220 of the capsule endoscope 221 of the fifth embodiment, a propelling mechanism 272, in place of the vibration motor 222, a weight 273, in place of the weight 223, and a control unit 274, in place of the control unit 226. In this case, the casing 270 includes a casing body 270a, in place of the casing body 220a of the casing 220. Other elements are the same as the first embodiment and the same elements are represented by the same reference numbers.

The casing 270 is a capsule-shaped member formed in a size easily insertable into the subject 100 and provided with a dome-shaped member 10b attached to a front-end part of the casing body 270a. The weight 273 is fixed to a rear-end part of the casing body 270a. On the other hand, other elements of the capsule endoscope 271 are placed at predetermined position in the casing body 270a. The casing 270 provided with such casing body 270a and dome-shaped member 10b has specific gravity smaller than the specific gravity of the liquid 2a and the center of gravity is placed at a rear portion.

The propelling mechanism 272 is configured to horizontally propel the capsule endoscope 271 in the liquid 2a. Concretely, the propelling mechanism 272 includes a screw 272a for rotating in the liquid 2a to generate a propelling power, a drive shaft 272b for rotatably supporting the screw 272a, and a drive unit 272c for rotating the screw 272a via the drive shaft 272b. In this case, the screw 272a is disposed in the pipe 270d formed near the rear-end part of the casing body 270a. The pipe 270d passes the liquid 2a therethrough when propelling the casing 270 in the liquid 2a by the rotation of the screw 272a. According to the control of the control unit 274, the drive unit 272c rotates the screw 272a to propel the casing 270 in the liquid 2a to change the position and direction of the imaging field in the digestive canal.

The control unit 274 is configured to control the drive of each elements of the capsule endoscope 271. Concretely, the control unit 274 has the same function as the control unit 226 of the capsule endoscope 221, and further, controls the drive of the drive unit 272c of the propelling mechanism 272, in place of the drive unit 224b of the vibration motor 222. In this case, the control unit 271 performs radio communications with the workstation 280, controls the drive of the drive unit 272c based on the control signal input from the communication processing unit 17 and received from the workstation 280, and propels the casing 270 in the liquid 2a to change the position and direction of the imaging field in the subject 100.

Figure 52:
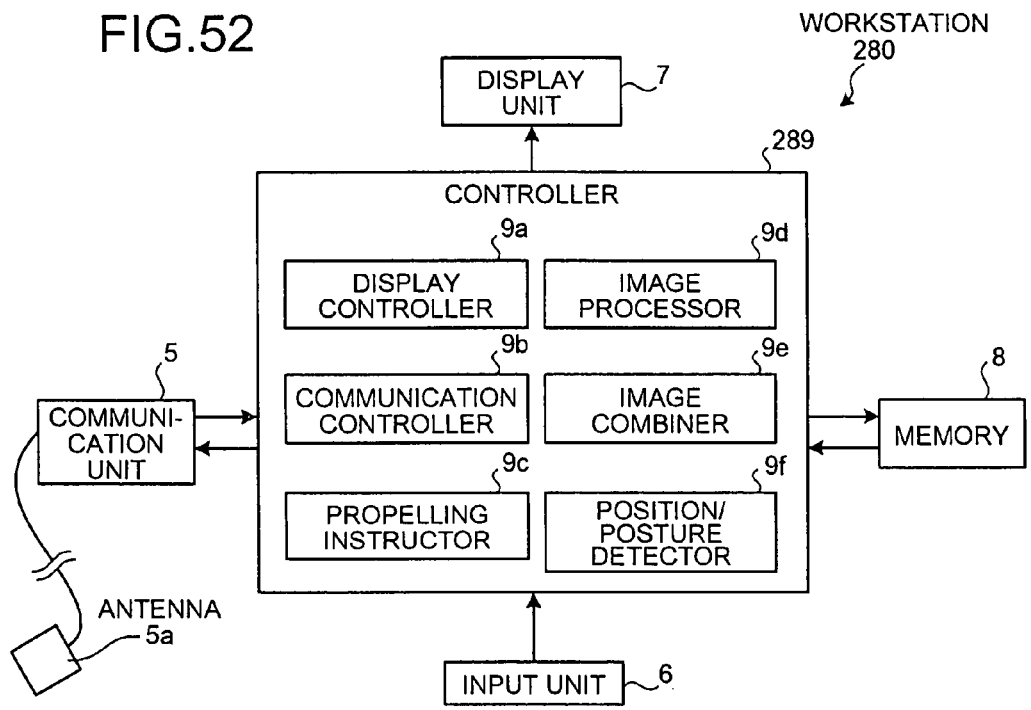
FIG. 52 is a block diagram schematically showing a configuration example of a workstation according to the sixth embodiment.

Next, a structure of the workstation 280 will be explained. FIG. 52 is a block diagram schematically showing a configuration example of the workstation 280. As shown in FIG. 52, the workstation 280 includes a control unit 289, in place of the control unit 239 of the workstation 230. The control unit 289 includes a propelling instructor 289h, in place of the specific gravity switching instruction unit 239h and the operation instruction unit 239i of the above described controller 239. Other elements are same as those of the fifth embodiment and the same elements are represented by the same reference numbers.

The control unit 289 has the substantially same function as the control unit 239 of the above described workstation 230. In this case, the control unit 289 includes a drive control function for starting or stopping to propel the capsule endoscope 271 in the liquid 2a, in place of the above described specific gravity switch instructing function and the vibration instructing function. Concretely, the propelling instructor 289h generates a control signal for starting or stopping to propel the capsule endoscope 221 in the liquid 2a according to the instruction information input by the input unit 6. The control signal generated by the propelling instructor 289h is sent by radio to the capsule endoscope 271 via the communication unit 5 or the like.

Figure 53:
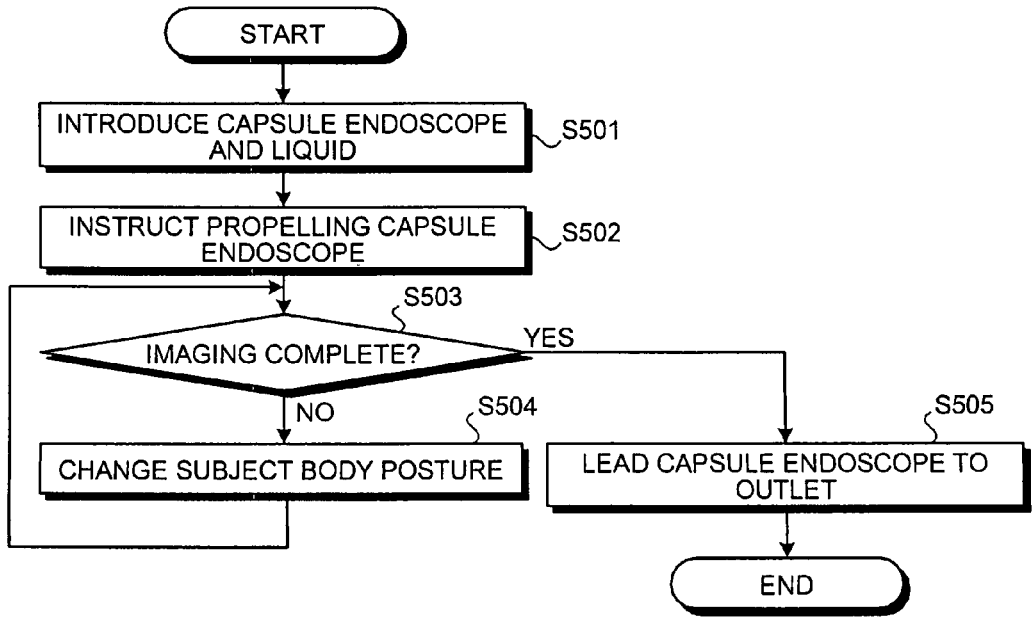
FIG. 53 is a flow chart showing a procedure for observing an inside of digestive canal of a subject with an image inside the digestive canal by the body-insertable device according to the sixth embodiment.
Figure 54:
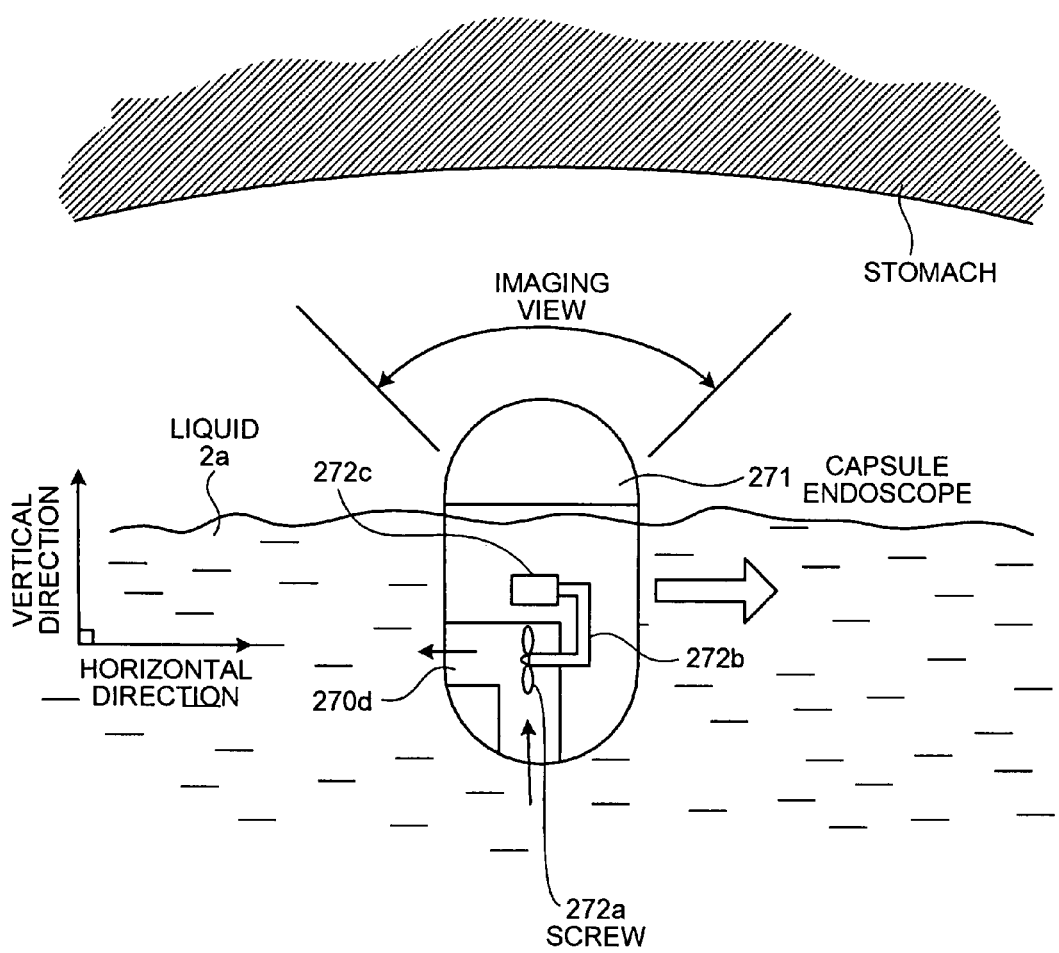
FIG. 54 is a schematic view showing an operation of the body-insertable device for changing a position or direction of an imaging field by moving a casing forwardly in liquid.

Next, a procedure of observing the digestive canal of the subject (for example, inside of the stomach) with an image taken by the capsule endoscope 271 will be described. FIG. 53 is a flowchart showing a procedure of observing the digestive canal of the subject 100 with an image in the digestive canal taken by the capsule endoscope 271 introduced in the subject 100. FIG. 54 is a schematic view showing an operation of the capsule endoscope 271 for propelling the casing 270 in the liquid 2a to change the position and direction of the imaging field.

As shown in FIG. 53, firstly the examiner starts an imaging operation of the capsule endoscope 271 by the workstation 280 or predetermined starter, introduces the capsule endoscope 271 into the subject 100, and introduces the liquid 2a with the use of the feeder 2 into the subject 100 (step S501). In this case, the capsule endoscope 221 and the liquid 2a are swallowed through the mouth of the subject 100, for example, and reach to a desired digestive canal in subject 100. The examiner operates workstation 280 for showing an image taken by the capsule endoscope 271 and finds the position of the capsule endoscope 271 in the subject 100 by seeing the image. The examiner may operate the workstation 280 to start the imaging operation of the capsule endoscope 271 after the capsule endoscope 271 is introduced into the subject.

Then, the examiner operates the input unit of the workstation 280 and instructs an operation of the capsule endoscope 271 (step S502). In this case, the control unit 289 receives instruction information for starting propelling operation of the capsule endoscope 271 from the input unit 6. The propelling instructor 289h generates a control signal that instructs to start propelling based on the instruction information. The control signal generated in this way is sent to the capsule endoscope 271 by a radio communication drive of the communication unit 5. In this case, the control unit 274 of the capsule endoscope 271 starts the drive of the drive unit 272c of the propelling mechanism 272 based on the control signal from the workstation 280 to propel the casing 270 in the liquid 2a. As shown in FIG. 54, such a capsule endoscope 271 is propelled while floating at the surface of the liquid 2a with the imaging field directed upward in the condition. With this, the capsule endoscope 271 sequentially takes images in the digestive canal while changing the position and direction of the imaging field.

When the body posture of the subject 100 is changed to another body posture and imaging of the digestive canal as an observed region is continued (step S503, No), the examiner changes the current body posture of the subject 100 (for example, a supine position) to another desired body posture (for example, a right lateral supine position) (step S504). Then, the examiner repeats the above described procedure subsequent to step S503.

The examiner may implement the procedure of steps S102 and S103 after step S501, similarly to the first embodiment. With this, for example, the stomach can be extended with the foaming agent. Further, the examiner may additionally introduce the liquid 2a after the procedure of step S502. With this, the capsule endoscope 271 can be vertically displaced, similarly to the above described first embodiment.

Since at least one of the position and posture of the capsule endoscope 271 in the digestive canal as an observed region is changed, the capsule endoscope 271 can take images of substantially entire area in the digestive canal. The examiner can observe every part of the desired digestive canal as an observed region of the subject 100 by displaying the images taken by the capsule endoscope 271 on the workstation 280.

Then, when the observation of the digestive canal as an observed region is completed and imaging in the digestive canal is to be ended (step S503, Yes), the examiner leads the capsule endoscope 271 to the outlet port of the digestive canal (step S505). In this case, the capsule endoscope 271 is led to the outlet port by peristalsis of the digestive canal or the flow of the liquid 2a and moves into the following digestive canal. With this, the capsule endoscope 271 completes imaging the digestive canal as an observed region. Then, the capsule endoscope 271 takes images in the digestive canals while being moved in the subject 100 by peristalsis of each digestive canal or the flow of the liquid 2a and is discharged to the outside of the subject 100.

The examiner can observe each digestive canal of the subject 100 by displaying the images taken by the capsule endoscope 271 on the workstation 280. On the other hand, the examiner may operates the workstation 280 and send a control signal for stopping the imaging operation to stop the imaging operation of the capsule endoscope 271 that has completed to image the desired observed region. Further, the examiner may operate the workstation 280 and send a control signal for stopping the propelling operation to stop the propelling operation of the capsule endoscope 271 that has completed to image the desired observed region.

Figure 55:
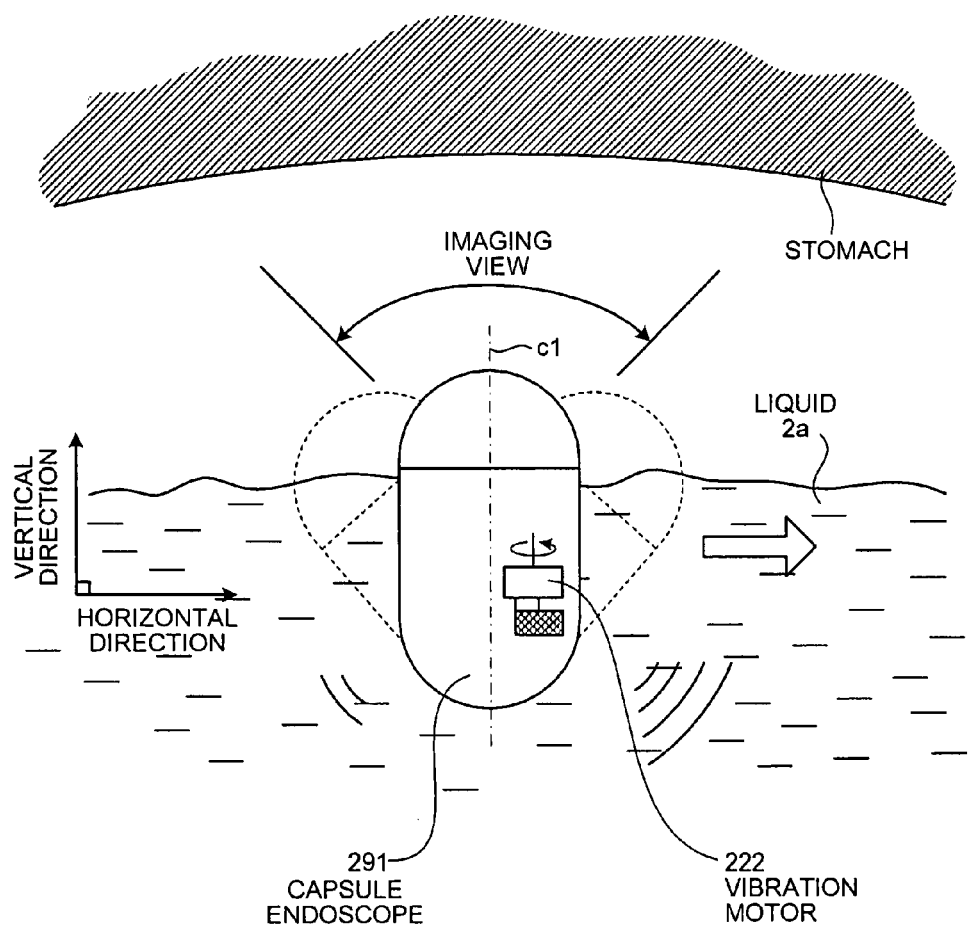
FIG. 55 is a schematic view showing an operation of a body-insertable device of another first aspect according to the sixth embodiment.
Figure 56:
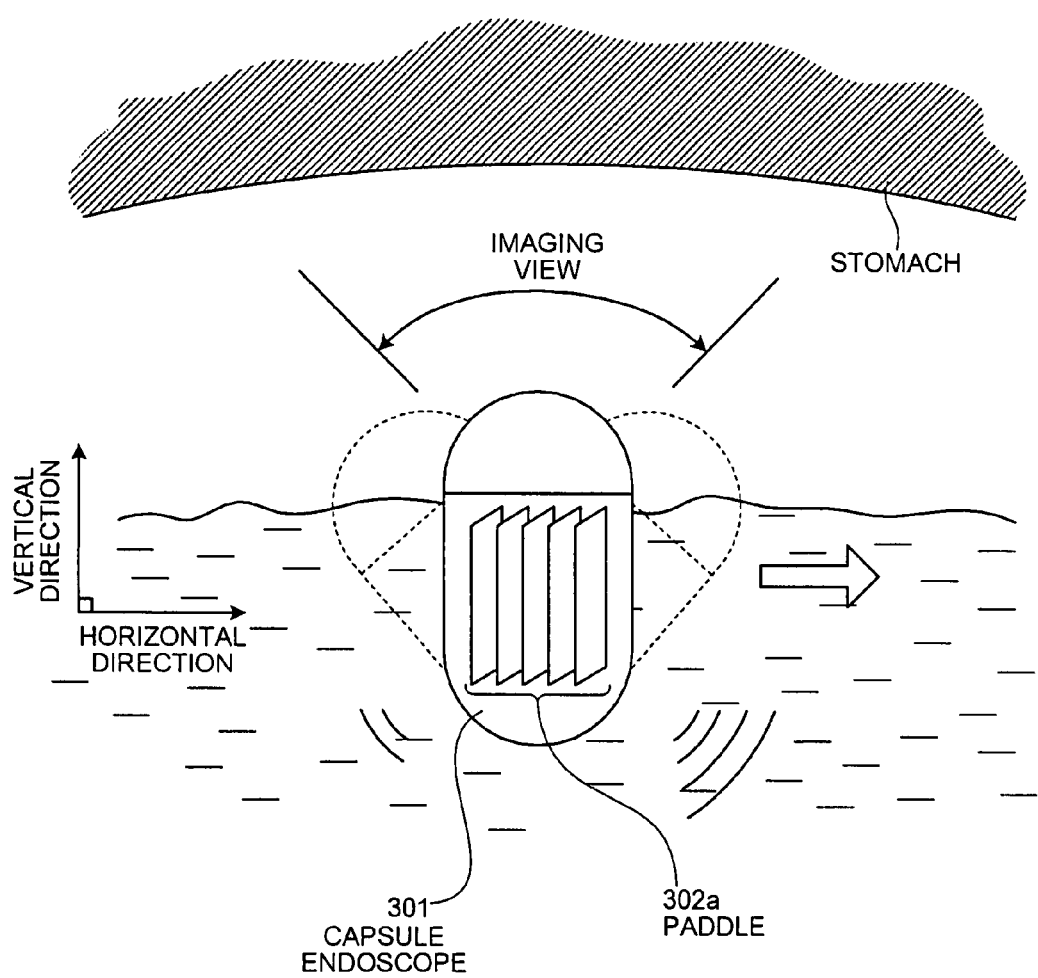
FIG. 56 is a schematic view showing an operation of a body-insertable device of another second aspect according to the sixth embodiment.
Figure 57:
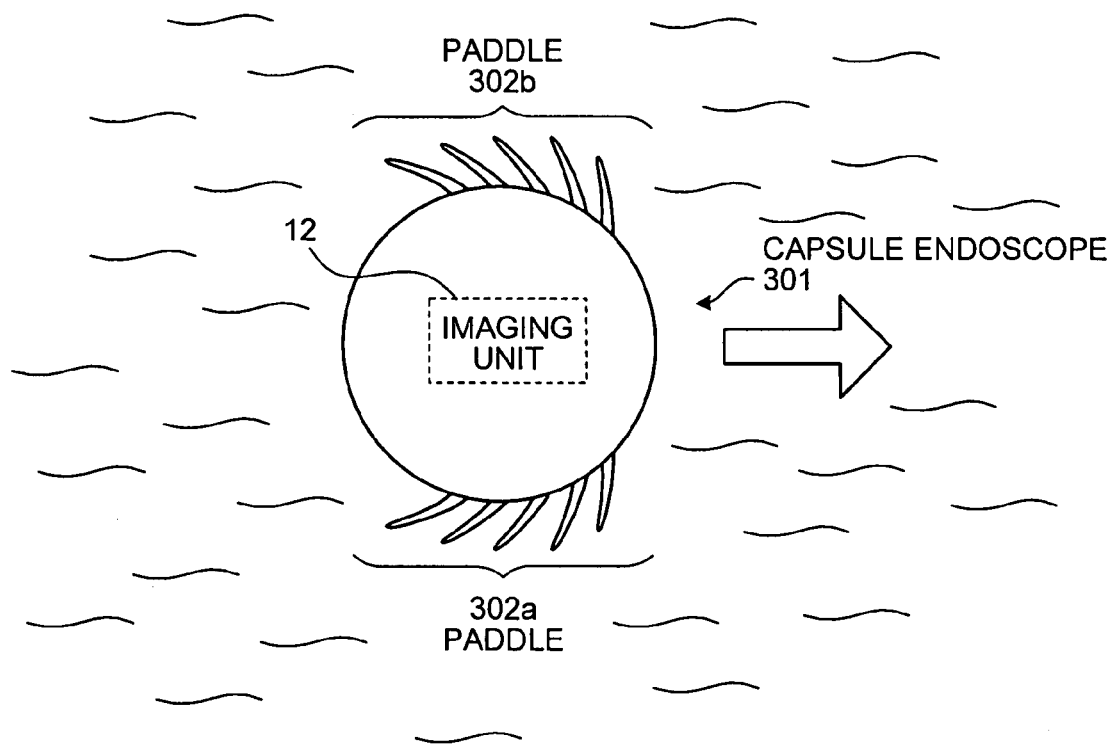
FIG. 57 is a schematic view exemplifying the body-insertable device of FIG. 56 as seen from the above.

The capsule endoscope of the sixth embodiment of the present invention propels in the liquid 2a by the propelling power obtained by the rotation of the screw 272a; however, it should not be limited to this, and the capsule endoscope may be propelled with use of the vibration of the casing in the liquid 2a. Concretely, for example, as shown in FIG. 55, the capsule endoscope 291 may include vibration motor 222 in the casing in a manner of displacing the drive axis with respect to the major axis C1 of the casing. Such capsule endoscope 291 disproportionately vibrates the casing by the drive of the vibration motor 222 so that the capsule endoscope 291 is propelled in the liquid 2a due to the disproportional vibration of the casing. Further, for example, as shown in FIGS. 56 and 57, a capsule endoscope 301 having fin-shaped paddles 302a, 302b on the outside wall of the casing in which the vibration motor is disposed may be employed. Such capsule endoscope 301 can be propelled while wobbling in the liquid 2a by the effect of the paddles 302a, 302b, since the vibration of the casing made by the drive of the vibration motor lets the paddles 302a, 302b paddle the liquid 2a.

As described above, in the sixth embodiment of the present invention an imaging unit for imaging inside view of the digestive canal of the subject is fixed inside the casing, a motor for generating propelling power for the casing in the liquid is disposed in the casing, and the motor drive propels the casing in the liquid so that the position and direction of the imaging field can be changed. A vibration motor is disposed in the casing and fin-shaped paddles are disposed outside wall of the casing. With this structure, the vibration motor vibrates the casing and the paddles work as if paddling the liquid so as to propel the casing in the liquid and this changes the position and direction of the imaging field. Accordingly, the position and direction of the imaging field can be easily changed in the liquid introduced in the digestive canal so that the body-insertable device and the body-insertable device system which provide the same effect as above described first embodiment can be easily obtained.

The specific gravity switching function described as a capsule endoscope in the fifth embodiment may be applied not only to capsule endoscopes including a vibration motor or a propelling mechanism in a casing thereof but also to capsule endoscope whose movements in liquid are controlled by magnetic force described in the first to fourth embodiments.

Further, according to the all embodiments and each modifications of the present invention, an acceleration sensor or an angular rate sensor installed in a capsule endoscope are employed in order to detect the position and posture of the capsule endoscope in the subject; however, it should not be limited to this, and a capsule endoscope may include a distance sensor therein in order to detect the position and posture by the distance sensor. That is, an optical or ultrasonic distance sensor may be installed in the capsule endoscope to detect distance from the stomach wall, for example and based on the detected distance information, variations in sizes of a plurality of images in sizes due to the distance are corrected so that the images can be combined.

Figure 58:
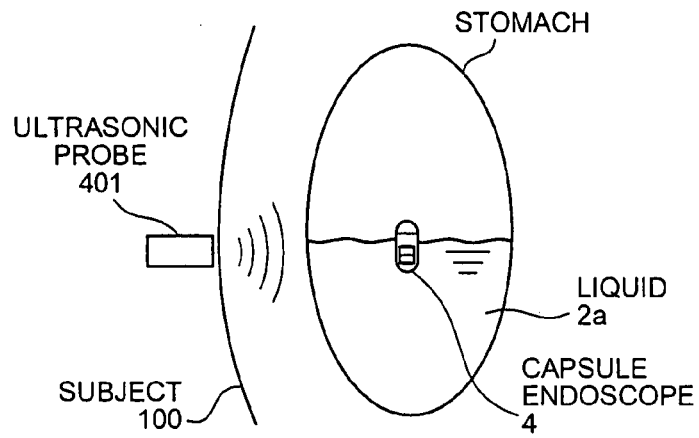
FIG. 58 is a schematic view showing a configuration example of an ultrasonic position detector.
Figure 59:
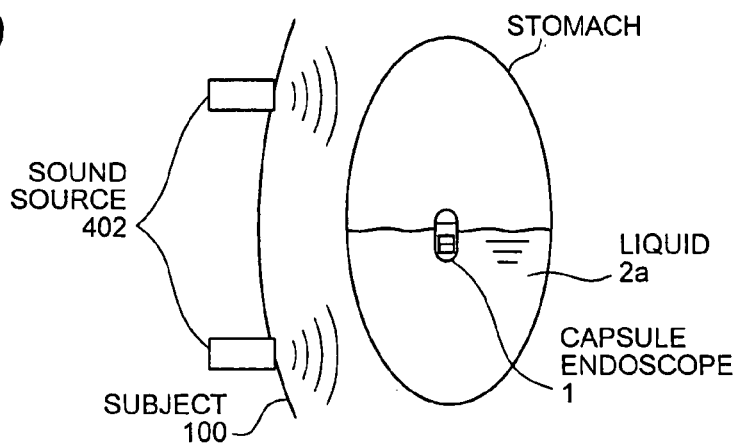
FIG. 59 is a schematic view showing a configuration example of a sonic position detector.
Figure 60:
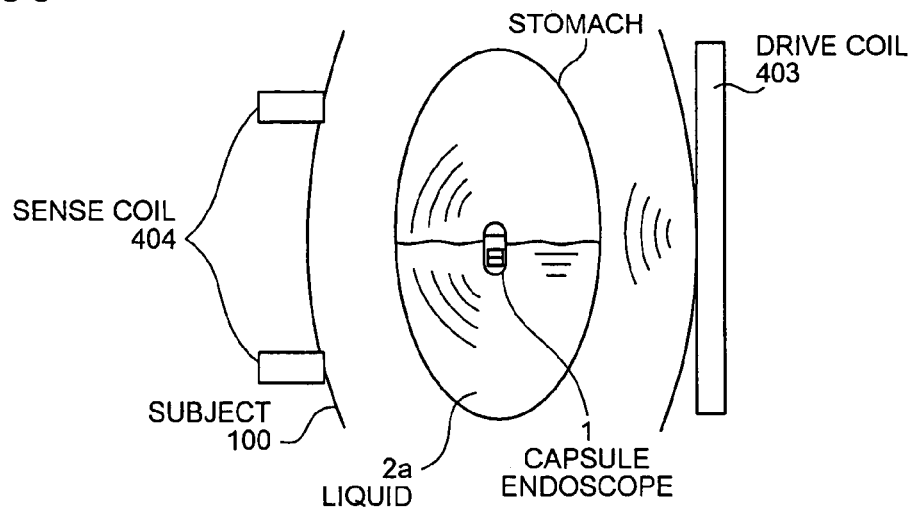
FIG. 60 is a schematic view showing a configuration example of a magnetic position detector.

Further, the position detector for detecting the position and posture of the capsule endoscope is not limited to an installed type and may be disposed outside the subject 100. FIGS. 58 to 60 are schematic views showing configuration examples of a position detector disposed outside the subject 100. FIG. 58 shows a ultrasonic position detector for detecting the position of the capsule endoscope 1 with use of cross-sectional image detection by an ultrasonic probe 401, for example. Since the stomach of the subject 100 contains liquid 2a, it helps to transmit ultrasonic wave from the ultrasonic probe 401 so that the position of the capsule endoscope 1 in the stomach can be detected from its cross-sectional images. Since the distance between the stomach wall and the capsule endoscope 1 can be detected by using ultrasonic wave, such information is useful for combining a plurality of images.

FIG. 59 shows a sonic position detector. Here, for example, a lavalier microphone is installed in the capsule endoscope 1 and sound sources 402 are disposed at a plurality of places outside the subject 100. Based on the strength of sound detected by the lavalier microphone in the capsule endoscope 1, distance from the sound sources 402 at the plurality of places is calculated and the position of the capsule endoscope 1 can be detected by the calculated distance.

FIG. 60 shows a magnetic position detector. Here, for example, an inductive coil is installed in the capsule endoscope 1 and a drive coil 403 is disposed outside the subject 100 to apply its magnetic field to the inductive coil. An inductive magnetic field is generated by a resonance system of the inductive coil in the capsule endoscope 1 and a condenser, and the position of the capsule endoscope 1 can be detected by detecting the strength of the inductive magnetic field by the sense coil 404 disposed outside the subject 100. In this case of the capsule endoscope 1, an inductive magnetic field is generated by the magnetic field from the drive coil 403 disposed outside the subject 100 and power of the capsule endoscope 1 is not used so that it is effective for energy saving. Further, a magnetic field generator may be provided in the capsule endoscope 1 and a magnetic field detector may be provided outside the subject 100. With this structure, a magnetic field detector such as an MI element can be disposed outside the subject 100 so that a large supersensitive detector may be employed. Further, in contrast, a magnetic field may be generated outside the subject 100 and the magnetic field may be detected on the side of the capsule endoscope 1. With this structure, energy consumption in the capsule endoscope 1 can be made smaller than the case of providing a magnetic field generator in the capsule endoscope 1.

According to all embodiments and each of modifications of the present invention, a permanent magnet as a driver for varying at least one of the position and posture of the casing of the capsule endoscope is disposed inside the casing; however, it should not be limited to this and a capsule endoscope with a permanent magnet selected according to a body type of the patient may be employed.

Figure 61:
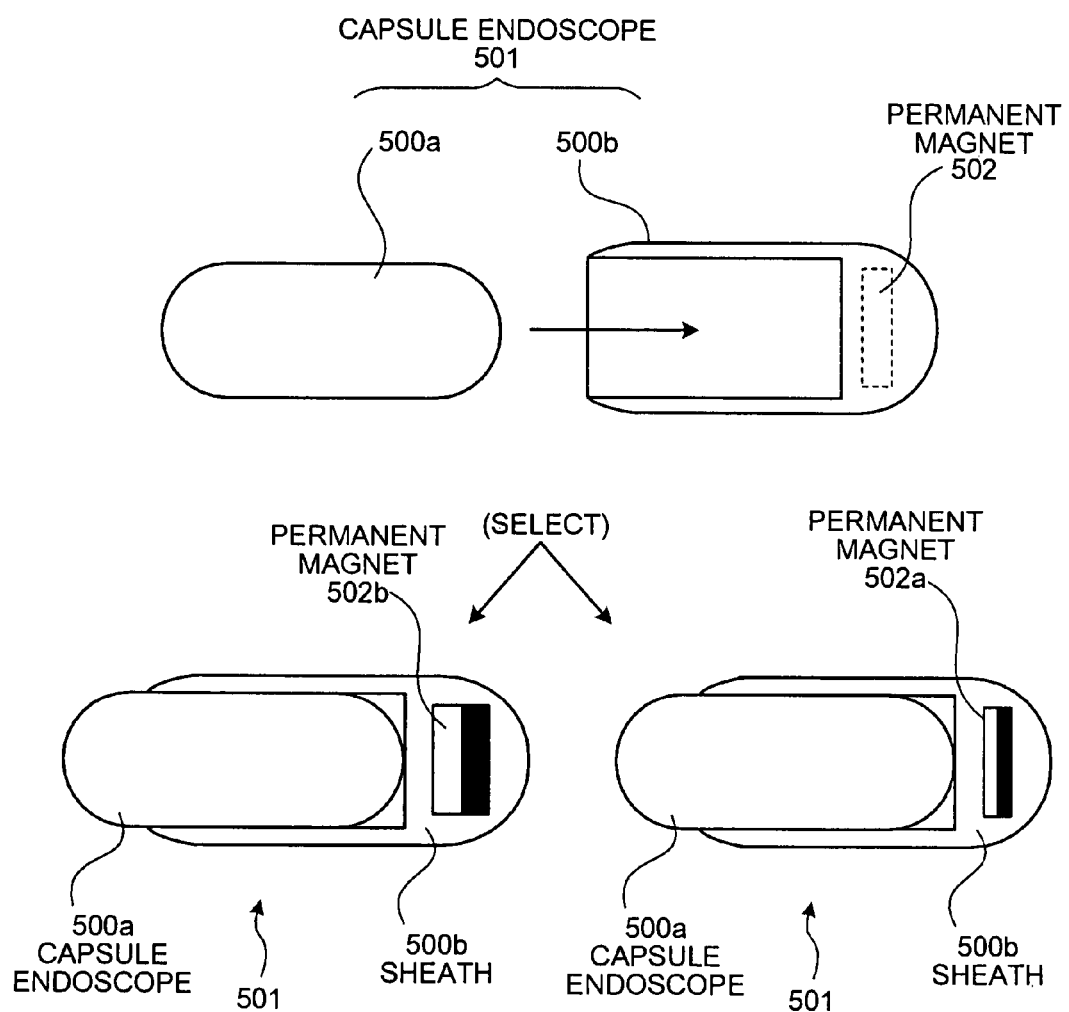
FIG. 61 is a schematic view showing a configuration example of a capsule endoscope in which a permanent magnet is removable from a casing.

FIG. 61 shows a schematic diagram showing a configuration example of a capsule endoscope in which a permanent magnet is removably attached to the casing. As shown in FIG. 61, the capsule endoscope 501 is formed by removably covering a capsule body 500a with a sheath 500b in which a permanent magnet 502 is installed. The capsule body 500a has a structure similar to that of the capsule endoscope 1 from which the permanent magnet 11 is removed. The sheath 500b includes the permanent magnet 502 installed therein and an inserting unit for removably inserting capsule body 500a therein. A plurality of sheaths 500b are prepared for each magnetic force (that is, the size of the permanent magnet) of the permanent magnet to be installed. In other words, a plurality of sheaths 500b are prepared for each selected permanent magnets according to body types of patients.

Figure 62:
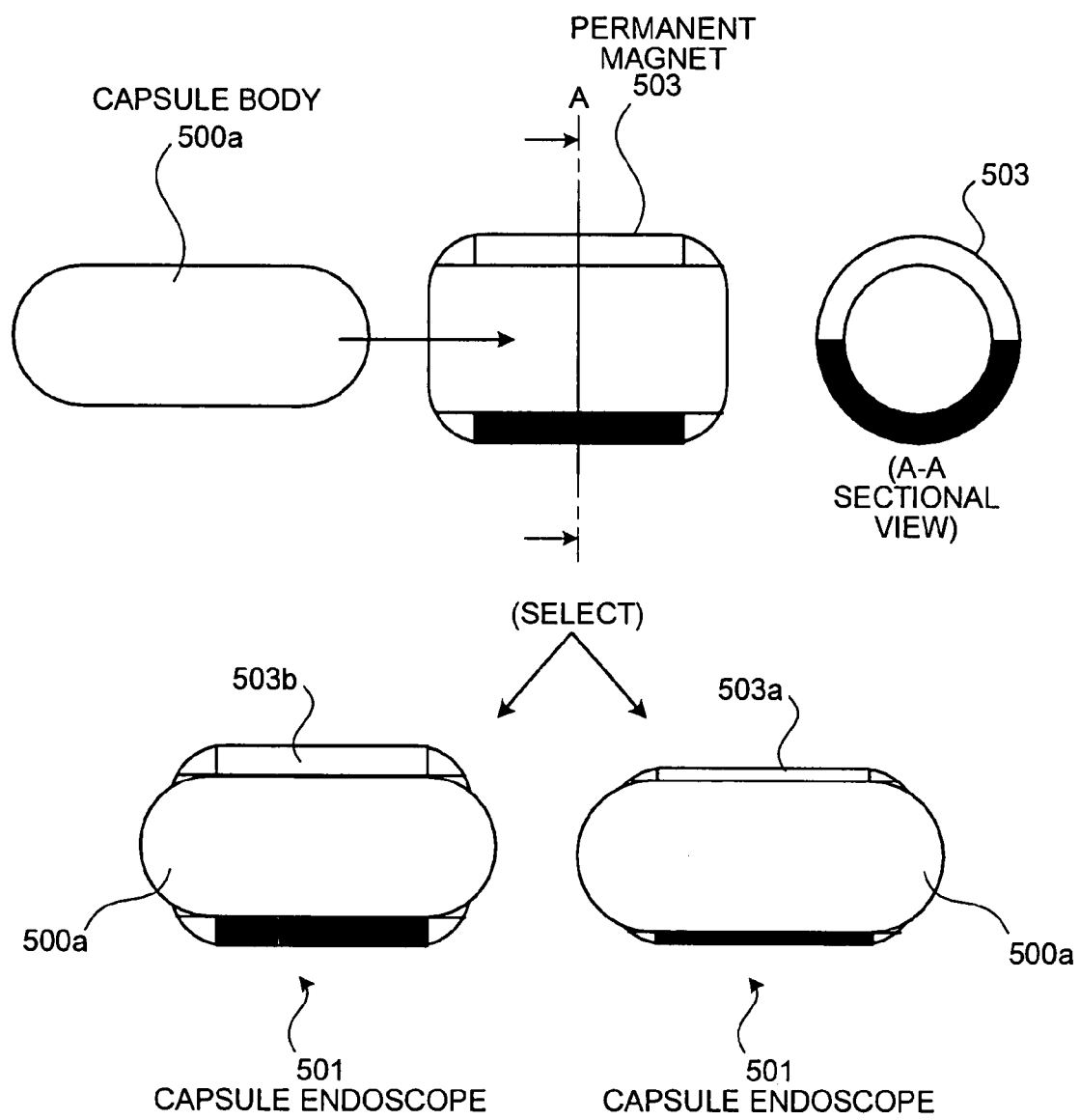
FIG. 62 is a schematic view showing a configuration example of a capsule endoscope in which a cylindrical permanent magnet is removable from a casing.

Further, such a capsule endoscope 501 may be formed by selectively attaching cylindrical permanent magnets in different size (that is, magnetic forces) to the capsule body 500a. FIG. 62 is a schematic view showing a configuration example of a capsule endoscope formed by removably attaching a cylindrical permanent magnet to a capsule body. As shown in FIG. 62, the capsule endoscope 501 is formed by removably covering the capsule body 500a with a cylindrical permanent magnet 503. As shown in the sectional view seen from the line A-A of FIG. 62, the permanent magnet 503 is a cylindrical permanent magnet and one half is magnetized to be north pole and the other half is magnetized to be south pole. The capsule body 500a is removably inserted into the permanent magnet 503. A plurality of the cylindrical permanent magnet 503 are prepared for every sizes (that is, each permanent magnet selected according to body types of patients).

Here, when the size of the permanent magnet to be disposed to the capsule endoscope 501 is changed, a sheath 500b to cover the capsule body 500a is selected according to the body type of the patient among a plurality of sheaths including permanent magnets in different sizes. Then, as shown in FIG. 61, the selected sheath 500*b* removably covers the capsule body 500*a*. By selecting a sheath including a permanent magnet in this way, the capsule endoscope 501 with the capsule body 500*a* covered by the sheath 500*b* including the permanent magnet 502*a* having a relatively small magnetic force can be selectively formed, or the capsule endoscope 501 with the capsule body 500*a* covered by the sheath 500*b* including permanent magnet 502*b* having a relatively large magnetic force compared to the permanent magnet 502*a* can be selectively formed. With this structure, the size of a magnet in the capsule endoscope 501 can be changed (selected) according to the patient's body type.

Or, a cylindrical permanent magnet 503 for covering the capsule body 500*a* is selected among the group of cylindrical permanent magnets in different sizes according to the body type of the patient, and then, as shown in FIG. 62, the capsule body 500*a* is removably covered by the selected permanent magnet 503. By selecting the cylindrical permanent magnet in this way, the capsule endoscope 501 with the capsule body 500*a* covered by the permanent magnet 503*a* having a relatively small magnetic force can be selectively formed, or a capsule endoscope 501 with the capsule body 500*a* covered by the permanent magnet 503*b* having a relatively large magnetic force compared to the permanent magnet 503*a* can be selectively formed. With this structure, the sizes of the magnet in the capsule endoscope 501 can be changed (selected) according to the body type of the patient.

Further, such sheath 500*b* has an RFID tag (not shown) in which specific information for specifying the installed permanent magnet 502 is recorded. Or, the capsule body 500*a* for being removably attached into the cylindrical permanent magnet 503 has an RFID tag (not shown) in which specific information for specifying the permanent magnet 503 is recorded. The above described workstation or capsule guidance device may include a reader for reading the specific information from the RFID tag and recognize the size of permanent magnet 502 in the sheath 500*b* or the size of the cylindrical permanent magnet 503 covering the capsule body 500*a* based on the specific information read by the RFID tag of the sheath 502. Before generating a magnetic field toward the capsule endoscope 501 inserted in the subject 100 to lead, the workstation or the capsule guidance device recognizes the size of the permanent magnet 502 or the permanent magnet 503 and controls the strength of the magnetic field to be generated to the capsule endoscope 501 based on the recognitions.

The method how the above described workstation or the capsule guidance device recognizes the size or the like of the permanent magnet 502 or the permanent magnet 503 in the capsule endoscope 501 is not limited to the above method using the RFID tag and other method may be applied. Concretely, when leading the capsule endoscope 501 is started, the size or the like of the selected permanent magnet may be input to the capsule guidance device or the workstation to recognize the size of the permanent magnet. Or, a visible marker may be provided on a member in which the permanent magnet 502 is installed (the sheath 500*b* or the capsule body 500*a*) and the marker may be read by a reader provided to the workstation or the capsule guidance device to recognize the size of the permanent magnet. In addition, a marker for identifying the size of the permanent magnet may be provided in the imaging field of the capsule body 500*a* and the marker may be read from the image taken by the capsule body 500*a* to recognize the size of the permanent magnet.

Here, when a capsule guidance device in which an electrical magnet for generating a magnetic field toward the capsule endoscope 501 in the subject 100 is deposed in planar arrangement is used, magnetic field becomes smaller at where there is more distance from the electrical magnet. Therefore, a patient with a big build (that is, subject 100) cannot obtain sufficient magnetic force, magnetism, or torque inside the body. Further, when the permanent magnet in the capsule endoscope is enlarged for a patient with a big build, it becomes difficult to introduce the capsule endoscope which is larger than need into patient with a small build.

However, in the capsule endoscope 501 having above described structure, the size of the permanent magnet can be changed (selected) in accordance with the body type of the patient. Further, the capsule guidance device recognizes the size of the permanent magnet in the capsule endoscope 501 and properly adjusts the strength of the magnetic field generated toward the capsule endoscope 501. As a result, the capsule endoscope 501 in body can be led under a proper condition according to the body type of a patient.

Figure 63:
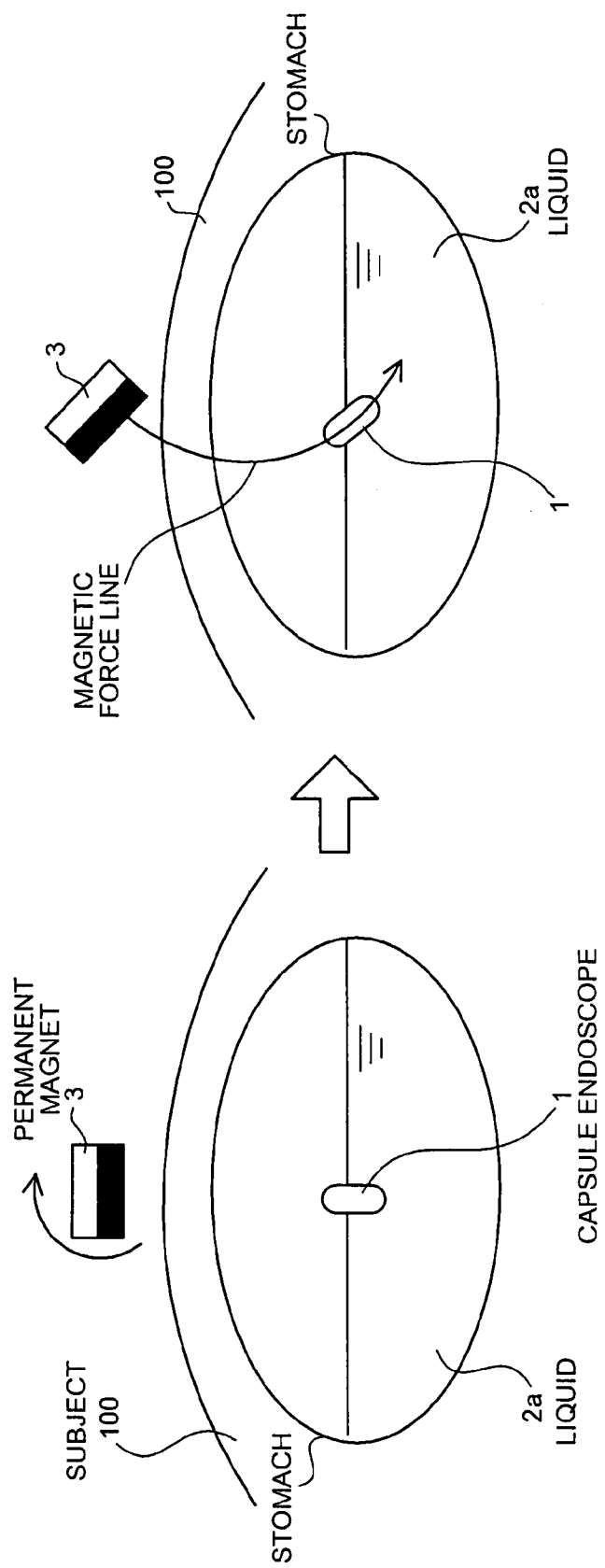
FIG. 63 is a schematic view showing an operation of a capsule endoscope for changing its posture by turning around but not displacing an external permanent magnet.

On the other hand, according to the first embodiment and its modification of the present invention, the posture of the capsule endoscope in the subject 100 is moved by moving the external permanent magnet 3 on the body surface of the subject 100; however, the present invention is not limited to this. The posture of the capsule endoscope in the subject 100 may be changed by changing the orientation of the permanent magnet 3 at a position without changing the position of the permanent magnet 3 on the body surface of the subject 100. Concretely, as shown in FIG. 63, the external permanent magnet 3 magnetically captures the capsule endoscope 1 in the liquid 2 introduced in the stomach of the subject 100 (by the magnetic fore generated by the permanent magnet 3) and the orientation of the external permanent magnet 3 is changed on the subject 100 without moving the position. In this case, the permanent magnet 3 changes the direction of magnetic force line toward the capsule endoscope 1 so that the posture of the capsule endoscope 1 is changed. Further, in FIG. 63, the permanent magnet 3 is disposed above the liquid in the subject 100 in a vertical direction; however, the permanent magnet 3 may be disposed in a direction opposite to the case in FIG. 63 (under the liquid in the subject 100 in a vertical direction). Further, electromagnet in an array as shown in FIGS. 32 and 35 may be employed in place of the permanent magnet 3. In this case, a magnetic field for magnetically capturing the capsule endoscope 1 may be generated by the vertical magnetic field generators 81*a*, 201*a* and the direction of the capsule endoscope 1 may be changed by the magnetic field generated by the horizontal magnetic field generators 81*b*, 201*b*. Further, an electrical magnet as shown in FIG. 27 may be employed in place of the permanent magnet 3. In this case, a magnetic field for magnetically capturing the capsule endoscope 1 may be generated by the vertical magnetic field generators 61 and the magnetic field generated by the horizontal magnetic field generator 62 may be changed by the rotary table 63 so that the direction of the capsule endoscope 1 may be changed.

Further, according to the first and third embodiments and their modifications of the present invention, the amount of the liquid 2*a* in the subject 100 at a standing posture or sitting posture is adjusted, and then the vertical direction of the capsule endoscope in the subject 100 is changed; however, the present invention is not limited to this and the horizontal position and posture of the capsule endoscope in the subject 100 at the standing posture or sitting posture may be changed. In this case, when the permanent magnet 3 is put closer to the side of the stomach of the subject 100 at the standing posture or sitting posture, the horizontal position and posture of the capsule endoscope in the subject 100 at the standing posture or sitting posture can be controlled.

Figure 64:
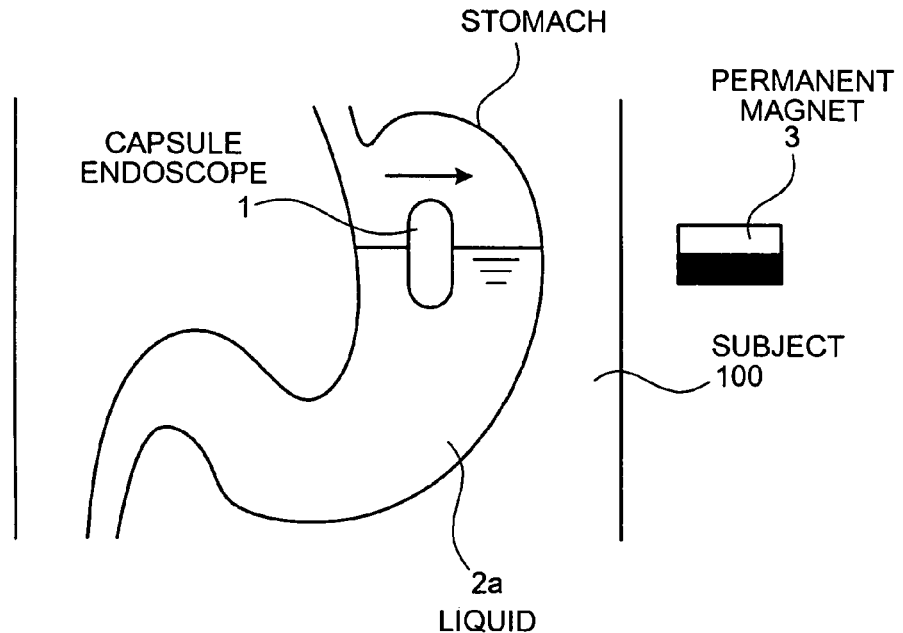
FIG. 64 is a schematic view showing an operation of moving the capsule endoscope horizontally toward the external permanent magnet when the capsule endoscope is in a subject which is sitting or standing.
Figure 65:
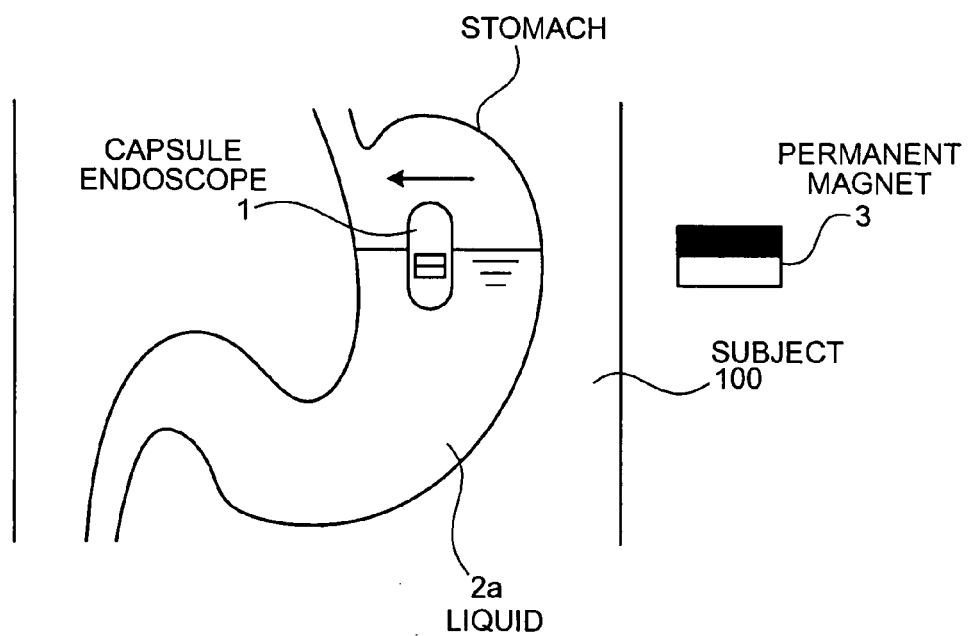
FIG. 65 is a schematic view showing an operation of moving the capsule endoscope horizontally away from the external permanent magnet when the capsule endoscope is in a subject which is sitting or standing.
Figure 66:
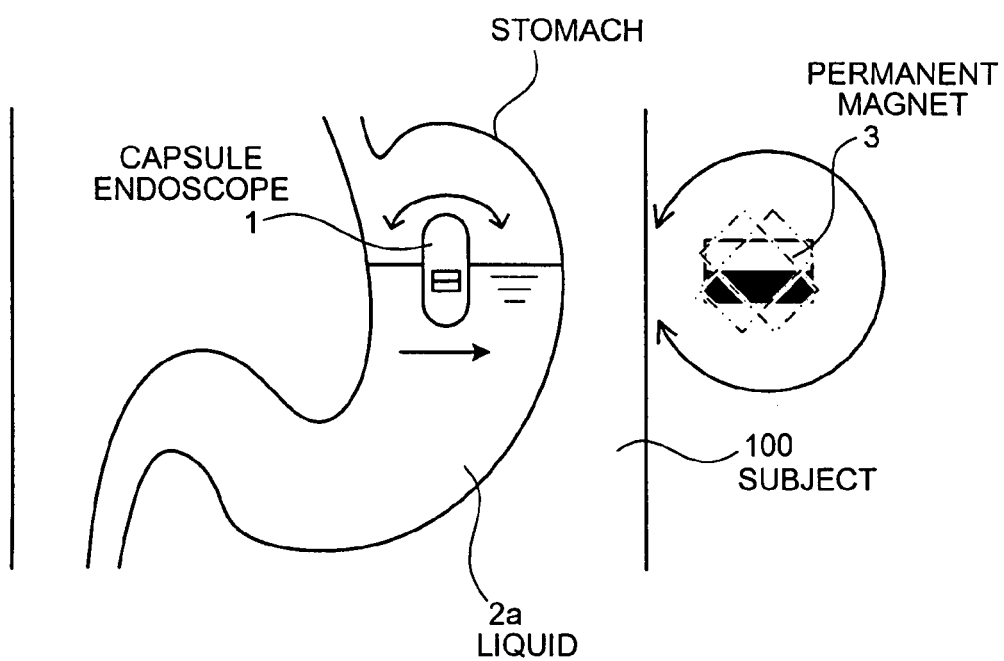
FIG. 66 is a schematic view showing an operation of changing a posture of the capsule endoscope which is in a subject which is sitting or standing.

Concretely, for example, as shown in FIG. 64, when the permanent magnet 3 is put closer to the side (side in a horizontal direction) of the stomach of the subject 100 at the standing posture or sitting posture so as to draw the permanent magnet of the capsule endoscope 1 introduced into the stomach of the subject 100, the capsule endoscope 1 horizontally moves toward the permanent magnet 3. At this time, it is desirable that the center of gravity of the capsule endoscope 1 is set such that the magnetization direction of the permanent magnet 11 in the capsule endoscope 1 in the liquid in the subject 100 becomes 10 degree or larger with respect to the liquid surface under a condition in which no magnetic field is generated outside the subject 100 (center of gravity is displaced from the center of the capsule endoscope 1 toward the direction with 10 degree or larger with respect to the magnetization direction of the permanent magnet 11). When the capsule endoscope 1 is led, the permanent magnet 3 is put closer to the subject 100 so that the magnetization direction of the permanent magnet 3 and the magnetization direction of the permanent magnet 11 direct in opposite directions. Here, since there is not major change in the magnetization direction of the permanent magnet 11 before and after the generation of the magnet field, the controllability is improved. In addition, magnetic torque is not required to be generated so leading becomes more efficient and the permanent magnet 11 and the permanent magnet 3 can be downsized. Further, for example, as shown in FIG. 65, when the external permanent magnet 3 is put closer to the capsule endoscope 1 of the subject 100 in an opposite direction to the permanent magnet in the capsule endoscope 1, the capsule endoscope 1 moves horizontally away from the permanent magnet 3. Here, under a condition in which there is no magnetic field is generated outside 100, the center of gravity is placed such that the magnetization direction of the permanent magnet 11 in the capsule endoscope 1 in the liquid in the subject 100 becomes 10 degree or larger with respect to the liquid surface (the center of gravity is displaced from the center of the capsule endoscope 1 toward the direction with 10 degree or larger with respect to the magnetization direction of the permanent magnet 11). The permanent magnet 3 is put closer to the subject 100 to make the magnetization direction of the permanent magnet 3 and the magnetization of the permanent magnet 11 the same direction. Here, desirably, the vertical position of the permanent magnet 3 is at the level of the liquid surface. With such a structure, efficient and secure control is realized. Although not shown in the drawings, when the permanent magnet 3 is put closer to the liquid in the subject 100 from the upward or downward in a vertical conation, the same effect can be obtained by putting the permanent magnet 3 closer to the subject 100 such that the magnetization direction of the permanent magnet 3 and the magnetization direction of the permanent magnet 11 are opposite. On the other hand, when the orientation of the permanent magnet 3 is changed when putting the permanent magnet 3 closer to the subject 100 from the side of the stomach, for example, as shown in FIG. 66, the capsule endoscope 1 in the subject 100 moves horizontally while changing the imaging field (that is, while changing its posture). As described above, by putting the permanent magnet 3 close to the side of the stomach, at least one of the position and posture of the capsule endoscope introduced in the stomach of the subject 100 at a standing or sitting posture can be controlled. It is substantially the same when using an electrical magnet, in place of the permanent magnet 3. Further, under a condition in which there is no magnetic field outside the subject 100, when the center of gravity is set such that the magnetization direction of the permanent magnet 11 in the capsule endoscope 1 in the liquid in the subject 100 is 10 degree or larger with respect to the liquid surface (the center of gravity is displaced from the center of the capsule endoscope 1 toward the direction with 10 degree or larger with respect to the magnetization direction of the permanent magnet 11), the case of generating magnetic attracting force and the case of generating magnetic repulsive force can be switched by switching between the conditions shown in FIGS. 64 and 65 (switching the orientation of the permanent magnet 3). When an electrical magnet is used in place of the permanent magnet 3, switching of the magnetic attracting force and the magnetic repulsive force can be realized by switching the direction of current to be applied to the electrical magnet. Further, although not shown in the drawings, the permanent magnet 11 is placed at one side of the liquid in the subject 100 (vertical direction) and when the vertical position is changed (vertical position changing unit), a case of generating magnetic attracting force and a case of generating a magnetic repulsive force toward the capsule endoscope 1 can be switched. For example, when the permanent magnet 3 is put at the same level with the water level and magnetic repulsive force is applied to the capsule endoscope 1 (when the magnetization direction of the permanent magnet 11 of the capsule endoscope 1 and the magnetization direction of the permanent magnet 3 are the same) and the permanent magnet 3 is moved vertically, the relation of the positions where the magnetic attracting forces are generated by the permanent magnet 3 and permanent magnet 11 changes. Accordingly, the magnetic repulsive force and the magnetic attracting force can be switched.

Figure 67:
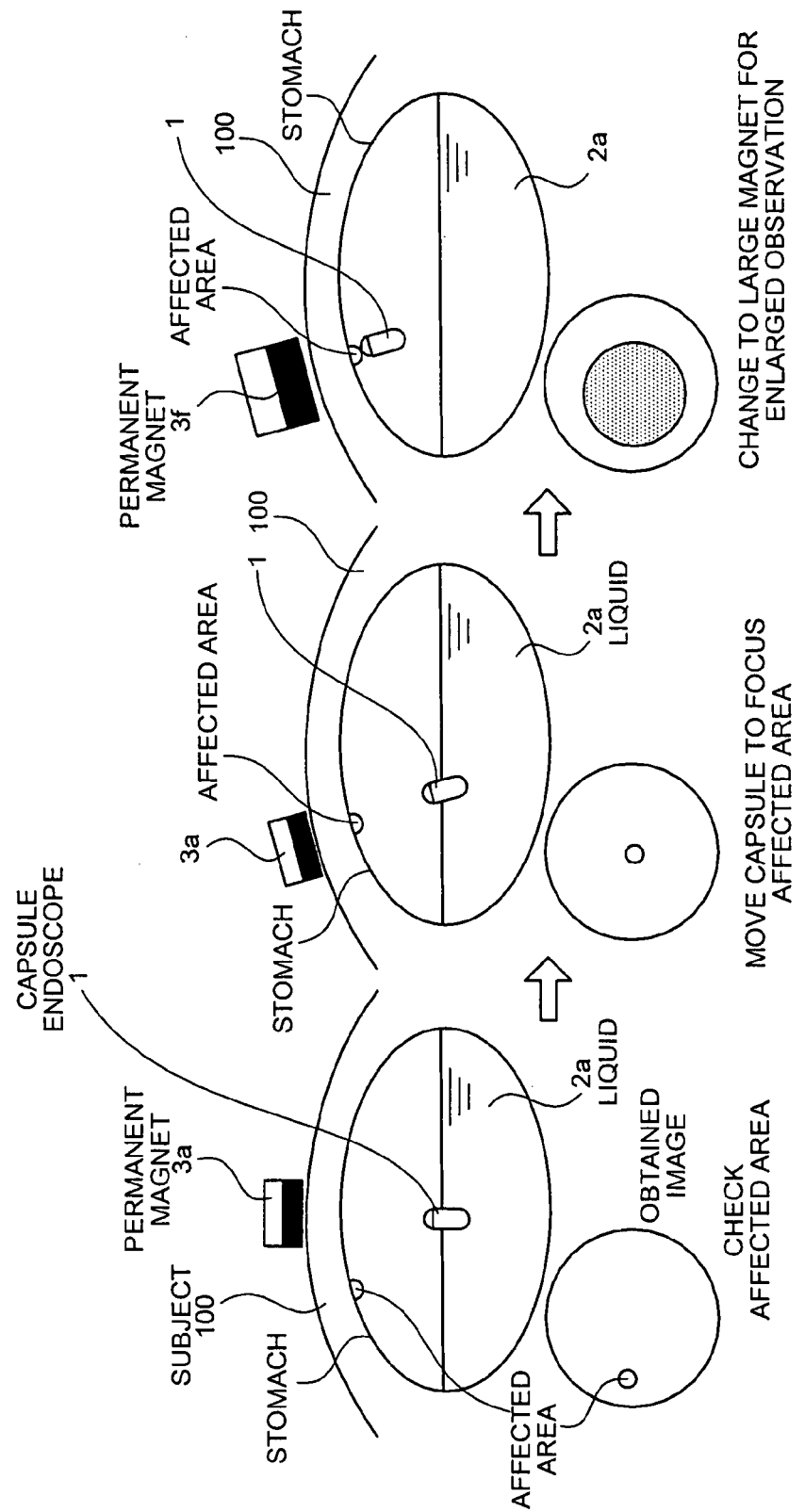
FIG. 67 is a schematic view showing a control of a position and posture of the capsule endoscope for observation by enlarging the view of affected area.

On the other hand, according to the first embodiment of the present invention, at least one of the position and posture of the capsule endoscope 1 of the subject 100 is controlled by using permanent magnet for leading the normal capsule endoscope; however the present invention is not limited to this and an enlarged image of the desired portion such as the affected area may be observed by attracting the capsule endoscope 1 by a permanent magnet having larger magnetic force. FIG. 67 is a schematic view showing a control of a position and posture of a capsule endoscope for observing enlarged view of an affected area. As shown in FIG. 67, the position and posture of the capsule endoscope 1 is changed by a leading permanent magnet 3*a* so that an obtained image is focused on the affected area of the stomach wall. Then, the leading permanent magnet 3*a* is switched to a permanent magnet 3*f* having a strong magnetic force for enlarging observation. For such permanent magnet for enlarging observation, a plurality of permanent magnets in different sizes (that is different strength of magnetic force) are prepared in advance, from one with smallest (weak) magnetic force to one with magnetic force sufficient for enlarging the affected area (the capsule endoscope 1 is drawn to the affected area).

Further, according to the fourth embodiment of the present invention, at least one of the position and posture of the capsule endoscope 51 in the liquid 2*a* is changed by the vertical magnetic field generator 61 and the horizontal magnetic field generator 62; however, the present invention is not limited to this, and, in the capsule guidance device 60, at least one of the position and posture of the capsule endoscope in the liquid 2*a* may be changed by a plurality of (desirably, three or more) electromagnet arranged symmetrically on a plane, in place of the vertical magnetic field generator 61 and the horizontal magnetic field generator 62.

Figure 68:
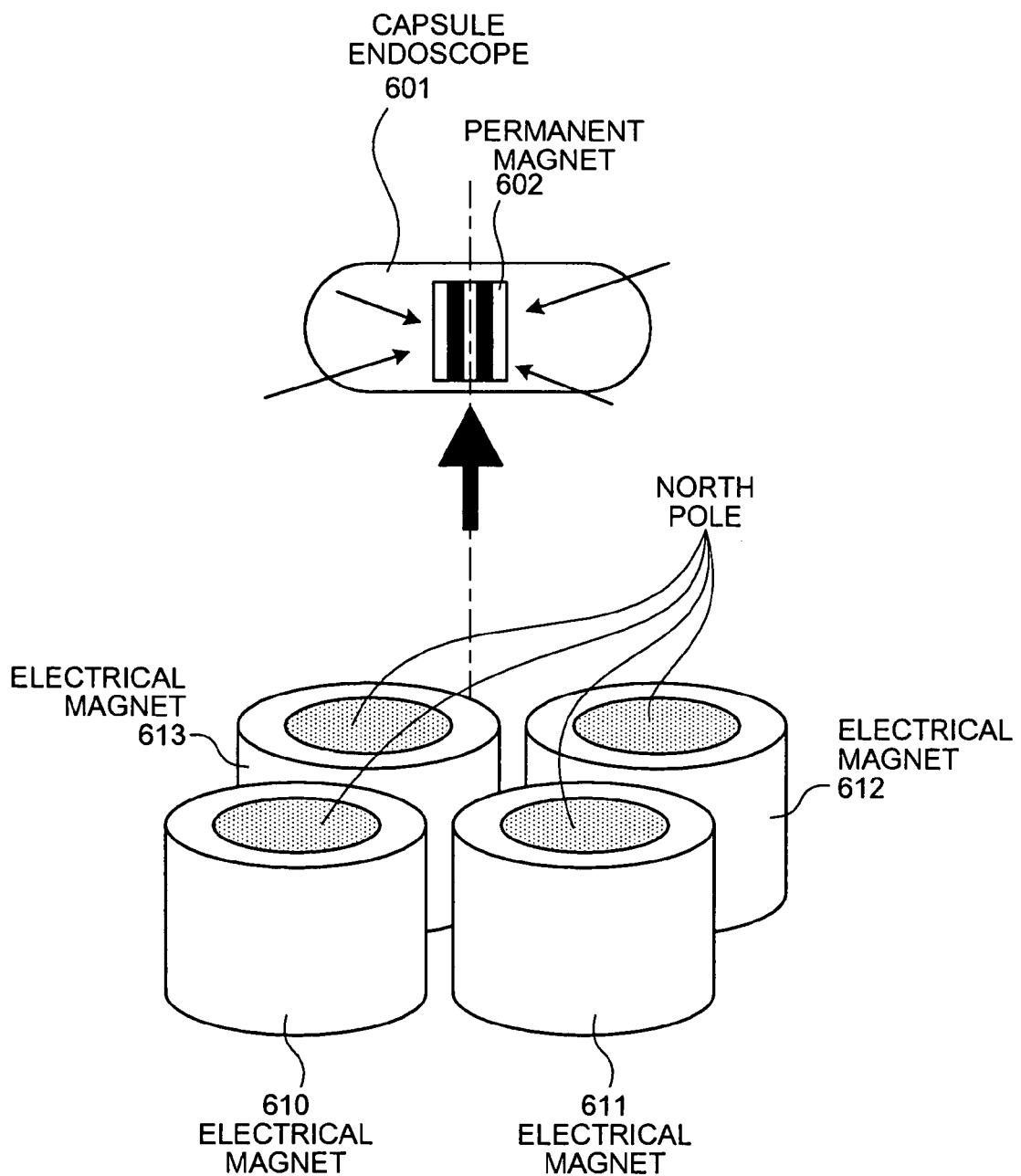
FIG. 68 is a schematic view showing a configuration example of a plurality of electromagnet for capturing the capsule endoscope on a symmetric axis.

In this case, in the capsule guidance device 60, as shown in FIG. 68, four electromagnet 610 to 613 are arranged symmetrically on a plane (in detail, on the rotary table 63). The number of the electromagnet to be arranged symmetrically should be two or more and should not be limited to 4. Further, the number of electromagnet to be arranged is desirably three or more.

Figure 69:
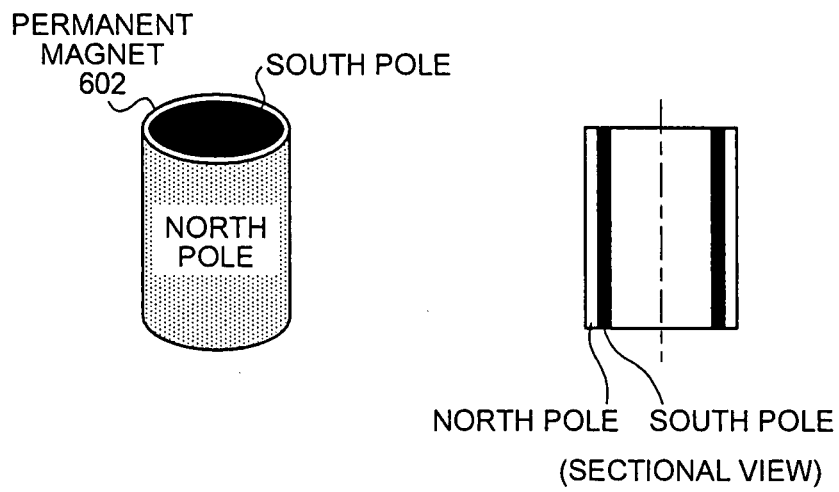
FIG. 69 is a schematic view showing a cylindrical permanent magnet provided inside the capsule endoscope.

Further, the capsule endoscope 601 lead by such capsule guidance device 60 has, as shown in FIG. 69, a cylindrical shape and is disposed with a permanent magnet 602 whose inside and outside are magnetized. The permanent magnet 602 is as shown in the sectional view in FIG. 69, magnetized to north at outer portion and magnetized to be south pole at inner portion.

As shown in FIG. 68, since such a capsule endoscope 601 receives repulsive force from the electrical magnet 610 to 63 the capsule endoscope 601 is magnetically captured (trapped) on the symmetric axis of the electromagnet 610 to 613. Further, the capsule endoscope 601 receives repulsive force form the electromagnet 610 to 613 in a direction of symmetric axis.

Figure 70:
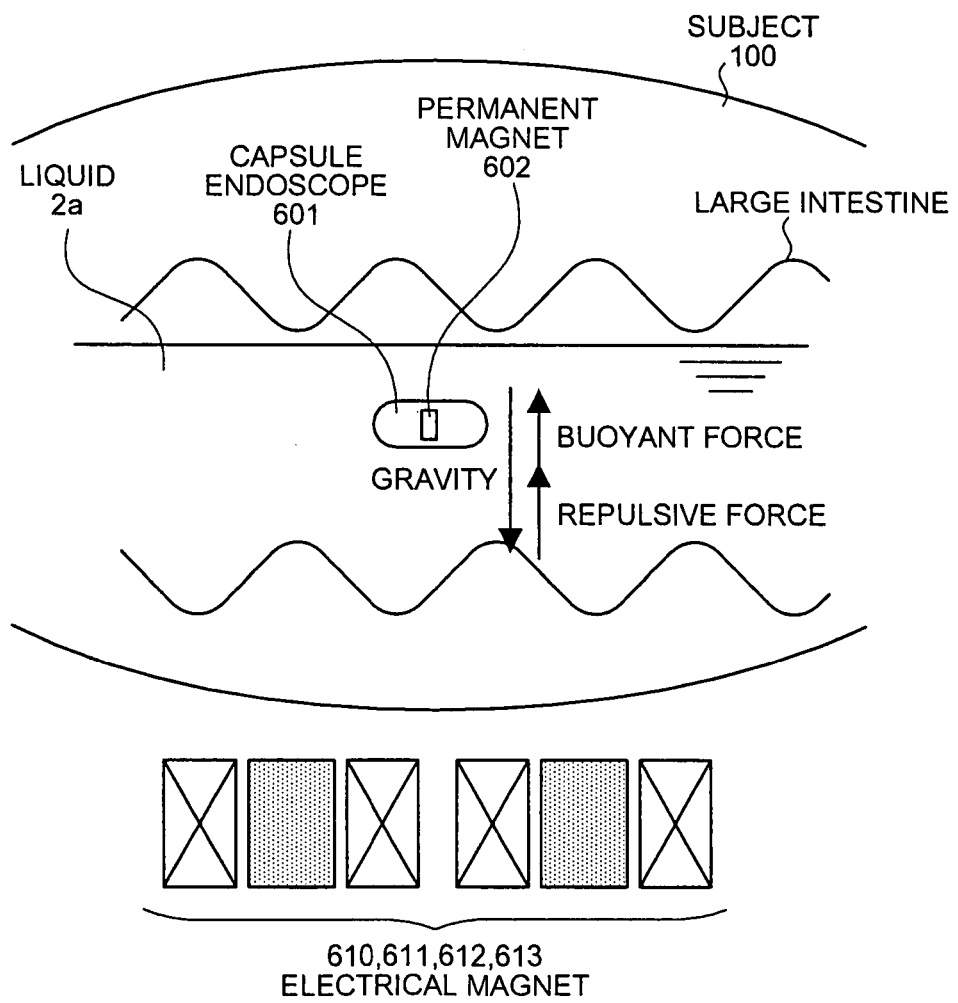
FIG. 70 is a schematic view showing an operation for capturing the capsule endoscope which has a greater specific gravity than liquid on a symmetric axis to control its position.

Here, when the specific gravity of the capsule endoscope 601 is made greater than that of the liquid 2a, as shown in FIG. 70, the capsule endoscope 601 is captured at a position where the sum of the buoyant force and repulsive force is equal to the specific gravity. When the capsule endoscope 601 is separated from the electrical magnet 610 to 613 due to disturbance, repulsive force becomes small and the capsule endoscope 601 moves toward the electrical magnet 610 to 613. Further, due to disturbance, when the capsule endoscope 601 moves close to the electromagnet 610 to 613, the repulsive force becomes larger and the capsule endoscope 601 moves away from the electromagnet 610 to 613. Therefore, control of positions of the capsule endoscope 601 which is less influenced by disturbance and is stable is obtained. By changing the magnetic field strength generated by the electromagnet 610 to 613, the stability on a horizontal plane can be changed. Further, although not shown, the permanent magnet in the capsule endoscope 601 may be a permanent magnet 11 provided to the capsule endoscope 1 in FIG. 2, and not limited to a cylindrical magnet in FIG. 68. In this case, under a condition in which there is no magnetic field is generated outside the subject 100, the center of gravity of the capsule endoscope 1 is set such that the magnetization direction of the permanent magnet 11 of the capsule endoscope 1 in the liquid in the subject 100 has 10 degree or larger with respect to the liquid surface (the center of gravity is displaced from the center of the capsule endoscope 1 toward the direction having 10 degree or larger with respect to the magnetization direction of the permanent magnet 11), and regarding the magnetic field generated by the magnetic field generator, the magnetic field strength generated at any position on a horizontal plane is set smaller than the magnetic field strength at any position at the area. The magnetic field can be generated by the electromagnet 610 to 613 in FIG. 68 or a later described ring-shaped permanent magnet in FIG. 71. With this, since the capsule endoscope 1 can be captured at a position having weak magnetic field on a horizontal plane and the posture of the capsule endoscope 1 is kept due to the position of the center of gravity, repulsive force can be kept generated.

Further, although not shown, by changing the magnetic field strength of the electromagnet 610 to 613, the vertical position of the capsule endoscope 601 can be controlled and the horizontal position can be controlled by the position of the electromagnet 610 to 613. Further, although not shown, when a magnetic field balance changing unit for changing the balance of the magnetic fields generated by the electromagnet 610 to 613, the position and posture of the capsule endoscope 601 in a horizontal direction can be controlled. Firstly, the inclination of the electromagnet 610 to 613 is changed by a magnetic field generator inclination changing unit. With this, since the position of weak magnetic field on a horizontal plane is moved, the position of the capsule endoscope 1 changes. Further, when the inclination of the magnetic field generator increases, the posture of the capsule endoscope 1 changes. Further, the relative position of the electromagnet 610 to 613 is changed by the relative position changing unit. With this, since position of the weak magnetic field on a horizontal plane is moved, the position of the capsule endoscope 1 changes. Further, for the same reason, the position and posture of the capsule endoscope 601 can be controlled by adjusting the outputs of the electromagnet 610 to 613. Further, the position of weak magnetic field on a horizontal plane may be moved by arranging the plurality of electromagnet as an array state on a substantially horizontal plane and changing the current applied to each electrical magnet.

Figure 71:
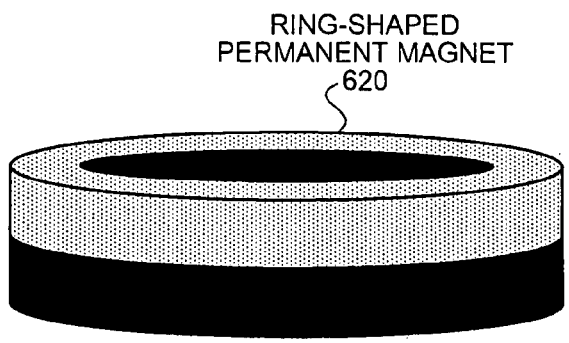
FIG. 71 is a schematic view showing a ring-shaped permanent magnet, in place of the electrical magnet, for capturing the capsule endoscope on a symmetrical axis.
Figure 72:
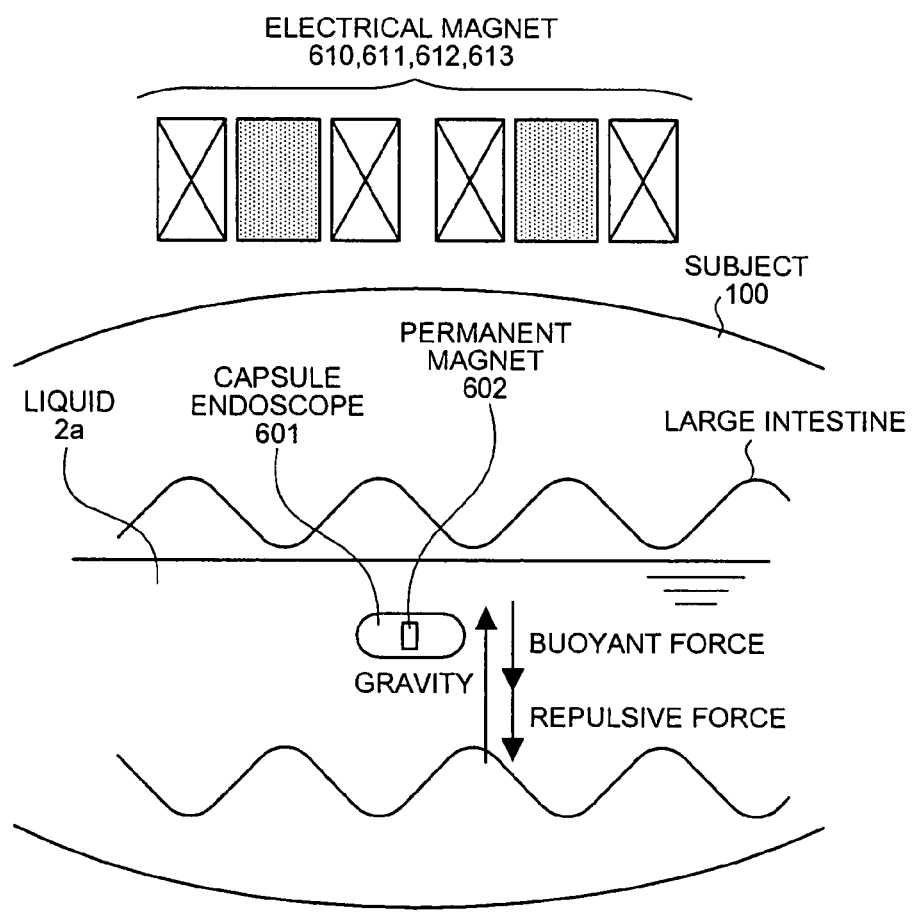
FIG. 72 is a schematic view showing an operation for capturing the capsule endoscope which has a smaller specific gravity than the liquid on a symmetric axis to control its position.

As a modification of such capsule guidance device 60, the ring-shaped permanent magnet 620 shown in FIG. 71 may be disposed, in place of the electromagnet 610 to 613. Further, although not shown, two electromagnet arranged in a same axis may be provided to magnetize the two electromagnet in different direction for each. With this, a region with weak magnetic field strength may be formed on the axis of the two coils. Further, a magnetic field generator 201 as shown in FIG. 35 may be provided. By magnetizing the horizontal magnetic field generators 201b, 201c in the same direction, a magnetic field having weaker magnetic field strength of the central axis of the magnetic field generator 201 compared to the peripheral region can be generated. Further, by magnetizing the vertical magnetic field generator 201a in a direction opposite to the horizontal magnetic field generators 201b, 201c, the magnetic field strength of the central axis can be weakened. Further, when the specific gravity of the capsule endoscope 601 is smaller than the specific gravity of the liquid 2a, as shown in FIG. 72, the electromagnet 610 to 613 are disposed vertically above the liquid in the subject 100. In this case, the capsule endoscope 601 in the liquid 2a is captured at a position where the sum of the buoyant force and repulsive force and specific gravity are balanced. Also, in this case, similarly to FIG. 68, under a condition in which no magnetic field is generated outside the subject 100, the position of the center of gravity of the capsule endoscope 1 is set such that the magnetization direction of the permanent magnet 11 of the capsule endoscope 1 in the liquid in the subject 100 has 10 degree or larger. The same effect can be obtained regarding the stability against the disturbance in a vertical direction. Further, although not shown, when the electrical magnet does not generate magnetic repulsive force, the posture of the capsule endoscope 1 can be controlled by generating magnetic field in a direction opposite to the magnetic field which is generated by the electrical magnet (magnetic field direction switching unit) and changing the directions. Further, not only for the present modification, when the vertical position is controlled by the magnetic attracting force or magnetic repulsive force, the specific gravity of the capsule endoscope 1 compared to that of the liquid is desirably close to 1. When the specific gravity is close to 1, since the magnetic attracting force and the magnetic repulsive force required for leading the capsule endoscope 1 is small, the controllability is improved and the magnetic field generator is downsized so that the operability can also be improved.

Figure 73:
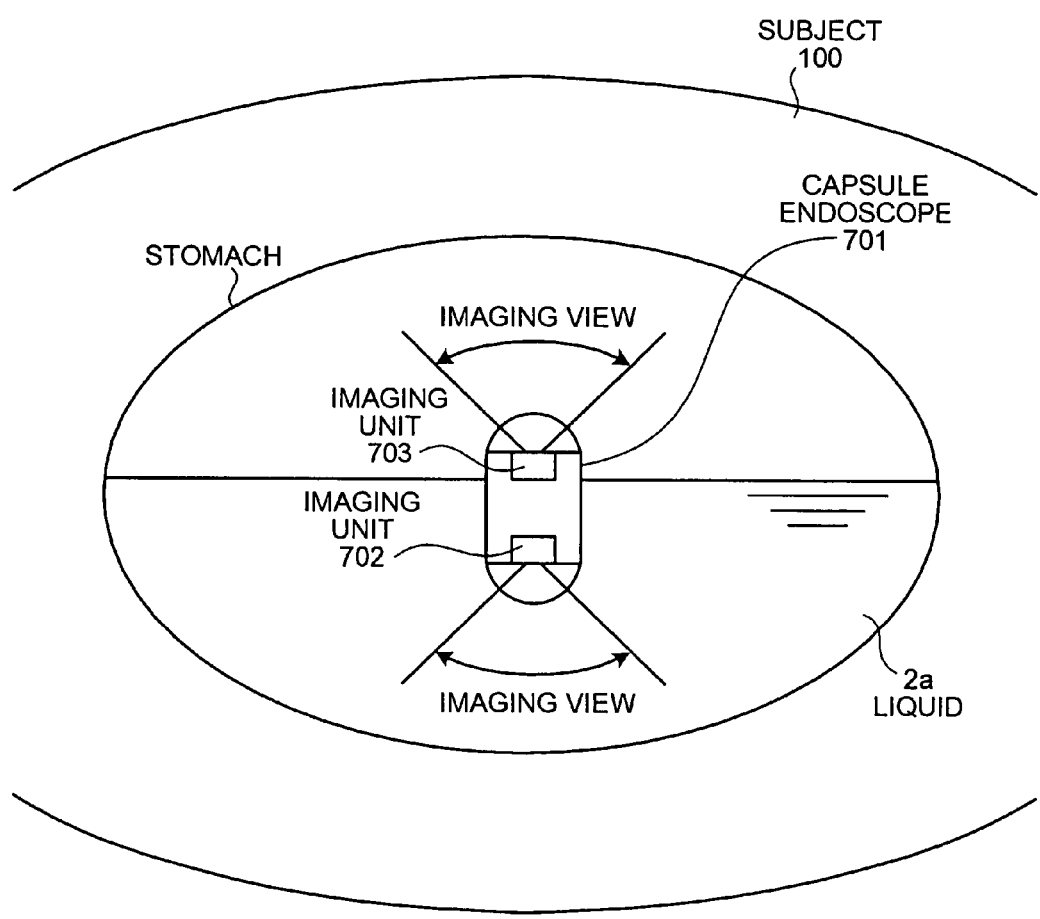
FIG. 73 is a schematic view showing a configuration example of the capsule endoscope having a plurality of imaging units which have different imaging fields.

On the other hand, according to the first to fourth embodiments and modifications of the present invention, a capsule endoscope having an imaging field at an end of a casing is employed; however, the present invention is not limited to this, and a capsule endoscope having a plurality of imaging units of different imaging fields fixed in the case may be employed. In this case, a capsule endoscope 701 having different imaging fields includes imaging units 702, 703 at both ends of a casing, as shown in FIG. 73. Other elements are substantially the same as the capsule endoscopes according to the first to fourth embodiments and modifications. In this case, the imaging unit 702 images, for example, stomach wall in the liquid 2a and, at the same time, the imaging unit 703 images stomach wall out of the liquid. With the capsule endoscope 701 having such structure, since the conditions in the liquid and out of the liquid are imaged at the same time, the efficiency of the observation improves and the inspection time is reduced. Further, since the vertical position of the capsule endoscope 701 can be controlled by the water level of the liquid 2a while the imaging fields in and out of the liquid are maintained, the observation capability is improved.

Figure 74:
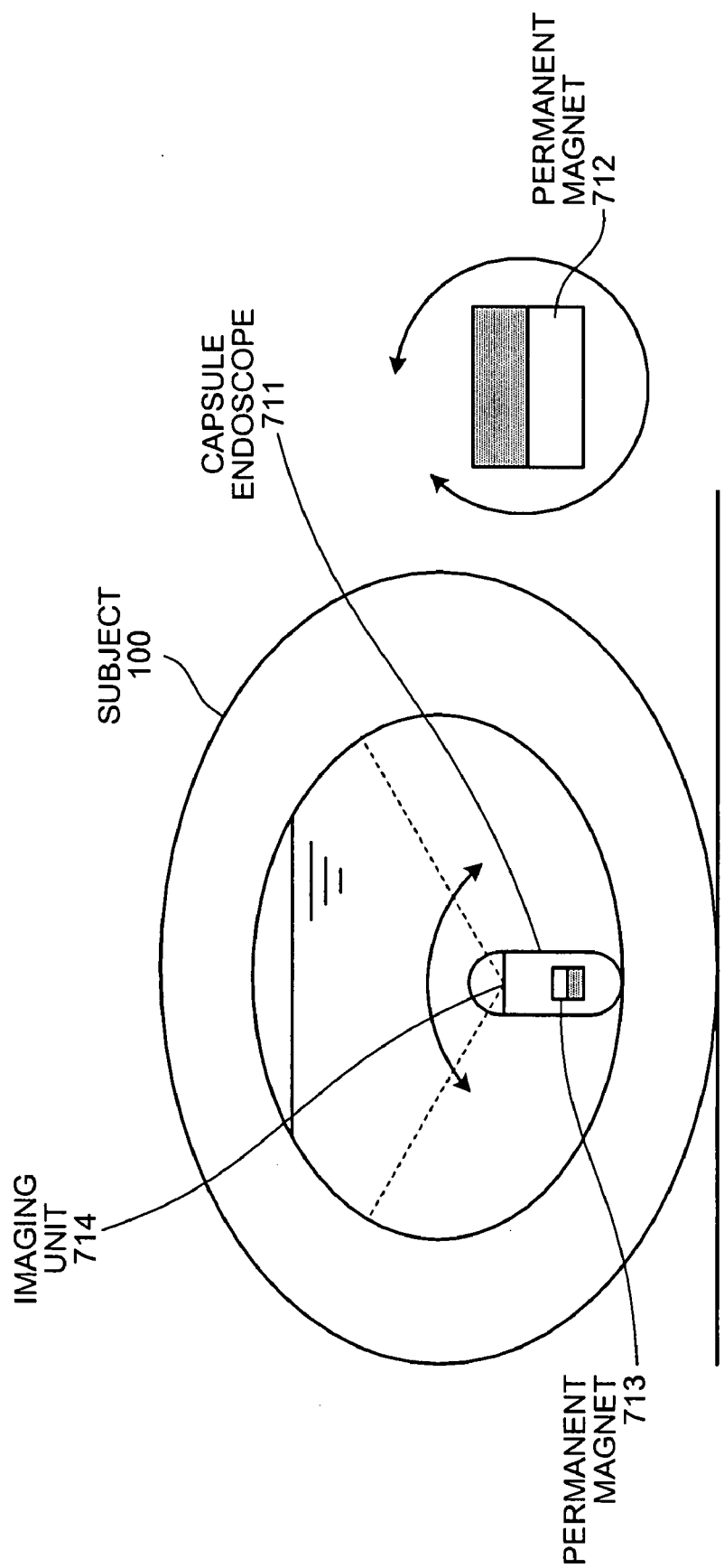
FIG. 74 is a schematic view showing a specific example for changing the direction of the capsule endoscope by changing the posture of the permanent magnet when the capsule endoscope contacts with an inner wall of an internal organ.

Further, as shown in FIG. 74, when the specific gravity of the capsule endoscope 711 is larger than the specific gravity of the liquid, a permanent magnet 712 outside the subject 100 is placed in a direction of side face (horizontal) with respect to the liquid in the subject 100 and the posture of the permanent magnet 712 is changed so as to change the direction of the capsule endoscope 711 in the subject 100 (in the liquid) and to change the direction of the imaging unit 714 (imaging field) of the capsule endoscope 711. In this case, since the capsule endoscope 711 contacts with the stomach wall, the direction of the capsule endoscope 711 (imaging field) can be certainly changed with the contact point of the capsule endoscope 711 and the stomach wall as a supporting point.

Figure 75:
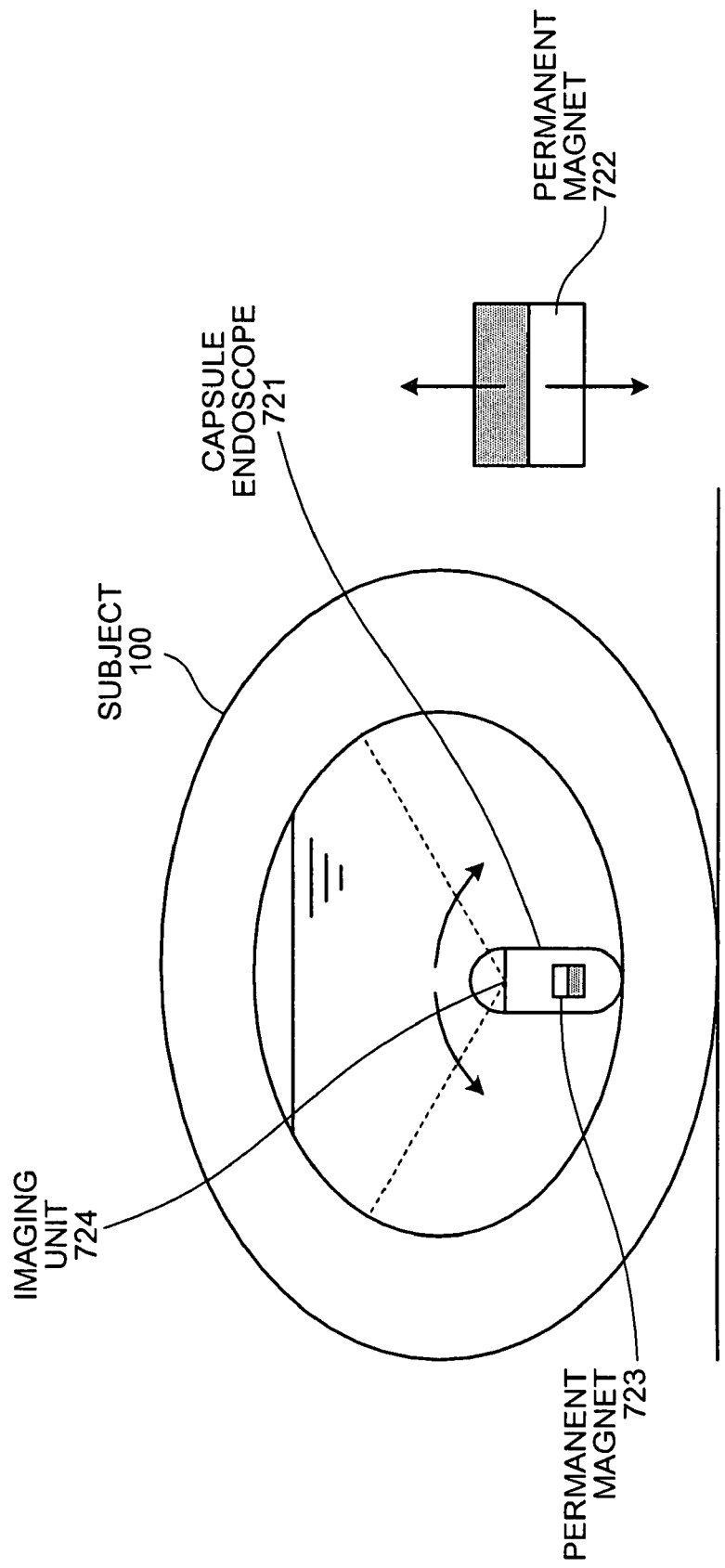
FIG. 75 is a schematic view showing a specific example for changing the direction of the capsule endoscope by displacing the permanent magnet vertically when the capsule endoscope contacts with an inner wall of an internal organ.

Further, as shown in FIG. 75, when the specific gravity of the capsule endoscope 721 including the permanent magnet 723 is larger than the specific gravity of the liquid, the permanent magnet 722 outside the subject 100 may be placed in a direction of side face (horizontal) with respect to the liquid in the subject 100, and the direction of the imaging unit 724 (imaging field) of the capsule endoscope 721 may be changed by changing the vertical position of the permanent magnet 722 so as to change the direction of the capsule endoscope 721 in the subject 100 (in the liquid). In this case, also, since the capsule endoscope 721 contacts with the stomach wall, the direction of the capsule endoscope 721 can be certainly changed with the contact point of the capsule endoscope 721 and the stomach wall as a supporting point. Here, when the vertical direction of movement of the permanent magnet 722 is changed to downward in a vertical direction (downward in FIG. 75), the capsule endoscope 721 in the subject 100 can reverse its orientation.

Figure 76:
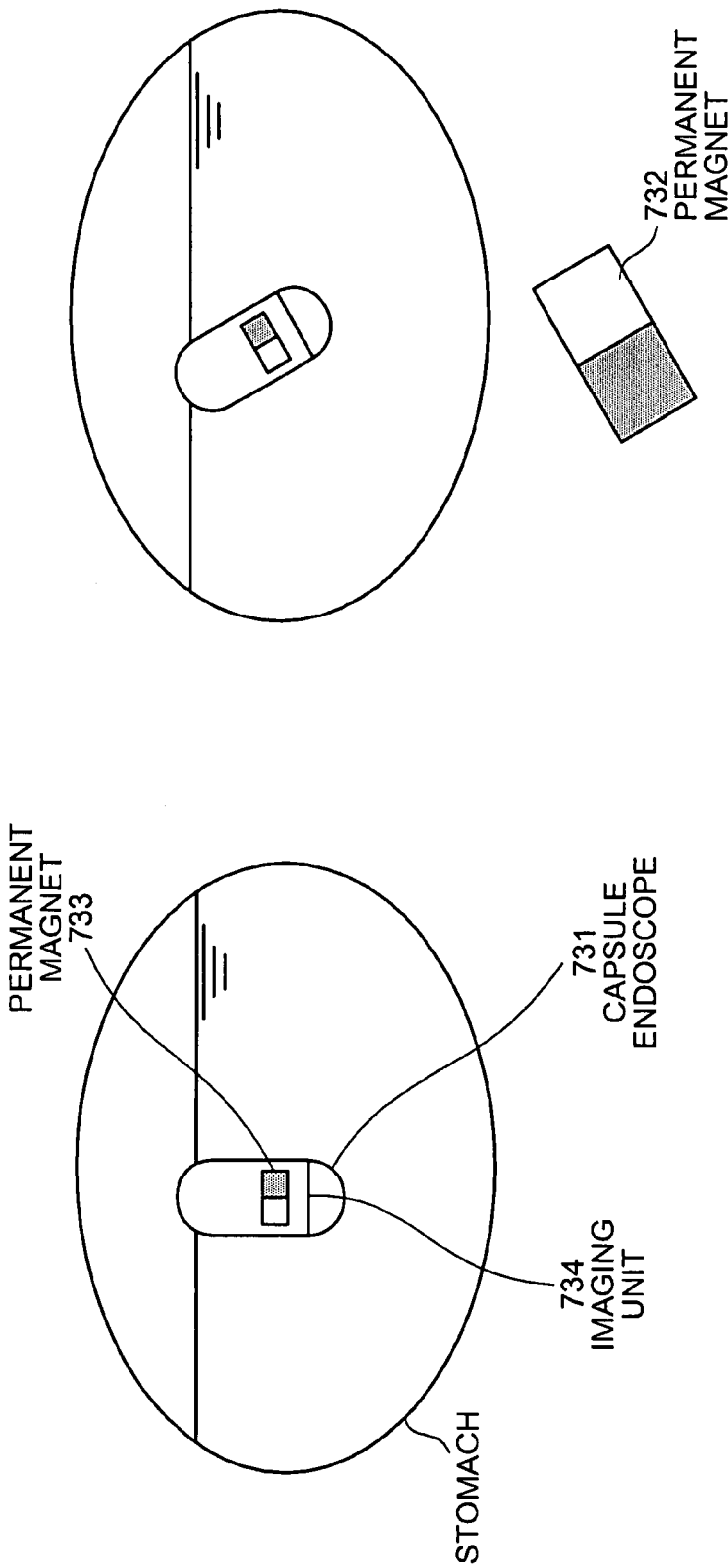
FIG. 76 is a schematic view showing another specific example for changing the direction and posture of the capsule endoscope when the capsule endoscope has a smaller specific gravity than liquid.

Further, as shown in FIG. 76, when the specific gravity of the capsule endoscope 731 including the permanent magnet 733 is smaller than the specific gravity of the liquid, the imaging unit 734 and the permanent magnet 73 are disposed so that the direction of the imaging unit 734 (imaging field) of the capsule endoscope 731 is vertical with respect to the magnetization direction of the permanent magnet 733. Also, under a condition in which there is no magnetic field applied to the capsule endoscope 731 in the liquid in the subject 100 from outside the subject 100, the center of gravity of the capsule endoscope 731 is set such that the magnetization direction of the permanent magnet 733 of the capsule endoscope 731 in a floating condition becomes substantially parallel to the liquid surface. As a result, the position and posture of the capsule endoscope 731 can be controlled by putting the permanent magnet 732 placed outside the subject 100 close to the capsule endoscope 731 in the subject 100. Generally, when the magnetization direction of the permanent magnet 733 and the direction of the imaging unit 734 are substantially perpendicular to each other, the freedom of rotation around the magnetization direction of the permanent magnet 733 cannot be determined uniquely even when a magnetic field is generated toward the permanent magnet 733. However, the direction of the capsule endoscope 731 can be determined uniquely when a magnetic field is generated by defining the freedom around the magnetization direction of the permanent magnet 733 based on the balance of the position of the center of gravity of the capsule endoscope 731 (displacing the center of gravity from the center of the capsule endoscope 731 in a direction perpendicular to the magnetization direction of the permanent magnet 733). With this, the direction of the imaging field of the imaging unit 734 of the capsule endoscope 731 can be certainly changed. Further, the permanent magnet 732 outside the subject 100 may be put closer to the liquid in the subject 100 from the above in a vertical direction. Further, the horizontal position of the capsule endoscope 731 in the subject 100 can be controlled by changing the horizontal position of the permanent magnet 732. Here, the controllability is high since the direction of the imaging unit 734 can be determined uniquely without relying on orientation on a horizontal plane of the magnetization direction of the permanent magnet 732 put close to the subject 100. In FIG. 76, the permanent magnet 732 is put close to the liquid in the subject from underneath in a vertical direction; however, the permanent magnet 732 may be put close from the side in a horizontal direction. Here, the same effect as the FIG. 76 can be obtained regarding the control of the horizontal condition by setting the magnetization direction of the permanent magnet 732 and a horizontal plane close to be parallel.

According to the first to fourth embodiments and modifications of the present invention, a permanent magnet is provided as a magnetic field response unit in a capsule endoscope and the position and posture of the capsule endoscope are controlled by its magnetic field; however, the present invention is not limited to this, and the permanent magnet as the magnetic field responding unit is to respond to the magnetic field so it may be an electrical magnet, electromagnetic material, or electromagnetic material and may be a battery or the like for operating the capsule endoscope functions.

Further, according to the first to fourth embodiments and modifications of the present invention, the position, posture, and direction of movement of the magnetic field generator such as permanent magnet, electrical magnet, or the like are specified; however the present invention is not limited to this and the magnetic field generator may be held by the examiner or may be mounted to a mechanism such as the arm and the stage. For example, the mechanism such as an arm or stage includes a horizontal position changing unit for changing the horizontal direction of the magnetic field generator, a vertical position changing unit for changing the vertical positions, a posture changing unit for changing the posture, and a distance changing unit for changing the distance between the magnetic field generator and the subject, or the like.

According to the present invention, since buoyant force of the liquid works on a body-insertable device and the gravity generated on the body-insertable device is canceled as much as the mount of the buoyant force, a drive unit for changing at least one of the position and posture of the body-insertable device can be downsized. With this structure, the body-insertable device it self can be downsized so that the facility of the body-insertable device for introducing into a subject can be improved. Further, a body-insertable device, a body-insertable device system, and an in-vivo observation method in which at least one of the position and direction of the imaging field in the subject can be actively controlled and desired observed region in the subject can be certainly observed in a short period of time are realized.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

Industrial Applicability

As described above, the body-insertable device system and the in-vivo observation method according to the present invention are effective for observing inside an internal organ of a subject with an image taken by the body-insertable device such as a capsule endoscope introduced in the internal organ. Particularly, at least one of the position and direction of the imaging field in the subject can be actively controlled by actively controlling at least one of the position and posture of the body-insertable device in the internal organ. Also, a desired observed region of the subject can be certainly observed in a short period of time.

What is claimed is:

1. A body-insertable device system, comprising:
a casing to be introduced into a subject and including at least one imaging unit having a specific observing direction for the subject;
liquid to be introduced into the subject; and
a drive unit which changes a position of the casing in the liquid,
wherein a specific gravity of the casing is smaller than a specific gravity of the liquid, and the drive unit includes:
a magnetic material provided in the casing;
a magnetic field generator which generates a magnetic field for the magnetic material and is placed outside of the subject; and
a horizontal position controller which causes the magnetic field generator to generate a magnetic attracting force in a horizontal direction for the magnetic material to control a horizontal position of the casing in the liquid,
wherein the drive unit includes a vertical position controller which causes the magnetic field generator to generate a magnetic attracting force in a vertical direction for the magnetic material to control a vertical position of the casing in the liquid, and the vertical position controller causes the casing to be kept under a liquid surface of the liquid and the horizontal position controller changes the horizontal position of the casing in the liquid, and
wherein the drive unit includes a position detector for detecting a position of the casing in the subject; and the vertical position controller controls the magnetic field generator based on the position detection result of the position detector to control the vertical position of the casing in the liquid.

2. The body-insertable device system according to claim 1, wherein the vertical position controller controls strength of the magnetic field generated by the magnetic field generator for the magnetic material.

3. The body-insertable device system according to claim 2, wherein the magnetic field generator is an electrical magnet, and
the vertical position controller changes current applied to the electrical magnet to control the strength of the magnetic field generated by the magnetic field generator.

4. The body-insertable device system according to claim 2, wherein the drive unit includes a magnetic field response detector which detects whether or not the casing has responded to the magnetic field generated by the magnetic field generator, and
the vertical position controller controls, based on the detection result of the magnetic field response detector, the strength of the magnetic field generated by the magnetic field generator.

5. The body-insertable device system according to claim 1, wherein the magnetic field generator is placed under the liquid in the subject in a vertical direction.

6. The body-insertable device system according to claim 1, wherein the magnetic material has a specific magnetization direction, and
center of gravity of the casing is set such that the magnetization direction and a liquid surface of the liquid have an angular difference of 10 degrees or larger when the magnetic field generator is not generating magnetic field.

7. The body-insertable device system according to claim 1, further comprising an image combining unit which combines images taken by the imaging unit,
wherein the drive unit includes a position/posture detector which detects a position and posture of the casing in the subject; and
the image combining unit combines the images taken by the imaging unit based on a result detected by the position/posture detector.

8. The body-insertable device system according to claim 1, wherein a region into which the casing is introduced is stomach.

9. An in-vivo observation method, comprising:
a casing introducing step of introducing a casing for obtaining an image into a subject;
a liquid introducing step of introducing liquid into the subject; and
a position changing step of changing a position of the casing in the liquid introduced in the casing introducing step, wherein
a magnetic material is provided in the casing and a specific gravity of the casing is smaller than a specific gravity of the liquid,
the position changing step changes the position of the casing by a magnetic field generated for the magnetic material by a magnetic field generator placed outside the subject, and
the position changing step includes generating a magnetic attracting force in a horizontal direction for the magnetic material to control a horizontal position of the casing in the liquid,
the position changing step includes
generating a magnetic attracting force in a vertical direction for the magnetic material to control a vertical position of the casing in the liquid, and
keeping the casing under a liquid surface of the liquid and changing the horizontal position of the casing in the liquid, and
a detecting step of detecting a position of the casing in the subject,
wherein the position changing step includes controlling the magnetic attracting force based on the position detection result of the detecting step to control the vertical position of the casing in the liquid.

10. The in-vivo observation method according to claim 9 wherein the position changing step includes controlling strength of the magnetic attracting force in the vertical direction to control the vertical position of the casing in the liquid.

11. The in-vivo observation method according to claim 10, wherein the position changing step includes changing current applied to an electrical magnet to control the strength of the magnetic attracting force.

12. The in-vivo observation method according to claim 10, further comprising a detecting step of detecting whether or not the casing has responded to the magnetic field, and
the position changing step includes controlling, based on the detection result of the detecting step, the strength of the magnetic attracting force.

13. The in-vivo observation method according to claim 9 wherein the magnetic field is generated from underside of the liquid in the subject in a vertical direction.

14. The in-vivo observation method according to claim 9, wherein the magnetic material has a specific magnetization direction, and center of gravity of the casing is set such that the magnetization direction and a liquid surface of the liquid have an angular difference of 10 degrees or larger when the magnetic field generator is not generating magnetic field.

15. The in-vivo observation method according to claim 9, further comprising
a position/posture detecting step of detecting a position and posture of the casing in the subject, and
an image combining step of combining images taken by the imaging unit based on a result detected by the position/posture detecting step.

16. The in-vivo observation method according to claim 9, wherein a region into which the casing is introduced is stomach.

* * * * *